(12) United States Patent
Kovach et al.

(10) Patent No.: US 9,988,394 B2
(45) Date of Patent: Jun. 5, 2018

(54) OXABICYCLOHEPTANE PRODRUGS

(71) Applicant: Lixte Biotechnology, Inc., East Setauket, NY (US)

(72) Inventors: John S. Kovach, East Setauket, NY (US); Robert Volkmann, Mystic, CT (US); Anthony Marfat, Mystic, CT (US)

(73) Assignee: Lixte Biotechnology Inc., East Setauket, NY (US)

( * ) Notice: Subject to any disclaimer, the term of this patent is extended or adjusted under 35 U.S.C. 154(b) by 0 days. days.

(21) Appl. No.: 15/154,304

(22) Filed: May 13, 2016

(65) Prior Publication Data

US 2016/0333024 A1 Nov. 17, 2016

Related U.S. Application Data

(60) Provisional application No. 62/162,501, filed on May 15, 2015.

(51) Int. Cl.

| | | |
|---|---|---|
| *C07D 493/08* | (2006.01) | |
| *A61K 31/495* | (2006.01) | |
| *A61K 31/337* | (2006.01) | |
| *C07D 493/22* | (2006.01) | |
| *A61K 31/496* | (2006.01) | |
| *A61K 9/00* | (2006.01) | |
| *A61K 47/02* | (2006.01) | |
| *A61K 45/06* | (2006.01) | |
| *A61K 31/34* | (2006.01) | |

(52) U.S. Cl.
CPC .......... *C07D 493/08* (2013.01); *A61K 9/0019* (2013.01); *A61K 9/0053* (2013.01); *A61K 31/337* (2013.01); *A61K 31/34* (2013.01); *A61K 31/496* (2013.01); *A61K 45/06* (2013.01); *A61K 47/02* (2013.01); *C07D 493/22* (2013.01)

(58) Field of Classification Search
CPC .. C07D 493/08; C07D 493/22; A61K 31/495; A61K 31/337
USPC ............................................ 549/398; 514/85
See application file for complete search history.

(56) References Cited

U.S. PATENT DOCUMENTS

| | | | |
|---|---|---|---|
| 5,206,386 | A | 4/1993 | Narayanan |
| 7,998,957 | B2 | 8/2011 | Kovach et al. |
| 8,058,268 | B2 | 11/2011 | Kovach |
| 8,143,445 | B2 | 3/2012 | Kovach et al. |
| 8,227,473 | B2 | 7/2012 | Kovach et al. |
| 8,329,719 | B2 | 12/2012 | Kovach |
| 8,426,444 | B2 | 4/2013 | Kovach et al. |
| 8,455,688 | B2 | 6/2013 | Kovach et al. |
| 8,541,458 | B2 | 9/2013 | Kovach et al. |
| 8,822,461 | B2 | 9/2014 | Kovach et al. |
| 9,079,917 | B2 | 7/2015 | Kovach et al. |
| 9,526,915 | B2 | 12/2016 | Kovach |
| 2008/0267947 | A1 | 10/2008 | Cirrito et al. |
| 2016/0264593 | A1* | 9/2016 | Kovach .................. A61K 45/06 |
| 2016/0303115 | A1 | 10/2016 | Kovach et al. |
| 2016/0333024 | A1 | 11/2016 | Kovach |

FOREIGN PATENT DOCUMENTS

| | | |
|---|---|---|
| WO | WO 2007/092414 A2 | 8/2007 |
| WO | WO 2008/097561 A1 | 8/2008 |
| WO | WO 2009/020565 A1 | 2/2009 |
| WO | WO 2009/045440 A1 | 4/2009 |
| WO | WO 2010/014141 A1 | 2/2010 |
| WO | WO 2010/014220 A1 | 2/2010 |
| WO | WO 2010/014254 A1 | 2/2010 |
| WO | WO 2010/147612 A1 | 12/2010 |
| WO | WO 2012/162535 A1 | 11/2012 |
| WO | WO 2014/005080 A1 | 1/2014 |
| WO | WO 2014/005084 A1 | 1/2014 |
| WO | WO 2014/137741 A1 | 9/2014 |
| WO | WO 2014/149494 A1 | 9/2014 |
| WO | WO 2014/168941 A1 | 10/2014 |
| WO | WO 2015/073802 A1 | 5/2015 |
| WO | WO 2015/196073 A1 | 12/2015 |
| WO | WO 2016/014783 A1 | 1/2016 |
| WO | WO 2016/040877 A1 | 3/2016 |
| WO | WO 2016/061193 A1 | 4/2016 |
| WO | WO 2016/134257 A1 | 8/2016 |
| WO | WO 2016/186963 A1 | 11/2016 |

OTHER PUBLICATIONS

Thiery et al. "Hepatocellular . . . " Hepatology, abstract (1999)I.*
International Search Report dated Jan. 29, 2015 in connection with PCT International Application No. PCT/US2014/065669.
Written Opinion of the International Searching Authority dated Jan. 29, 2015in connection with PCT International Application No. PCT/US2014/065669.
International Preliminary Report on Patentability Chapter I dated May 17, 2016 in connection with PCT International Application No. PCT/US2014/065669.
Office Action dated Mar. 23, 2017 in connection with U.S. Appl. No. 15/036,760.

(Continued)

*Primary Examiner* — Niloofar Rahmani
(74) *Attorney, Agent, or Firm* — Andrea L. C. Reid; Dechert LLP

(57) ABSTRACT

The present invention provides a compound having the structure:

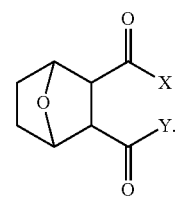

16 Claims, 22 Drawing Sheets

(56) References Cited

OTHER PUBLICATIONS

International Search Report dated Oct. 17, 2016 in connection with PCT International Application No. PCT/US2016/032123.
Written Opinion of the International Searching Authority dated Oct. 17, 2016 in connection with PCT International Application No. PCT/US2016/032123.
Office Action dated Feb. 17, 2017 in connection with U.S. Appl. No. 15/154,304.
Thjiery, J.P. et al. (1999) Hepatocellular carcinoma cell lines from diethylnitrosamine phenobarbital-treated rats. Characterization and sensitivity to endothall, a protein serine/threonine phosphatase-2A inhibitor. Hepatology May 1, 1999 (Abstract only).

\* cited by examiner

A.
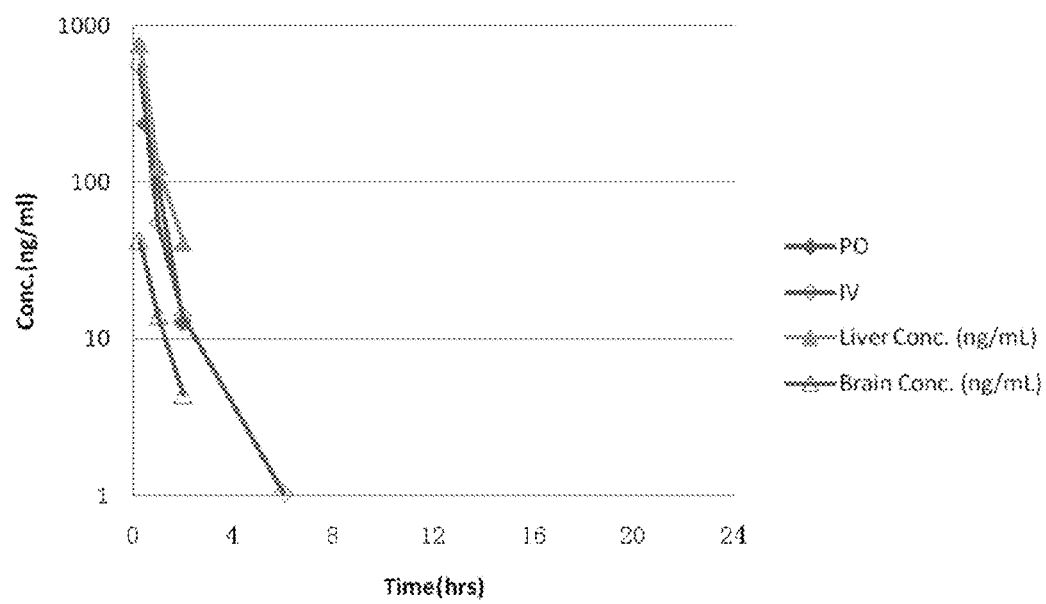
B.
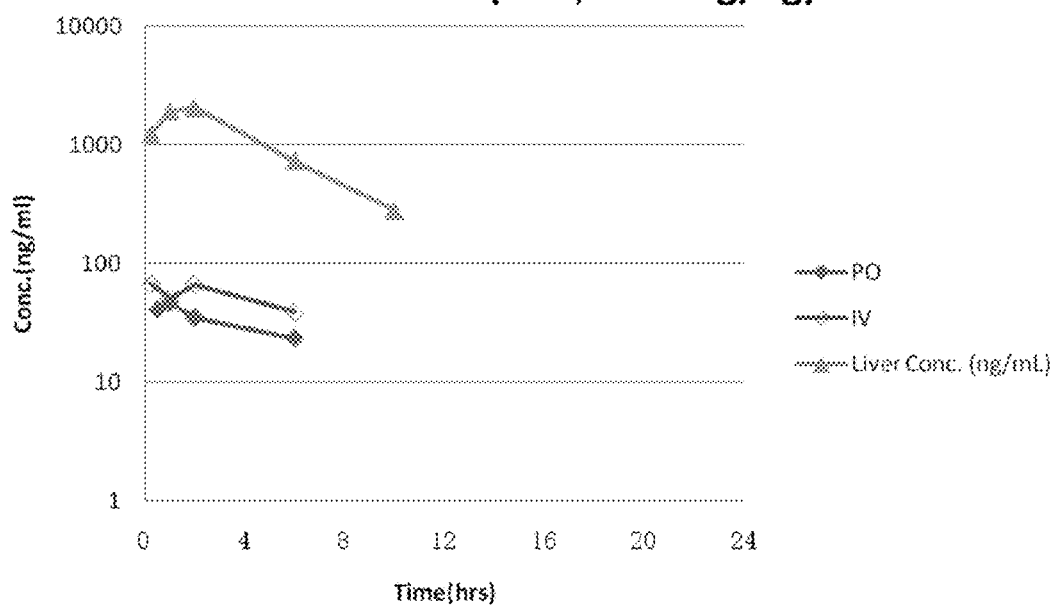
Fig. 1A-B

C.
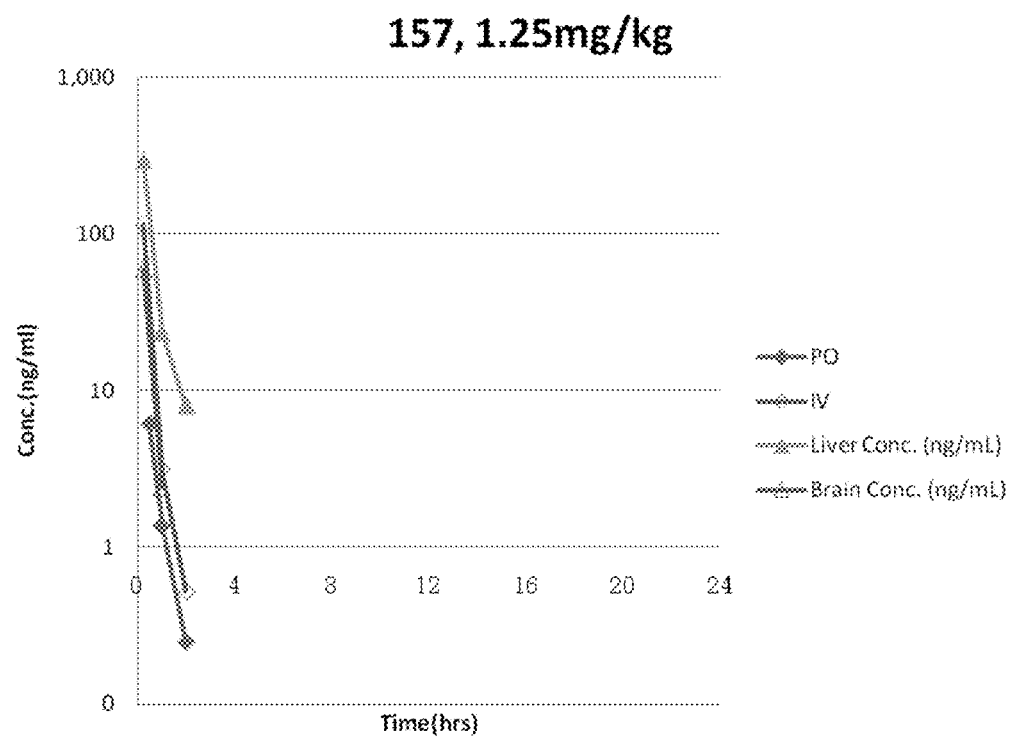
D.
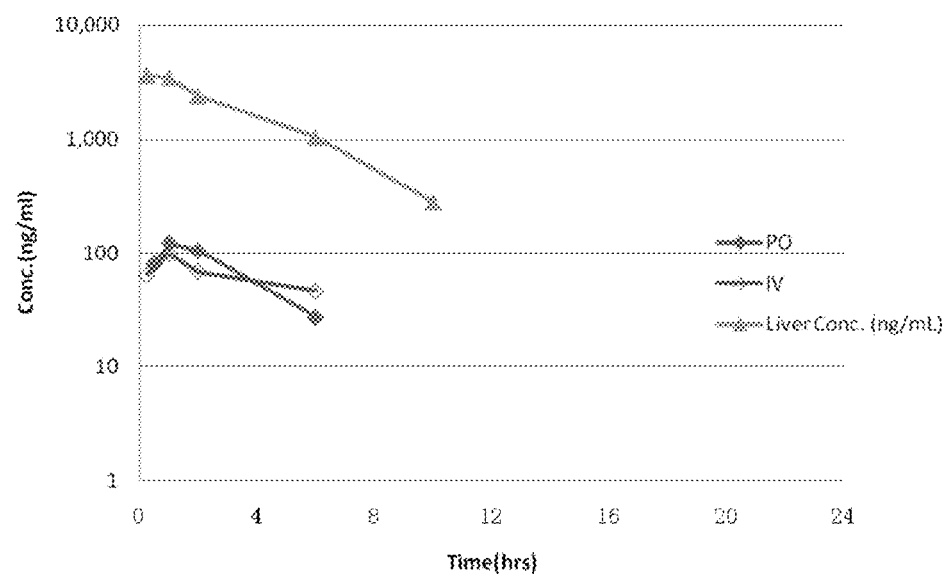
Fig. 1C-D

A.
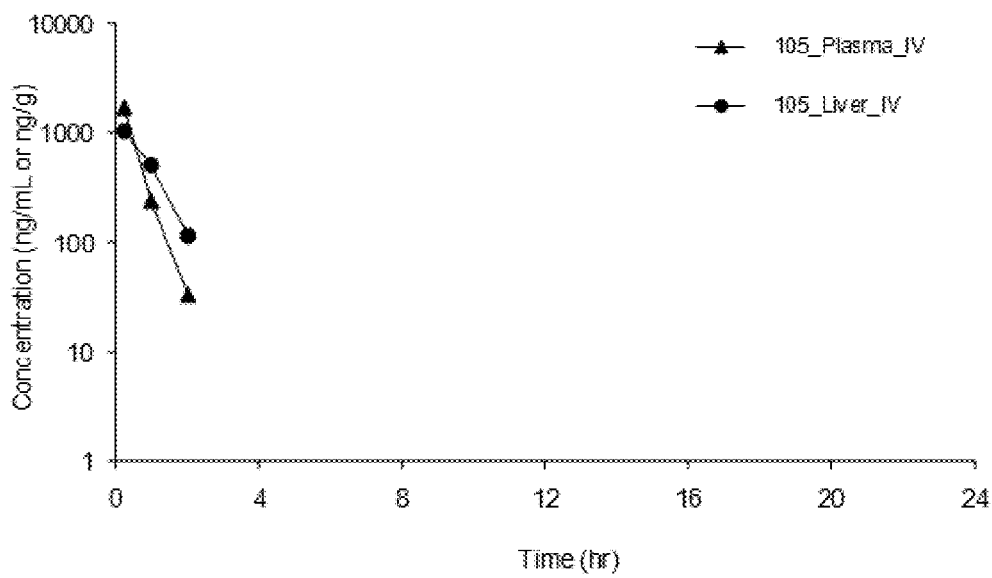
B.
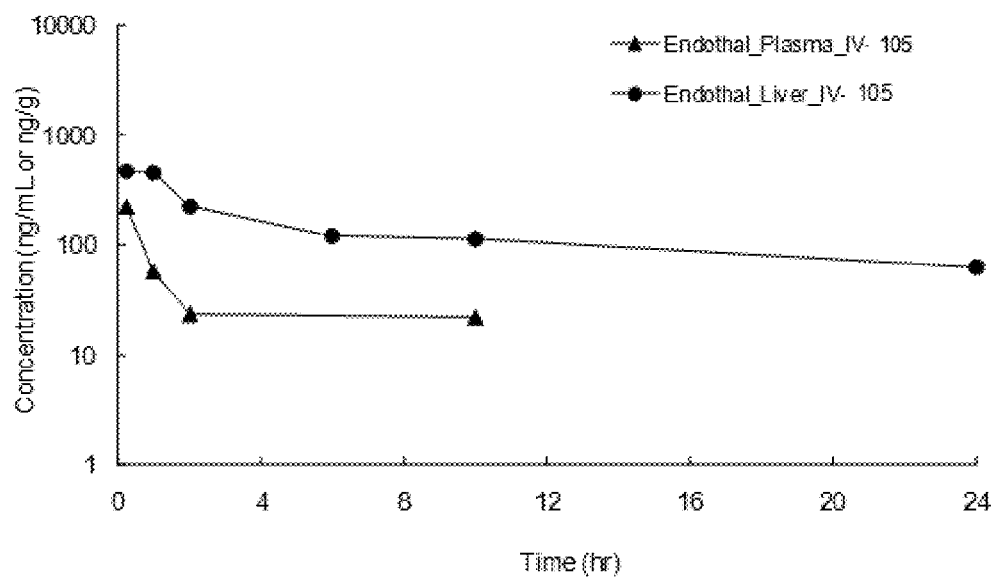
Fig. 2A-B

C.

A.
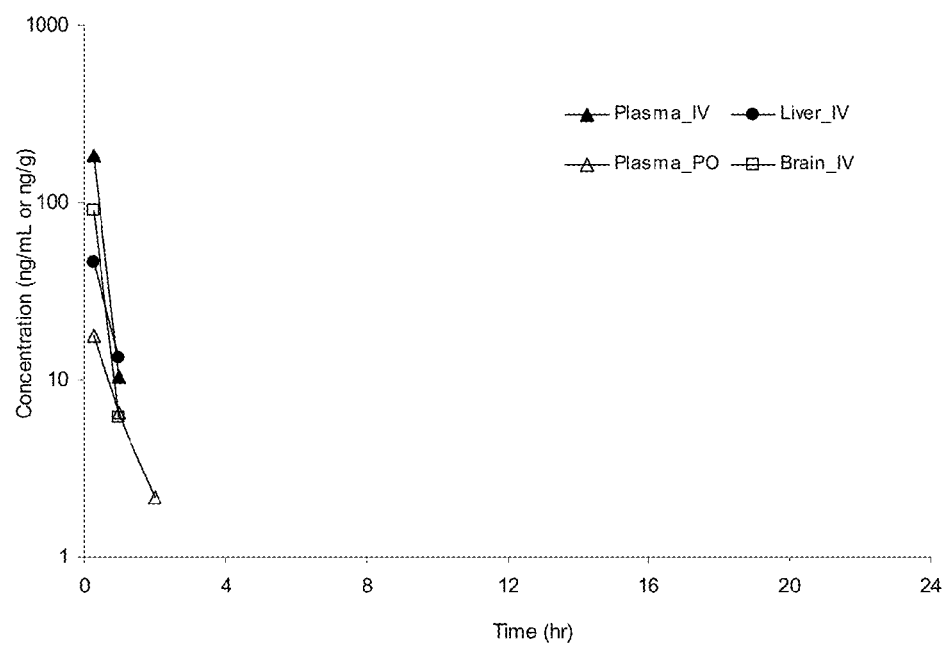
B.
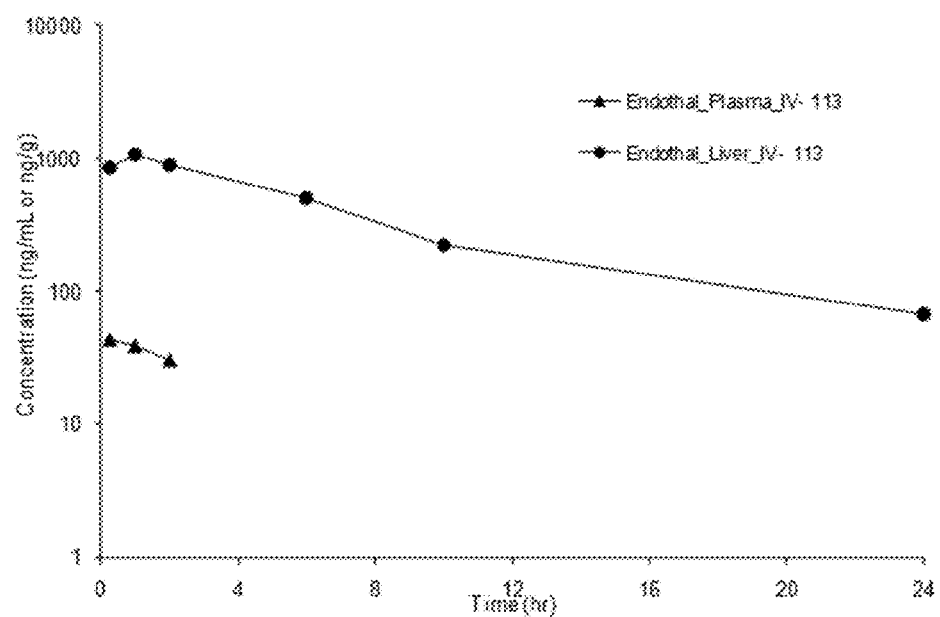
Fig. 3A-B

C.
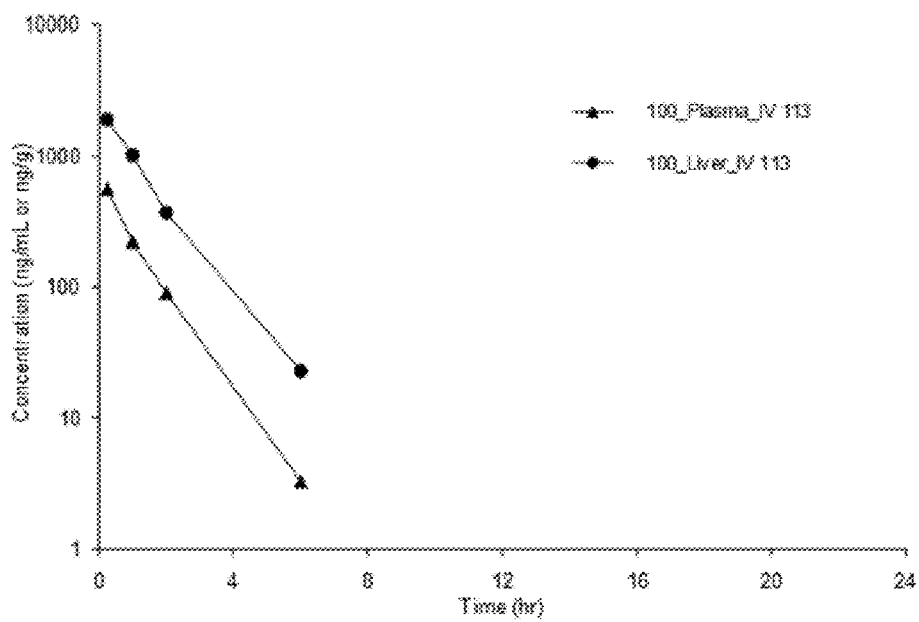
D.
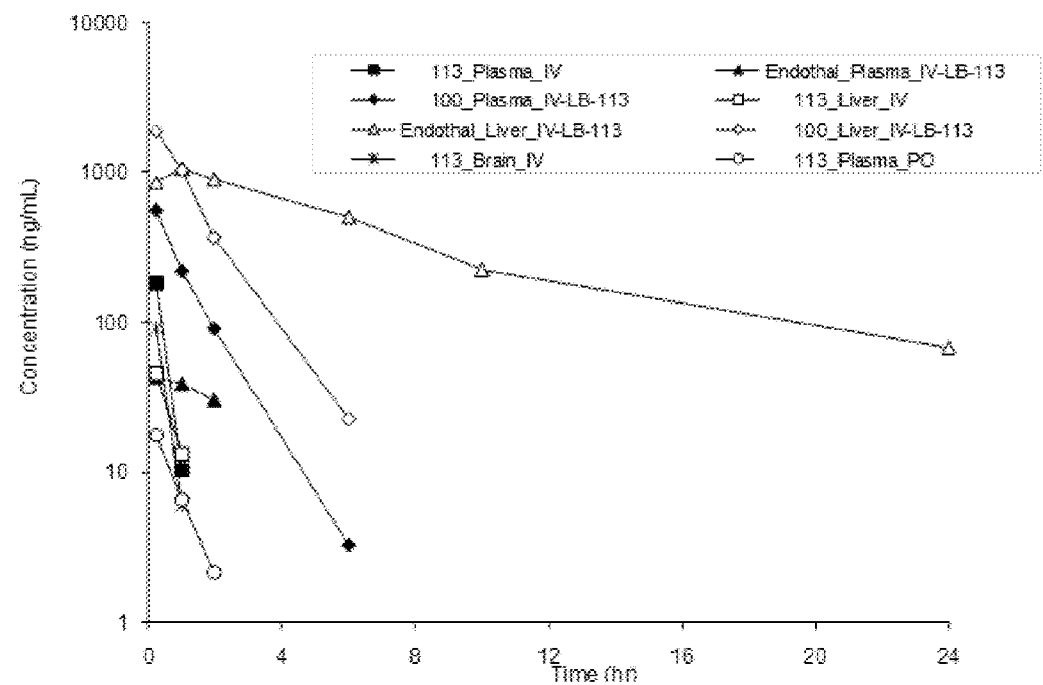
Fig. 3C-D

A.
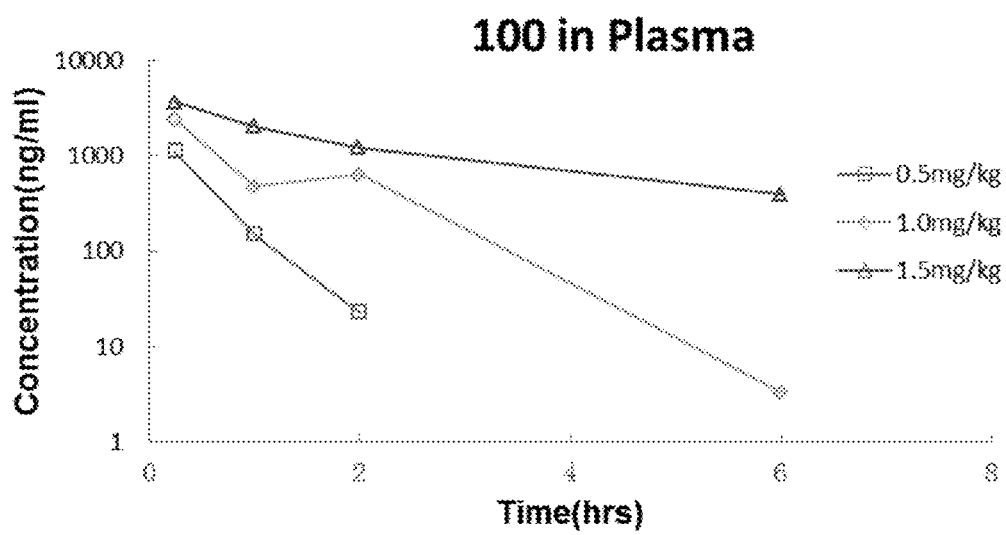
B.
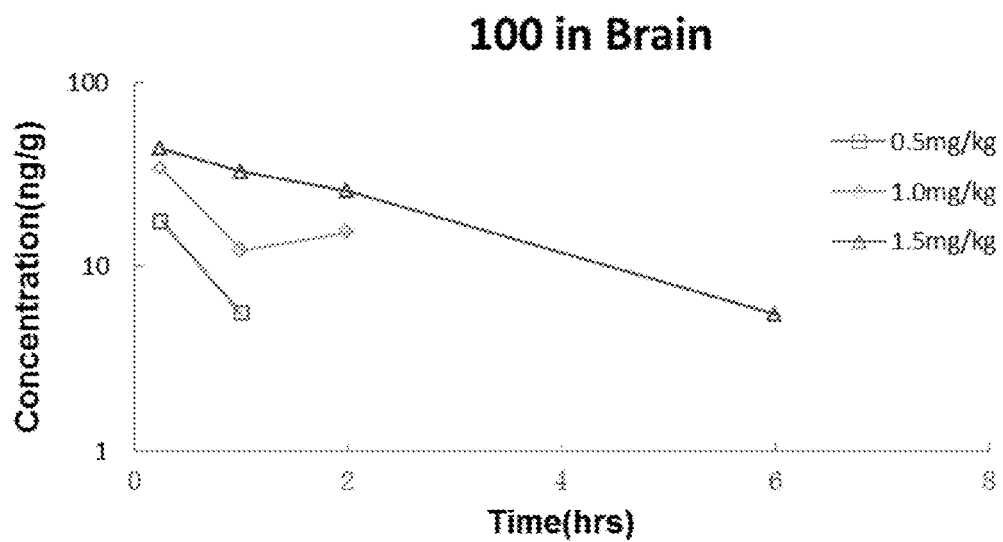
Fig. 4A-B

C.
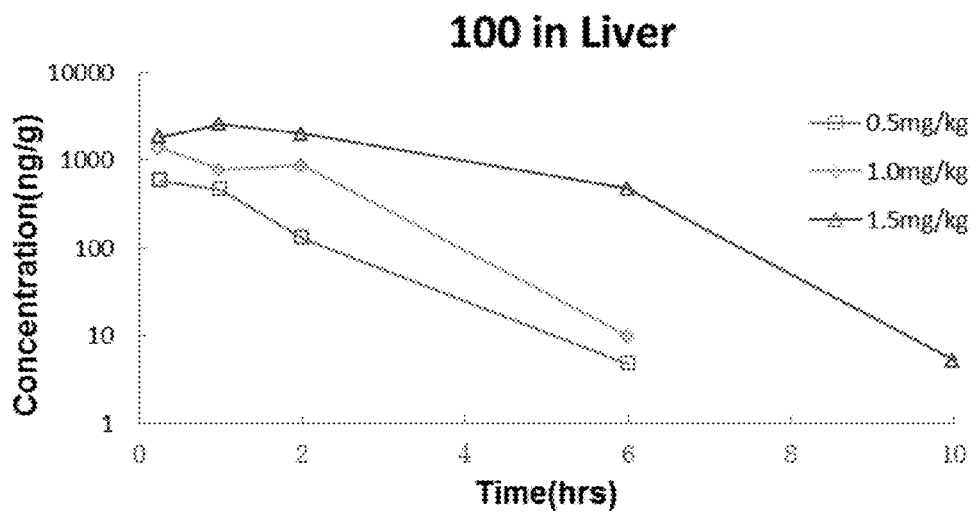
D.
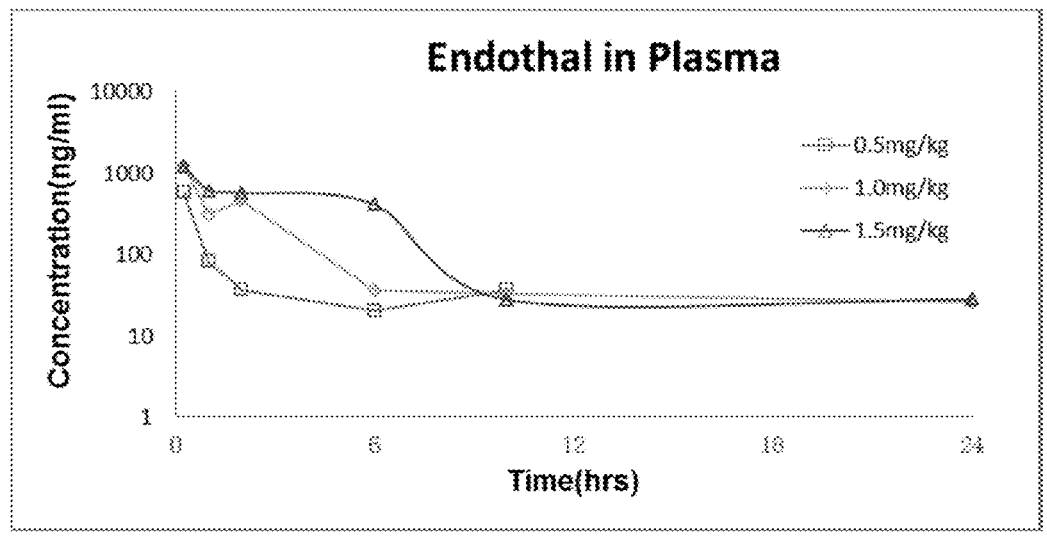
Fig. 4C-D

E.

| Test Article | Species | NADPH-Dependent CL$_{int}$ (µl min$^{-1}$ mg$^{-1}$) | NADPH-Dependent T$_{1/2}$ (min) | NADPH-Free CL$_{int}$ (µl min$^{-1}$ mg$^{-1}$) | NADPH-Free T$_{1/2}$ (min) | Comment |
|---|---|---|---|---|---|---|
| verapamil | Rat | 26.8 | 25.9 | <0.72 | >960 | high clearance control |
| | Human | 14.3 | 48.6 | <0.72 | >960 | |
| | Monkey | 89.2 | 7.77 | <0.72 | >960 | |
| warfarin | Rat | <0.72 | >960 | <0.72 | >960 | low clearance control |
| | Human | <0.72 | >960 | <0.72 | >960 | |
| | Monkey | <0.72 | >960 | <0.72 | >960 | |
| LB-151 | Rat | <0.72 | >960 | <0.72 | >960 | |
| | Human | 0.8 | 831 | 1.2 | 562 | |
| | Monkey | <0.72 | >960 | <0.72 | >960 | |
| LB-100 POM Ester | Rat | 13.7 | 50.8 | 10.0 | 69.3 | |
| | Human | 10.0 | 69.2 | 10.7 | 64.5 | |
| | Monkey | 113.3 | 6.1 | 108 | 6.4 | |
| LB-100 Carbonate | Rat | 12.2 | 56.8 | 12.6 | 55.0 | |
| | Human | 7.75 | 89.5 | 9.66 | 71.7 | |
| | Monkey | 39.7 | 17.5 | 48.2 | 14.4 | |

| Test Article | Species | T₁/₂ (min) | % remaining parent at last time point (240 min) | Comment |
|---|---|---|---|---|
| Propantheline | Dog | 157 | 43.8 | High Clint control |
| Propantheline | Human | 61 | 9.2 | |
| Propantheline | Monkey | 52 | 7.5 | |
| Enalapril | Rat | 20.9 | 0.0 | |
| LB-100 Carbonate | Dog | 9.0 | 0.0 | |
| LB-100 Carbonate | Human | 9.0 | 0.0 | |
| LB-100 Carbonate | Monkey | 9.0 | 0.0 | |
| LB-100 Carbonate | Rat | 9.0 | 0.0 | |
| LB-100 POM Ester | Dog | 20.6 | 0.0 | |
| LB-100 POM Ester | Human | 7.7 | 0.0 | |
| LB-100 POM Ester | Monkey | 6.1 | 0.0 | |
| LB-100 POM Ester | Rat | 14.2 | 0.0 | |
| LB-151 | Dog | 536 | 76.8 | |
| LB-151 | Human | 958 | 82.0 | |
| LB-151 | Monkey | 547 | 76.8 | |
| LB-151 | Rat | 197 | 45.3 | |

T₁/₂ - Half-Life

| Test Article | Test Conc. | Assay Duration | mean A→B $P_{app}$ ($10^{-6}$ cm s$^{-1}$) | mean B→A $P_{app}$ ($10^{-6}$ cm s$^{-1}$) | Efflux Ratio | Comment |
|---|---|---|---|---|---|---|
| ranitidine | 10 µM | 2 hr | 0.054 | 1.8 | 32.6 | low permeability control |
| warfarin | 10 µM | 2 hr | 15.1 | 30.9 | 2.0 | high permeability control |
| talinolol | 10 µM | 2 hr | 0.021 | 2.9 | 139 | P-gp efflux control |
| LB-151 | 10 µM | 2 hr | 0.18 | 8.8 | 48.7 | |
| LB-100 Pom Ester | 10 µM | 2 hr | 0.19 | 28.3 | 152 | |
| LB-100 Carbonate | 10 µM | 2 hr | 0.12 | 11.2 | 95.1 | |

Papp: apparent permeability rate coefficient
Efflux Ratio: $P_{app}$ (B→A) / $P_{app}$ (A→B)

Fig. 9

OXABICYCLOHEPTANE PRODRUGS

This application claims the benefit of U.S. Provisional Application No. 62/162,501, filed May 15, 2015, the contents of which are hereby incorporated by reference.

Throughout this application various publications are referenced. The disclosures of these documents in their entireties are hereby incorporated by reference into this application in order to more fully describe the state of the art to which this invention pertains.

BACKGROUND OF THE INVENTION

Retinoids, metabolites of vitamin A, have been examined therapeutically against a variety of tumors, including gliomas (Yung et al. 1996). Nuclear receptor co-repressor (N-CoR) is closely associated with the retinoid receptor and is released upon ligand binding to the receptor (Bastien et al. 2004). By preventing the action of protein phosphatase-1 and protein phosphatase-2A (PP2A), anti-phosphatases increase the phosphorylated form of N-CoR and promote its subsequent cytoplasmic translocation (Hermanson et al. 2002).

The phosphatase inhibitor, cantharidin, has anti-tumor activity against human cancers of the liver (hepatomas) and of the upper gastrointestinal tract but is toxic to the urinary tract (Wang, 1989). Cantharidin acts as a protein phosphatase inhibitor, which prompted a more general interest in compounds with this type of chemical structure (Li and Casida 1992). Previously, it had been found that the simpler congener and its hydrolysis product (commercially available as the herbicide, Endothal) are hepatotoxic (Graziani and Casida, 1997). Binding studies have shown that the action of certain cantharidin homologs is direct on protein phosphatase-2A and indirect on protein phosphatase-1 (Honkanen et al., 1993; Li et al., 1993).

Of the known congeners of this type of compound, only the parent, cantharidin and its bis(normethyl)-derivative, norcantharidin, have seen any use as anti-cancer drug substances and only norcantharidin is used as an anti-neoplastic agent (Tsauer et al. 1997).

Despite these successes, few compounds of this type have been screened for anti-tumor or cytotoxic activity. Currently, there is a significant need to develop inhibitors of protein phosphatases that are more active, less toxic and more specific in action than the known substances mentioned above. In particular, the need is present for diseases such as high-grade malignant gliomas of children and adults.

Diffuse intrinsic pontine glioma (DIPG) is a non-operable cancer of the brainstem in children for which no treatment other than radiation has offered any extension of life, with survival with best care being about 12 months. Multiple trials of adjuvant chemotherapy have not significantly improved outcomes (Warren et al. 2011; Hawkins et al. 2011). There are about 300 new cases diagnosed annually in the United States. Glioblastoma multiforme (GBM) is an aggressive brain cancer occurring in about 20,000 adults annually in the US for which standard treatment (primary surgery, followed by 6-weeks of radiation plus temozolomide, followed by daily oral temozolomide) has only increased average lifespan from less than one year to about 18 months despite 50 years of testing experimental therapies (Stupp et al. 2009). There is an urgent need for new treatments of these gliomas.

Many chemotherapeutic agents used to treat cancer exhibit serious toxicity, resulting in unwanted side effects for patients and reducing efficacy by limiting the doses that can be safely administered. Prodrugs, which are converted to the active drug in vivo, can offer many advantages over parent drugs such as increased solubility, enhanced stability, improved bioavailability, reduced side effects, better selectivity and improved entry of the drug to certain tissues. Activation of prodrugs can involve many enzymes through a variety of mechanisms including hydrolytic activation (Yang, Y. et al. 2011). Enzymes involved in the hydrolytic activation of prodrugs include carboxylesterases and amidases.

Endothal is the common name for 7-oxabicyclo[2.2.1] heptane-2,3-dicarboxylic acid. It is an inhibitor of PP2A, an enzyme present in both plants and animals that is involved in the dephosphorylation of proteins. Endothal is structurally similar to cantharidin, a chemical compound secreted by many species of blister beetle. Endothal is known as an active defoliant and potent contact herbicide used in many agricultural situations. It is considered effective as a pre-harvest desiccant and as a selective pre-emergence herbicide. Endothal has been tested against a limited number of human cancer cell lines (Thiery J. P. et al. 1999).

SUMMARY OF THE INVENTION

The present invention provides a compound having the structure:

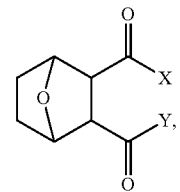

wherein

X is X is $OR_1$, $NR_2R_3$, OH, O-alkyl, O-alkenyl, O-alkynyl, O-aryl, O-alkylaryl, O-heteroaryl,

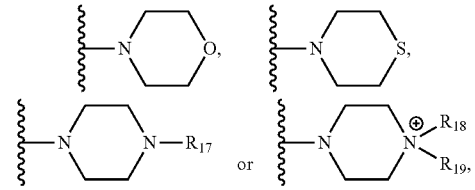

wherein $R_1$ is H, alkyl, alkenyl, alkynyl, aryl, alkylaryl, heteroaryl, alkylaryl, ($C_1$-$C_4$ alkyl)-O(CO)$R_4$, ($C_1$-$C_4$ alkyl)-O(CO)O$R_4$, O($C_1$-$C_4$ alkyl)-OP(O)(O$R_4$)$_2$, ($C_1$-$C_4$ alkyl)-OP(O)(O($C_1$-$C_4$ alkyl)-O(CO)O$R_4$)$_2$, ($C_1$-$C_4$ alkyl)-OP(O)(O($C_1$-$C_4$ alkyl)-O(CO)$R_4$)$_2$, ($C_1$-$C_4$ alkyl)NR$_4$R$_5$, ($C_1$-$C_4$ alkyl)NC(O)R$_4$, ($C_1$-$C_4$ alkyl)C(O)OR$_4$, ($C_1$-$C_4$ alkyl)OC(O)aryl($C_1$-$C_4$ alkyl)P(O)(OR$_4$)$_2$, ($C_1$-$C_4$ alkyl)OC(O)($C_2$-$C_4$ alkenyl)CO$_2$R$_4$, ($C_1$-$C_4$ alkyl)OC(O)($C_1$-$C_4$ alkyl)NH$_2$, ($C_1$-$C_4$ alkyl)C(O)NR$_4$R$_5$,

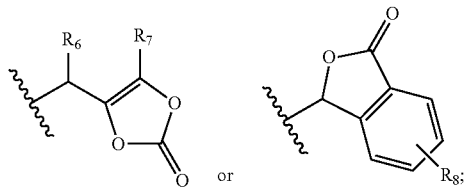

or

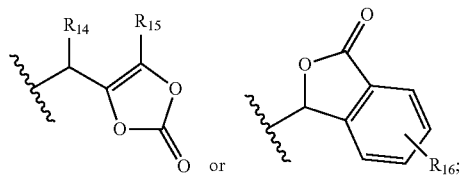

$R_2$ and $R_3$ are each independently H, alkyl, alkenyl, alkynyl, aryl, alkylaryl, heteroaryl, $(C_1\text{-}C_4 \text{ alkyl})\text{-}O(CO)R_4$, $(C_1\text{-}C_4 \text{ alkyl})\text{-}O(CO)OR_4$, $O(C_1\text{-}C_4 \text{ alkyl})\text{-}OP(O)(OR_4)_2$, $(C_1\text{-}C_4 \text{ alkyl})\text{-}OP(O)(O(C_1\text{-}C_4 \text{ alkyl})\text{-}O(CO)OR_4)_2$, $(C_1\text{-}C_4 \text{ alkyl})\text{-}OP(O)(O(C_1\text{-}C_4 \text{ alkyl})\text{-}O(CO)R_4)_2$, $(C_1\text{-}C_4 \text{ alkyl})NR_4R_5$, $(C_1\text{-}C_4 \text{ alkyl})NC(O)R_4$, $(C_1\text{-}C_4 \text{ alkyl})C(O)OR_4$, $(C_1\text{-}C_4 \text{ alkyl})OC(O)aryl(C_1\text{-}C_4 \text{ alkyl})P(O)(OR_4)_2$, $(C_1\text{-}C_4 \text{ alkyl})OC(O)(C_2\text{-}C_4 \text{ alkenyl})CO_2R_4$, $(C_1\text{-}C_4 \text{ alkyl})OC(O)(C_1\text{-}C_4 \text{ alkyl})NH_2$, $(C_1\text{-}C_4 \text{ alkyl})C(O)NR_4R_5$,

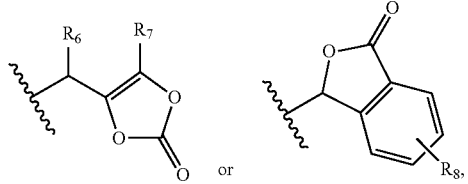

or $R_{17}$ is H, alkyl, hydroxyalkyl, alkenyl, alkenyl, alkynyl, aryl, alkylaryl, heteroaryl, alkylheteroaryl, $C(O)O\text{-}t\text{-}Bu$ or $—CH_2CN$;

$R_{18}$ is H or alkyl;

$R_{19}$ is $(C_1\text{-}C_4 \text{ alkyl})\text{-}O(CO)R_4$, $(C_1\text{-}C_4 \text{ alkyl})\text{-}O(CO)OR_4$, $(C_1\text{-}C_4 \text{ alkyl})\text{-}OP(O)(OR_4)_2$, $(C_1\text{-}C_4 \text{ alkyl})\text{-}OP(O)(O(C_1\text{-}C_4 \text{ alkyl})\text{-}O(CO)OR_4)_2$, $(C_1\text{-}C_4 \text{ alkyl})\text{-}OP(O)(O(C_1\text{-}C_4 \text{ alkyl})\text{-}O(CO)R_4)_2$, $(C_1\text{-}C_4 \text{ alkyl})NR_4R_5$, $(C_1\text{-}C_4 \text{ alkyl})NC(O)R_4$, $(C_1\text{-}C_4 \text{ alkyl})C(O)OR_4$, $(C_1\text{-}C_4 \text{ alkyl})OC(O)aryl(C_1\text{-}C_4 \text{ alkyl})P(O)(OR_4)_2$, $(C_1\text{-}C_4 \text{ alkyl})OC(O)(C_2\text{-}C_4 \text{ alkenyl})CO_2R_4$, $(C_1\text{-}C_4 \text{ alkyl})OC(O)(C_1\text{-}C_4 \text{ alkyl})NH_2$, $(C_1\text{-}C_4 \text{ alkyl})C(O)NR_4R_5$,

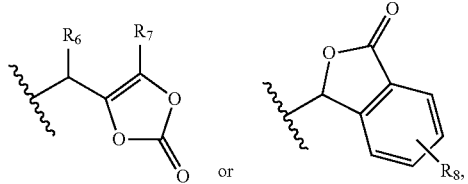

or wherein each occurrence of $R_4$ is, independently, H, alkyl, alkenyl, alkynyl, aryl or heteroaryl;

wherein each occurrence of $R_5$ is, independently, H, alkyl, alkenyl, alkynyl, aryl or heteroaryl;

wherein each occurrence of $R_6$ and $R_7$ is, independently, H, alkyl, alkenyl, alkynyl, aryl or heteroaryl;

wherein each occurrence of $R_8$ is, independently, H, halogen, alkyl, alkenyl, alkynyl, aryl or heteroaryl; and Y is $OR_9$ or $NR_{10}R_{11}$, wherein $R_9$ is H, alkyl, alkenyl, alkynyl, aryl, alkylaryl, heteroaryl, alkylaryl, $(C_1\text{-}C_4 \text{ alkyl})\text{-}O(CO)R_{12}$, $(C_1\text{-}C_4 \text{ alkyl})\text{-}O(CO)OR_{12}$, $(C_1\text{-}C_4 \text{ alkyl})\text{-}OP(O)(OR_{12})_2$, $(C_1\text{-}C_4$ alkyl)$\text{-}OP(O)(O(C_1\text{-}C_4 \text{ alkyl})\text{-}O(CO)OR_{12})_2$, $(C_1\text{-}C_4 \text{ alkyl})\text{-}OP(O)(O(C_1\text{-}C_4 \text{ alkyl})\text{-}O(CO)R_{12})_2$, $(C_1\text{-}C_4 \text{ alkyl})NR_{12}R_{13}$, $(C_1\text{-}C_4 \text{ alkyl})NC(O)R_{12}$, $(C_1\text{-}C_4 \text{ alkyl})C(O)OR_{12}$, $(C_1\text{-}C_4 \text{ alkyl})OC(O)aryl(C_1\text{-}C_4 \text{ alkyl})P(O)(OR_{12})_2$, $(C_1\text{-}C_4 \text{ alkyl})OC(O)(C_2\text{-}C_4 \text{ alkenyl})CO_2R_{12}$, $(C_1\text{-}C_4 \text{ alkyl})OC(O)(C_1\text{-}C_4 \text{ alkyl})NH_2$, $(C_1\text{-}C_4 \text{ alkyl})C(O)NR_{12}R_{13}$,

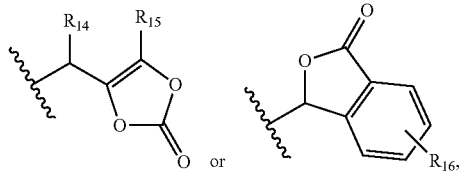

$R_{10}$ is H; and $R_{11}$ is $(C_1\text{-}C_4 \text{ alkyl})\text{-}O(CO)R_{12}$, $(C_1\text{-}C_4 \text{ alkyl})\text{-}O(CO)OR_{12}$, $(C_1\text{-}C_4 \text{ alkyl})\text{-}OP(O)(OR_{12})_2$, $(C_1\text{-}C_4 \text{ alkyl})\text{-}OP(O)(O(C_1\text{-}C_4 \text{ alkyl})\text{-}O(CO)OR_{12})_2$, $(C_1\text{-}C_4 \text{ alkyl})\text{-}OP(O)(O(C_1\text{-}C_4 \text{ alkyl})\text{-}O(CO)R_{12})_2$, $(C_1\text{-}C_4 \text{ alkyl})NR_{12}R_{13}$, $(C_1\text{-}C_4 \text{ alkyl})NC(O)R_{12}$, $(C_1\text{-}C_4 \text{ alkyl})C(O)OR_{12}$, $(C_1\text{-}C_4 \text{ alkyl})OC(O)aryl(C_1\text{-}C_4 \text{ alkyl})P(O)(OR_{12})_2$, $(C_1\text{-}C_4 \text{ alkyl})OC(O)(C_2\text{-}C_4 \text{ alkenyl})CO_2R_{12}$, $(C_1\text{-}C_4 \text{ alkyl})OC(O)(C_1\text{-}C_4 \text{ alkyl})NH_2$, $(C_1\text{-}C_4 \text{ alkyl})C(O)NR_{12}R_{13}$,

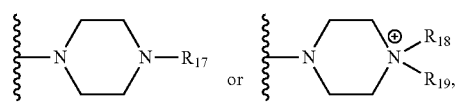

wherein each occurrence of $R_{12}$ is, independently, H, alkyl, alkenyl, alkynyl, aryl or heteroaryl;

wherein each occurrence of $R_{13}$ is, independently, H, alkyl, alkenyl, alkynyl, aryl or heteroaryl;

wherein each occurrence of $R_{14}$ and $R_{15}$ is, independently, H, alkyl, alkenyl, alkynyl, aryl or heteroaryl;

wherein each occurrence of $R_{16}$ is, independently, H, halogen, alkyl, alkenyl, alkynyl, aryl or heteroaryl, wherein when Y is $OR_9$ where $R_9$ is H, alkyl, alkenyl, alkynyl, aryl, alkylaryl, heteroaryl, alkylaryl, then X is

and when X is where $R_{17}$ is $CH_3$, then X is other than $—O(C_4 \text{ alkyl})\text{-}OP(O)(OEt)_2$ or $—NH(C_4 \text{ alkyl})\text{-}OP(O)(OEt)_2$, or a salt or ester of the compound.

The present invention also provides a compound having the structure:

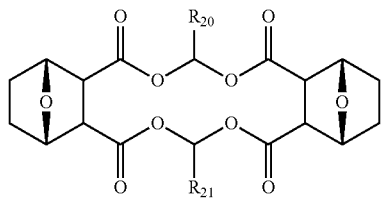

wherein R₂₀ and R₂₁ are each independently H, alkyl, hydroxyalkyl, alkenyl, alkynyl, aryl, alkylaryl, or heteroaryl,
or a salt or ester of the compound.

The present invention also provides a compound having the structure:

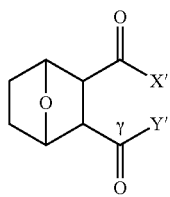

wherein
X' is OH, O(alkyl) or NR$_{22}$R$_{23}$;
R$_{22}$ is H, alkyl, alkenyl, alkynyl, aryl, alkylaryl, or heteroaryl;
R$_{23}$ is H, alkyl, alkenyl, alkynyl, aryl, alkylaryl, or heteroaryl, or R$_{22}$ and R$_{23}$ combine to form an N-methylpiperazine;
Y' is an anti-cancer agent A containing at least one amine nitrogen and the nitrogen on the anti-cancer agent covalently bonds directly to carbon γ, or
Y' is an anti-cancer agent A containing at least one hydroxyl oxygen and the oxygen on the anti-cancer agent covalently bonds directly to carbon γ, or
Y' is

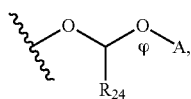

wherein A is an anti-cancer agent containing at least one carboxylic acid and the carbonyl carbon of the carboxylic acid on the anti-cancer agent covalently bonds directly to oxygen φ, and
R$_{24}$ is H or alkyl,
or a salt or ester of the compound.

BRIEF DESCRIPTION OF THE FIGURES

FIG. 1A: Concentration versus time curves of 153 in plasma following iv or po administration, and in liver and brain following iv administration of 153 to SD rats.

FIG. 1B: Concentration versus time curves of Endothal in plasma following iv or po administration, and in liver following iv administration of 153 to SD rats.

FIG. 1C: Concentration versus time curves of 157 in plasma following iv or po administration, and in, liver and brain following iv administration of 157 to SD rats.

FIG. 1D: Concentration versus time curves of Endothal in plasma following iv or po administration, and in liver following iv administration of 157 to SD rats.

FIG. 2A: Mean plasma and liver concentration-time profiles of 105 after IV dose of 1 mg/kg in SD rats (N=2/time point).

FIG. 2B: Mean plasma and liver concentration-time profile of Endothal after IV dose of 1 mg/kg 105 in male SD rats (N=2/time point).

FIG. 3A: Mean plasma, brain and liver concentration-time profile of 113 after IV or PO dose of 1.4 mg/kg in male SD rats (N=2/time point).

FIG. 3B: Mean plasma and liver concentration-time profile of Endothal after IV dose of 1.4 mg/kg 113 in male SD rats (N=2/time point)

FIG. 3C: Mean plasma and liver concentration-time profile of 100 after IV dose of 1.4 mg/kg 113 in male SD rats (N=2/time point)

FIG. 3D: Mean plasma, brain and liver concentration-time profile of 113, 100 and Endothal after IV or PO dose of 113 at 1.4 mg/kg in male SD rats (N=2/time point)

FIG. 4A: Concentration versus time curves of 100 in plasma following iv administration of 100 to SD rats.

FIG. 4B: Concentration versus time curves of 100 in brain following iv administration of 100 to SD rats.

FIG. 4C: Concentration versus time curves of 100 in liver following iv administration of 100 to SD rats.

FIG. 4D: Concentration versus time curves of endothal in plasma following iv administration of 100 to SD rats.

FIG. 5: Summary of results of liver S9 stability study for LB151, LB100 POM and LB-100 Cabronate.

FIG. 7: Summary of results of whole blood half-life studies for LB151, LB100 POM and LB-100 Cabronate.

FIG. 9: Summary of results of MDCK-MDR1 permeability studies for LB151, LB100 POM and LB-100 Cabronate.

DETAILED DESCRIPTION OF THE INVENTION

Figure 2C:
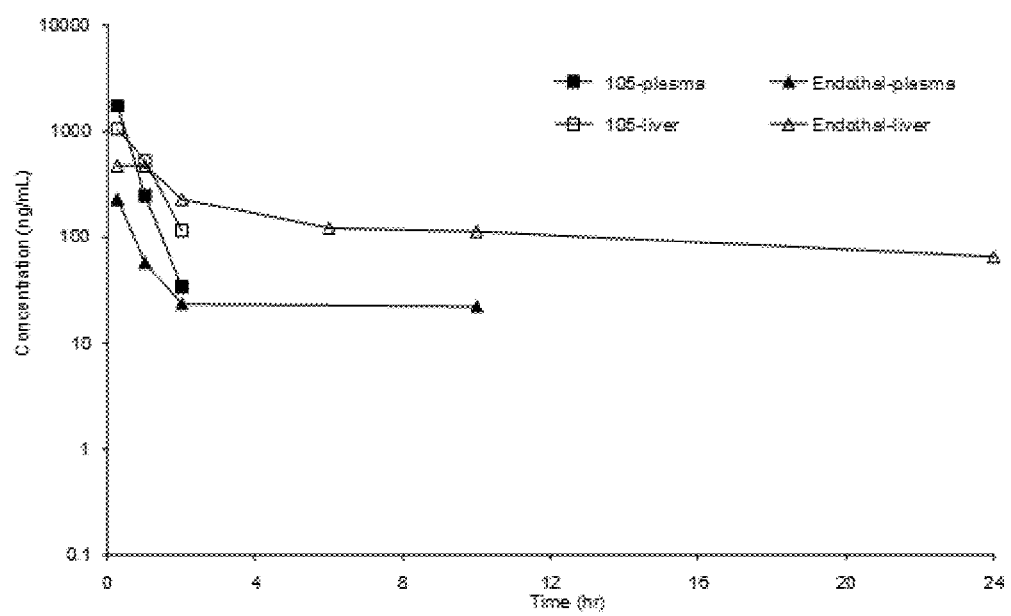
FIG. 2C: Mean plasma and liver concentration-time profile of 105 and Endothal after an IV dose of 1 mg/kg 105 in male SD rats (N=2/time point).

The present invention provides a compound having the structure:

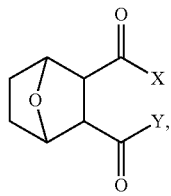

wherein
X is X is $OR_1$, $NR_2R_3$, OH, O-alkyl, O-alkenyl, O-alkynyl, O-aryl, O-alkylaryl, O-heteroaryl,

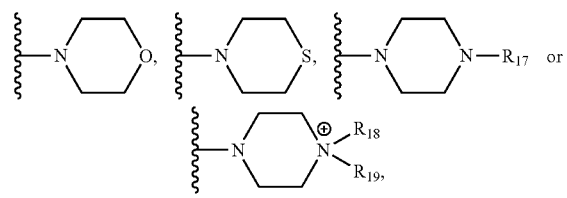

wherein $R_1$ is H, alkyl, alkenyl, alkynyl, aryl, alkylaryl, heteroaryl, alkylaryl, ($C_1$-$C_4$ alkyl)-O(CO)$R_4$, ($C_1$-$C_4$ alkyl)-O(CO)O$R_4$, O($C_1$-$C_4$ alkyl)-OP(O)(O$R_4$)$_2$, ($C_1$-$C_4$ alkyl)-OP(O)(O($C_1$-$C_4$ alkyl)-O(CO)O$R_4$)$_2$, ($C_1$-$C_4$ alkyl)-OP(O)(O($C_1$-$C_4$ alkyl)-O(CO)$R_4$)$_2$, ($C_1$-$C_4$ alkyl)NR$_4$R$_5$, ($C_1$-$C_4$ alkyl)NC(O)$R_4$, ($C_1$-$C_4$ alkyl)C(O)O$R_4$, ($C_1$-$C_4$ alkyl)OC(O)aryl($C_1$-$C_4$ alkyl)P(O)(O$R_4$)$_2$, ($C_1$-$C_4$ alkyl)OC(O)($C_2$-$C_4$ alkenyl)CO$_2$R$_4$, ($C_1$-$C_4$ alkyl)OC(O)($C_1$-$C_4$ alkyl)NH$_2$, ($C_1$-$C_4$ alkyl)C(O)NR$_4$R$_5$,

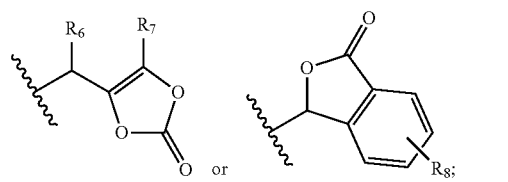

$R_2$ and $R_3$ are each independently H, alkyl, alkenyl, alkynyl, aryl, alkylaryl, heteroaryl, ($C_1$-$C_4$ alkyl)-O (CO)$R_4$, ($C_1$-$C_4$ alkyl)-O(CO)O$R_4$, O($C_1$-$C_4$ alkyl)-OP(O)(O$R_4$)$_2$, ($C_1$-$C_4$ alkyl)-OP(O)(O($C_1$-$C_4$ alkyl)-O (CO)O$R_4$)$_2$, ($C_1$-$C_4$ alkyl)-OP(O)(O($C_1$-$C_4$ alkyl)-O (CO)$R_4$)$_2$, ($C_1$-$C_4$ alkyl)NR$_4$R$_5$, ($C_1$-$C_4$ alkyl)NC(O) $R_4$, ($C_1$-$C_4$ alkyl)C(O)O$R_4$, ($C_1$-$C_4$ alkyl)OC(O)aryl ($C_1$-$C_4$ alkyl)P(O)(O$R_4$)$_2$, ($C_1$-$C_4$ alkyl)OC(O) ($C_2$-$C_4$ alkenyl)CO$_2$R$_4$, ($C_1$-$C_4$ alkyl)OC(O)($C_1$-$C_4$ alkyl)NH$_2$, ($C_1$-$C_4$ alkyl)C(O)NR$_4$R$_5$,

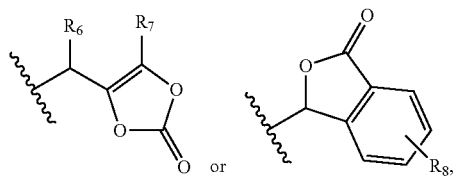

$R_{17}$ is H, alkyl, hydroxyalkyl, alkenyl, alkenyl, alkynyl, aryl, alkylaryl, heteroaryl, alkylheteroaryl, C(O)O-t-Bu or —CH$_2$CN;

$R_{18}$ is H or alkyl;

$R_{19}$ is ($C_1$-$C_4$ alkyl)-O(CO)$R_4$, ($C_1$-$C_4$ alkyl)-O(CO)O$R_4$, ($C_1$-$C_4$ alkyl)-OP(O)(O$R_4$)$_2$, ($C_1$-$C_4$ alkyl)-OP(O)(O ($C_1$-$C_4$ alkyl)-O(CO)O$R_4$)$_2$, ($C_1$-$C_4$ alkyl)-OP(O)(O ($C_1$-$C_4$ alkyl)-O(CO)$R_4$)$_2$, ($C_1$-$C_4$ alkyl)NR$_4$R$_5$, ($C_1$-$C_4$ alkyl)NC(O)$R_4$, ($C_1$-$C_4$ alkyl)C(O)O$R_4$, ($C_1$-$C_4$ alkyl) OC(O)aryl($C_1$-$C_4$ alkyl)P(O)(O$R_4$)$_2$, ($C_1$-$C_4$ alkyl)OC (O)($C_2$-$C_4$ alkenyl)CO$_2$R$_4$, ($C_1$-$C_4$ alkyl)OC(O)($C_1$-$C_4$ alkyl)NH$_2$, ($C_1$-$C_4$ alkyl)C(O)NR$_4$R$_5$,

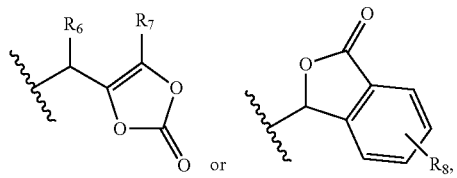

wherein each occurrence of $R_4$ is, independently, H, alkyl, alkenyl, alkynyl, aryl or heteroaryl;

wherein each occurrence of $R_5$ is, independently, H, alkyl, alkenyl, alkynyl, aryl or heteroaryl;

wherein each occurrence of $R_6$ and $R_7$ is, independently, H, alkyl, alkenyl, alkynyl, aryl or heteroaryl;

wherein each occurrence of $R_8$ is, independently, H, halogen, alkyl, alkenyl, alkynyl, aryl or heteroaryl; and Y is $OR_9$ or $NR_{10}R_{11}$, wherein $R_9$ is H, alkyl, alkenyl, alkynyl, aryl, alkylaryl, heteroaryl, alkylaryl, ($C_1$-$C_4$ alkyl)-O(CO)$R_{12}$, ($C_1$-$C_4$ alkyl)-O (CO)O$R_{12}$, ($C_1$-$C_4$ alkyl)-OP(O)(O$R_{12}$)$_2$, ($C_1$-$C_4$ alkyl)-OP(O)(O($C_1$-$C_4$ alkyl)-O(CO)O$R_{12}$)$_2$, ($C_1$-$C_4$ alkyl)-OP(O)(O($C_1$-$C_4$ alkyl)-O(CO)$R_{12}$)$_2$, ($C_1$-$C_4$ alkyl)NR$_{12}$R$_{13}$, ($C_1$-$C_4$ alkyl)NC(O)$R_{12}$, ($C_1$-$C_4$ alkyl) C(O)O$R_{12}$, ($C_1$-$C_4$ alkyl)OC(O)aryl($C_1$-$C_4$ alkyl)P(O) (O$R_{12}$)$_2$, ($C_1$-$C_4$ alkyl)OC(O)($C_2$-$C_4$ alkenyl)CO$_2$R$_{12}$, ($C_1$-$C_4$ alkyl)OC(O)($C_1$-$C_4$ alkyl)NH$_2$, ($C_1$-$C_4$ alkyl)C (O)NR$_{12}$R$_{13}$,

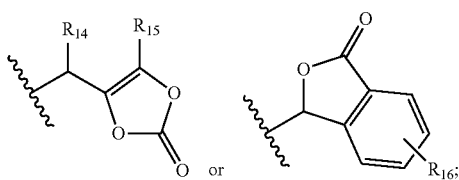 or $R_{10}$ is H; and
$R_{11}$ is $(C_1$-$C_4$ alkyl)-O(CO)$R_{12}$, $(C_1$-$C_4$ alkyl)-O(CO)OR$_{12}$, $(C_1$-$C_4$ alkyl)-OP(O)(OR$_{12}$)$_2$, $(C_1$-$C_4$ alkyl)-OP(O)(O($C_1$-$C_4$ alkyl)-O(CO)OR$_{12}$)$_2$, $(C_1$-$C_4$ alkyl)-OP(O)(O($C_1$-$C_4$ alkyl)-O(CO)R$_{12}$)$_2$, $(C_1$-$C_4$ alkyl)NR$_{12}$R$_{13}$, $(C_1$-$C_4$ alkyl)NC(O)R$_{12}$, $(C_1$-$C_4$ alkyl)C(O)OR$_{12}$, $(C_1$-$C_4$ alkyl)OC(O)aryl($C_1$-$C_4$ alkyl)P(O)(OR$_{12}$)$_2$, $(C_1$-$C_4$ alkyl)OC(O)($C_2$-$C_4$ alkenyl)CO$_2$R$_{12}$, $(C_1$-$C_4$ alkyl)OC(O)($C_1$-$C_4$ alkyl)NH$_2$, $(C_1$-$C_4$ alkyl)C(O)NR$_{12}$R$_{13}$,

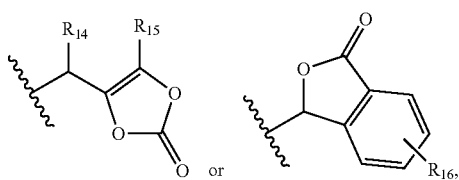 or wherein each occurrence of $R_{12}$ is, independently, H, alkyl, alkenyl, alkynyl, aryl or heteroaryl;
wherein each occurrence of $R_{13}$ is, independently, H, alkyl, alkenyl, alkynyl, aryl or heteroaryl;
wherein each occurrence of $R_{14}$ and $R_{15}$ is, independently, H, alkyl, alkenyl, alkynyl, aryl or heteroaryl;
wherein each occurrence of $R_{16}$ is, independently, H, halogen, alkyl, alkenyl, alkynyl, aryl or heteroaryl,
wherein when Y is OR$_9$ where $R_9$ is H, alkyl, alkenyl, alkynyl, aryl, alkylaryl, heteroaryl, alkylaryl, then X is

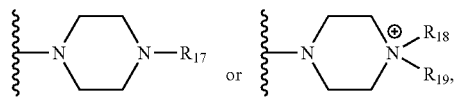

and
when X is

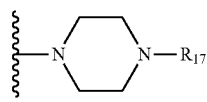

where $R_{17}$ is CH$_3$, then X is other than —O(C$_4$ alkyl)-OP(O)(OEt)$_2$ or —NH(C$_4$ alkyl)-OP(O)(OEt)$_2$,
or a salt or ester of the compound.
In some embodiments, Y is OR$_9$ or NR$_{10}$R$_{11}$,
wherein
$R_9$ is H, alkyl, alkenyl, alkynyl, aryl, alkylaryl, heteroaryl, alkylaryl, $(C_1$-$C_4$ alkyl)-O(CO)R$_{12}$, $(C_1$-$C_4$ alkyl)-O(CO)OR$_{12}$, $(C_1$-$C_4$ alkyl)-OP(O)(O($C_1$-$C_4$ alkyl)-O(CO)OR$_{12}$)$_2$, $(C_1$-$C_4$ alkyl)-OP(O)(O($C_1$-$C_4$ alkyl)-O(CO)R$_{12}$)$_2$, $(C_1$-$C_4$ alkyl)NR$_{12}$R$_{13}$, $(C_1$-$C_4$ alkyl)NC(O)R$_{12}$, $(C_1$-$C_4$ alkyl)C(O)OR$_{12}$, $(C_1$-$C_4$ alkyl)OC(O)aryl($C_1$-$C_4$ alkyl)P(O)(OR$_{12}$)$_2$, $(C_1$-$C_4$ alkyl)OC(O)($C_2$-$C_4$ alkenyl)CO$_2$R$_{12}$, $(C_1$-$C_4$ alkyl)OC(O)($C_1$-$C_4$ alkyl)NH$_2$, $(C_1$-$C_4$ alkyl)C(O)NR$_{12}$R$_{13}$,

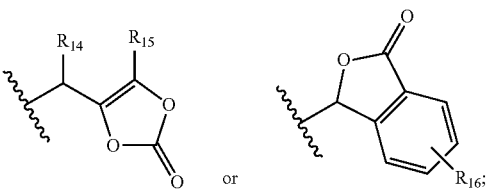 or $R_{10}$ is H; and
$R_{11}$ is $(C_1$-$C_4$ alkyl)-O(CO)R$_{12}$, $(C_1$-$C_4$ alkyl)-O(CO)OR$_{12}$, $(C_1$-$C_4$ alkyl)-OP(O)(OR$_{12}$)$_2$, $(C_1$-$C_4$ alkyl)-OP(O)(O($C_1$-$C_4$ alkyl)-O(CO)OR$_{12}$)$_2$, $(C_1$-$C_4$ alkyl)-OP(O)(O($C_1$-$C_4$ alkyl)-O(CO)R$_{12}$)$_2$, $(C_1$-$C_4$ alkyl)NR$_{12}$R$_{13}$, $(C_1$-$C_4$ alkyl)NC(O)R$_{12}$, $(C_1$-$C_4$ alkyl)C(O)OR$_{12}$, $(C_1$-$C_4$ alkyl)OC(O)aryl($C_1$-$C_4$ alkyl)P(O)(OR$_{12}$)$_2$, $(C_1$-$C_4$ alkyl)OC(O)($C_2$-$C_4$ alkenyl)CO$_2$R$_{12}$, $(C_1$-$C_4$ alkyl)OC(O)($C_1$-$C_4$ alkyl)NH$_2$, $(C_1$-$C_4$ alkyl)C(O)NR$_{12}$R$_{13}$,

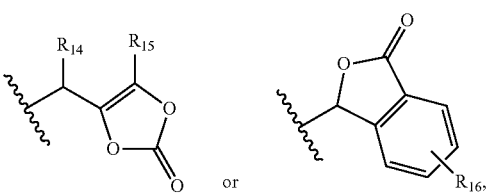 or wherein each occurrence of $R_{12}$ is, independently, H, alkyl, alkenyl, alkynyl, aryl or heteroaryl;
wherein each occurrence of $R_{13}$ is, independently, H, alkyl, alkenyl, alkynyl, aryl or heteroaryl;
wherein each occurrence of $R_{14}$ and $R_{15}$ is, independently, H, alkyl, alkenyl, alkynyl, aryl or heteroaryl;
wherein each occurrence of $R_{16}$ is, independently, H, halogen, alkyl, alkenyl, alkynyl, aryl or heteroaryl,
In some embodiments, X is OR$_1$ or NR$_2$R$_3$,
wherein R$_1$ is H, alkyl, alkenyl, alkynyl, aryl, alkylaryl, heteroaryl, alkylaryl, $(C_1$-$C_4$ alkyl)-O(CO)R$_4$, $(C_1$-$C_4$ alkyl)-O(CO)OR$_4$, O($C_1$-$C_4$ alkyl)-OP(O)(OR$_4$)$_2$, $(C_1$-$C_4$ alkyl)-OP(O)(O($C_1$-$C_4$ alkyl)-O(CO)OR$_4$)$_2$, $(C_1$-$C_4$ alkyl)-OP(O)(O($C_1$-$C_4$ alkyl)-O(CO)R$_4$)$_2$, $(C_1$-$C_4$ alkyl)NR$_4$R$_5$, $(C_1$-$C_4$ alkyl)NC(O)R$_4$, $(C_1$-$C_4$ alkyl)C(O)OR$_4$, $(C_1$-$C_4$ alkyl)OC(O)aryl($C_1$-$C_4$ alkyl)P(O)(OR$_4$)$_2$, $(C_1$-$C_4$ alkyl)OC(O) ($C_2$-$C_4$ alkenyl)CO$_2$R$_4$, $(C_1$-$C_4$ alkyl)OC(O)($C_1$-$C_4$ alkyl)NH$_2$, $(C_1$-$C_4$ alkyl)C(O)NR$_4$R$_5$,

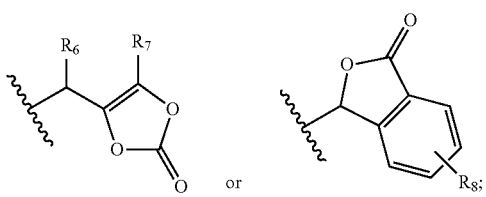 or

R$_2$ and R$_3$ are each independently H, alkyl, alkenyl, alkynyl, aryl, alkylaryl, heteroaryl, $(C_1$-$C_4$ alkyl)-O(CO)R$_4$, $(C_1$-$C_4$ alkyl)-O(CO)OR$_4$, O($C_1$-$C_4$ alkyl)-OP (O)(OR₄)₂, (C₁-C₄ alkyl)-OP(O)(O(C₁-C₄ alkyl)-O (CO)OR₄)₂, (C₁-C₄ alkyl)-OP(O)(O(C₁-C₄ alkyl)-O (CO)R₄)₂, (C₁-C₄ alkyl)NR₄R₅, (C₁-C₄ alkyl)NC(O) R₄, (C₁-C₄ alkyl) C(O)OR₄, (C₁-C₄ alkyl)OC(O)aryl (C₁-C₄ alkyl)P(O)(OR₄)₂, (C₁-C₄ alkyl)OC(O)(C₂-C₄ alkenyl)CO₂R₄, (C₁-C₄ alkyl)OC(O)(C₁-C₄ alkyl)NH₂, (C₁-C₄ alkyl)C(O)NR₄R₅,

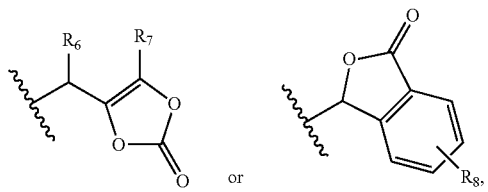

or wherein each occurrence of R₄ is, independently, H, alkyl, alkenyl, alkynyl, aryl or heteroaryl;

wherein each occurrence of R₅ is, independently, H, alkyl, alkenyl, alkynyl, aryl or heteroaryl;

wherein each occurrence of R₆ and R₇ is, independently, H, alkyl, alkenyl, alkynyl, aryl or heteroaryl;

wherein each occurrence of R₈ is, independently, H, halogen, alkyl, alkenyl, alkynyl, aryl or heteroaryl.

In some embodiments, X is OH, O-alkyl, O-alkenyl, O-alkynyl, O-aryl, O-alkylaryl, O-heteroaryl; and Y is OR₉ or NR₁₀R₁₁, wherein R₉ is (C₁-C₄ alkyl)-O(CO)R₂, (C₁-C₄ alkyl)-O (CO)OR₁₂, (C₁-C₄ alkyl)-OP(O)(OR₁₂)₂, (C₁-C₄ alkyl)-OP(O)(O(C₁-C₄ alkyl)-O(CO)OR₁₂)₂, (C₁-C₄ alkyl)-OP(O)(O(C₁-C₄ alkyl)-O(CO)R₁₂)₂, (C₁-C₄ alkyl)NR₁₂R₁₃, (C₁-C₄ alkyl)NC(O)R₁₂, (C₁-C₄ alkyl) C(O)OR₁₂, (C₁-C₄ alkyl)OC(O)aryl(C₁-C₄ alkyl)P(O) (OR₁₂)₂, (C₁-C₄ alkyl)OC(O)(C₂-C₄ alkenyl)CO₂R₁₂, (C₁-C₄ alkyl)OC(O)(C₁-C₄ alkyl)NH₂, (C₁-C₄ alkyl)C (O) NR₁₂R₁₃,

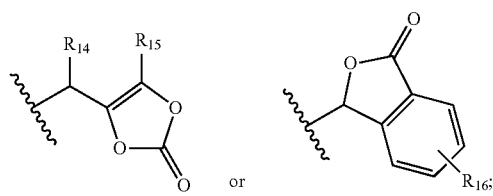

or

R₁₀ is H; and

R₁₁ is (C₁-C₄ alkyl)-O(CO)R₁₂, (C₁-C₄ alkyl)-O(CO) OR₁₂, (C₁-C₄ alkyl)-OP(O)(OR₁₂)₂, (C₁-C₄ alkyl)-OP (O)(O(C₁-C₄ alkyl)-O(CO)OR₁₂)₂, (C₁-C₄ alkyl)-OP (O)(O(C₁-C₄ alkyl)-O(CO)R₁₂)₂, (C₁-C₄ alkyl) NR₁₂R₁₃, (C₁-C₄ alkyl)NC(O)R₁, (C₁-C₄ alkyl)C(O) OR₁, (C₁-C₄ alkyl)OC(O)aryl(C₁-C₄ alkyl)P(O) (OR₂)₂, (C₁-C₄ alkyl)OC(O)(C₂-C₄ alkenyl)CO₂R₁₂, (C₁-C₄ alkyl)OC(O) (C₁-C₄ alkyl)NH₂, (C₁-C₄ alkyl)C (O)NR₁₂R₁₃,

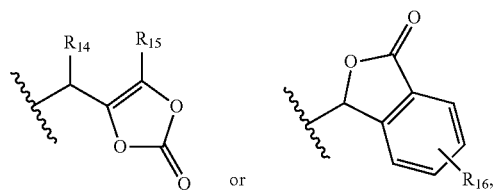

or wherein each occurrence of R₁₂ is, independently, H, alkyl, alkenyl, alkynyl, aryl or heteroaryl;

wherein each occurrence of R₁₃ is, independently, H, alkyl, alkenyl, alkynyl, aryl or heteroaryl;

wherein each occurrence of R₁₄ and R₁₅ is, independently, H, alkyl, alkenyl, alkynyl, aryl or heteroaryl;

wherein each occurrence of R₁₆ is, independently, H, halogen, alkyl, alkenyl, alkynyl, aryl or heteroaryl.

In some embodiments, the compound having the structure:

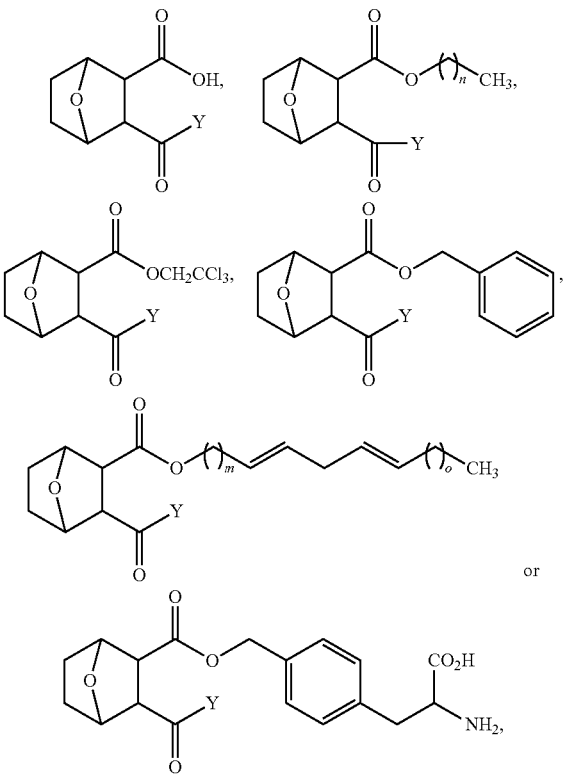

wherein each n=0-19, m=0-8 and o=0-6;

Y is OR₉ or NR₁₀R₁₁, wherein R₉ is (C₁-C₄ alkyl)-O(CO)R₂, (C₁-C₄ alkyl)-O (CO)OR₁₂, (C₁-C₄ alkyl)-OP(O)(OR₁₂)₂, (C₁-C₄ alkyl)-OP(O)(O(C₁-C₄ alkyl)-O(CO)OR₁₂)₂, (C₁-C₄ alkyl)-OP(O)(O(C₁-C₄ alkyl)-O(CO)R₁₂)₂, (C₁-C₄ alkyl)NR₁₂R₁₃, (C₁-C₄ alkyl)NC(O)R₁₂, (C₁-C₄ alkyl) C(O)OR₁₂, (C₁-C₄ alkyl)OC(O)aryl(C₁-C₄ alkyl)P(O) (OR₂)₂, (C₂-C₄ alkyl)OC(O)(C₂-C₄ alkenyl)CO₂R₁₂, (C₁-C₄ alkyl)OC(O)(C₁-C₄ alkyl)NH₂, (C₁-C₄ alkyl)C (O)NR₁₂R₁₃,

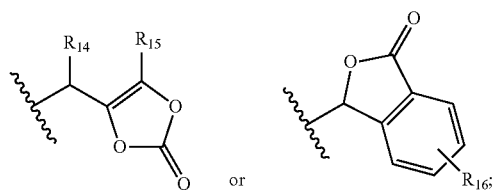

or

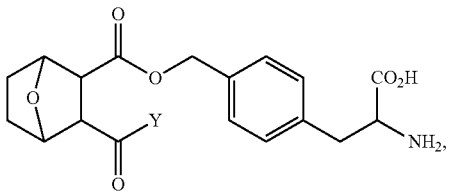

$R_{10}$ is H; and $R_{11}$ is $(C_1$-$C_4$ alkyl)-O(CO)$R_{12}$, $(C_1$-$C_4$ alkyl)-O(CO)OR$_{12}$, $(C_1$-$C_4$ alkyl)-OP(O)(OR$_{12}$)$_2$, $(C_1$-$C_4$ alkyl)-OP(O)(O($C_1$-$C_4$ alkyl)-O(CO)OR$_{12}$)$_2$, $(C_1$-$C_4$ alkyl)-OP(O)(O($C_1$-$C_4$ alkyl)-O(CO)R$_{12}$)$_2$, $(C_1$-$C_4$ alkyl)NR$_{12}$R$_{13}$, $(C_1$-$C_4$ alkyl)NC(O)R$_{12}$, $(C_1$-$C_4$ alkyl)C(O)OR$_{12}$, $(C_1$-$C_4$ alkyl)OC(O)aryl($C_1$-$C_4$ alkyl)P(O)(OR$_{12}$)$_2$, $(C_2$-$C_4$ alkyl)OC(O)($C_2$-$C_4$ alkenyl)CO$_2$R$_{12}$, $(C_1$-$C_4$ alkyl)OC(O)($C_1$-$C_4$ alkyl)NH$_2$, $(C_1$-$C_4$ alkyl)C(O)NR$_{12}$R$_{13}$,

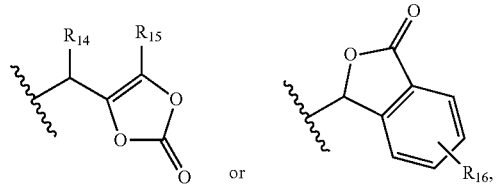

or wherein each occurrence of $R_{12}$ is, independently, H, alkyl, alkenyl, alkynyl, aryl or heteroaryl;

wherein each occurrence of $R_{13}$ is, independently, H, alkyl, alkenyl, alkynyl, aryl or heteroaryl;

wherein each occurrence of $R_{14}$ and $R_{15}$ is, independently, H, alkyl, alkenyl, alkynyl, aryl or heteroaryl;

wherein each occurrence of $R_{16}$ is, independently, H, halogen, alkyl, alkenyl, alkynyl, aryl or heteroaryl.

In some embodiments, the compound having the structure:

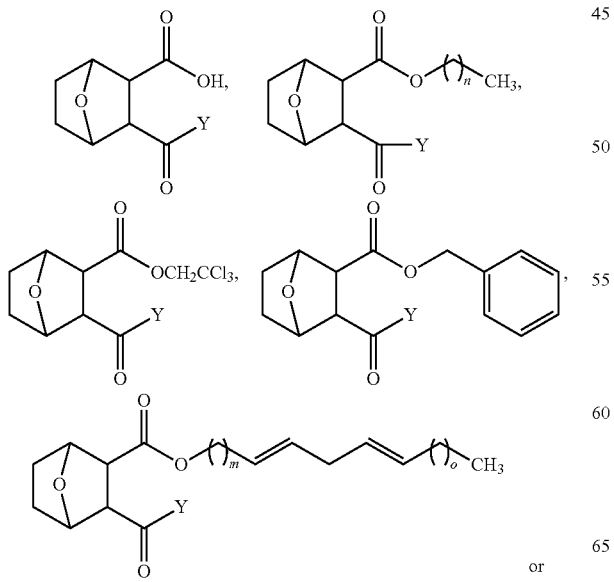

wherein each n=0-19, m=0-8 and n=0-6;

Y is OR$_9$, wherein R$_9$ is

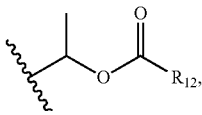 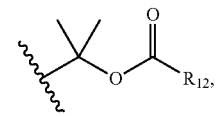

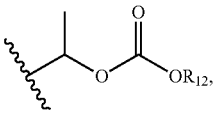 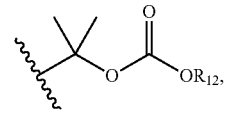

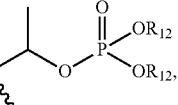 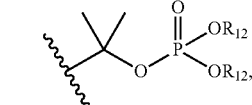

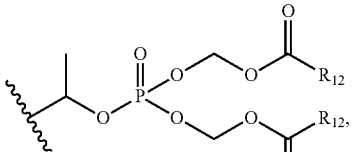

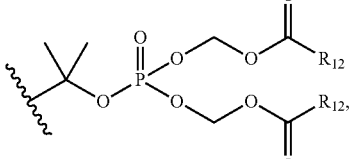

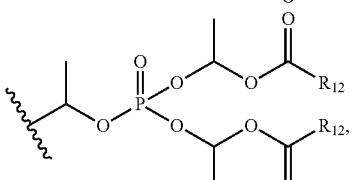

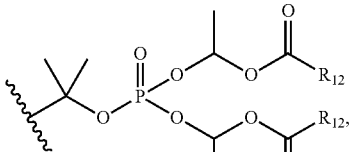

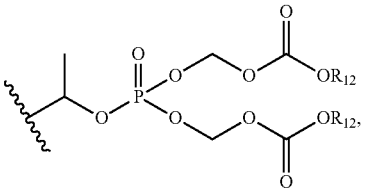

or

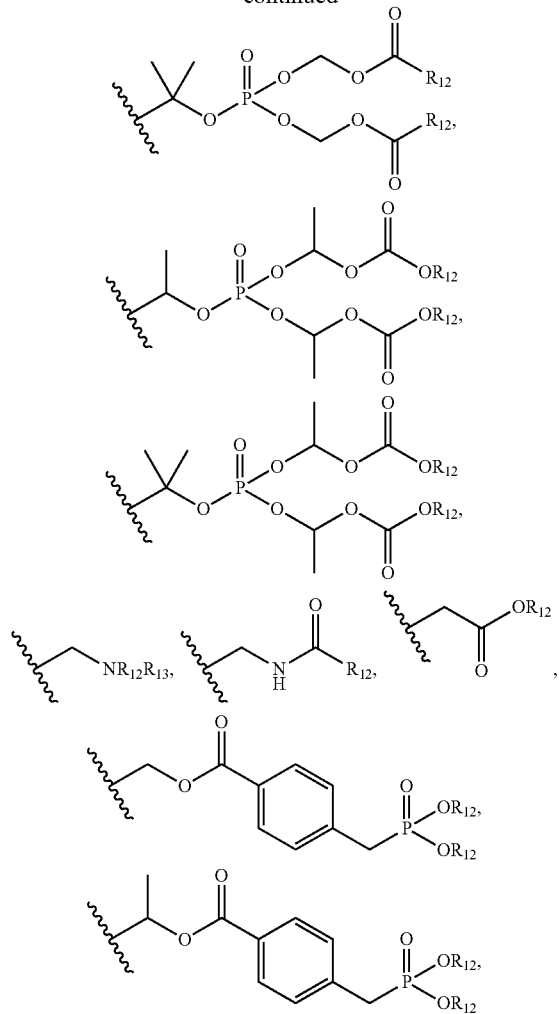
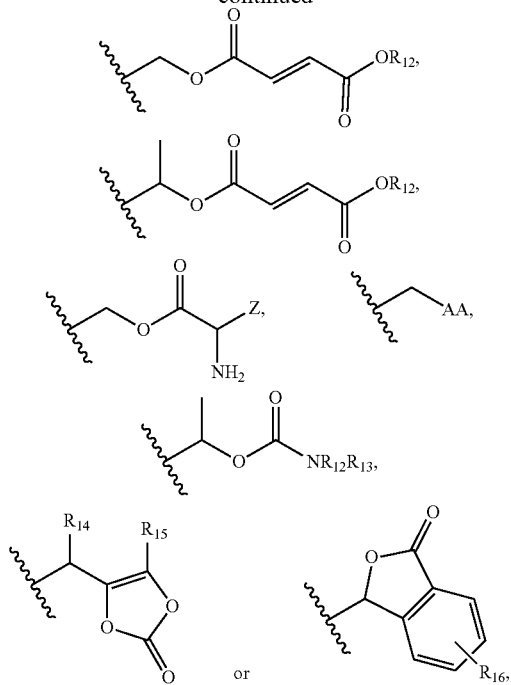

wherein each occurrence of $R_{12}$ is, independently, H, alkyl, alkenyl, alkynyl, aryl or heteroaryl;

wherein each occurrence of $R_{13}$ is, independently, H, alkyl, alkenyl, alkynyl, aryl or heteroaryl;

wherein each occurrence of $R_{14}$ and $R_{15}$ is, independently, H, alkyl, alkenyl, alkynyl, aryl or heteroaryl;

wherein each occurrence of $R_{16}$ is, independently, H, halogen, alkyl, alkenyl, alkynyl, aryl or heteroaryl;

Z is an amino acid substituent; and

AA is an amino acid moiety.

In some embodiments, the compound having the structure:

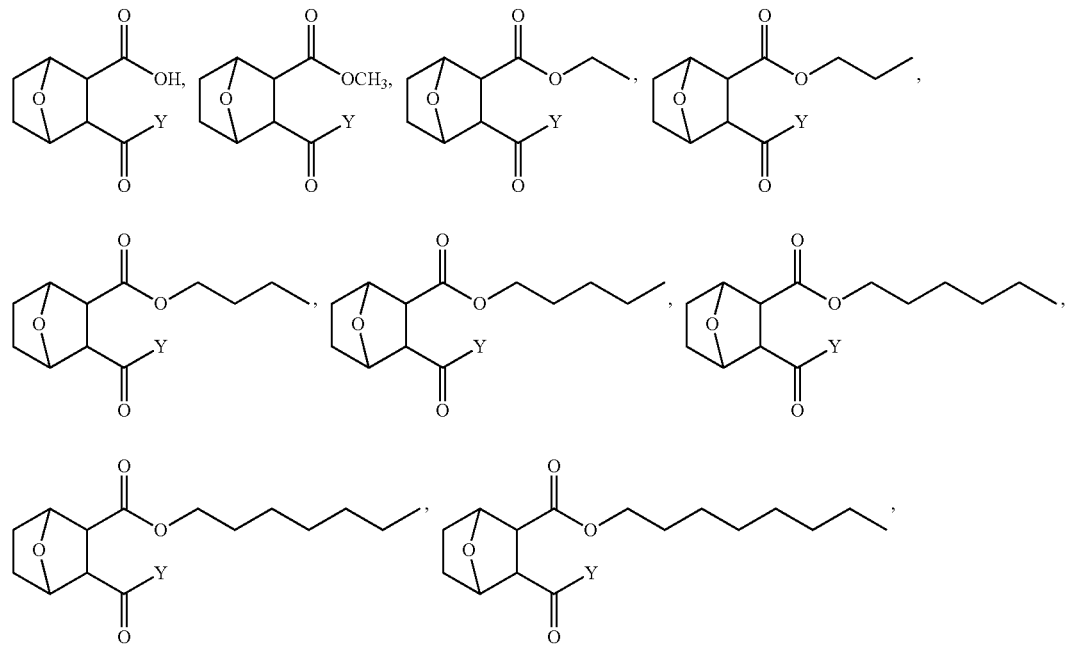

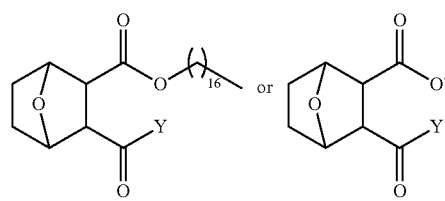
Y is OR$_9$,
 wherein R$_9$ is
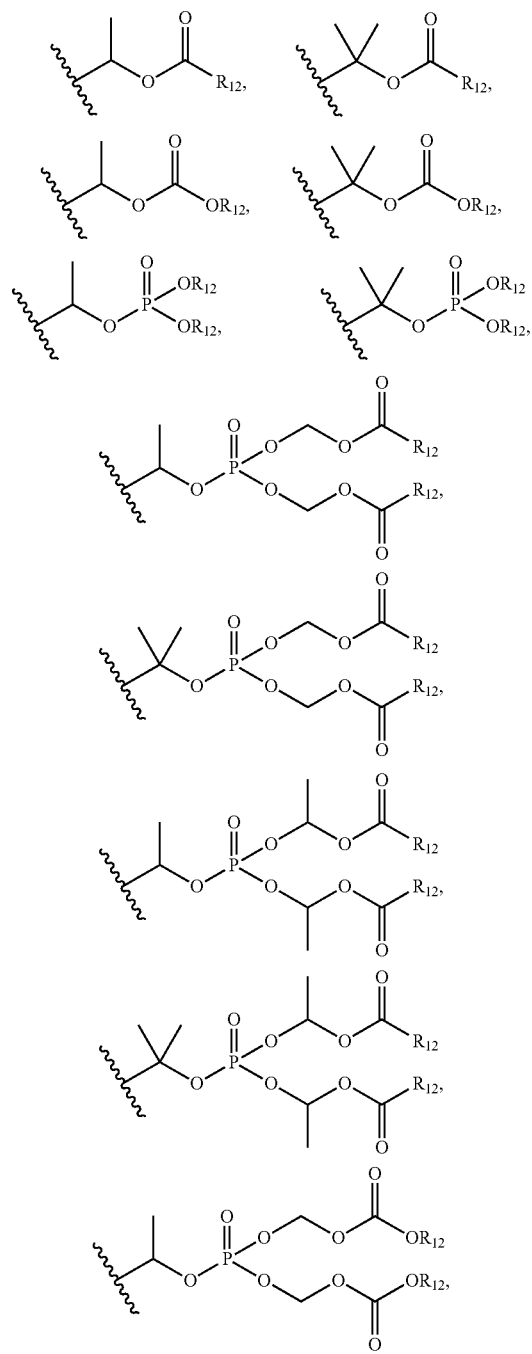
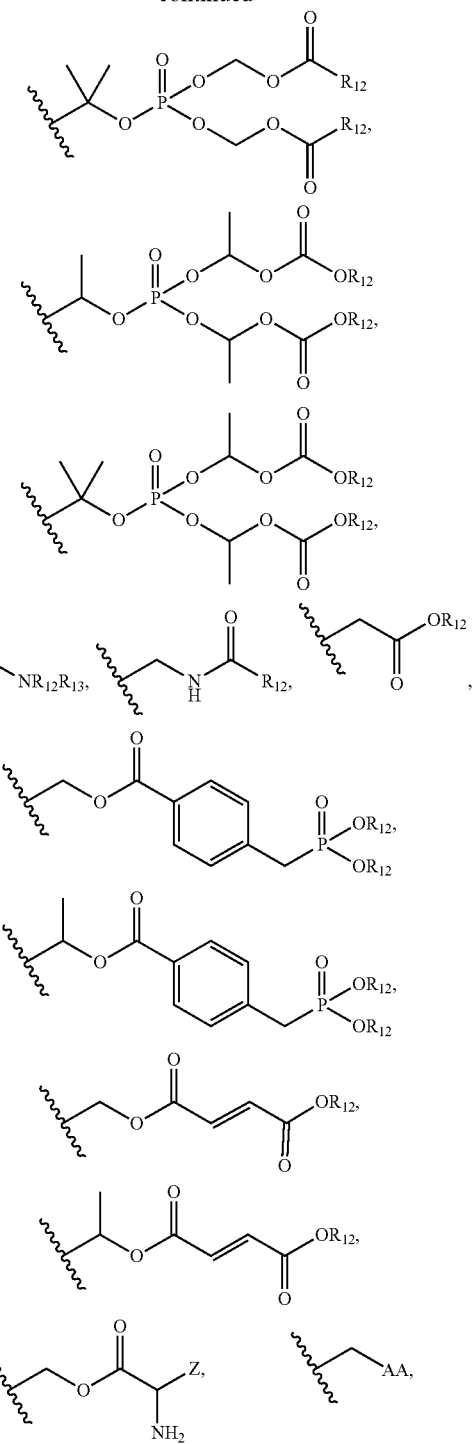

-continued

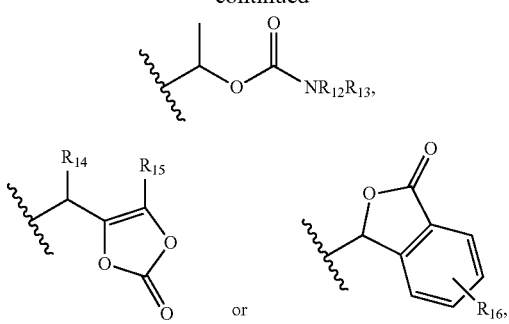

wherein each occurrence of $R_{12}$ is, independently, H, alkyl, alkenyl, alkynyl, aryl or heteroaryl;

wherein each occurrence of $R_{13}$ is, independently, H, alkyl, alkenyl, alkynyl, aryl or heteroaryl;

wherein each occurrence of $R_{14}$ and $R_{15}$ is, independently, H, alkyl, alkenyl, alkynyl, aryl or heteroaryl;

wherein each occurrence of $R_{16}$ is, independently, H, halogen, alkyl, alkenyl, alkynyl, aryl or heteroaryl;

Z is an amino acid substituent; and

AA is an amino acid moiety.

In some embodiments, the compound having the structure:

wherein

Each n=0-19, m=0-8 and n=0-6;

Y is $NR_{10}R_{11}$, wherein $R_{10}$ is H; and $R_{11}$ is

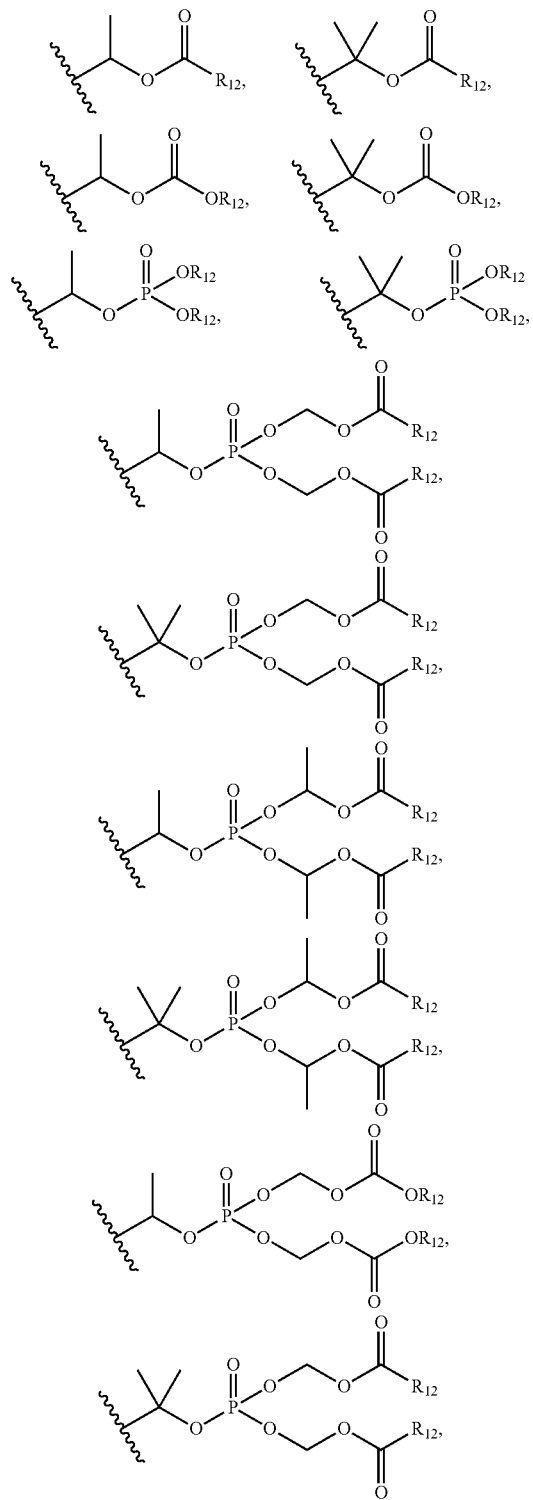

-continued

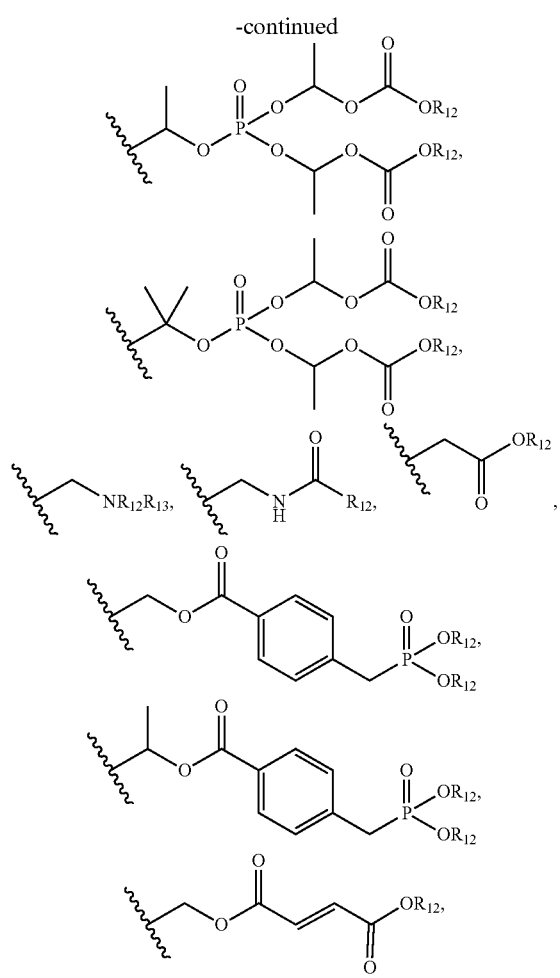

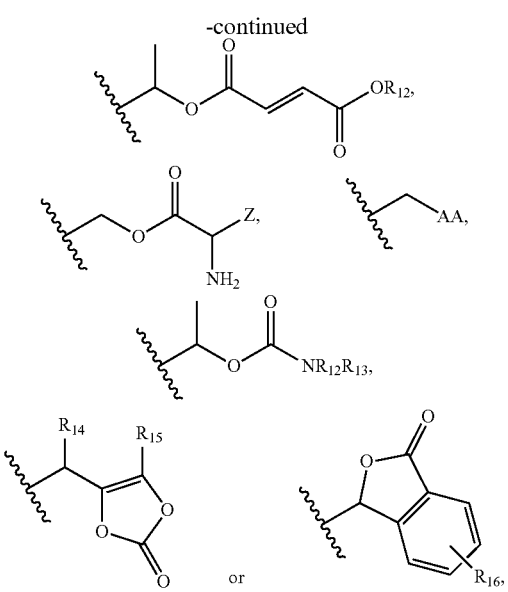

wherein each occurrence of $R_{12}$ is, independently, H, alkyl, alkenyl, alkynyl, aryl or heteroaryl;

wherein each occurrence of $R_{13}$ is, independently, H, alkyl, alkenyl, alkynyl, aryl or heteroaryl;

wherein each occurrence of $R_{14}$ and $R_{15}$ is, independently, H, alkyl, alkenyl, alkynyl, aryl or heteroaryl;

wherein each occurrence of $R_{16}$ is, independently, H, halogen, alkyl, alkenyl, alkynyl, aryl or heteroaryl;

Z is an amino acid substituent; and

AA is an amino acid moiety.

In some embodiments, the compound having the structure:

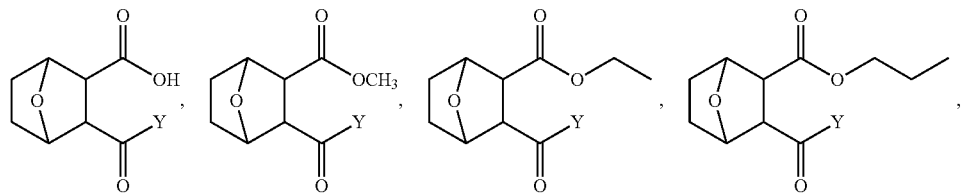

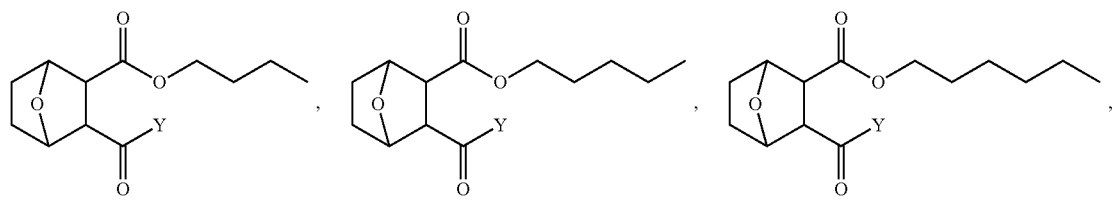

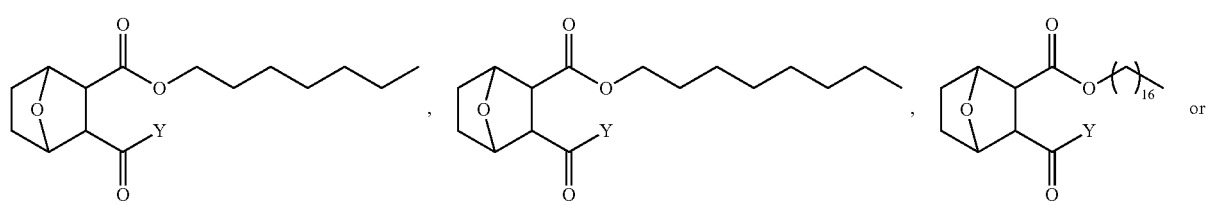

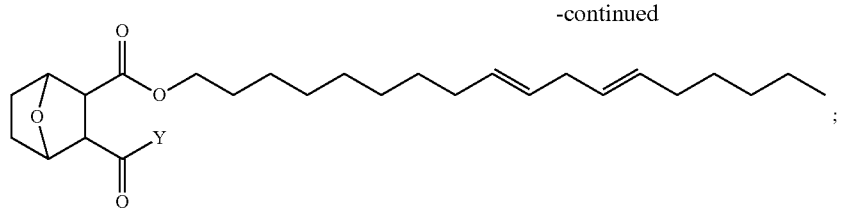
and
Y is $NR_{10}R_{11}$,
wherein
$R_{10}$ is H; and
$R_{11}$ is
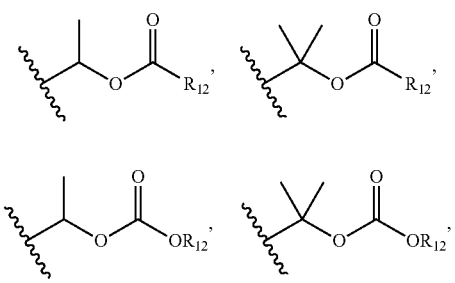
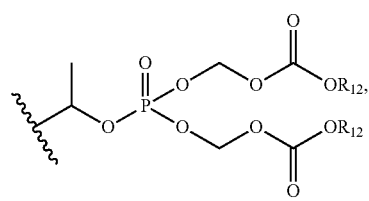
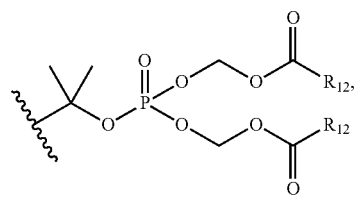
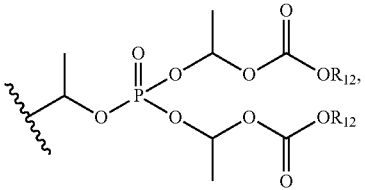
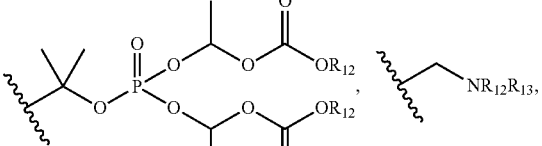
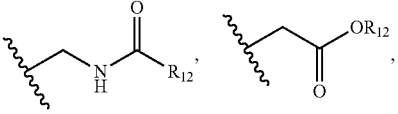
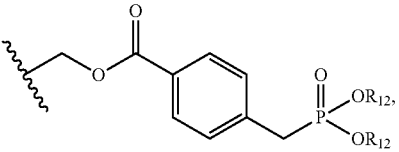
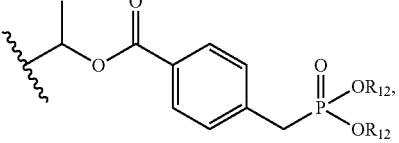
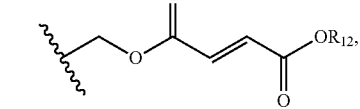

-continued

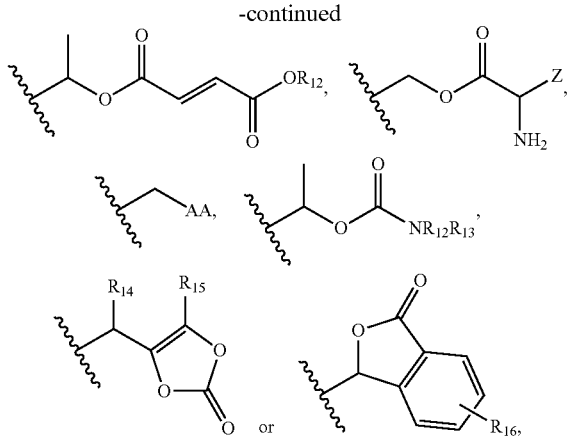

wherein each occurrence of $R_{12}$ is, independently, H, alkyl, alkenyl, alkynyl, aryl or heteroaryl;
wherein each occurrence of $R_{13}$ is, independently, H, alkyl, alkenyl, alkynyl, aryl or heteroaryl;
wherein each occurrence of $R_{14}$ and $R_{15}$ is, independently, H, alkyl, alkenyl, alkynyl, aryl or heteroaryl;
wherein each occurrence of $R_{16}$ is, independently, H, halogen, alkyl, alkenyl, alkynyl, aryl or heteroaryl;
Z is an amino acid substituent; and
AA is an amino acid moiety.

In some embodiments, the compound having the structure:

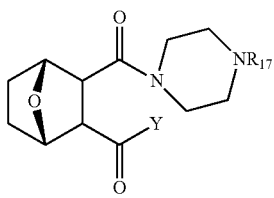

wherein
$R_{17}$ is H, alkyl, hydroxyalkyl, alkenyl or alkylaryl;
Y is $OR_9$ or $NR_{10}R_{11}$,
wherein $R_9$ is $(C_1$-$C_4$ alkyl)-$O(CO)R_{12}$, $(C_1$-$C_4$ alkyl)-$O(CO)OR_{12}$, $(C_1$-$C_4$ alkyl)-$OP(O)(OR_{12})_2$, $(C_1$-$C_4$ alkyl)-$OP(O)(O(C_1$-$C_4$ alkyl)-$O(CO)OR_{12})_2$, $(C_1$-$C_4$ alkyl)-$OP(O)(O(C_1$-$C_4$ alkyl)-$O(CO)R_{12})_2$, $(C_1$-$C_4$ alkyl)$NR_{12}R_{13}$, $(C_1$-$C_4$ alkyl)$NC(O)R_{12}$, $(C_1$-$C_4$ alkyl)$C(O)OR_{12}$, $(C_1$-$C_4$ alkyl)$OC(O)$aryl$(C_1$-$C_4$ alkyl)$P(O)(OR_{12})_2$, $(C_1$-$C_4$ alkyl)$OC(O)(C_2$-$C_4$ alkenyl)$CO_2R_{12}$, $(C_1$-$C_4$ alkyl)$OC(O)(C_1$-$C_4$ alkyl)$NH_2$, $(C_1$-$C_4$ alkyl)$C(O) NR_{12}R_{13}$,

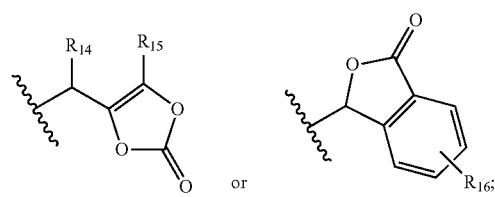

$R_{10}$ is H; and
$R_{11}$ is $(C_1$-$C_4$ alkyl)-$O(CO)R_{12}$, $(C_1$-$C_4$ alkyl)-$O(CO)OR_{12}$, $(C_1$-$C_4$ alkyl)-$OP(O)(OR_{12})_2$, $(C_1$-$C_4$ alkyl)-$OP(O)(O(C_1$-$C_4$ alkyl)-$O(CO)OR_{12})_2$, $(C_1$-$C_4$ alkyl)-$OP(O)(O(C_1$-$C_4$ alkyl)-$O(CO)R_{12})_2$, $(C_1$-$C_4$ alkyl) $NR_{12}R_{13}$, $(C_1$-$C_4$ alkyl)$NC(O)R_{12}$, $(C_1$-$C_4$ alkyl)$C(O) OR_{12}$, $(C_1$-$C_4$ alkyl)$OC(O)$aryl$(C_1$-$C_4$ alkyl)$P(O) (OR_{12})_2$, $(C_1$-$C_4$ alkyl)$OC(O)(C_2$-$C_4$ alkenyl)$CO_2R_{12}$, $(C_1$-$C_4$ alkyl)$OC(O)(C_1$-$C_4$ alkyl)$NH_2$, $(C_1$-$C_4$ alkyl)$C (O)NR_{12}R_{13}$,

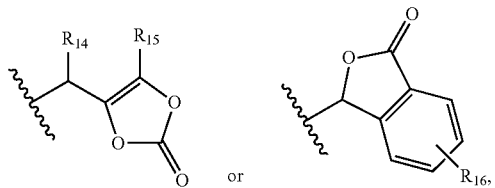

wherein each occurrence of $R_{12}$ is, independently, H, halogen, alkyl, alkenyl, alkynyl, aryl or heteroaryl;
wherein each occurrence of $R_{13}$ is, independently, H, alkyl, alkenyl, alkynyl, aryl or heteroaryl;
wherein each occurrence of $R_{14}$ and $R_{15}$ is, independently, H, alkyl, alkenyl, alkynyl, aryl or heteroaryl;
wherein each occurrence of $R_{16}$ is, independently, H, halogen, alkyl, alkenyl, alkynyl, aryl or heteroaryl.

In some embodiments, the compound having the structure:

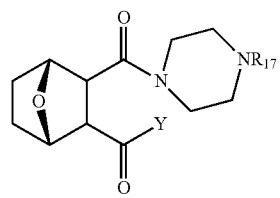

wherein
$R_{17}$ is H, alkyl, hydroxyalkyl, alkenyl or alkylaryl; and
Y is $OR_9$,
wherein $R_9$ is

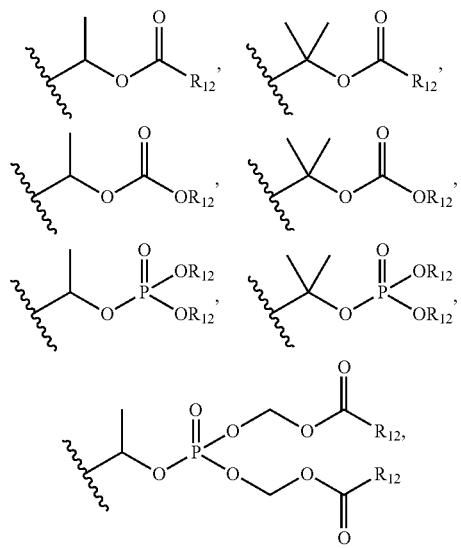

-continued

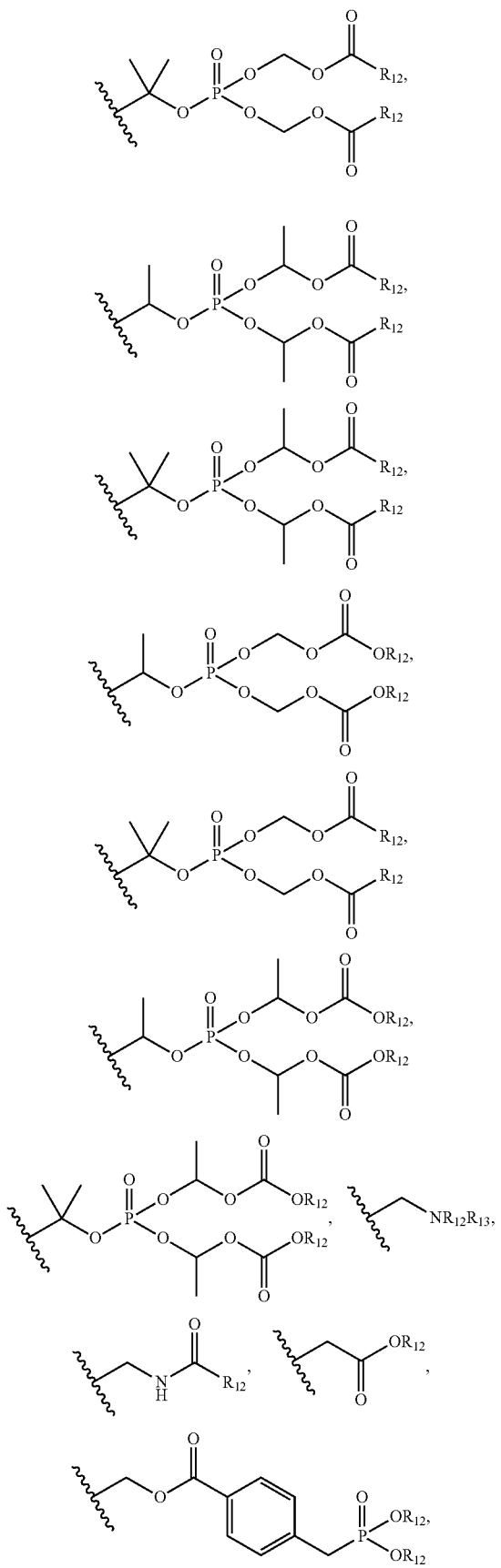

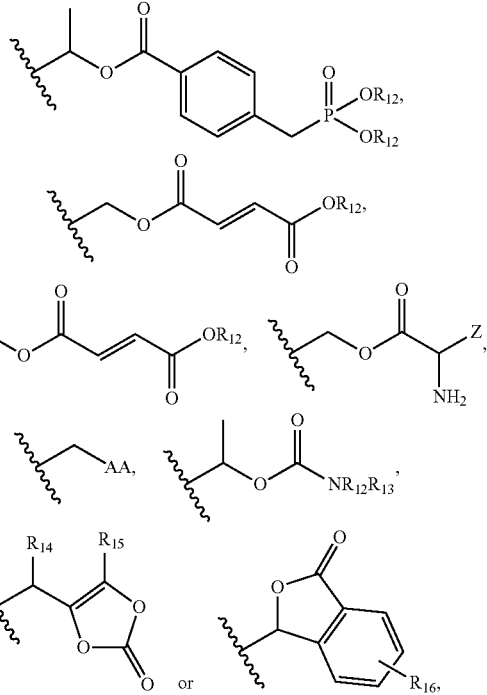

wherein each occurrence of $R_{12}$ is, independently, H, halogen, alkyl, alkenyl, alkynyl, aryl or heteroaryl;
wherein each occurrence of $R_{13}$ is, independently, H, alkyl, alkenyl, alkynyl, aryl or heteroaryl;
wherein each occurrence of $R_{14}$ and $R_{15}$ is, independently, H, alkyl, alkenyl, alkynyl, aryl or heteroaryl;
wherein each occurrence of $R_{16}$ is, independently, H, halogen, alkyl, alkenyl, alkynyl, aryl or heteroaryl;
Z is an amino acid substituent; and
AA is an amino acid moiety.

In some embodiments, the compound having the structure:

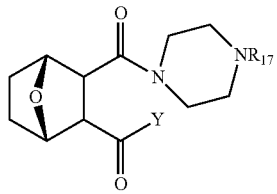

wherein
$R_{17}$ is H, methyl, ethyl, $CH_2CH_2OH$, $CH_2$(phenyl); and
Y is $OR_9$,
wherein $R_9$ is

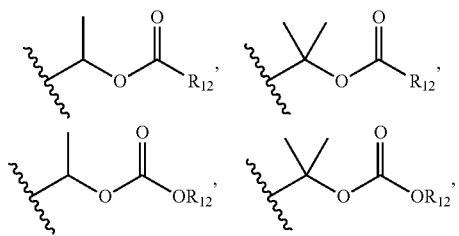

wherein each occurrence of $R_{12}$ is, independently, H, alkyl, alkenyl, alkynyl, aryl or heteroaryl;

wherein each occurrence of $R_{13}$ is, independently, H, alkyl, alkenyl, alkynyl, aryl or heteroaryl;

wherein each occurrence of $R_{14}$ and $R_{15}$ is, independently, H, alkyl, alkenyl, alkynyl, aryl or heteroaryl;

wherein each occurrence of $R_{16}$ is, independently, H, halogen, alkyl, alkenyl, alkynyl, aryl or heteroaryl;

Z is an amino acid substituent; and

AA is an amino acid moiety.

In some embodiments, the compound having the structure:

31
-continued
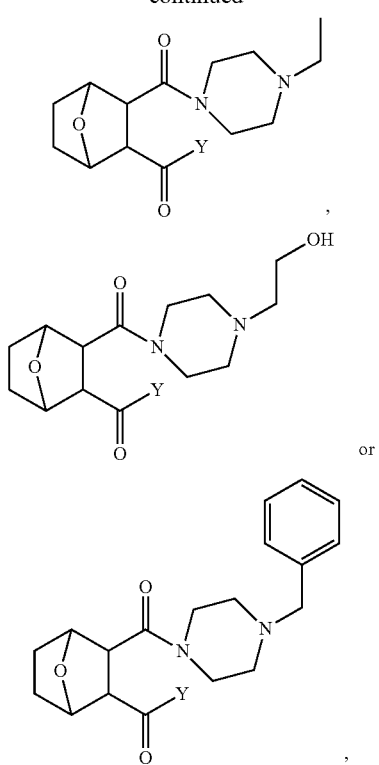
wherein
Y is OR$_9$,
wherein R$_9$ is
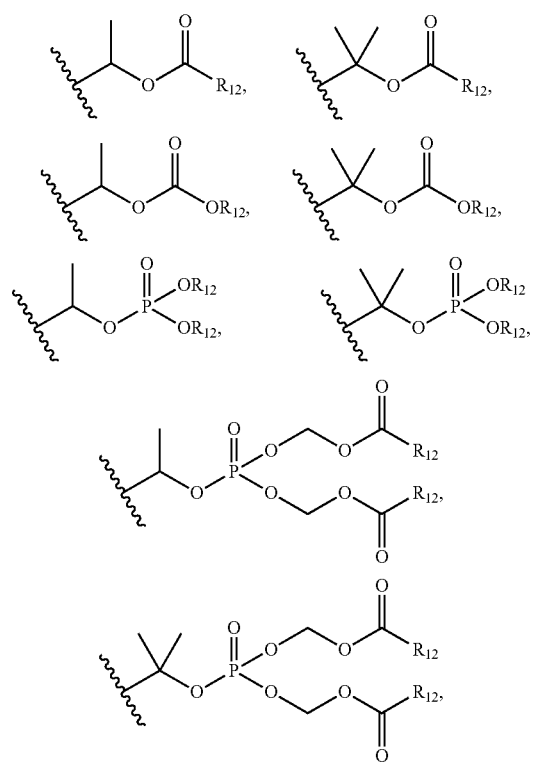
32
-continued
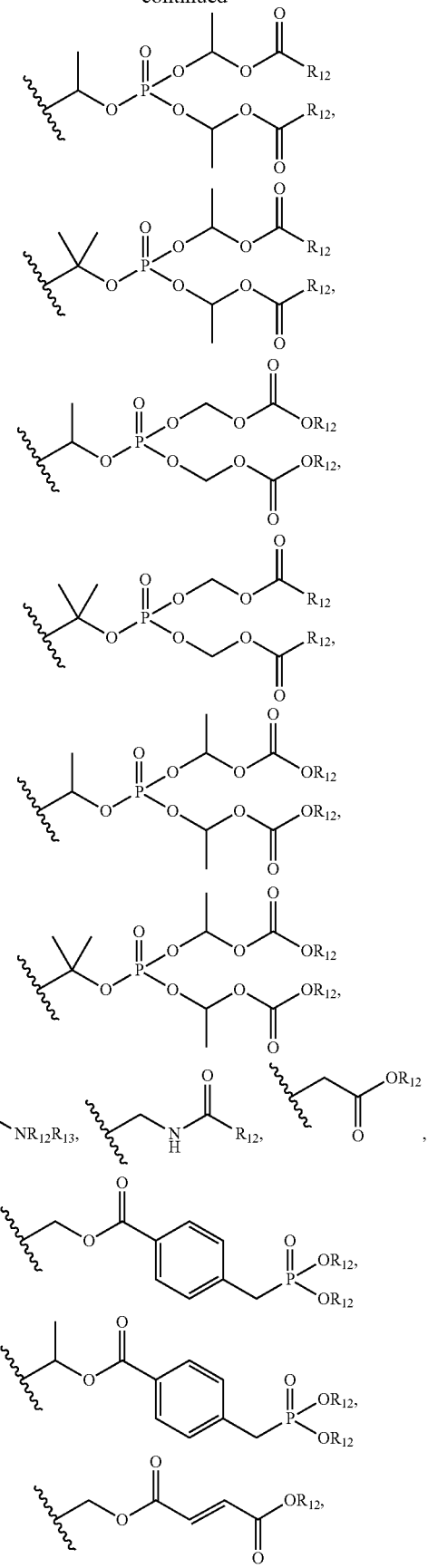

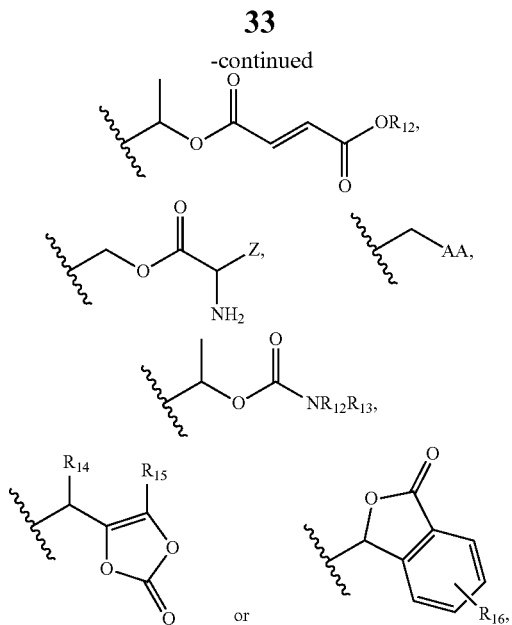

wherein each occurrence of $R_{12}$ is, independently, H, alkyl, alkenyl, alkynyl, aryl or heteroaryl;

wherein each occurrence of $R_{13}$ is, independently, H, alkyl, alkenyl, alkynyl, aryl or heteroaryl;

wherein each occurrence of $R_{14}$ and $R_{15}$ is, independently, H, alkyl, alkenyl, alkynyl, aryl or heteroaryl;

wherein each occurrence of $R_{16}$ is, independently, H, halogen, alkyl, alkenyl, alkynyl, aryl or heteroaryl;

Z is an amino acid substituent; and

AA is an amino acid moiety.

In some embodiments, the compound having the structure:

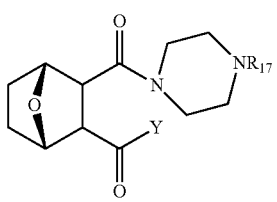

wherein
$R_{17}$ is H, alkyl, hydroxyalkyl, alkenyl or alkylaryl; and
Y is $NR_{10}R_{11}$,
wherein
$R_{10}$ is H; and
$R_{11}$ is

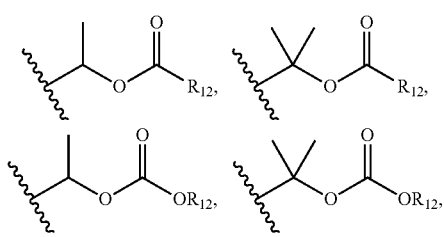

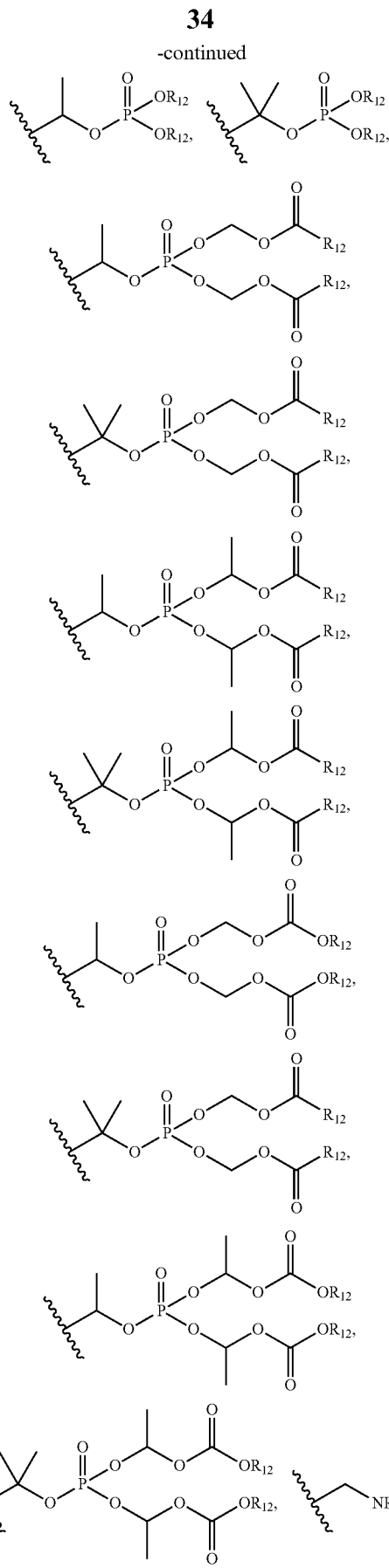

-continued

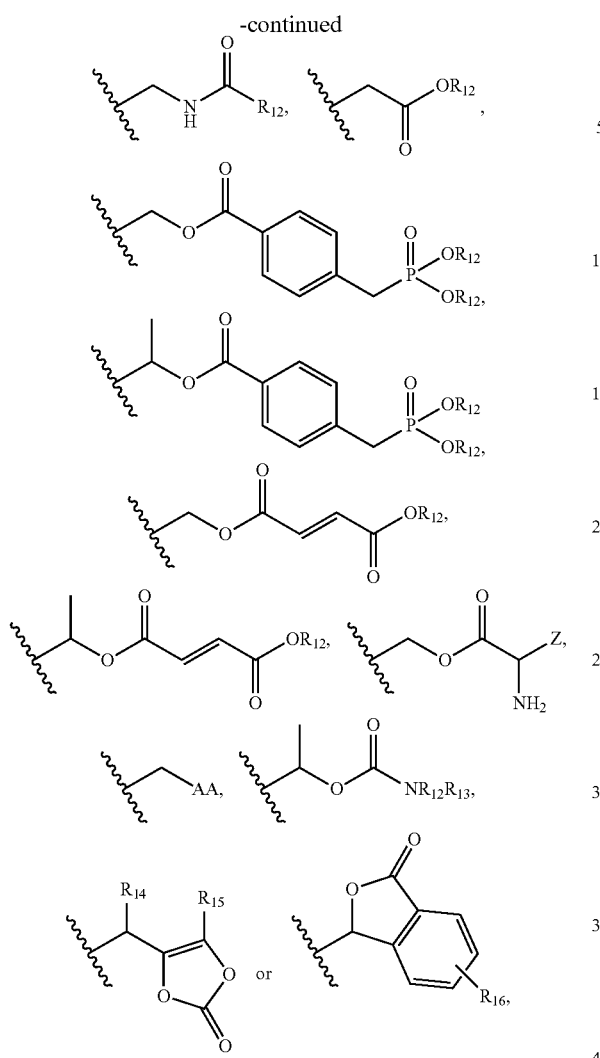

wherein each occurrence of $R_{12}$ is, independently, H, alkyl, alkenyl, alkynyl, aryl or heteroaryl;

wherein each occurrence of $R_{13}$ is, independently, H, alkyl, alkenyl, alkynyl, aryl or heteroaryl;

wherein each occurrence of $R_{14}$ and $R_{15}$ is, independently, H, alkyl, alkenyl, alkynyl, aryl or heteroaryl;

wherein each occurrence of $R_{16}$ is, independently, H, halogen, alkyl, alkenyl, alkynyl, aryl or heteroaryl;

Z is an amino acid substituent; and

AA is an amino acid moiety.

In some embodiments, the compound having the structure:

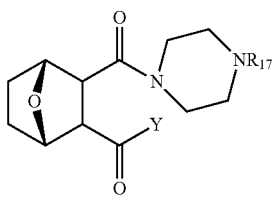

wherein $R_{17}$ is H, methyl, ethyl, $CH_2CH_2OH$, $CH_2$(phenyl); and

Y is $NR_{10}R_{11}$, wherein $R_{10}$ is H; and $R_{11}$ is

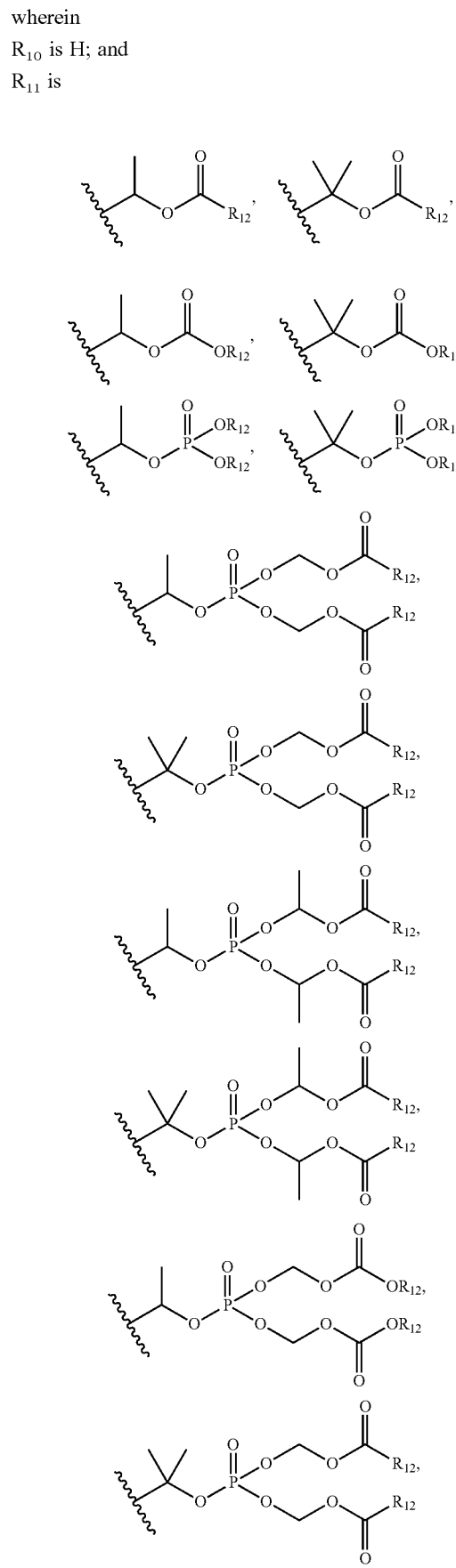

-continued

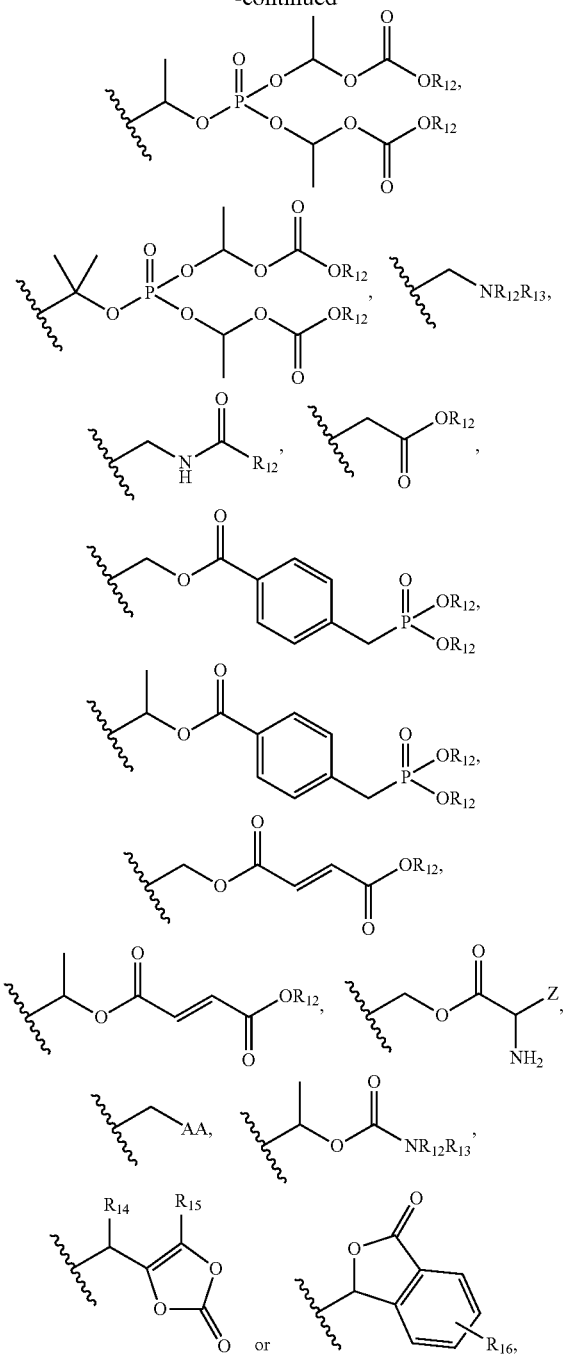

wherein each occurrence of $R_{12}$ is, independently, H, alkyl, alkenyl, alkynyl, aryl or heteroaryl;
wherein each occurrence of $R_{13}$ is, independently, H, alkyl, alkenyl, alkynyl, aryl or heteroaryl;
wherein each occurrence of $R_{14}$ and $R_{15}$ is, independently, H, alkyl, alkenyl, alkynyl, aryl or heteroaryl;
wherein each occurrence of $R_{16}$ is, independently, H, halogen, alkyl, alkenyl, alkynyl, aryl or heteroaryl;
Z is an amino acid substituent; and
AA is an amino acid moiety.

In some embodiments, the compound having the structure:

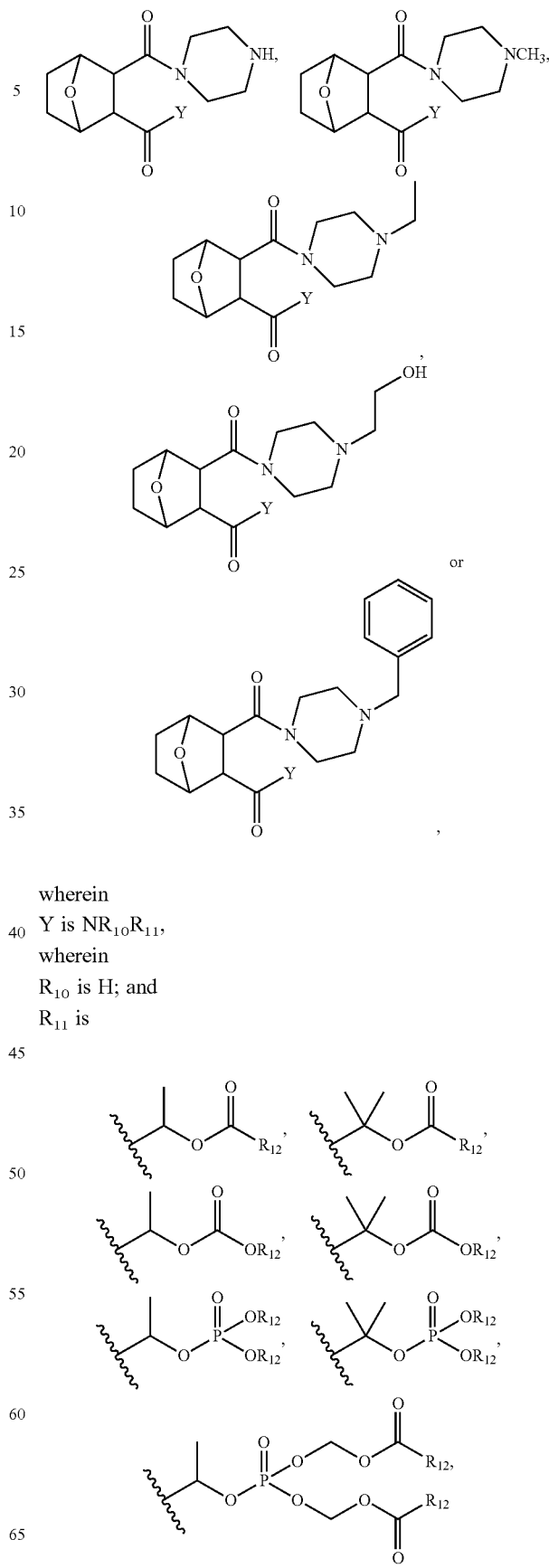

wherein
Y is $NR_{10}R_{11}$,
wherein
$R_{10}$ is H; and
$R_{11}$ is

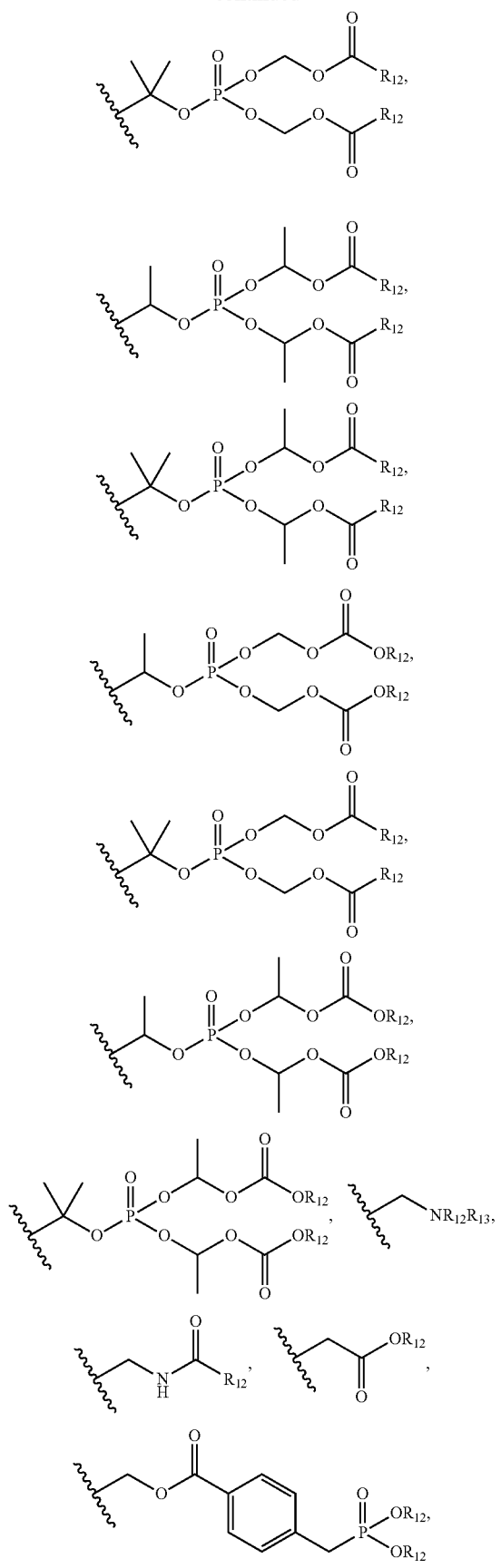
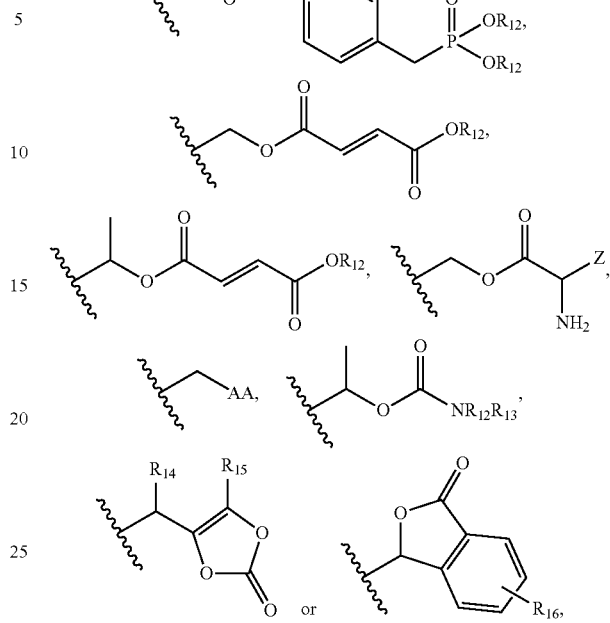

wherein each occurrence of $R_{12}$ is, independently, H, alkyl, alkenyl, alkynyl, aryl or heteroaryl;

wherein each occurrence of $R_{13}$ is, independently, H, alkyl, alkenyl, alkynyl, aryl or heteroaryl;

wherein each occurrence of $R_{14}$ and $R_{15}$ is, independently, H, alkyl, alkenyl, alkynyl, aryl or heteroaryl;

wherein each occurrence of $R_{16}$ is, independently, H, halogen, alkyl, alkenyl, alkynyl, aryl or heteroaryl;

Z is an amino acid substituent; and

AA is an amino acid moiety.

In some embodiments, the compound wherein

X is $OR_1$ or $NR_2R_3$, wherein $R_1$ is ($C_1$-$C_4$ alkyl)-O(CO)$R_4$, ($C_1$-$C_4$ alkyl)-O (CO)O$R_4$, ($C_1$-$C_4$ alkyl)-OP(O)(O$R_4$), ($C_1$-$C_4$ alkyl)-OP(O)(O($C_1$-$C_4$ alkyl)-O(CO)O$R_4$)$_2$, ($C_1$-$C_4$ alkyl)-OP(O)(O($C_1$-$C_4$ alkyl)-O(CO)$R_4$)$_2$, ($C_1$-$C_4$ alkyl)N$R_4R_5$, ($C_1$-$C_4$ alkyl)NC(O)$R_4$, ($C_1$-$C_4$ alkyl)C(O)O$R_4$, ($C_1$-$C_4$ alkyl)OC(O)aryl($C_1$-$C_4$ alkyl)P(O)(O$R_4$)$_2$, ($C_1$-$C_4$ alkyl)OC(O)($C_2$-$C_4$ alkenyl)CO$_2R_4$, ($C_1$-$C_4$ alkyl)OC(O)($C_1$-$C_4$ alkyl)NH$_2$, ($C_1$-$C_4$ alkyl)C(O)N$R_4R_5$, $R_2$ is H; and $R_3$ is ($C_1$-$C_4$ alkyl)-O(CO)$R_4$, ($C_1$-$C_4$ alkyl)-O(CO)O$R_4$, ($C_1$-$C_4$ alkyl)-OP(O)(O$R_4$)$_2$, ($C_1$-$C_4$ alkyl)-OP(O)(O($C_1$-$C_4$ alkyl)-O(CO)O$R_4$)$_2$, ($C_1$-$C_4$ alkyl)-OP(O)(O($C_1$-$C_4$ alkyl)-O(CO)$R_4$)$_2$, ($C_1$-$C_4$ alkyl)N$R_4R_5$, ($C_1$-$C_4$ alkyl)NC(O)$R_4$, ($C_1$-$C_4$ alkyl)C(O)O$R_4$, ($C_1$-$C_4$ alkyl)OC(O)aryl($C_1$-$C_4$ alkyl)P(O)(O$R_4$)$_2$, ($C_1$-$C_4$ alkyl)OC (O)(C$_2$-C$_4$ alkenyl)CO$_2$R$_4$, (C$_1$-C$_4$ alkyl)OC(O)(C$_1$-C$_4$ alkyl)NH$_2$, (C$_1$-C$_4$ alkyl)C(O)NR$_4$R$_5$,

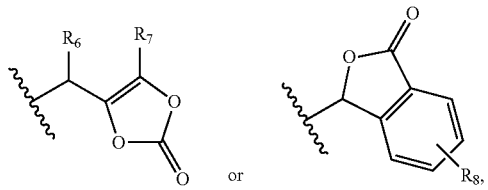

or wherein each occurrence of R$_4$ is, independently, H, alkyl, alkenyl, alkynyl, aryl or heteroaryl;
wherein each occurrence of R$_5$ is, independently, H, alkyl, alkenyl, alkynyl, aryl or heteroaryl;
wherein each occurrence of R$_6$ and R$_7$ is, independently, H, alkyl, alkenyl, alkynyl, aryl or heteroaryl;
wherein each occurrence of R$_8$ is, independently, H, halogen, alkyl, alkenyl, alkynyl, aryl or heteroaryl;
Y is OR$_9$ or NR$_{10}$R$_{11}$,
wherein R$_9$ is (C$_1$-C$_4$ alkyl)-O(CO)R$_{12}$, (C$_1$-C$_4$ alkyl)-O(CO)OR$_2$, (C$_1$-C$_4$ alkyl)-OP(O)(OR$_{12}$)$_2$, (C$_1$-C$_4$ alkyl)-OP(O)(O(C$_1$-C$_4$ alkyl)-O(CO)OR$_{12}$)$_2$, (C$_1$-C$_4$ alkyl)-OP(O)(O(C$_1$-C$_4$ alkyl)-O(CO)R$_{12}$)$_2$, (C$_1$-C$_4$ alkyl)NR$_{12}$R$_{13}$, (C$_1$-C$_4$ alkyl)NC(O)R$_{12}$, (C$_1$-C$_4$ alkyl)C(O)OR$_{12}$, (C$_1$-C$_4$ alkyl)OC(O)aryl(C$_1$-C$_4$ alkyl)P(O)(OR$_{12}$)$_2$, (C$_1$-C$_4$ alkyl)OC(O)(C$_2$-C$_4$ alkenyl)CO$_2$R$_{12}$, (C$_1$-C$_4$ alkyl)OC(O)(C$_1$-C$_4$ alkyl)NH$_2$, (C$_1$-C$_4$ alkyl)C(O)NR$_{12}$R$_{13}$,

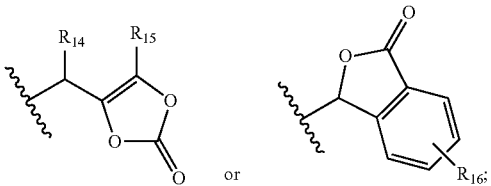

or

R$_{10}$ is H;
R$_{11}$ is (C$_1$-C$_4$ alkyl)-O(CO)R$_{12}$, (C$_1$-C$_4$ alkyl)-O(CO)OR$_{12}$, O(C$_1$-C$_4$ alkyl)-OP(O)(OR$_{12}$)$_2$, (C$_1$-C$_4$ alkyl)-OP(O)(O(C$_1$-C$_4$ alkyl)-O(CO)OR$_{12}$)$_2$, (C$_1$-C$_4$ alkyl)-OP(O)(O(C$_1$-C$_4$ alkyl)-O(CO)R$_{12}$)$_2$, (C$_1$-C$_4$ alkyl)NR$_{12}$R$_{13}$, (C$_1$-C$_4$ alkyl)NC(O)R$_{12}$, (C$_1$-C$_4$ alkyl)C(O)OR$_{12}$, (C$_1$-C$_4$ alkyl)OC(O)aryl(C$_1$-C$_4$ alkyl)P(O)(OR$_{12}$)$_2$, (C$_1$-C$_4$ alkyl)OC(O)(C$_2$-C$_4$ alkenyl)CO$_2$R$_{12}$, (C$_1$-C$_4$ alkyl)OC(O) (C$_1$-C$_4$ alkyl)NH$_2$, (C$_1$-C$_4$ alkyl)C(O)NR$_{12}$R$_{13}$,

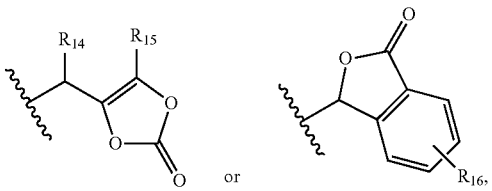

or wherein each occurrence of R$_{12}$ is, independently, H, alkyl, alkenyl, alkynyl, aryl or heteroaryl;
wherein each occurrence of R$_{13}$ is, independently, H, alkyl, alkenyl, alkynyl, aryl or heteroaryl;
wherein each occurrence of R$_{14}$ and R$_{15}$ is, independently, H, alkyl, alkenyl, alkynyl, aryl or heteroaryl;
wherein each occurrence of R$_{16}$ is, independently, H, halogen, alkyl, alkenyl, alkynyl, aryl or heteroaryl.

In some embodiments, the compound wherein
X is OR$_1$,
wherein R$_1$ is (C$_1$-C$_4$ alkyl)-O(CO)R$_4$, (C$_1$-C$_4$ alkyl)-O(CO)OR$_4$, (C$_1$-C$_4$ alkyl)-OP(O)(OR$_4$)$_2$, (C$_1$-C$_4$ alkyl)-OP(O)(O(C$_1$-C$_4$ alkyl)-O(CO)OR$_4$)$_2$, (C$_1$-C$_4$ alkyl)-OP(O)(O(C$_1$-C$_4$ alkyl)-O(CO)R$_4$)$_2$, (C$_1$-C$_4$ alkyl)NR$_4$R$_5$, (C$_1$-C$_4$ alkyl)NC(O)R$_4$, (C$_1$-C$_4$ alkyl)C(O)OR$_4$, (C$_1$-C$_4$ alkyl)OC(O)aryl(C$_1$-C$_4$ alkyl)P(O)(OR$_4$)$_2$, (C$_1$-C$_4$ alkyl)OC(O)(C$_2$-C$_4$ alkenyl)CO$_2$R$_4$, (C$_1$-C$_4$ alkyl)OC(O)(C$_1$-C$_4$ alkyl)NH$_2$, (C$_1$-C$_4$ alkyl)C(O)NR$_4$R$_5$,

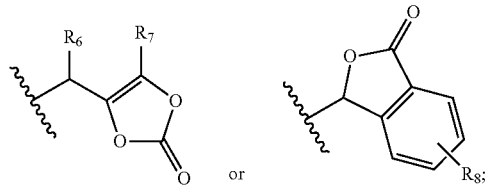

or wherein each occurrence of R$_4$ is, independently, H, halogen, alkyl, alkenyl, alkynyl, aryl or heteroaryl;
wherein each occurrence of R$_5$ is, independently, H, alkyl, alkenyl, alkynyl, aryl or heteroaryl;
wherein each occurrence of R$_6$ and R$_7$ is, independently, H, alkyl, alkenyl, alkynyl, aryl or heteroaryl;
wherein each occurrence of R$_8$ is, independently, H, halogen, alkyl, alkenyl, alkynyl, aryl or heteroaryl;
Y is OR$_9$,
wherein (C$_1$-C$_4$ alkyl)-O(CO)R$_{12}$, (C$_1$-C$_4$ alkyl)-O(CO)OR$_{12}$, (C$_1$-C$_4$ alkyl)-OP(O)(OR$_{12}$)$_2$, (C$_1$-C$_4$ alkyl)-OP(O)(O(C$_1$-C$_4$ alkyl)-O(CO)OR$_{12}$)$_2$, (C$_1$-C$_4$ alkyl)-OP(O)(O(C$_1$-C$_4$ alkyl)-O(CO)R$_{12}$)$_2$, (C$_1$-C$_4$ alkyl)NR$_{12}$R$_{13}$, (C$_1$-C$_4$ alkyl)NC(O)R$_{12}$, (C$_1$-C$_4$ alkyl)C(O)OR$_{12}$, (C$_1$-C$_4$ alkyl)OC(O)aryl(C$_1$-C$_4$ alkyl)P(O)(OR$_{12}$)$_2$, (C$_1$-C$_4$ alkyl)OC(O)(C$_2$-C$_4$ alkenyl)CO$_2$R$_{12}$, (C$_1$-C$_4$ alkyl)OC(O)(C$_1$-C$_4$ alkyl)NH$_2$, (C$_1$-C$_4$ alkyl)C(O)NR$_{12}$R$_{13}$,

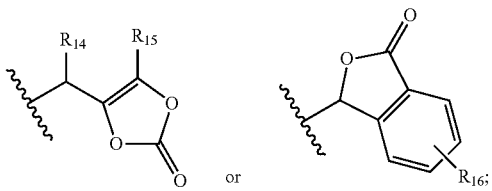

or wherein each occurrence of R$_{12}$ is, independently, H, halogen, alkyl, alkenyl, alkynyl, aryl or heteroaryl;
wherein each occurrence of R$_{13}$ is, independently, H, alkyl, alkenyl, alkynyl, aryl or heteroaryl;
wherein each occurrence of R$_{14}$ and R$_{15}$ is, independently, H, alkyl, alkenyl, alkynyl, aryl or heteroaryl;
wherein each occurrence of R$_{16}$ is, independently, H, halogen, alkyl, alkenyl, alkynyl, aryl or heteroaryl.

In some embodiments, the compound wherein
X is OR$_1$,
wherein R$_1$ is (C$_1$-C$_4$ alkyl)-O(CO)R$_4$, (C$_1$-C$_4$ alkyl)-O(CO)OR$_4$, (C$_1$-C$_4$ alkyl)-OP(O)(OR$_4$)$_2$, (C$_1$-C$_4$ alkyl)-OP(O)(O(C$_1$-C$_4$ alkyl)-O(CO)OR$_4$)$_2$, (C$_1$-C$_4$ alkyl)-OP(O)(O(C$_1$-C$_4$ alkyl)-O(CO) R)$_2$, (C$_1$-C$_4$ alkyl)NR$_4$R$_5$, (C$_1$-C$_4$ alkyl)NC(O)R$_4$, (C$_1$-C$_4$ alkyl)C(O)OR$_4$, (C$_1$-C$_4$ alkyl)OC(O)aryl(C$_1$-C$_4$ alkyl)P(O)(OR$_4$)$_2$, (C$_1$-C$_4$ alkyl)OC(O)($C_2$-$C_4$ alkenyl)$CO_2R_4$, ($C_1$-$C_4$ alkyl)OC(O)($C_1$-$C_4$ alkyl)$NH_2$, ($C_1$-$C_4$ alkyl)C(O)$NR_4R_5$,

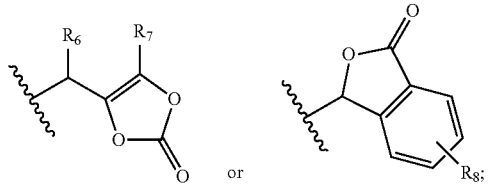

wherein each occurrence of $R_4$ is, independently, H, alkyl, alkenyl, alkynyl, aryl or heteroaryl;

wherein each occurrence of $R_5$ is, independently, H, alkyl, alkenyl, alkynyl, aryl or heteroaryl;

wherein each occurrence of $R_6$ and $R_7$ is, independently, H, alkyl, alkenyl, alkynyl, aryl or heteroaryl;

wherein each occurrence of $R_8$ is, independently, H, halogen, alkyl, alkenyl, alkynyl, aryl or heteroaryl;

Y is $NR_{10}R_{11}$, wherein $R_{10}$ is H;

$R_{11}$ is ($C_1$-$C_4$ alkyl)-O(CO)$R_{12}$, ($C_1$-$C_4$ alkyl)-O(CO)$OR_{12}$, ($C_1$-$C_4$ alkyl)-OP(O)($OR_{12}$)$_2$, ($C_1$-$C_4$ alkyl)-OP(O)(O($C_1$-$C_4$ alkyl)-O(CO)$OR_{12}$)$_2$, ($C_1$-$C_4$ alkyl)-OP(O)(O($C_1$-$C_4$ alkyl)-O(CO)$R_{12}$)$_2$, ($C_1$-$C_4$ alkyl)$NR_{12}R_{13}$, ($C_1$-$C_4$ alkyl)NC(O)$R_{12}$, ($C_1$-$C_4$ alkyl)C(O)$OR_{12}$, ($C_1$-$C_4$ alkyl)OC(O)aryl($C_1$-$C_4$ alkyl)P(O)($OR_{12}$)$_2$, ($C_1$-$C_4$ alkyl)OC(O)($C_2$-$C_4$ alkenyl)$CO_2R_{12}$, ($C_1$-$C_4$ alkyl)OC(O)($C_1$-$C_4$ alkyl)$NH_2$, ($C_1$-$C_4$ alkyl)C(O)$NR_{12}R_{13}$,

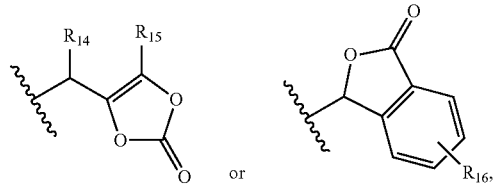

wherein each occurrence of $R_{12}$ is, independently, H, alkyl, alkenyl, alkynyl, aryl or heteroaryl;

wherein each occurrence of $R_{13}$ is, independently, H, alkyl, alkenyl, alkynyl, aryl or heteroaryl;

wherein each occurrence of $R_{14}$ and $R_{15}$ is, independently, H, alkyl, alkenyl, alkynyl, aryl or heteroaryl;

wherein each occurrence of $R_{16}$ is, independently, H, halogen, alkyl, alkenyl, alkynyl, aryl or heteroaryl.

In some embodiments, the compound wherein

X is $NR_2R_3$, wherein $R_2$ is H; and $R_3$ is ($C_1$-$C_4$ alkyl)-O(CO)$R_4$, ($C_1$-$C_4$ alkyl)-O(CO)$OR_4$, ($C_1$-$C_4$ alkyl)-OP(O)($OR_4$)$_2$, ($C_1$-$C_4$ alkyl)-OP(O)(O($C_1$-$C_4$ alkyl)-O(CO)$OR_4$)$_2$, ($C_1$-$C_4$ alkyl)-OP(O)(O($C_1$-$C_4$ alkyl)-O(CO)$R_4$)$_2$, ($C_1$-$C_4$ alkyl)$NR_4R_5$, ($C_1$-$C_4$ alkyl)NC(O)$R_4$, ($C_1$-$C_4$ alkyl)C(O)$OR_4$, ($C_1$-$C_4$ alkyl)OC(O)aryl($C_1$-$C_4$ alkyl)P(O)($OR_4$)$_2$, ($C_1$-$C_4$ alkyl)OC(O)($C_2$-$C_4$ alkenyl)$CO_2R_4$, ($C_1$-$C_4$ alkyl)OC(O)($C_1$-$C_4$ alkyl)$NH_2$, ($C_1$-$C_4$ alkyl)C(O)$NR_4R_5$,

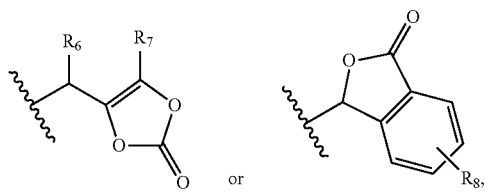

wherein each occurrence of $R_4$ is, independently, H, alkyl, alkenyl, alkynyl, aryl or heteroaryl;

wherein each occurrence of $R_5$ is, independently, H, alkyl, alkenyl, alkynyl, aryl or heteroaryl;

wherein each occurrence of $R_6$ and $R_7$ is, independently, H, alkyl, alkenyl, alkynyl, aryl or heteroaryl;

wherein each occurrence of $R_8$ is, independently, H, halogen, alkyl, alkenyl, alkynyl, aryl or heteroaryl;

Y is $NR_{10}R_{11}$, wherein $R_{10}$ is H;

$R_{11}$ is ($C_1$-$C_4$ alkyl)-O(CO)$R_{12}$, ($C_1$-$C_4$ alkyl)-O(CO)$OR_{12}$, ($C_1$-$C_4$ alkyl)-OP(O)($OR_{12}$)$_2$, ($C_1$-$C_4$ alkyl)-OP(O)(O($C_1$-$C_4$ alkyl)-O(CO)$OR_{12}$)$_2$, ($C_1$-$C_4$ alkyl)-OP(O)(O($C_1$-$C_4$ alkyl)-O(CO)$R_{12}$)$_2$, ($C_1$-$C_4$ alkyl)$NR_{12}R_{13}$, ($C_1$-$C_4$ alkyl)NC(O)$R_{12}$, ($C_1$-$C_4$ alkyl)C(O)$OR_{12}$, ($C_1$-$C_4$ alkyl)OC(O)aryl($C_1$-$C_4$ alkyl)P(O)($OR_{12}$)$_2$, ($C_1$-$C_4$ alkyl)OC(O)($C_2$-$C_4$ alkenyl)$CO_2R_{12}$, ($C_1$-$C_4$ alkyl)OC(O)($C_1$-$C_4$ alkyl)$NH_2$, ($C_1$-$C_4$ alkyl)C(O)$NR_{12}R_{13}$,

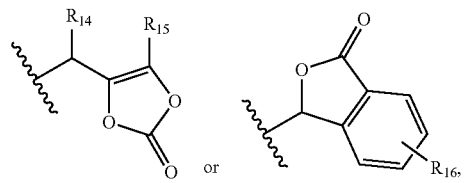

wherein each occurrence of $R_{12}$ is, independently, H, alkyl, alkenyl, alkynyl, aryl or heteroaryl;

wherein each occurrence of $R_{13}$ is, independently, H, alkyl, alkenyl, alkynyl, aryl or heteroaryl;

wherein each occurrence of $R_{14}$ and $R_{15}$ is, independently, H, alkyl, alkenyl, alkynyl, aryl or heteroaryl;

wherein each occurrence of $R_{16}$ is, independently, H, halogen, alkyl, alkenyl, alkynyl, aryl or heteroaryl.

In some embodiments, the compound wherein $R_9$ is

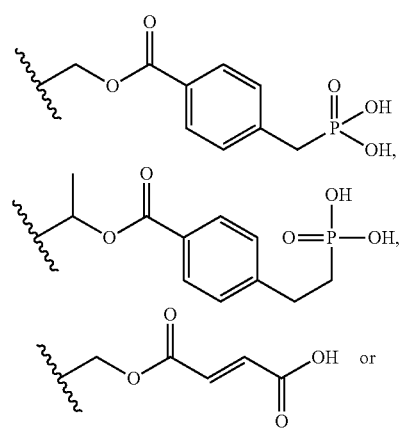

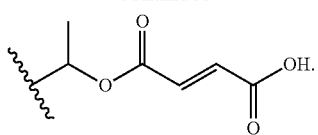
In some embodiments, the compound wherein R₉ is
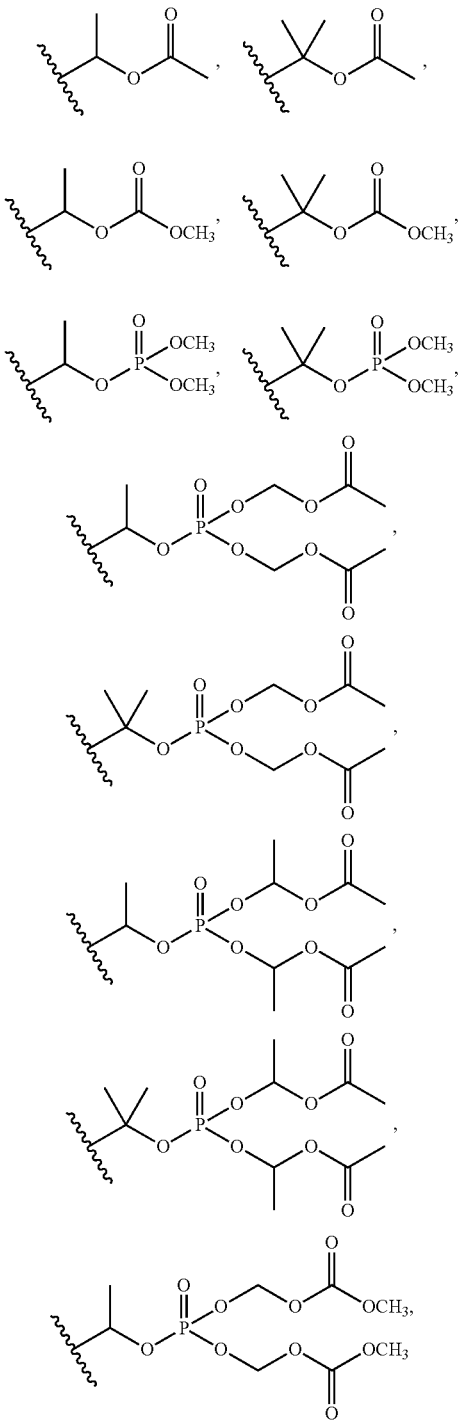
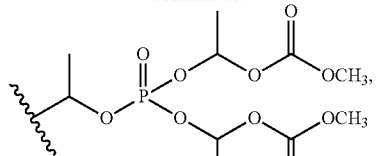
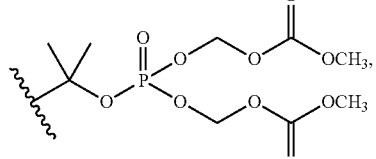
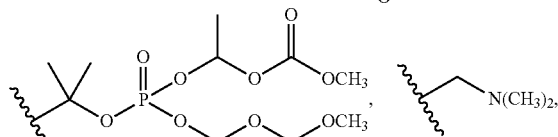
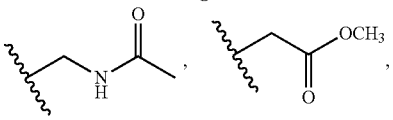
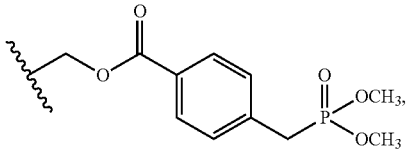
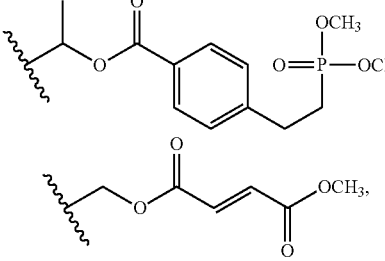
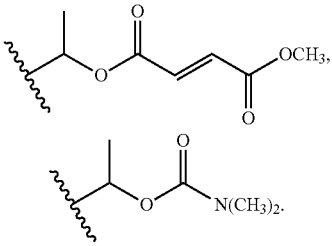
In some embodiments, the compound wherein R₉ is
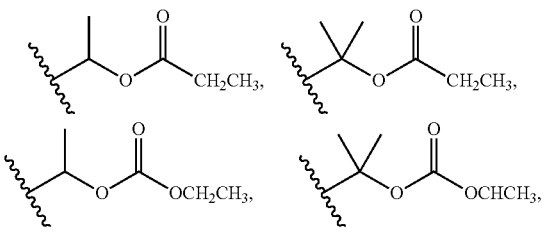

-continued
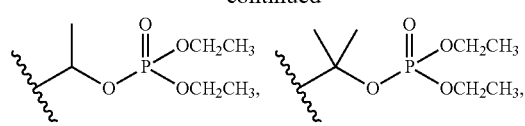
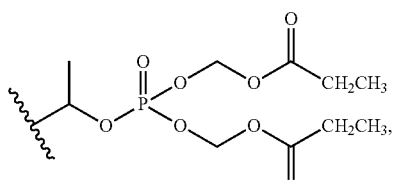
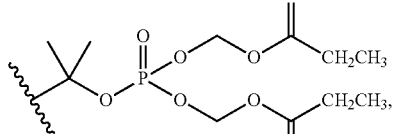
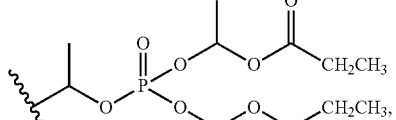
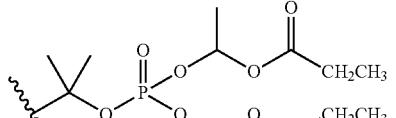
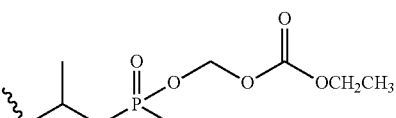
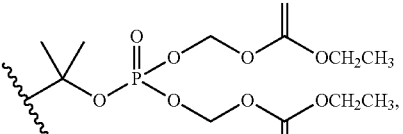
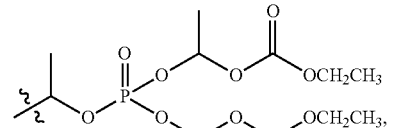
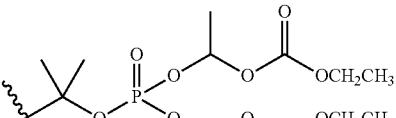
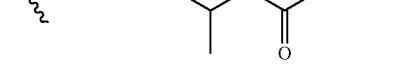
-continued
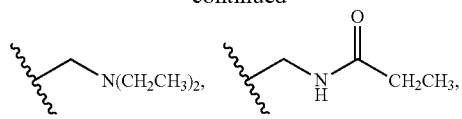
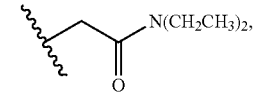
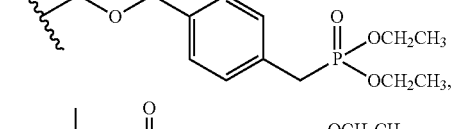
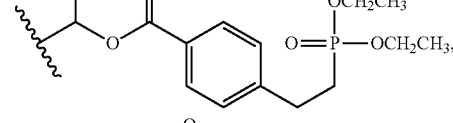
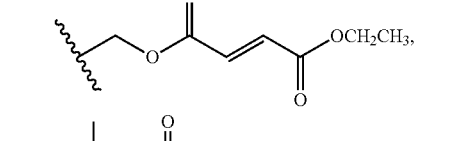
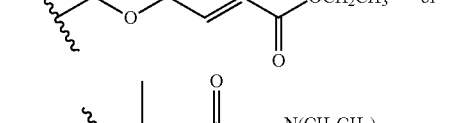 or
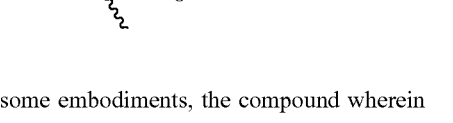
In some embodiments, the compound wherein $R_9$ is
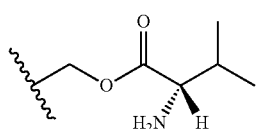 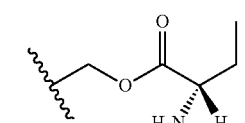
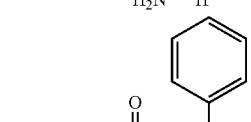 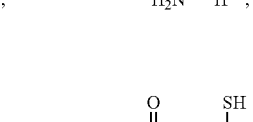
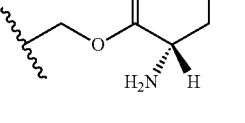 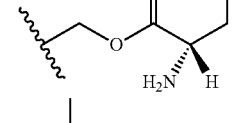
, or

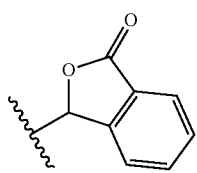
In some embodiments, the compound wherein
$R_{10}$ is H; and
$R_{11}$ is
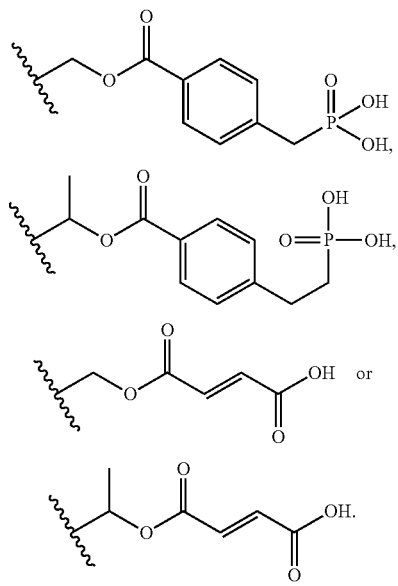
In some embodiments, the compound wherein
$R_{10}$ is H; and
$R_{11}$ is
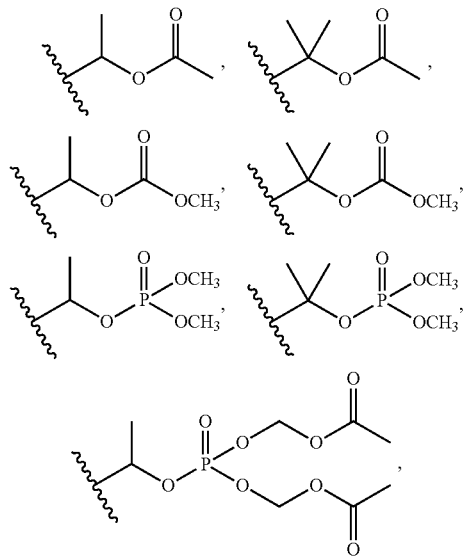
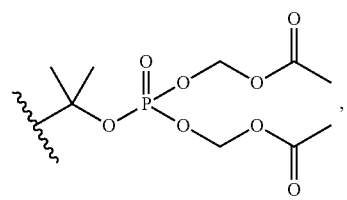
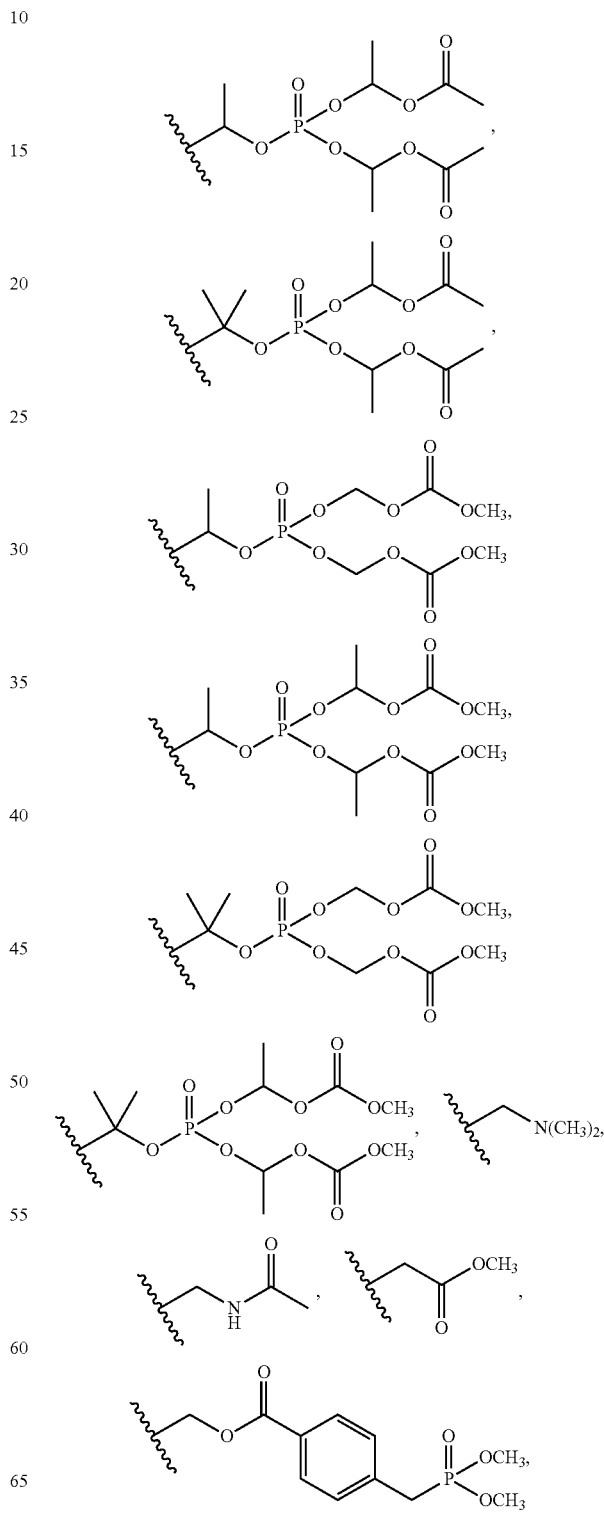

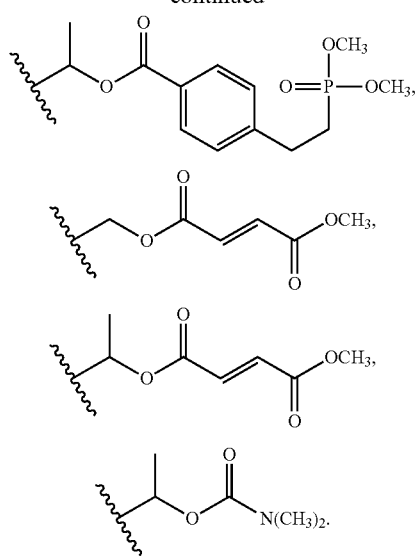
In some embodiments, the compound wherein
$R_{10}$ is H; and
$R_{11}$ is
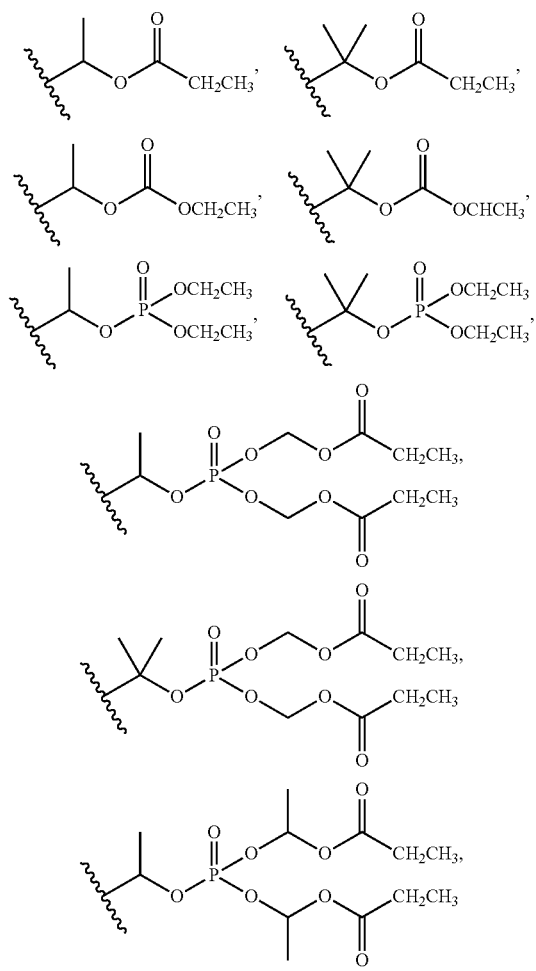
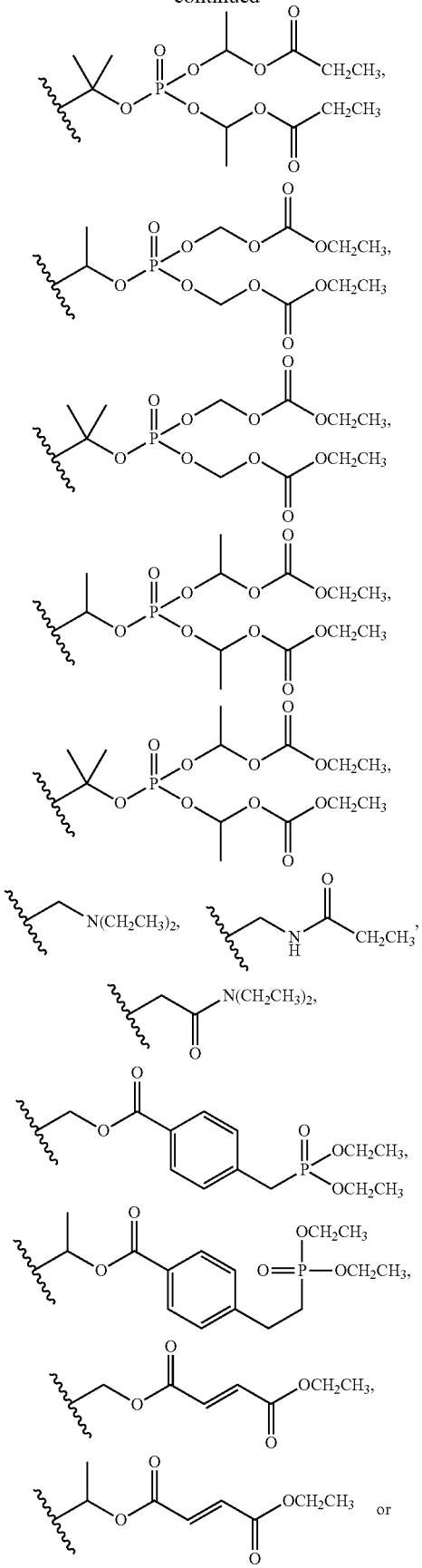

-continued
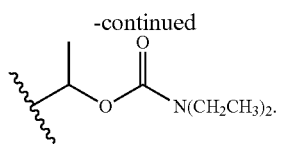
In some embodiments, the compound wherein
$R_{10}$ is H; and
$R_{11}$ is
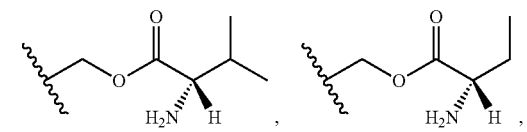
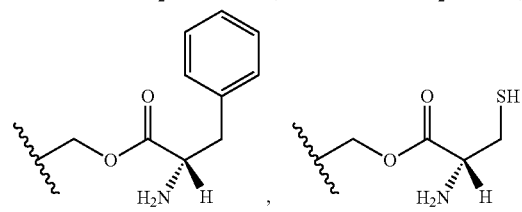
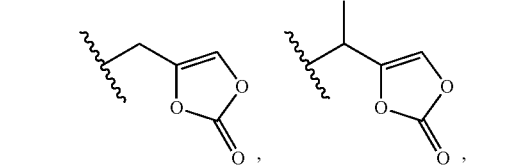
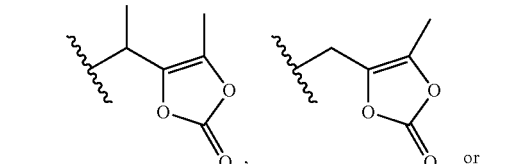 or
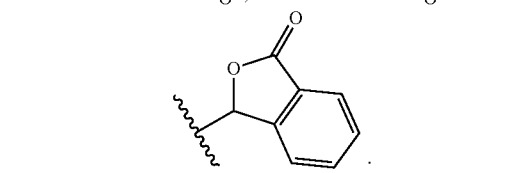.
In some embodiments, the compound wherein
$R_1$ and $R_9$ are each, independently,
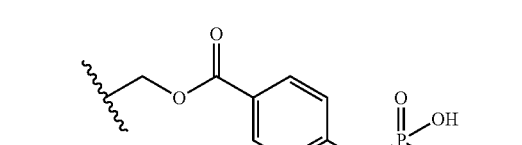
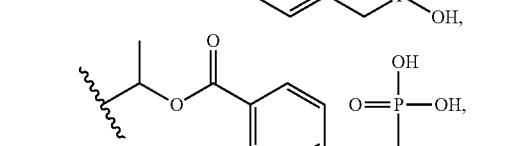
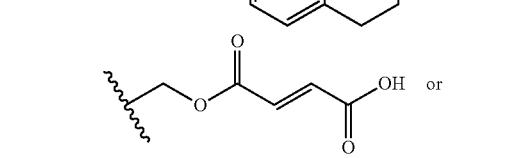 or
-continued
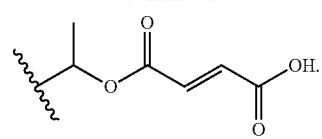
In some embodiments, the compound wherein
$R_1$ and $R_9$ are each, independently,
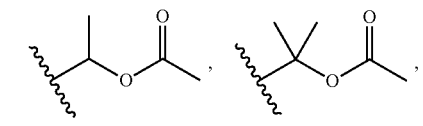
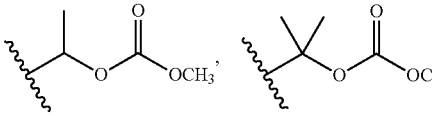
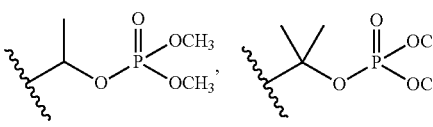
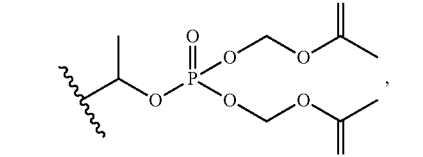
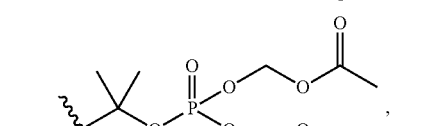
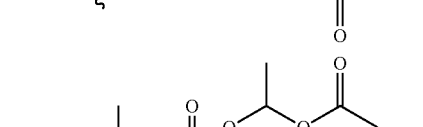
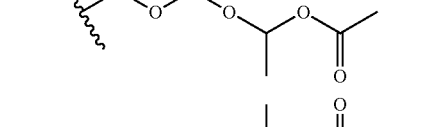
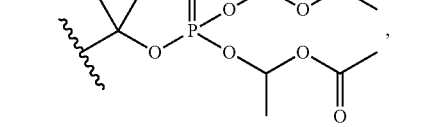
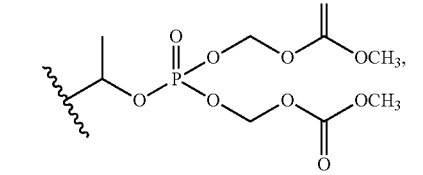

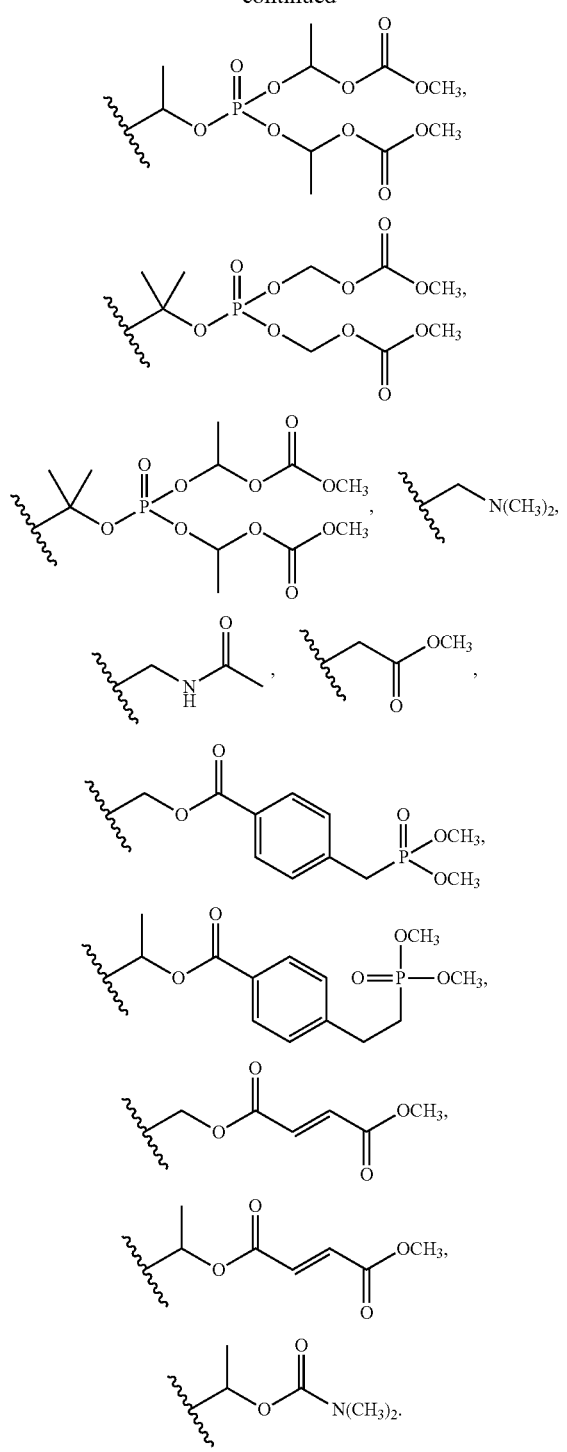
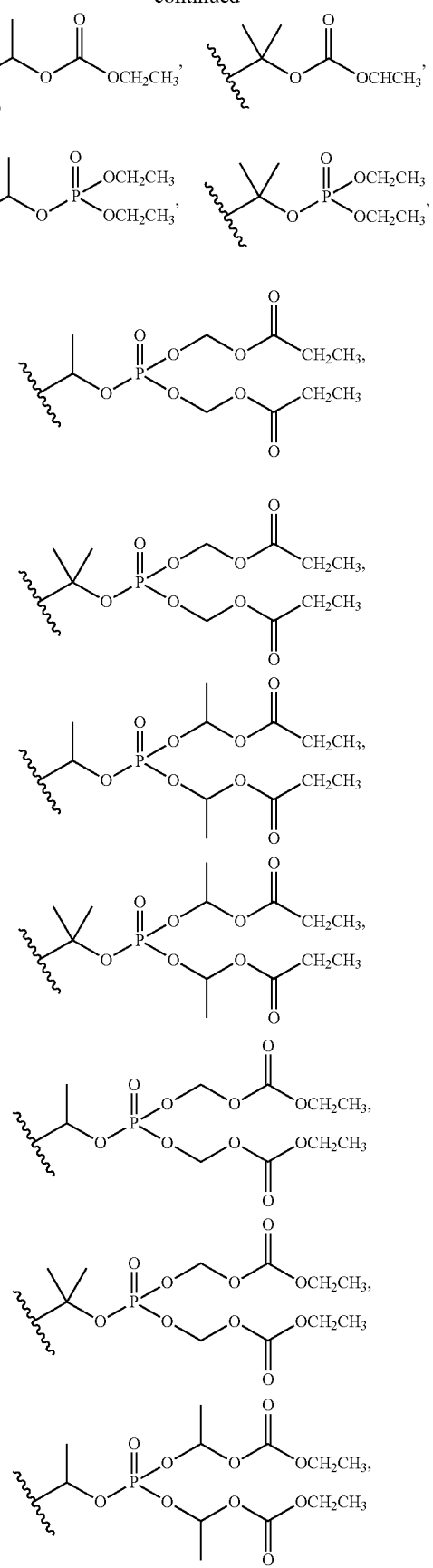
In some embodiments, the compound wherein $R_1$ and $R_9$ are each, independently,
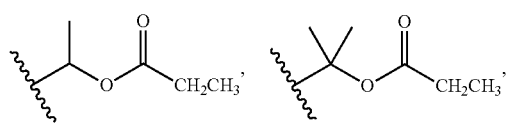
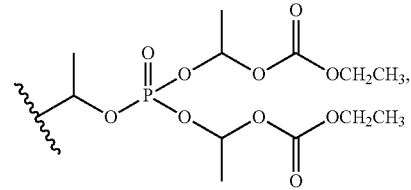

-continued
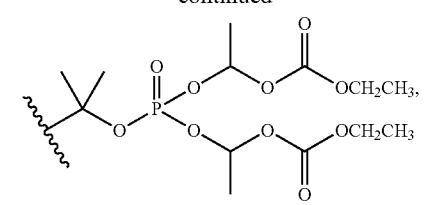
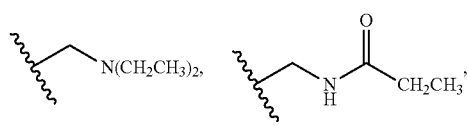
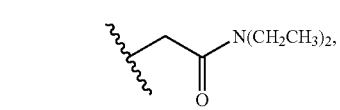
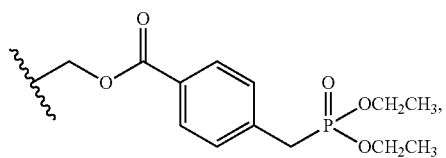
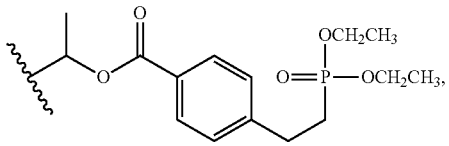
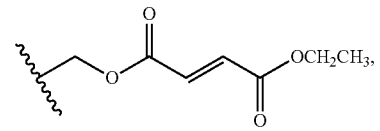
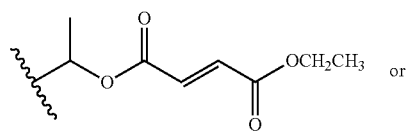
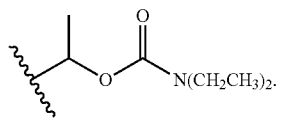
In some embodiments, the compound wherein $R_1$ and $R_9$ are each, independently,
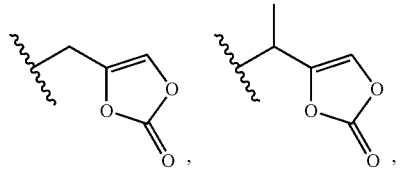
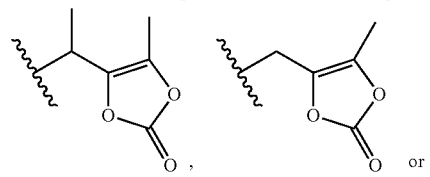
-continued
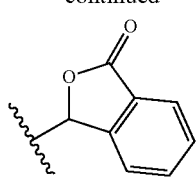
In some embodiments, the compound wherein $R_3$ and $R_{11}$ are each, independently,
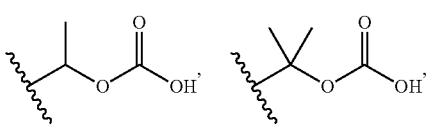
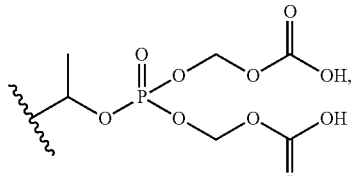
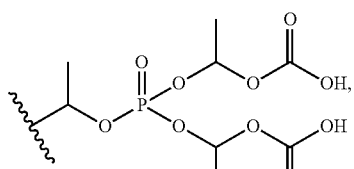
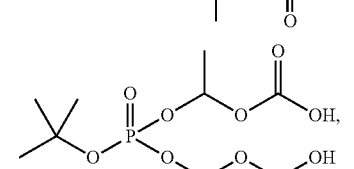
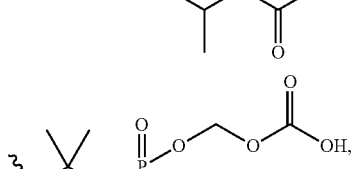
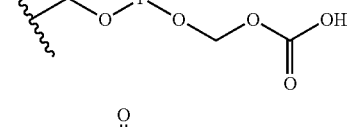
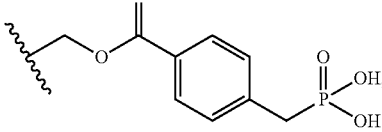
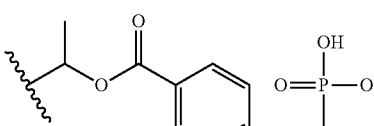
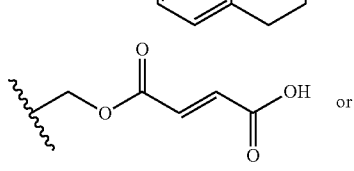

-continued
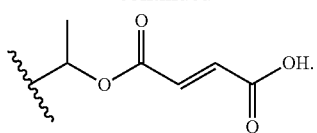
In some embodiments, the compound wherein $R_3$ and $R_{11}$ are each, independently,
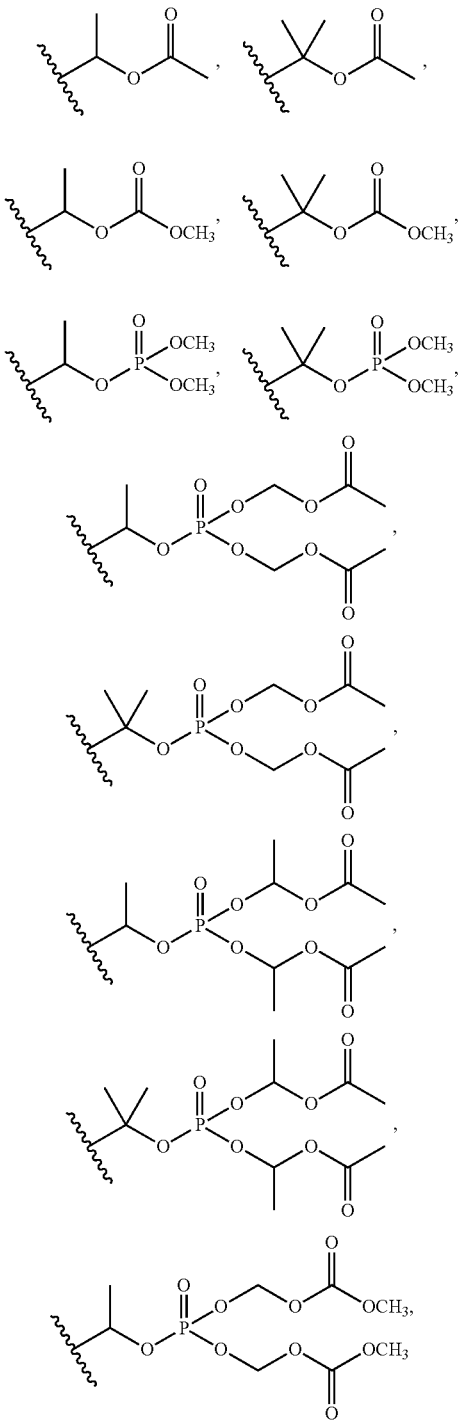
-continued
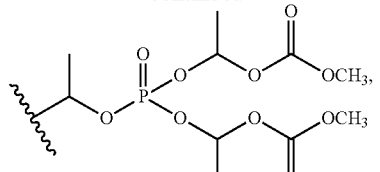
In some embodiments, the compound wherein $R_3$ and $R_{11}$ are each, independently,
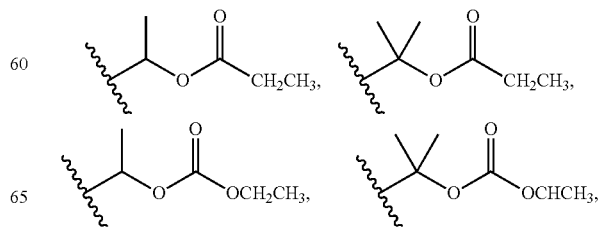

-continued
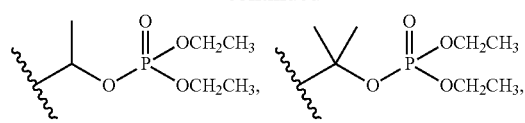
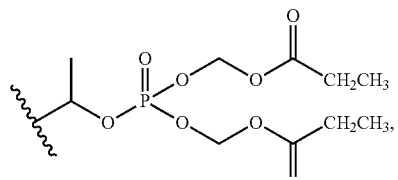
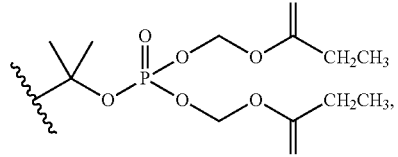
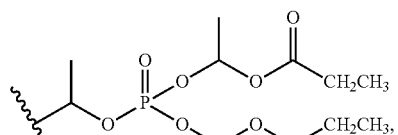
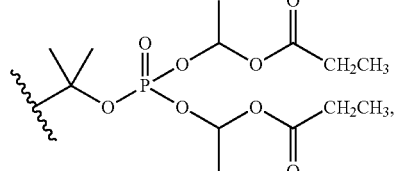
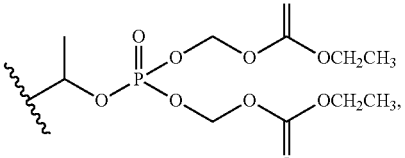
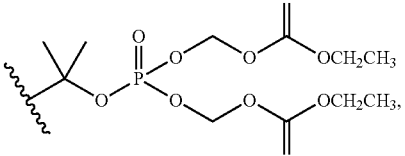
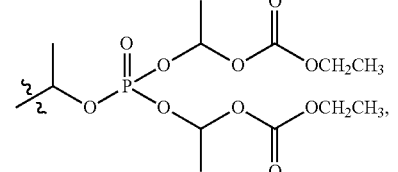
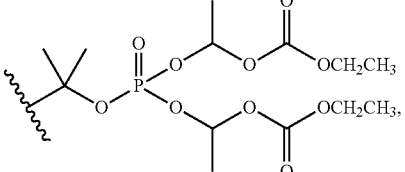
-continued
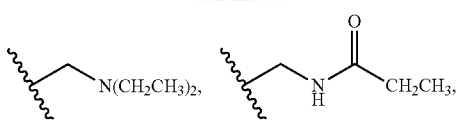
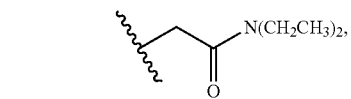
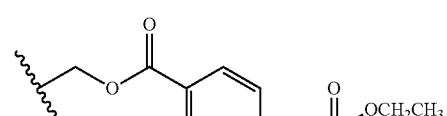
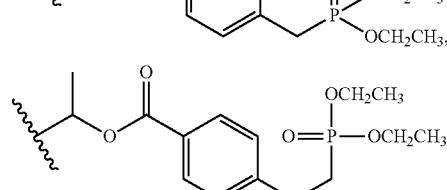
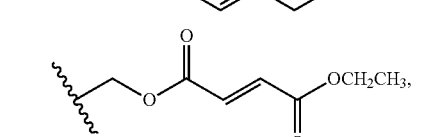
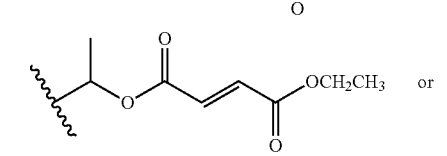
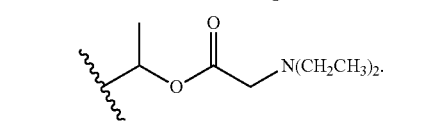
In some embodiments, the compound wherein $R_3$ and $R_{11}$ are each, independently,
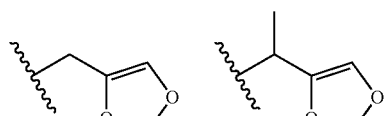
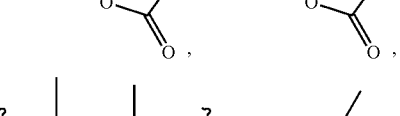
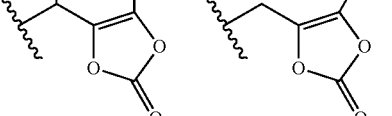
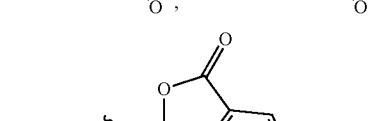
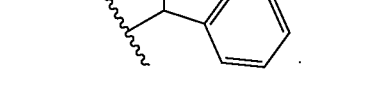
In some embodiments, the compound having the structure:

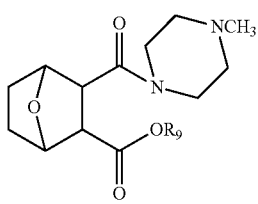
wherein
R₉ is
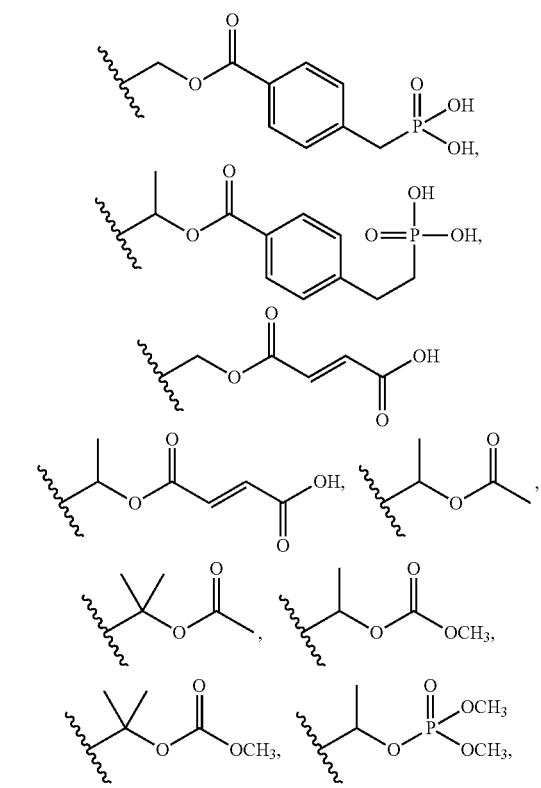
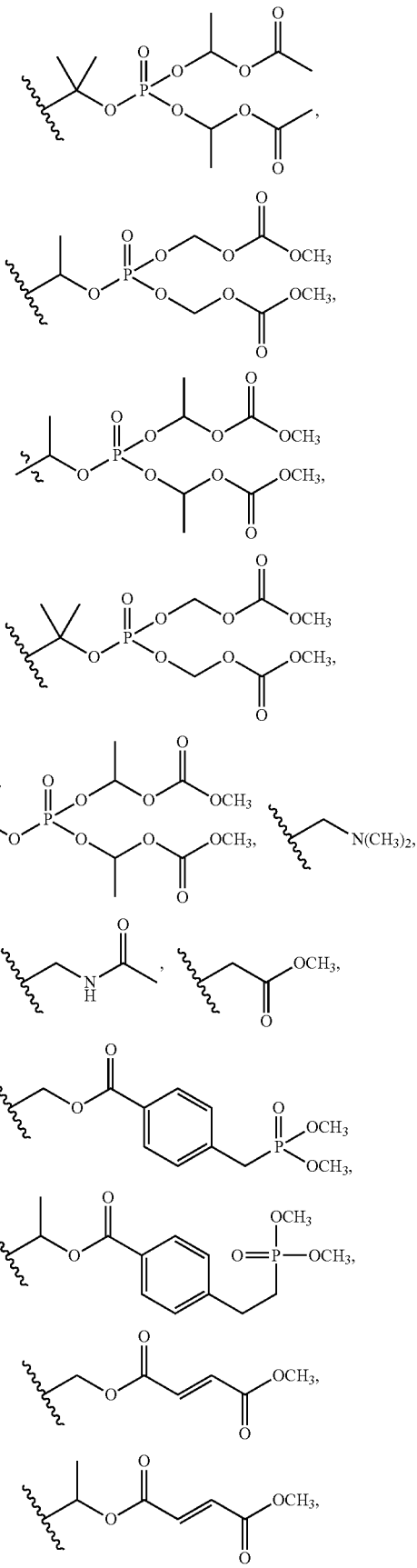

65
-continued
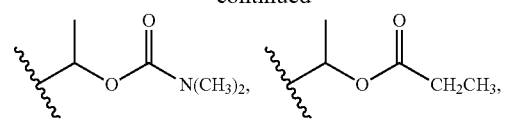
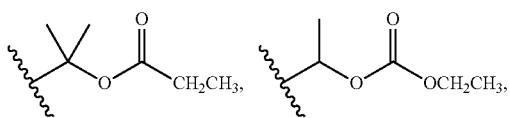
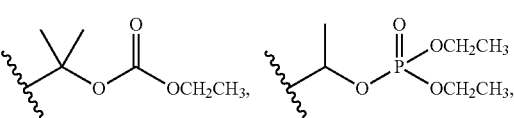
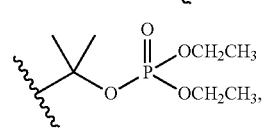
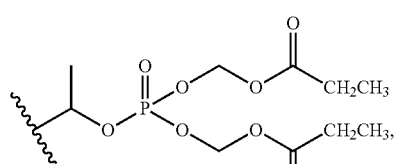
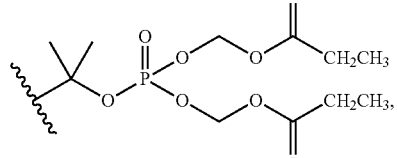
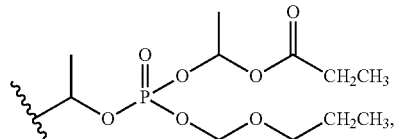
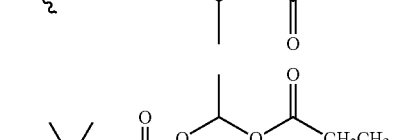
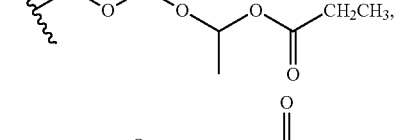
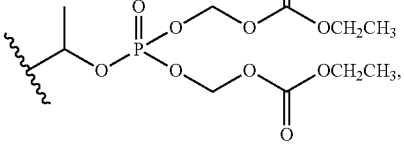
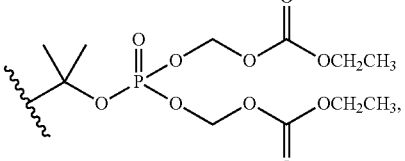
66
-continued
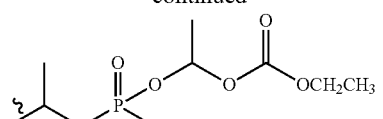
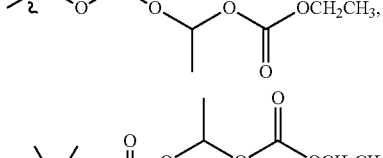
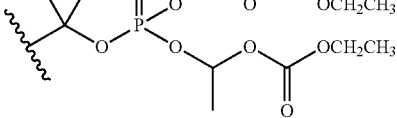
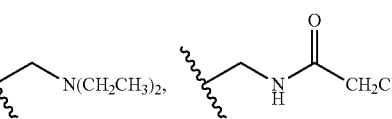
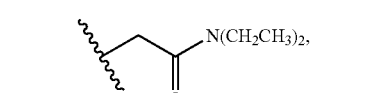
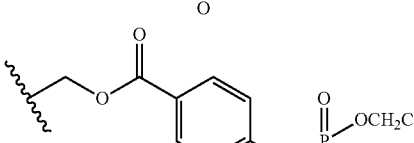
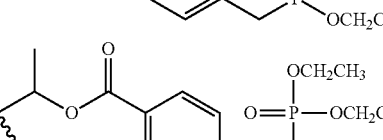
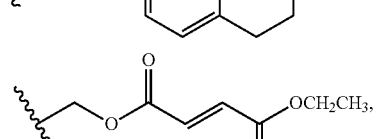
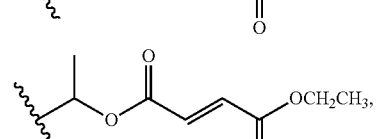
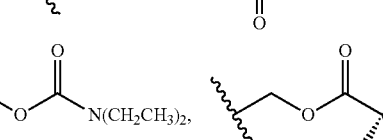
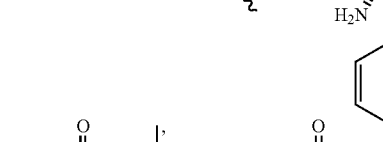
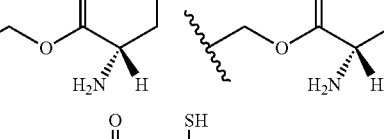
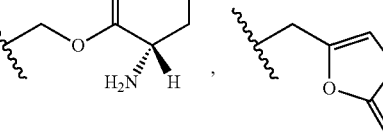

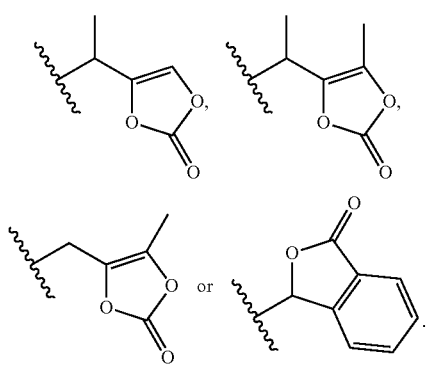
In some embodiments, the compound having the structure:
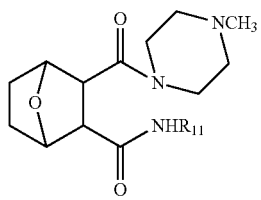
wherein
$R_{11}$ is
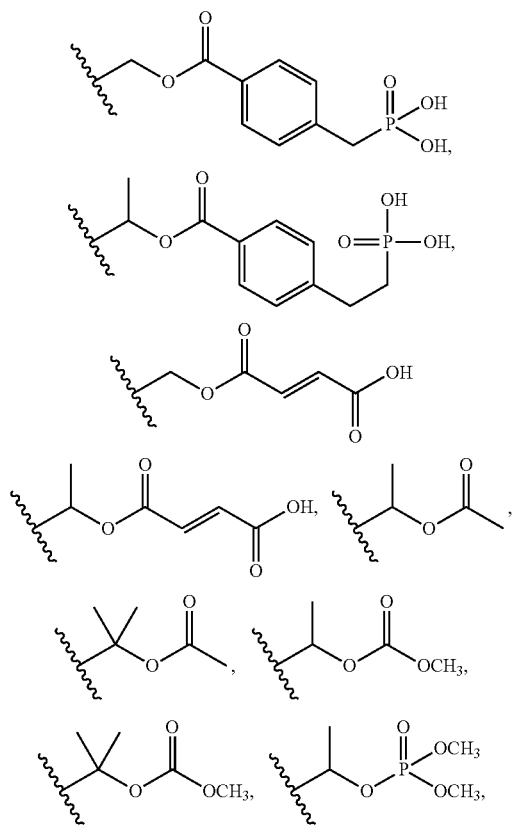
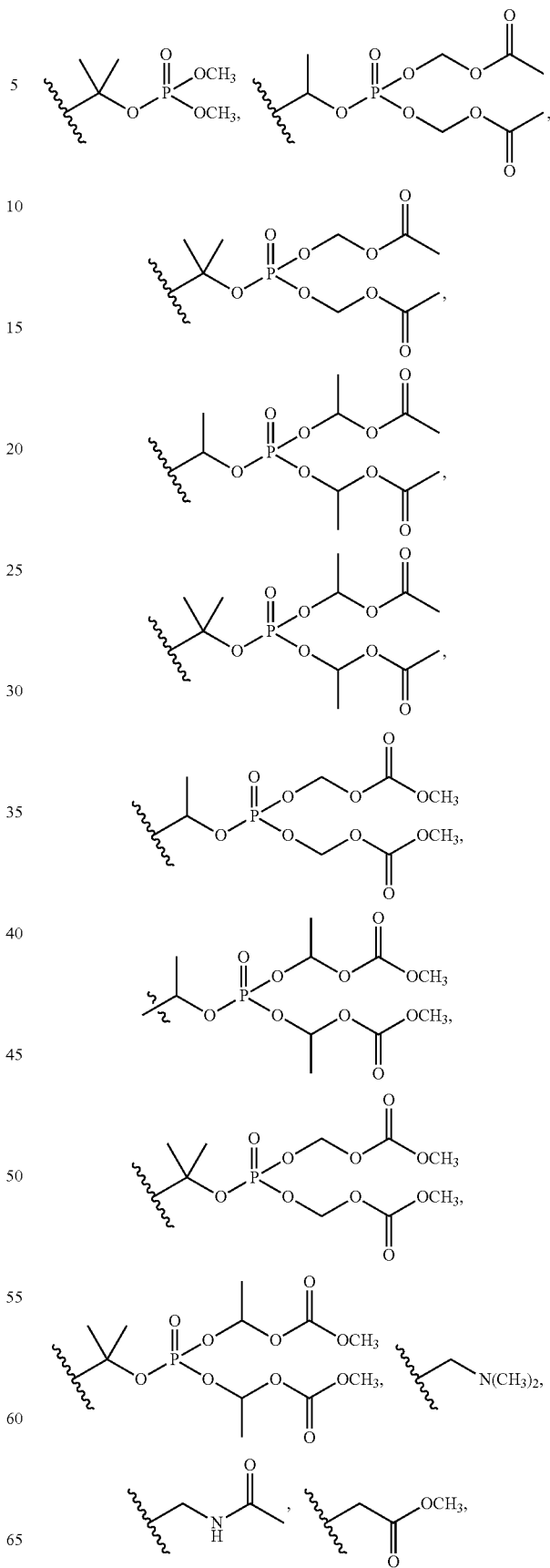

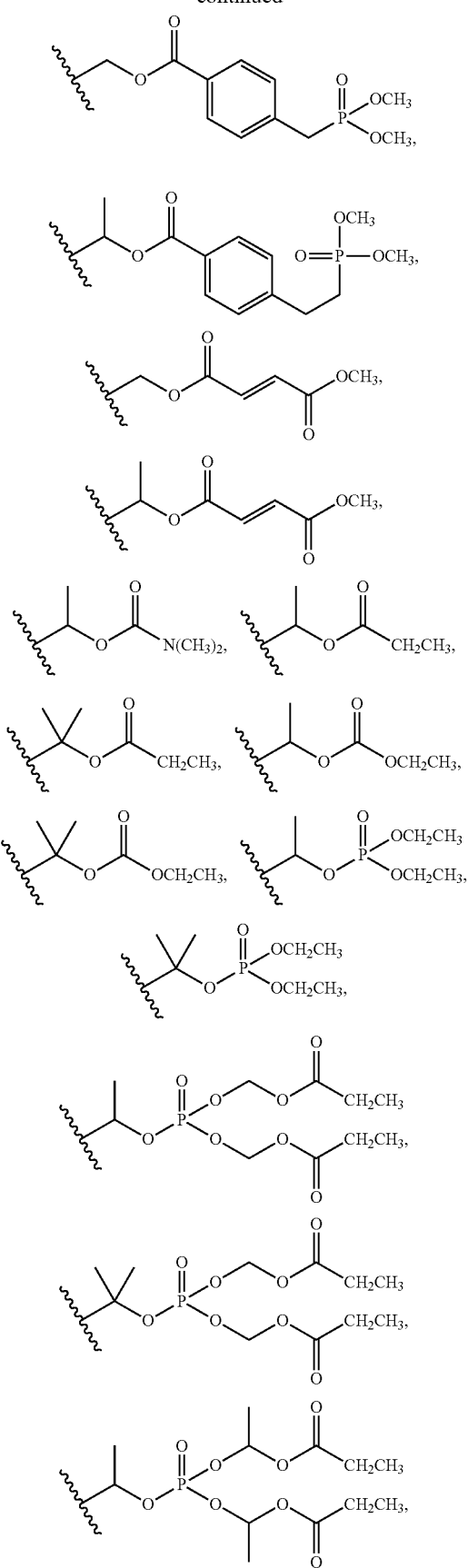
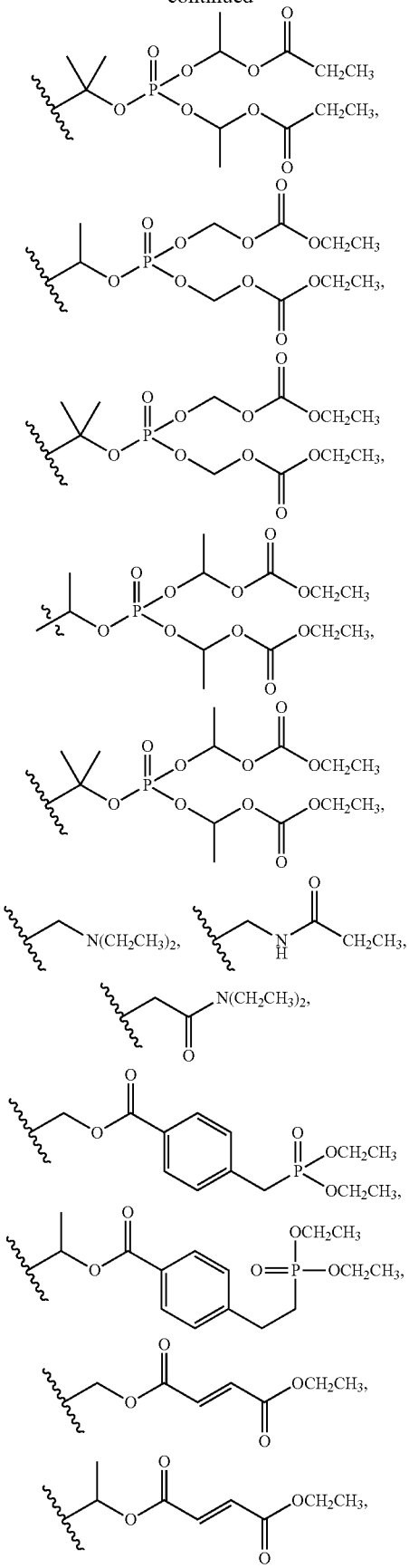

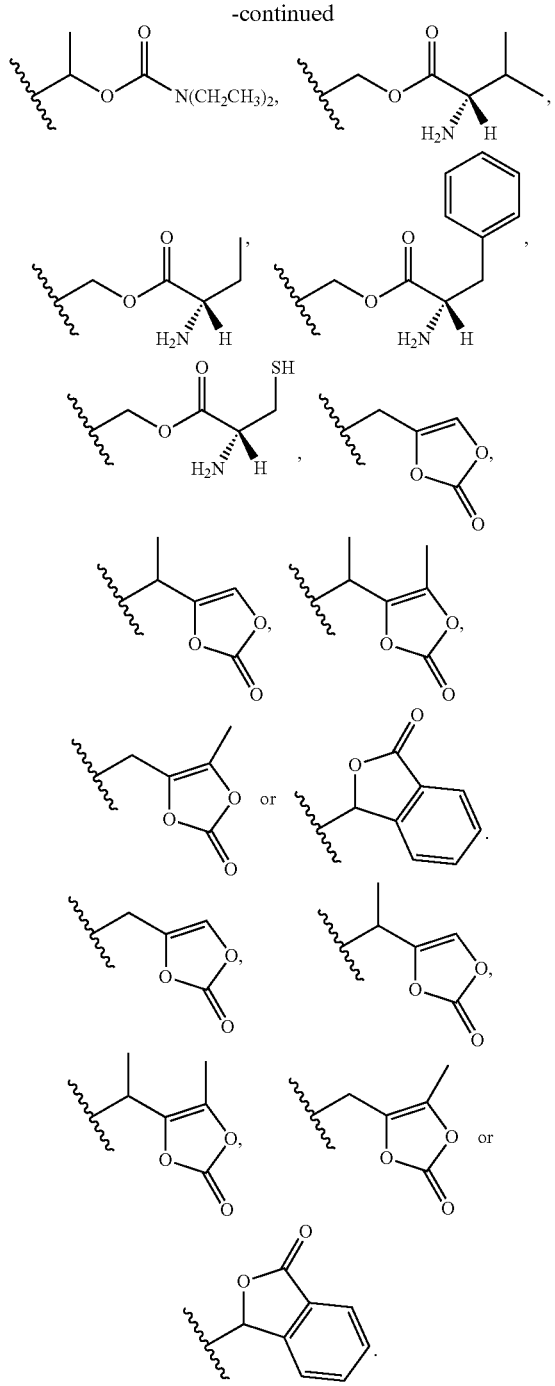
In some embodiments, the compound having the structure:
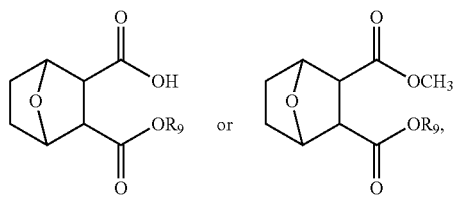
wherein $R_9$ is
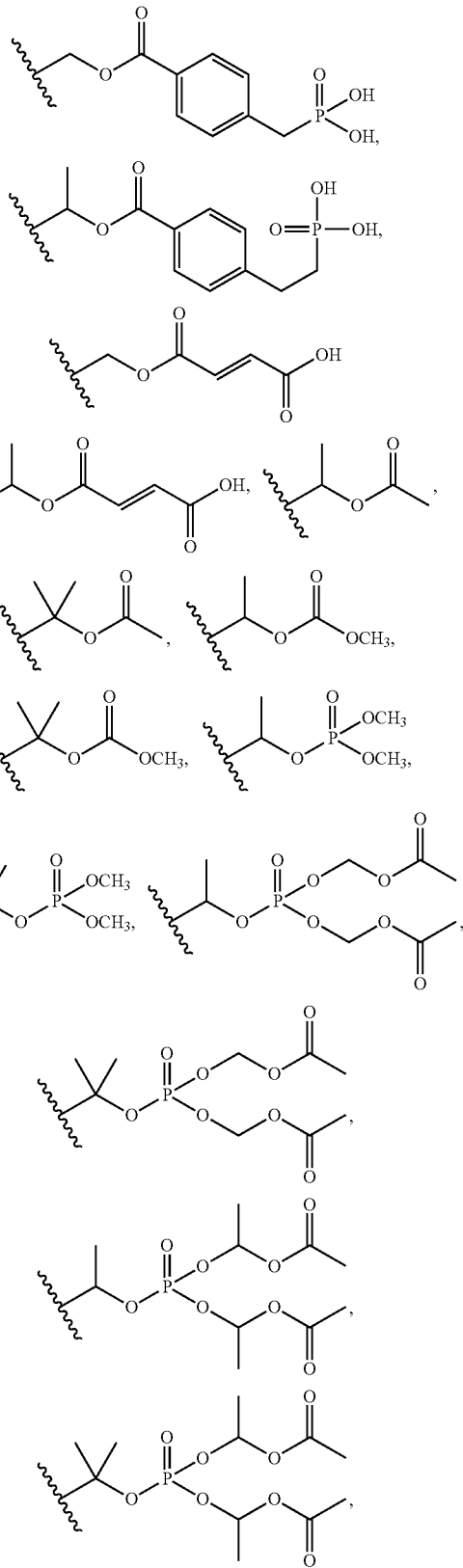

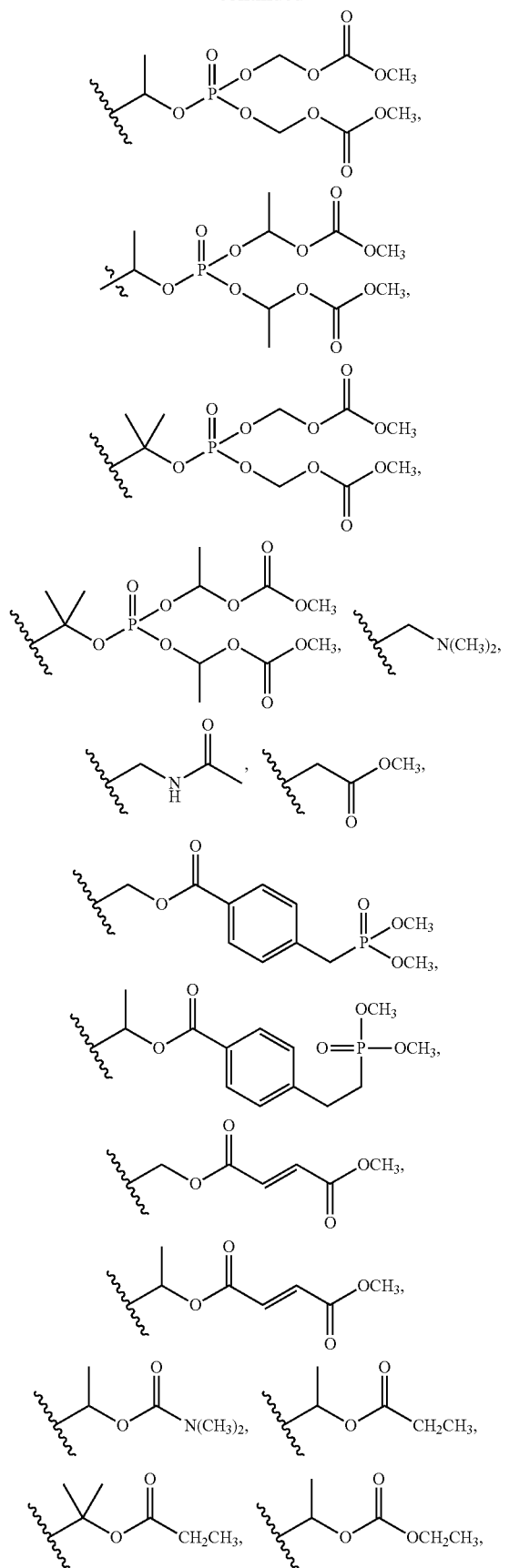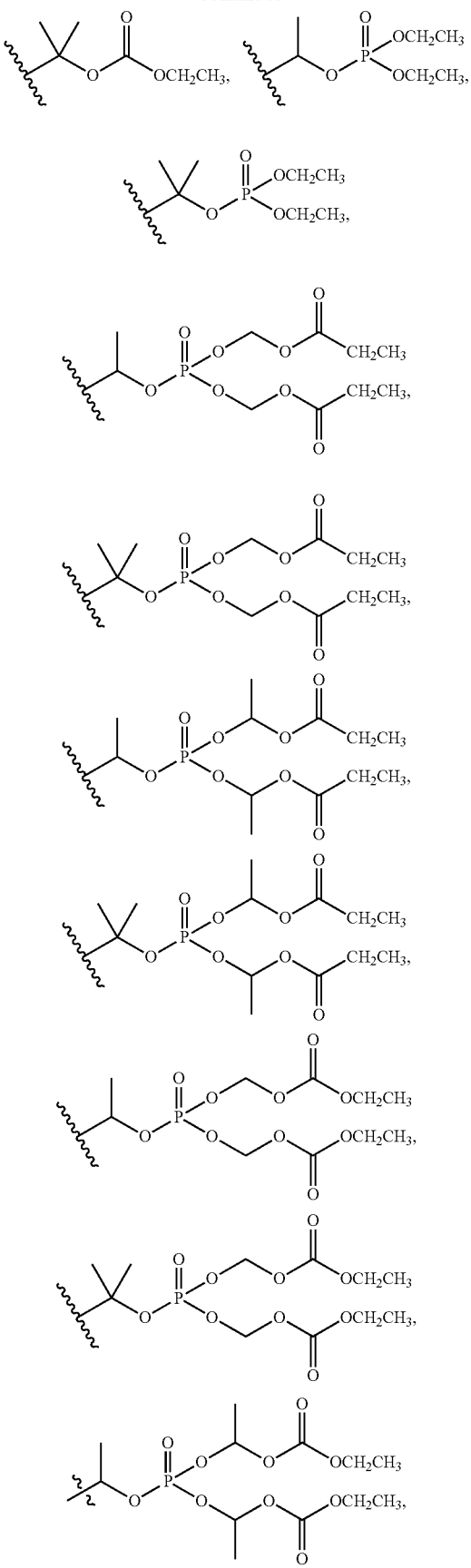

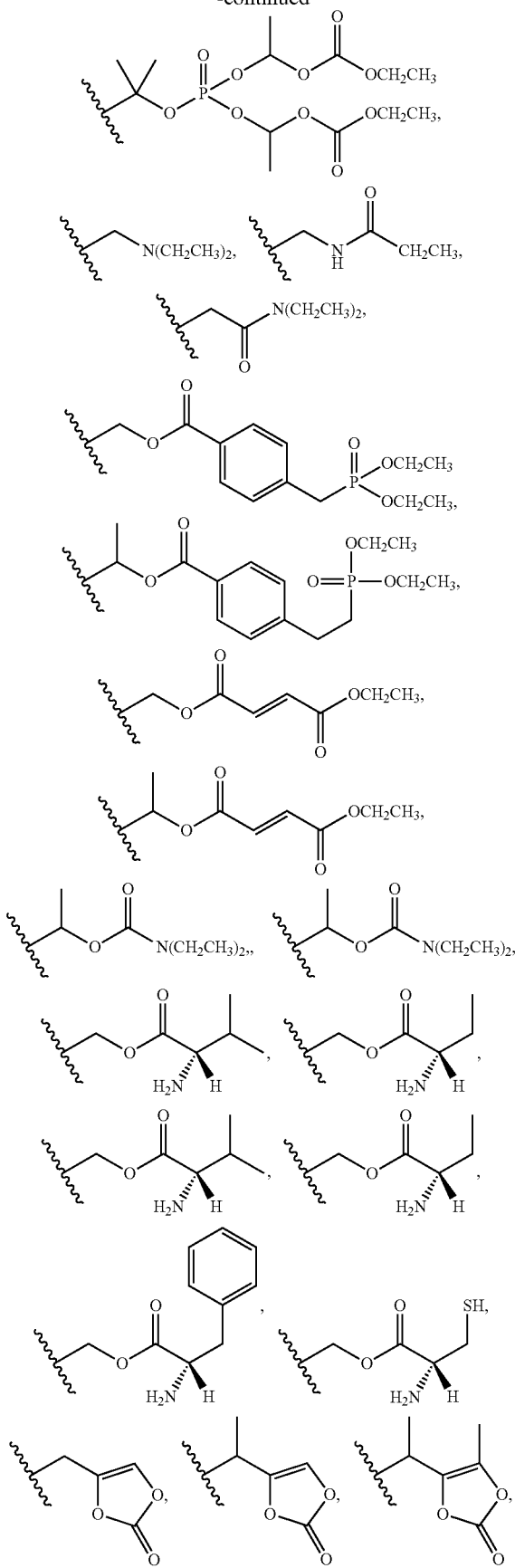
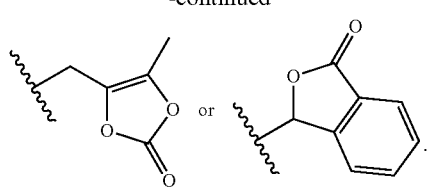
In some embodiments, the compound having the structure:
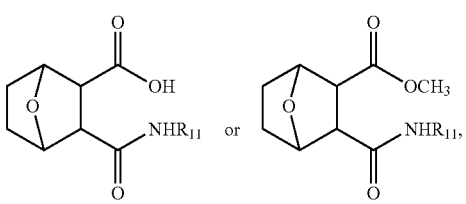
wherein $R_{11}$ is
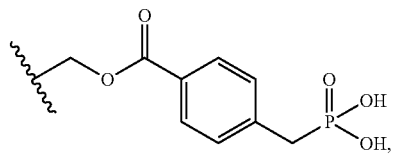
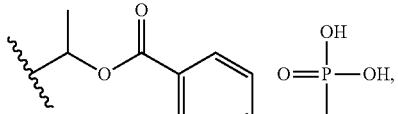
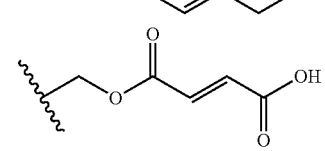
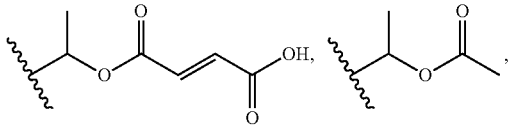
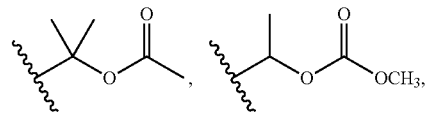
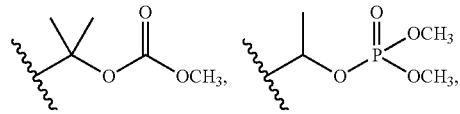
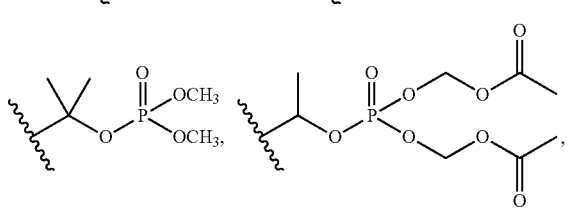

77
-continued
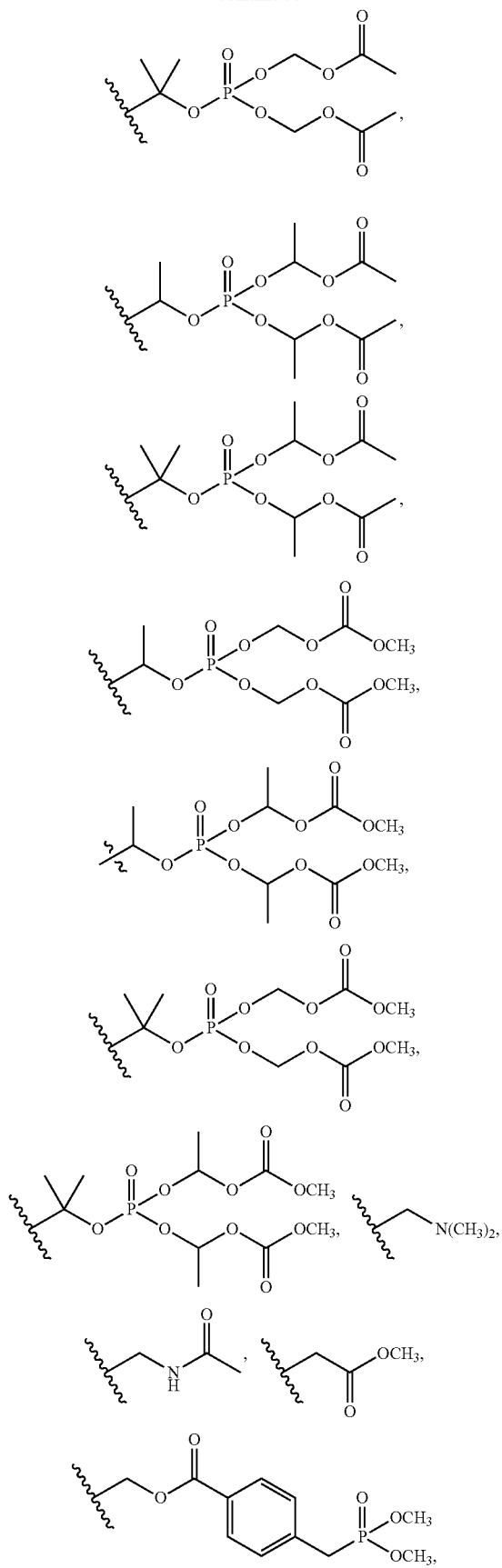
78
-continued
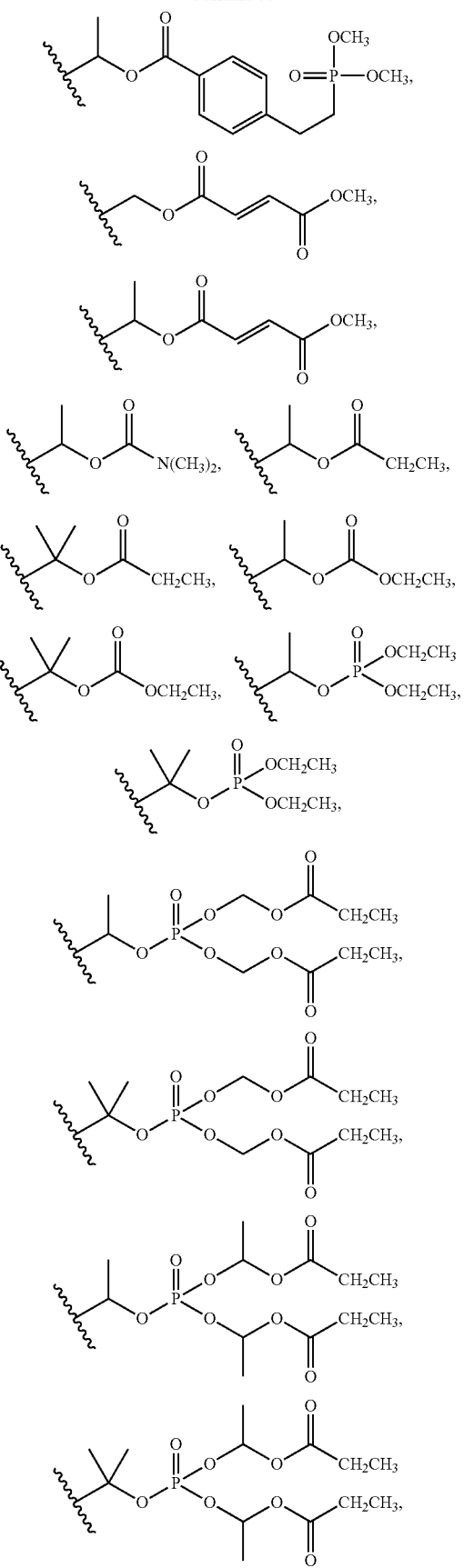

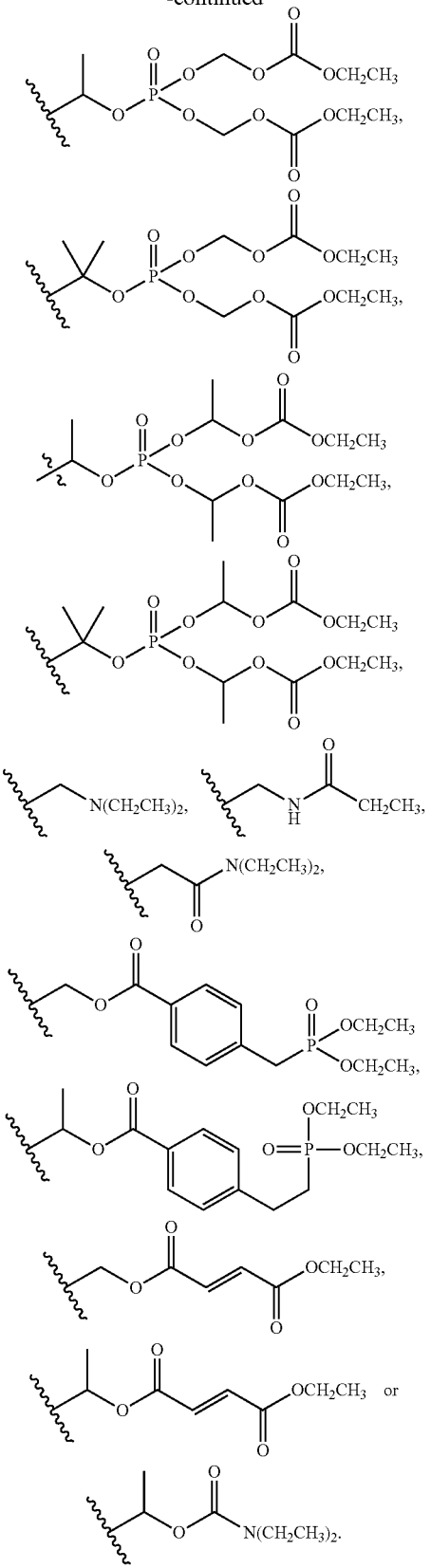

In some embodiments, the compound having the structure:

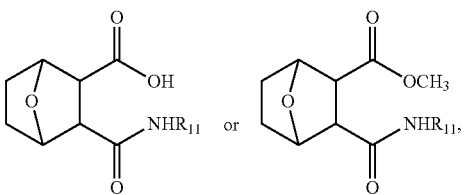

wherein
$R_{11}$ is

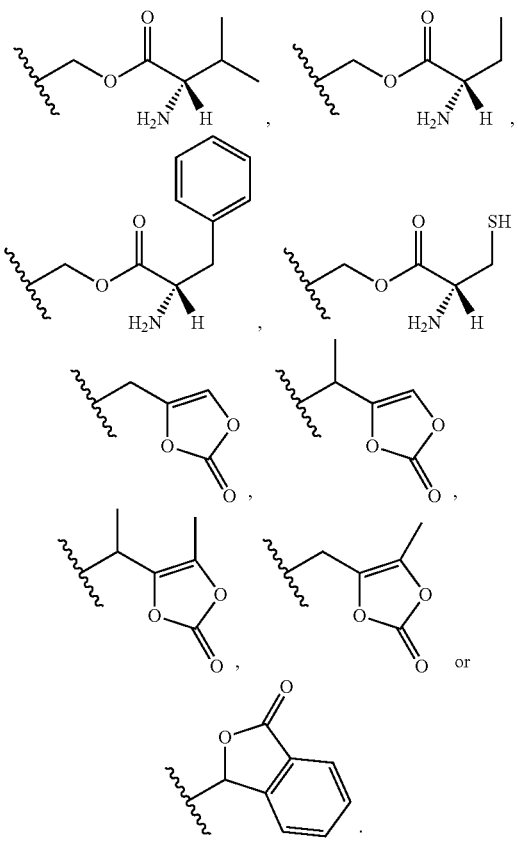

In some embodiments, the compound having the structure:

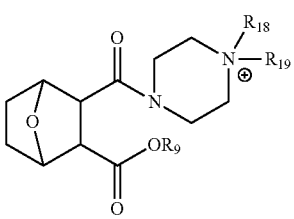

wherein
$R_{18}$ is H or alkyl;
$R_{19}$ is $(C_1$-$C_4$ alkyl)-O(CO)$R_4$, $(C_1$-$C_4$ alkyl)-O(CO)O$R_4$, $(C_1$-$C_4$ alkyl)-OP(O)(O$R_4$)$_2$, $(C_1$-$C_4$ alkyl)-OP(O)(O$(C_1$-$C_4$ alkyl)-O(CO)O$R_4$)$_2$, $(C_1$-$C_4$ alkyl)-OP(O)(O$(C_1$-$C_4$ alkyl)-O(CO)$R_4$)$_2$, $(C_2$-$C_4$ alkyl)N$R_4$$R_5$, $(C_1$-$C_4$ alkyl)NC(O)$R_4$, $(C_1$-$C_4$ alkyl)C(O)O$R_4$, $(C_1$-$C_4$ alkyl)

OC(O)aryl($C_1$-$C_4$ alkyl)P(O)(O$R_4$)$_2$, ($C_1$-$C_4$ alkyl)OC(O)($C_2$-$C_4$ alkenyl)CO$_2$$R_4$, ($C_1$-$C_4$ alkyl)OC(O)($C_1$-$C_4$ alkyl)NH$_2$, ($C_1$-$C_4$ alkyl)C(O)N$R_4$$R_5$,

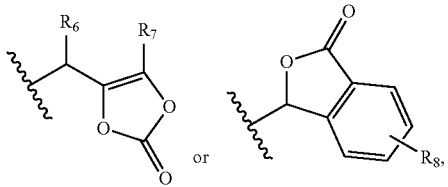

wherein each occurrence of $R_4$ is, independently, H, alkyl, alkenyl, alkynyl, aryl or heteroaryl;
wherein each occurrence of $R_5$ is, independently, H, alkyl, alkenyl, alkynyl, aryl or heteroaryl;
wherein each occurrence of $R_6$ and $R_7$ is, independently, H, alkyl, alkenyl, alkynyl, aryl or heteroaryl;
wherein each occurrence of $R_8$ is, independently, H, halogen, alkyl, alkenyl, alkynyl, aryl or heteroaryl; and
$R_9$ is H, alkyl, alkenyl, alkynyl, aryl, alkylaryl, heteroaryl, alkylaryl, ($C_1$-$C_4$ alkyl)-O(CO)$R_{12}$, ($C_1$-$C_4$ alkyl)-O(CO)O$R_{12}$, ($C_1$-$C_4$ alkyl)-OP(O)(O$R_{12}$)$_2$, ($C_1$-$C_4$ alkyl)-OP(O)(O($C_1$-$C_4$ alkyl)-O(CO)O$R_{12}$)$_2$, ($C_1$-$C_4$ alkyl)-OP(O)(O($C_1$-$C_4$ alkyl)-O(CO)$R_{12}$)$_2$, ($C_1$-$C_4$ alkyl)N$R_{12}$$R_{13}$, ($C_1$-$C_4$ alkyl)NC(O)$R_{12}$, ($C_1$-$C_4$ alkyl)C(O)O$R_{12}$, ($C_1$-$C_4$ alkyl)OC(O)aryl($C_1$-$C_4$ alkyl)P(O)(O$R_{12}$)$_2$, ($C_1$-$C_4$ alkyl)OC(O)($C_2$-$C_4$ alkenyl)CO$_2$$R_{12}$, ($C_1$-$C_4$ alkyl)OC(O)($C_1$-$C_4$ alkyl)NH$_2$, ($C_1$-$C_4$ alkyl)C(O)N$R_{12}$$R_{13}$,

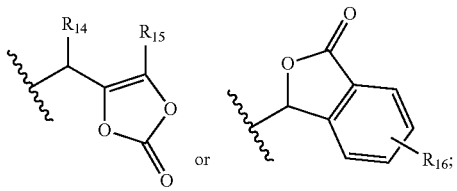

wherein each occurrence of $R_{12}$ is, independently, H, alkyl, alkenyl, alkynyl, aryl or heteroaryl;
wherein each occurrence of $R_{13}$ is, independently, H, alkyl, alkenyl, alkynyl, aryl or heteroaryl,
or a salt or ester of the compound.
In some embodiments, the compound having the structure:

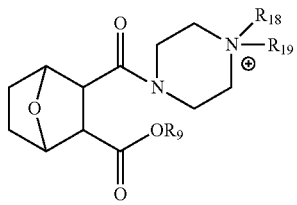

wherein
$R_{18}$ is H or alkyl;
$R_{19}$ is ($C_1$-$C_4$ alkyl)-O(CO)$R_4$, ($C_1$-$C_4$ alkyl)-O(CO)O$R_4$, ($C_1$-$C_4$ alkyl)-OP(O)(O$R_4$)$_2$, ($C_1$-$C_4$ alkyl)-OP(O)(O($C_1$-$C_4$ alkyl)-O(CO)O$R_4$)$_2$, ($C_1$-$C_4$ alkyl)-OP(O)(O($C_1$-$C_4$ alkyl)-O(CO)$R_4$)$_2$, ($C_1$-$C_4$ alkyl)N$R_4$$R_5$, ($C_1$-$C_4$ alkyl)NC(O)$R_4$, ($C_1$-$C_4$ alkyl)C(O)O$R_4$, ($C_1$-$C_4$ alkyl)OC(O)aryl($C_1$-$C_4$ alkyl)P(O)(O$R_4$)$_2$, ($C_1$-$C_4$ alkyl)OC(O)($C_2$-$C_4$ alkenyl)CO$_2$$R_4$, ($C_1$-$C_4$ alkyl)OC(O)($C_1$-$C_4$ alkyl)NH$_2$, ($C_1$-$C_4$ alkyl)C(O)N$R_4$$R_5$,

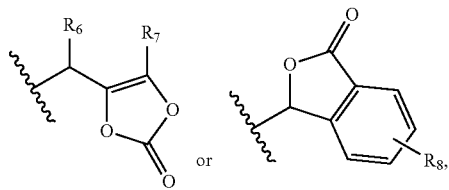

wherein each occurrence of $R_4$ is, independently, H, alkyl, alkenyl, alkynyl, aryl or heteroaryl;
wherein each occurrence of $R_5$ is, independently, H, alkyl, alkenyl, alkynyl, aryl or heteroaryl;
wherein each occurrence of $R_6$ and $R_7$ is, independently, H, alkyl, alkenyl, alkynyl, aryl or heteroaryl;
wherein each occurrence of $R_8$ is, independently, H, halogen, alkyl, alkenyl, alkynyl, aryl or heteroaryl; and
$R_9$ is H, alkyl, alkenyl, alkynyl, aryl, alkylaryl, heteroaryl, or alkylaryl.
In some embodiments, the compound wherein $R_9$ is H or alkyl.
In some embodiments, the compound wherein
$R_9$ is —H,
—CH$_3$
—CH$_2$CH$_3$,
—CH$_2$CH$_2$CH$_3$,
—CH$_2$CH$_2$CH$_2$CH$_3$,
—CH$_2$CH$_2$CH$_2$CH$_2$CH$_3$,
—CH$_2$CH$_2$CH$_2$CH$_2$CH$_2$CH$_3$,
—CH$_2$CH$_2$CH$_2$CH$_2$CH$_2$CH$_2$CH$_3$,
—CH$_2$CH$_2$CH$_2$CH$_2$CH$_2$CH$_2$CH$_2$CH$_3$,
—CH$_2$CH$_2$CH$_2$CH$_2$CH$_2$CH$_2$CH$_2$CH$_2$CH$_3$,
—CH$_2$CH$_2$CH$_2$CH$_2$CH$_2$CH$_2$CH$_2$CH$_2$CH$_2$CH$_3$,
—CH$_2$CH$_2$CH$_2$CH$_2$CH$_2$CH$_2$CH$_2$CH$_2$CH$_2$CH$_2$CH$_2$CH$_2$CH$_2$CH$_3$, or
—CH$_2$CH$_2$CH$_2$CH$_2$CH$_2$CH$_2$CH$_2$CH$_2$=CHCH$_2$CH=CHCH$_2$CH$_2$CH$_2$CH$_3$.
In some embodiments, the compound wherein
$R_{18}$ is —H or —CH$_3$; and
$R_{19}$ is ($C_1$-$C_4$ alkyl)-O(CO)$R_4$ or ($C_1$-$C_4$ alkyl)-O(CO)O$R_4$.
In some embodiments, the compound wherein
$R_{18}$ is —H or —CH$_3$; and
$R_{19}$ is —CH$_2$—O(CO)CH$_3$, —CH(CH$_3$)—O(CO)CH$_3$, —CH$_2$—O(CO)OCH$_3$, —CH(CH$_3$)—O(CO) OCH$_3$.
In some embodiments, the compound wherein $R_9$ is

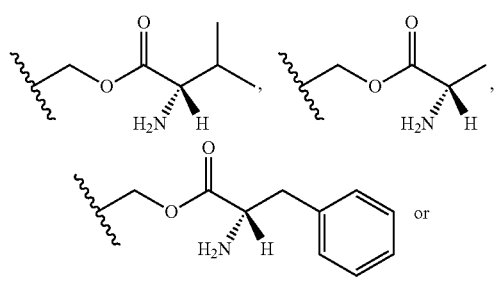

-continued

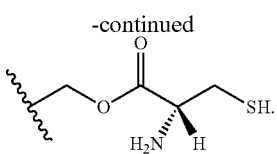

The present invention also provides a compound having the structure:

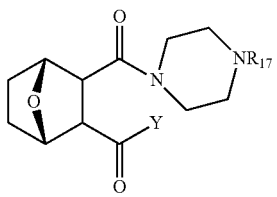

wherein
$R_{17}$ is H, alkyl, hydroxyalkyl, alkenyl, alkenyl, alkynyl, aryl, alkylaryl, heteroaryl, alkylheteroaryl, C(O)O-t-Bu or —$CH_2CN$;
Y is $OR_9$, wherein $R_9$ is ($C_1$-$C_4$ alkyl)-O(CO)$R_{12}$ or ($C_1$-$C_4$ alkyl)-O(CO)O$R_{12}$,
  wherein each occurrence of $R_{12}$ is, independently, H, alkyl, alkenyl, alkynyl, aryl or heteroaryl.
In some embodiments, the compound wherein
$R_{17}$ is H, methyl, ethyl, $CH_2CH_2OH$, CH (phenyl); and
Y is ORG, wherein $R_9$ is ($C_1$-$C_4$ alkyl)-O(CO)$R_{12}$ or ($C_1$-$C_4$ alkyl)-O(CO)O$R_{12}$,
  wherein each occurrence of $R_{12}$ is, independently, H, alkyl, alkenyl, alkynyl, aryl or heteroaryl.
In some embodiments, the compound wherein
$R_{17}$ is H, methyl, ethyl, $CH_2CH_2OH$, $CH_2$(phenyl); and
Y is $OR_9$, wherein $R_9$ is ($C_1$-$C_4$ alkyl)-O(CO)$R_{12}$ or ($C_3$-$C_4$ alkyl)-O(CO)O$R_{12}$,
  wherein each occurrence of $R_{12}$ is an alkyl.
In some embodiments, the compound wherein
$R_{17}$ is methyl; and
Y is $OR_9$, wherein $R_9$ is ($C_1$-$C_4$ alkyl)-O(CO)$R_{12}$ or ($C_1$-$C_4$ alkyl)-O(CO)O$R_{12}$,
  wherein each occurrence of $R_{12}$ is an alkyl.
In some embodiments, the compound having the structure

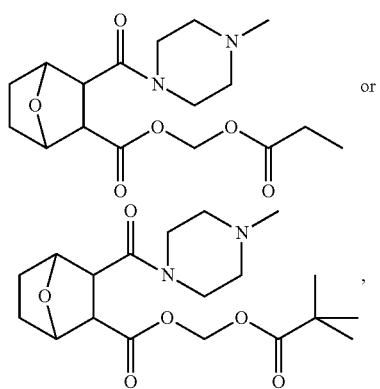

or a salt of the compound.

In some embodiments, the compound having the structure

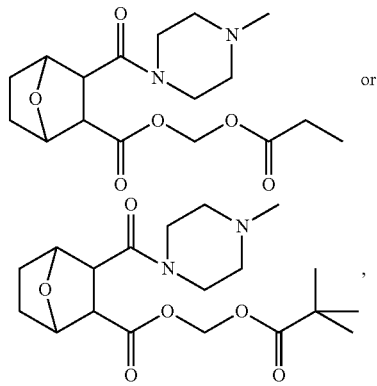

or a salt of the compound.

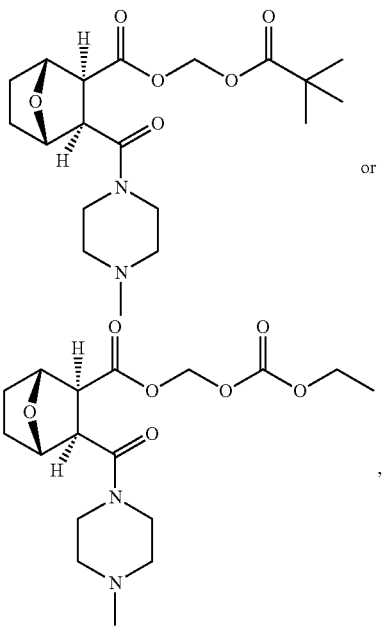

or a salt of the compound.

The present invention also provides a compound having the structure:

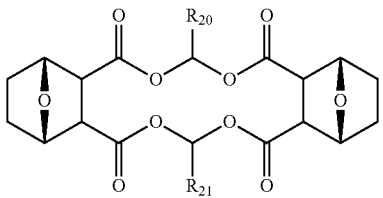

wherein $R_{20}$ and $R_{21}$ are each independently H, alkyl, hydroxyalkyl, alkenyl, alkynyl, aryl, alkylaryl, or heteroaryl,
or a salt or ester of the compound.
In some embodiments, the above compound wherein $R_{20}$ and $R_{21}$ are each independently H, methyl, ethyl, $CH_2CH_2OH$, or $CH_2$(phenyl)

In some embodiments, the above compound wherein $R_{20}$ and $R_{21}$ are both H.

In some embodiments, the above compound wherein $R_{20}$ and $R_{21}$ are both methyl.

The present invention provides a pharmaceutical composition comprising a compound of the present invention and a pharmaceutically acceptable carrier.

The present invention provides a pharmaceutical composition comprising a compound of the present invention or a pharmaceutically acceptable salt thereof and a pharmaceutically acceptable carrier.

The present invention provides a pharmaceutical composition comprising a compound of the present invention or a pharmaceutically acceptable salt thereof and an anticancer agent, and at least one pharmaceutically acceptable carrier.

In some embodiments, the pharmaceutical composition wherein the pharmaceutically acceptable carrier comprises a liposome.

In some embodiments, the pharmaceutical composition wherein the compound is contained in a liposome or microsphere, or the compound and the anti-cancer agent are contained in a liposome or microsphere.

The present invention also provides a method for in vivo delivery of endothal to a target cell in a subject, the method comprising administering to the subject a compound of the present invention, wherein one or two bonds in the compound are subject to in vivo hydrolytic cleavage in the subject, so as to thereby deliver endothal to the target cell in the subject.

In some embodiments of the above method, the compound has the structure

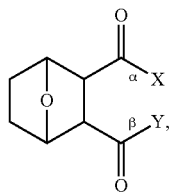

wherein one or both of bond α and bond β is subject to in vivo hydrolytic cleavage in the subject.

In some embodiments of the above method, the compound has the structure

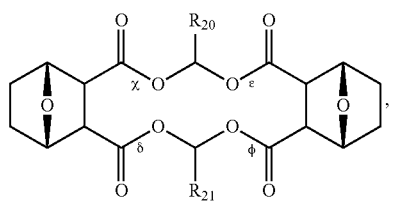

wherein one or more of bonds χ, δ, ε, and φ are subject to in vivo hydrolytic cleavage in the subject.

In some embodiments of the above method, wherein the delivery of the endothal to the target cell in the subject is effective to treat a disease in the subject afflicted with the disease.

In some embodiments of the above method, wherein the disease is cancer.

In some embodiments of the above method, wherein the cancer is a breast cancer, colon cancer, large cell lung cancer, adenocarcinoma of the lung, small cell lung cancer, stomach cancer, liver cancer, ovary adenocarcinoma, pancreas carcinoma, prostate carcinoma, promylocytic leukemia, chronic myelocytic leukemia, acute lymphocytic leukemia, colorectal cancer, ovarian cancer, lymphoma, non-Hodgkin's lymphoma or Hodgkin's lymphoma.

In some embodiments of the above method, wherein the cancer is a brain cancer.

In some embodiments of the above method, wherein the brain cancer is a glioma, pilocytic astrocytoma, low-grade diffuse astrocytoma, anaplastic astrocytoma, glioblastoma multiforme, oligodendroglioma, ependymoma, meningioma, pituitary gland tumor, primary CNS lymphoma, medulloblastoma, craniopharyngioma, or diffuse intrinsic pontine glioma.

In some embodiments of the above method, further comprising administering to the subject an anti-cancer agent.

In some embodiments of the above method, wherein the anti-cancer agent is selected from x-radiation or ionizing radiation.

In some embodiments of the above method, wherein the target cell is a cancer cell.

In some embodiments of the above method, wherein the cancer cell is a breast cancer, colon cancer, large cell lung cancer, adenocarcinoma of the lung, small cell lung cancer, stomach cancer, liver cancer, ovary adenocarcinoma, pancreas carcinoma, prostate carcinoma, promylocytic leukemia, chronic myelocytic leukemia, acute lymphocytic leukemia, colorectal cancer, ovarian cancer, lymphoma, non-Hodgkin's lymphoma or Hodgkin's lymphoma cell.

In some embodiments of the above method, wherein the cancer cell is a brain cancer cell.

In some embodiments of the above method, wherein the brain cancer cell is a glioma, pilocytic astrocytoma, low-grade diffuse astrocytoma, anaplastic astrocytoma, glioblastoma multiforme, oligodendroglioma, ependymoma, meningioma, pituitary gland tumor, primary CNS lymphoma, medulloblastoma, craniopharyngioma, or diffuse intrinsic pontine glioma cell.

In some embodiments of the above method, wherein the target cell is in the brain of the subject.

In some embodiments of the above method, wherein the endothal is delivered to a target cell in the brain of the subject.

In some embodiments of the above method, the hydrolytic cleavage of the α and/or β bond is facilitated by a carboxylesterase or an amidase in the subject.

In some embodiments of the above method, wherein the hydrolytic cleavage of the χ, δ, ε, and φ bond is facilitated by a carboxylesterase or an amidase in the subject.

The present invention also provides a compound having the structure:

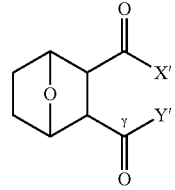

wherein
X' is OH, O(alkyl) or $NR_{22}R_{23}$;
$R_{22}$ is H, alkyl, alkenyl, alkynyl, aryl, alkylaryl, or heteroaryl;

$R_{23}$ is H, alkyl, alkenyl, alkynyl, aryl, alkylaryl, or heteroaryl, or $R_{22}$ and $R_{23}$ combine to form an N-methylpiperazine;

Y' is an anti-cancer agent A containing at least one amine nitrogen and the nitrogen on the anti-cancer agent covalently bonds directly to carbon γ, or Y' is an anti-cancer agent A containing at least one hydroxyl oxygen and the oxygen on the anti-cancer agent covalently bonds directly to carbon γ, or Y' is

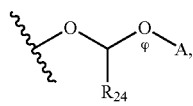

wherein A is an anti-cancer agent containing at least one carboxylic acid and the carbonyl carbon of the carboxylic acid on the anti-cancer agent covalently bonds directly to oxygen φ, and $R_{24}$ is H or alkyl, or a salt or ester of the compound.

In some embodiments, the compound having the structure:

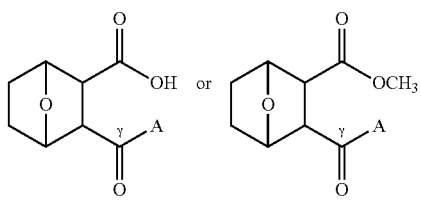

wherein

A is an anti-cancer agent containing at least one amine nitrogen and the nitrogen on the anti-cancer agent covalently bonds directly to carbon γ, or A is an anti-cancer agent containing at least one hydroxyl oxygen and the oxygen on the anti-cancer agent covalently bonds directly to carbon γ.

In some embodiments, the compound having the structure:

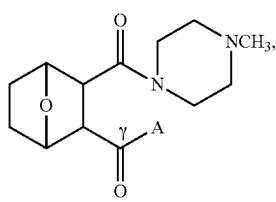

wherein

A is an anti-cancer agent containing at least one amine nitrogen and the nitrogen on the anti-cancer agent covalently bonds directly to carbon γ, or A is an anti-cancer agent containing at least one hydroxyl oxygen and the oxygen on the anti-cancer agent covalently bonds directly to carbon γ.

In some embodiments, the compound having the structure:

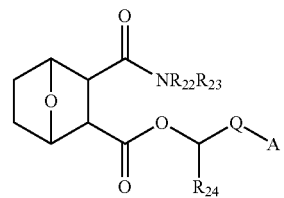

wherein

Q is NH or O;

$R_{22}$ is H, alkyl, alkenyl, alkynyl, aryl, alkylaryl, or heteroaryl;

$R_{23}$ is H, alkyl, alkenyl, alkynyl, aryl, alkylaryl, or heteroaryl, or $R_{22}$ and $R_{23}$ combine to form an N-methylpiperazine;

$R_{24}$ is H or alkyl; and

A is an anti-cancer agent containing at least one carboxylic acid or primary amide and the carbonyl carbon of the carboxylic acid or primary amide on the anti-cancer agent covalently bonds directly to Q, or a salt or ester of the compound.

In some embodiments, the compound having the structure:

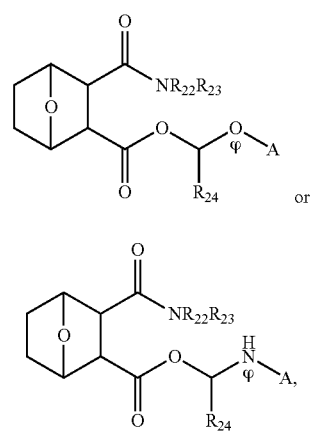

wherein $R_{22}$ is H, alkyl, alkenyl, alkynyl, aryl, alkylaryl, or heteroaryl;

$R_{23}$ is H, alkyl, alkenyl, alkynyl, aryl, alkylaryl, or heteroaryl, or $R_{24}$ is H or alkyl; and A is an anti-cancer agent containing at least one carboxylic acid and the carbonyl carbon of the carboxylic acid on the anti-cancer agent covalently bonds directly to oxygen φ, or A is an anti-cancer agent containing at least one primary amide and the carbonyl carbon of the primary amide on the anti-cancer agent covalently bonds directly to nitrogen φ, or a salt or ester of the compound.

In some embodiments, the compound having the structure:

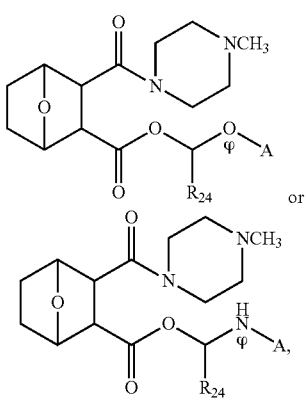

wherein

R$_{24}$ is H or alkyl; and

A is an anti-cancer agent containing at least one carboxylic acid and the carbonyl carbon of the carboxylic acid on the anti-cancer agent covalently bonds directly to oxygen φ, or A is an anti-cancer agent containing at least one primary amide and the carbonyl carbon of the primary amide on the anti-cancer agent covalently bonds directly to nitrogen φ, or or a salt or ester of the compound.

In some embodiments, the above compound wherein A is adenine, emtricitabine, vapreotide, troxacitabine, triptorelin, trimetrexate glucuronate, trimetrexate, tipifarnib, tiazofurin, thioguanine, squalamine lactate, piritrexim isethionate, pentetreotide, pemetrexed, peldesine, oxaliplatin, nelarabine, mitoguazone, methyl aminolevulinate, methotrexate, melphalan, leuprolide, lanreotide, idarubicin, histamine, goderelin, gemtuzumab ozogamicin, gemcitabine, fludarabine, epirubicin, eflornithine, doxorubicin, decitabine, 5-aza-2'-deoxycytidine, daunorubicin, dactinomycin, cytarabine, clofarabine, cladribine, cliengtide, cetrorelix acetate, cetrorelix, bleomycin, azacitidine, aminolevulinic acid, aminoglutethimide, amifostine, abarelix, amifostine, abarelix, phentermine, corticorelin, metyrosine or monomethyl auristatin E (MMAE).

In some embodiments, the above compound wherein A is abarelix, azacitidine, bleomycin, broxuridine, capecitabine, cetrorelix, cetrorelix acetate, cladribine, clofarabine, cytarabine, dactinomycin, dasatinib, daunorubicin, decitabine, docetaxel, doxorubicin, dromostanolone propionate, emtricitabine, epirubicin, estramustine, etoposide, etoposide phosphate, fludarabine, fulvestrant, gemcitabine, gemtuzumab ozogamicin, goserelin, goserelin acetate, irinotecan, irinotecan hydrochloride, irofulven, lanreotide acetate, lanreotide, leuprolide, leuprolide acetate, mitobronitol, mitolactol, mitoxantrone, mitoxantrone hydrochloride, motexafin gadolinium, nelarabine, paclitaxel, patupilone, pentostatin, plicamycin, plitidepsin, porfimer, porfimer sodium, squalamine lactate, streptozocin, taxol, temsirolimus, tezacitabine, teniposide, tiazofurin, trabectedin, treosulfan, triptorelin, troxacitabine, valrubicin or zosuquidar trihydrochloride.

In some embodiments, the above compound wherein A is acitretin, aminolevulinic acid, bexarotene, carboplatin, cetrorelix acetate, chlorambucil, cilengitide, corticorelin, eflornithine, exisulind, fumagillin irinotecan, melphalan, methotrexate, metyrosine, pemetrexed, pentetreotide, phenylbutyrate, porfimer, sulindac, verteporfin ortemozolomide.

In some embodiments, the compound having the structure:

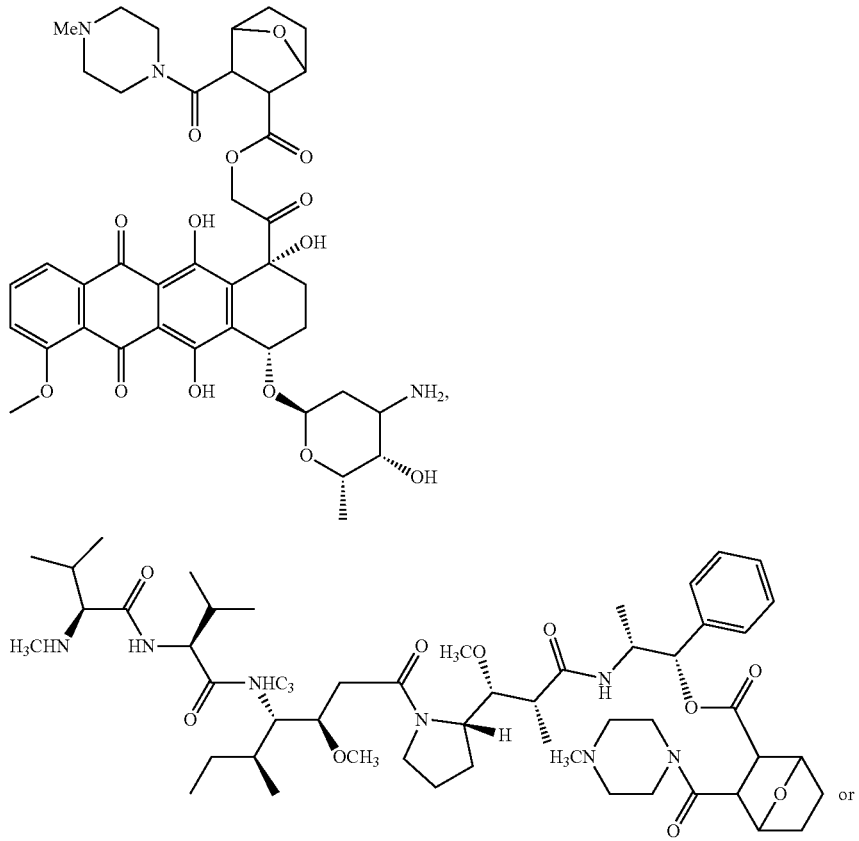

-continued

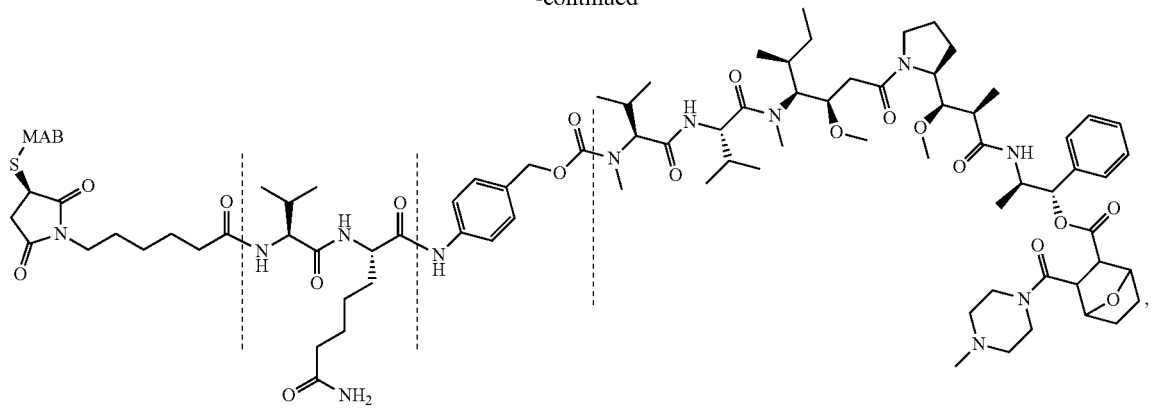

or salt or ester of the compound.

In some embodiments, the compound having the structure:

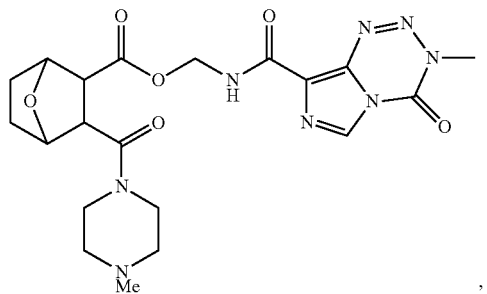 [SMILES: CN1CCN(C(=O)C2C3CCC(O3)C2C(=O)OCNC(=O)c2ncn3c(=O)n(C)nnc23)CC1]

or salt or ester of the compound.

The present invention also provides method for in vivo delivery of endothal and an anti-cancer agent to a cancer cell in a subject, the method comprising administering to the subject a compound of the present invention so as to thereby deliver endothal and the anti-cancer agent to the cancer cell in the subject.

In some embodiments of the above method, wherein the compound has the structure:

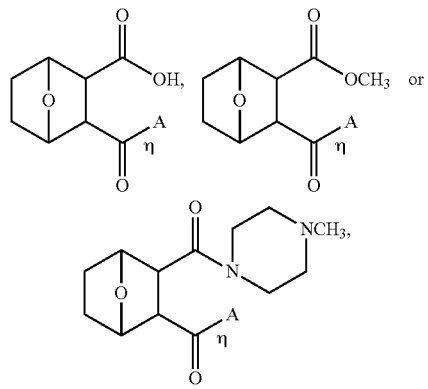

wherein bond η is subject to in vivo hydrolytic cleavage in the subject, so as to thereby deliver endothal and the anti-cancer agent to the cancer cell in the subject.

In some embodiments of the above method, wherein A is an anti-cancer agent containing at least one amine nitrogen and the nitrogen on the anti-cancer agent covalently bonds directly to carbon γ and the hydrolytic cleavage of the η bond is facilitated by an amidase in the subject.

In some embodiments of the above method, wherein A is an anti-cancer agent containing at least one hydroxyl oxygen and the oxygen on the anti-cancer agent covalently bonds directly to carbon γ and the hydrolytic cleavage of the η is facilitated by a carboxylesterase in the subject.

In some embodiments of the above method, wherein the compound has the structure:

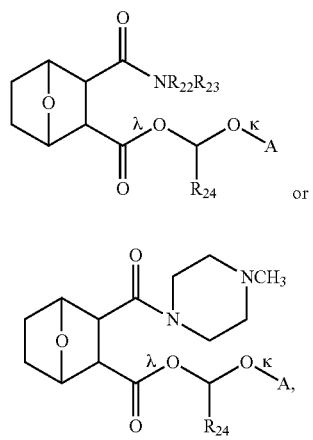

wherein bonds κ and λ are subject to in vivo hydrolytic cleavage in the subject, so as to thereby deliver endothal and the anti-cancer agent to the cancer cell in the subject.

In some embodiments of the above method, wherein the compound has the structure:

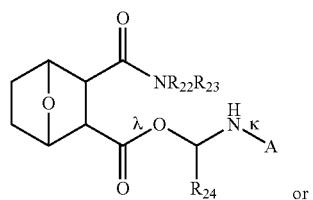

or

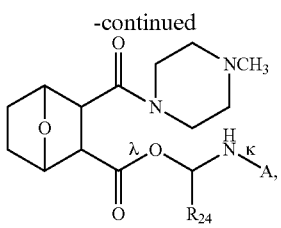

wherein bonds κ and λ are subject to in vivo hydrolytic cleavage in the subject, so as to thereby deliver endothal and the anti-cancer agent to the cancer cell in the subject.

In some embodiments of the above method, wherein the hydrolytic cleavage of the κ bond and/or the λ bond is facilitated by a carboxylesterase or amidase in the subject.

In some embodiments of the above method, wherein the delivery of the endothal and the anti-cancer agent to the cancer cell in the subject is effective to treat a cancer in a subject afflicted with the cancer.

In some embodiments of the above method, wherein the cancer is a breast cancer, colon cancer, large cell lung cancer, adenocarcinoma of the lung, small cell lung cancer, stomach cancer, liver cancer, ovary adenocarcinoma, pancreas carcinoma, prostate carcinoma, promylocytic leukemia, chronic myelocytic leukemia, acute lymphocytic leukemia, colorectal cancer, ovarian cancer, lymphoma, non-Hodgkin's lymphoma or Hodgkin's lymphoma.

In some embodiments of the above method, wherein the cancer is a brain cancer.

In some embodiments of the above method, wherein the brain cancer is a glioma, pilocytic astrocytoma, low-grade diffuse astrocytoma, anaplastic astrocytoma, glioblastoma multiforme, oligodendroglioma, ependymoma, meningioma, pituitary gland tumor, primary CNS lymphoma, medulloblastoma, craniopharyngioma, or diffuse intrinsic pontine glioma.

In some embodiments of the above method, wherein the cancer cell is a breast cancer, colon cancer, large cell lung cancer, adenocarcinoma of the lung, small cell lung cancer, stomach cancer, liver cancer, ovary adenocarcinoma, pancreas carcinoma, prostate carcinoma, promylocytic leukemia, chronic myelocytic leukemia, acute lymphocytic leukemia, colorectal cancer, ovarian cancer, lymphoma, non-Hodgkin's lymphoma or Hodgkin's lymphoma cell.

In some embodiments of the above method, wherein the cancer cell is a brain cancer cell.

In some embodiments of the above method, wherein the brain cancer cell is a glioma, pilocytic astrocytoma, low-grade diffuse astrocytoma, anaplastic astrocytoma, glioblastoma multiforme, oligodendroglioma, ependymoma, meningioma, pituitary gland tumor, primary CNS lymphoma, medulloblastoma, craniopharyngioma, or diffuse intrinsic pontine glioma cell.

In some embodiments of the above method, wherein the target cell is in the brain of the subject.

In some embodiments of the above method, wherein the endothal and anti-cancer agent are delivered to a cancer cell in the brain of the subject.

In some embodiments of the above method, the compound is co-administered with an anti-cancer agent.

The present invention provides a method of treating a subject afflicted with cancer comprising administering to the subject a therapeutically effective amount of the compound of the present invention.

The present invention provides a method of enhancing the anti-cancer activity of an anti-cancer agent in a subject afflicted with a cancer, comprising administering to the subject the compound of the present invention in an amount effective to enhance the anti-cancer activity of the anti-cancer agent.

The present invention provides a method of treating a subject afflicted with cancer comprising periodically administering to the subject:
a) an amount of the compound of the present invention or a pharmaceutically acceptable salt thereof, and
b) an anti-cancer agent,
wherein the amounts when taken together are more effective to treat the subject than when each agent at the same amount is administered alone.

The present invention provides for the use of the compound of the present invention or a pharmaceutically acceptable salt thereof and an anti-cancer agent in the preparation of a combination for treating a subject afflicted with cancer wherein the amount of the compound and the amount of the anti-cancer agent are administered simultaneously or contemporaneously.

The present invention provides a pharmaceutical composition comprising an amount of the compound of the present invention or a pharmaceutically acceptable salt thereof for use in treating a subject afflicted with cancer as an add-on therapy or in combination with, or simultaneously, contemporaneously or concomitantly with an anti-cancer agent.

In some embodiments, the compound of the present invention or a pharmaceutically acceptable salt thereof for use as an add-on therapy or in combination with an anti-cancer agent in treating a subject afflicted with cancer.

In some embodiments, the compound of the present invention or a pharmaceutically acceptable salt thereof and an anti-cancer agent for the treatment of a subject afflicted with cancer wherein the compound and the anti-cancer agent are administered simultaneously, separately or sequentially.

In some embodiments, a product containing an amount of the compound of the present invention or a pharmaceutically acceptable salt thereof and an amount of an anti-cancer agent for simultaneous, separate or sequential use in treating a subject afflicted cancer.

In some embodiments, the compound of the present invention or a pharmaceutically acceptable salt thereof for use in treating cancer.

In some embodiments, the compound of the present invention or a pharmaceutically acceptable salt thereof in combination with an anti-cancer agent for use in treating cancer.

In some embodiments of any of the above methods, uses, pharmaceutical compositions, compounds or products, the cancer is breast cancer, colon cancer, large cell lung cancer, adenocarcinoma of the lung, small cell lung cancer, stomach cancer, liver cancer, ovary adenocarcinoma, pancreas carcinoma, prostate carcinoma, promylocytic leukemia, chronic myelocytic leukemia, acute lymphocytic leukemia, colorectal cancer, ovarian cancer, lymphoma, non-Hodgkin's lymphoma or Hodgkin's lymphoma.

In some embodiments of any of the above methods, uses, pharmaceutical compositions, compounds or products, the cancer is brain cancer.

In some embodiments of any of the above methods, uses, pharmaceutical compositions, compounds or products, the brain cancer is a glioma, pilocytic astrocytoma, low-grade diffuse astrocytoma, anaplastic astrocytoma, glioblastoma multiforme, oligodendroglioma, ependymoma, meningioma, pituitary gland tumor, primary CNS lymphoma, medulloblastoma, craniopharyngioma, or diffuse intrinsic pontine glioma.

In some embodiments of any of the above methods, uses, pharmaceutical compositions, compounds or products, the compound crosses the blood brain barrier of the subject.

In some embodiments of any of the above methods, uses, pharmaceutical compositions, compounds or products, the compound and/or a metabolite of the compound crosses the blood brain barrier of the subject.

The present invention provides a method of inhibiting proliferation or inducing apoptosis of a cancer cell in a human subject, comprising administering to the subject:
a) the compound of the present invention, or a salt of the compound, in an amount effective to inhibit the proliferation or to induce apoptosis of the cancer cell, and
b) an anti-cancer agent in an amount effective to inhibit the proliferation or to induce apoptosis of the cancer cell.

The present invention provides a method of inhibiting proliferation or inducing apoptosis of a cancer cell in a human subject which overexpresses translationally controlled tumour protein (TCTP) comprising administering to the subject
a) the compound of the present invention, or a salt of the compound, in an amount effective to inhibit the proliferation or to induce apoptosis of the cancer cell, and
b) an anti-cancer agent in an amount effective to inhibit the proliferation or to induce apoptosis of the cancer cell.

In some embodiments of the above methods, the cancer cell does not overexpress N-CoR.

In some embodiments of any of the above methods, uses, pharmaceutical compositions, compounds or products, the anti-cancer agent is selected from x-radiation or ionizing radiation.

In some embodiments of any of the above methods, uses, pharmaceutical compositions, compounds or products, the anti-cancer agent is selected from a DNA damaging agent, a DNA intercalating agent, a microtubule stabilizing agent, a microtubule destabilizing agent, a spindle toxin, abarelix, aldesleukin, alemtuzumab, alitertinoin, allopurinol, altretamine, amifostin, anakinra, anastrozole, arsenic trioxide, asparaginase, azacitidine, bevacizumab, bexarotene, bleomycin, bortezomib, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin sodium, darbepoetin alfa, dasatinib, daunorubicin, daunomycin, decitabine, denileukin, dexrazoxane, docetaxel, doxorubicin, dromostanolone propionate, exulizumab, epirubicin, epoetin alfa, erlotinib, estramustine, etoposide phosphate, etoposide, VP-16, exemestane, fentanyl citrate, filgrastim, floxuridine, fludarabine, fluorouracil, fulvestrant, gefitinib, gemcitabine, gosereline acetate, histrelin acetate, hydroxyurea, ibritumomab tiuxetan, idarubicin, ifosfamide, imatinib mesylate, interferon alfa 2a, interferon alfa 2b, irinotecan, lapatinib ditosylate, lenalidomide, letrozole, leucovrin, leuprolide acetate, levamisole, lomustine, meclorethamine, megestrol acetate, melphalan, mercaptopurine, mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa 2b, pemetrexed disodium, pentostatin, pipobroman, plicamycin, mithramycin, porfimer sodium, procarbazine, quinacrine, rasburicase, rituximab, sargrmostim, sorafenib, streptozocin, sunitinib, sunitinib maleate, talc, tamoxifen, temozolomide, teniposide, VM-26, testolactone, thalidomide, thioguanine, G-TG, thiotepa, topotecan, toremifene, tositumomab, trastuzumab, tretinoin ATRA, uracil mustard, valrunicin, vinblastine, vincristine, vinorelbine, vorinostat, zoledronate, zoledronic acid, abraxane and brentuximab vedotin.

In some embodiments of any of the above methods, uses, pharmaceutical compositions, compounds or products, the subject is a human.

In some embodiments of any of the above methods, uses, pharmaceutical compositions, compounds or products, the cancer is any one of adrenocortical cancer, bladder cancer, osteosarcoma, cervical cancer, esophageal, gallbladder, head and neck cancer, lymphoma, Hodgkin's lymphoma, non-Hodgkin's lymphoma, renal cancer, melanoma, pancreatic cancer, rectal cancer, thyroid cancer, throat cancer, brain cancer, breast cancer, lung cancer, prostate cancer, melanoma, pancreatic cancer, colon cancer, large cell lung cancer, adenocarcinoma of the lung, small cell lung cancer, stomach cancer, liver cancer, ovary adenocarcinoma, pancreas carcinoma, prostate carcinoma, promylocytic leukemia, chronic myelocytic leukemia, acute lymphocytic leukemia, colorectal cancer, ovarian cancer or hepatocellular carcinoma.

In one embodiment, a pharmaceutical composition comprising the compound of the present invention. In one embodiment, a pharmaceutical composition comprising the compound of the present invention and a pharmaceutically acceptable carrier.

In one embodiment of the method, the compound of the present invention inhibits PP2A activity in the subject. In one embodiment of the method, the compound of the present invention inhibits PP2A activity in the brain of the subject. In one embodiment of the method, the compound of the present invention crosses the blood brain barrier of the subject.

In some embodiments, the compounds of the present invention are ester derivatives of compound 100 and serve as pro-drugs of compound 100.

In some embodiments, the compounds of the present invention are ester derivatives of 100 and serve as pro-drugs that can be converted into 100 by serum esterases and/or brain esterases.

In some embodiments, the compounds of the present invention are derivatives of compound 100 and serve as pro-drugs of endothal.

In some embodiments, the compounds of the present invention are derivatives of compound 100 and serve as pro-drugs that can be converted into endothal by serum esterases and/or brain esterases.

In some embodiments, the compounds of the present invention are derivatives of compound 100 and serve as pro-drugs that cross the blood brain barrier and deliver endothal to the brain.

Administration of a pro-drug of endothal is more effective at delivering endothal to targets cells in a subject than administration of endothal itself.

The metabolic profile of endothal is such that administration of a pro-drug of endothal is more effective at delivering endothal to targets cells in a subject than administration of endothal itself.

In some embodiments, the method wherein the compound is first converted to compound 100 in vivo, which in turn is converted to endothal in vivo.

The compounds disclosed herein act as prodrugs of endothal, altering metabolism by masking one or two acid groups with an amide or an ester moiety. The design of the prodrug will result in reduced toxicity and increased systemic exposure of endothal in the subject.

In some embodiments of the delivery method, a pharmaceutical composition comprising the compound and a pharmaceutically acceptable carrier.

As used herein, a "symptom" associated with a disease includes any clinical or laboratory manifestation associated with the disease and is not limited to what the subject can feel or observe.

As used herein, "treatment of the diseases", "treatment of the injury" or "treating", e.g. of a disease encompasses inducing inhibition, regression, or stasis of the disease or injury, or a symptom or condition associated with the disease or injury.

As used herein, "inhibition" of disease encompasses preventing or reducing the disease progression and/or disease complication in the subject.

As used herein, "overexpressing N-CoR" means that the level of the Nuclear receptor co-repressor (N-CoR) expressed in cells of the tissue tested are elevated in comparison to the levels of N-CoR as measured in normal healthy cells of the same type of tissue under analogous conditions. The nuclear receptor co-repressor (N-CoR) of the subject invention may be any molecule that binds to the ligand binding domain of the DNA-bound thyroid hormone receptor (T3R) and retinoic acid receptor (RAR) (U.S. Pat. No. 6,949,624, Liu et al.). Examples of tumors that overexpress N-CoR may include glioblastoma multiforme, breast cancer (Myers et al. 2005), colorectal cancer (Giannini and Cavallini 2005), small cell lung carcinoma (Waters et al 2004.) or ovarian cancer (Havrilesky et al. 2001).

As used herein, the term "amino acid moiety" or "AA" refers to any natural or unnatural amino acid including its salt form, ester derivative, protected amine derivative and/or its isomeric forms. Amino Acids comprise, by way of non-limiting example: Agmatine, Alanine Beta-Alanine, Arginine, Asparagine, Aspartic Acid, Cysteine, Glutamine, Glutamic Acid, Glycine, Histidine, Isoleucine, Leucine, Lysine, Methionine, Phenylalanine, Phenyl Beta-Alanine, Proline, Serine, Threonine, Tryptophan, Tyrosine, and Valine. The amino acids may be L or D amino acids. The amino acid may be attached via the acid to form an ester linker or via the amine to form a secondary amine linker.

As used herein, the term "amino acid moiety" refers to H, OH, alkyl, benzyl, methyl, ethyl, propyl, butyl, isopropyl, isobutyl, —$(CH_2)C(O)NH_2$, —$(CH_2)_2C(O)NH_2$, —$(CH_2)C(O)OH$, —$(CH_2)_2C(O)OH$, —$(CH_2)_5C(O)OH$, —$CH(CH_3)CH_2CH_3$, propyl, butyl, —$(CH_2CH_2CH_2)NH_2$, —$(CH_2)SH$, —$(CH_2CH_2)SH$, —$(CH_2)SCH_3$, —$(CH_2CH_2)SCH_3$, —$(CH_2CH_2)OH$, —$(CH_2)OH$, —$(CH_2)$-indole, —$(CH_2)$-thiophene, —$(CH_2)$-imidazole, —$CH(OH)CH_3$, —$CH(CH_3)C(SH)(CH_3)_2$, —$CH_2$(4-methoxyphenyl) or —$(CH_2)_3NHC(NH)NH_2$.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{20}$ alkyl, $C_2$-$C_{20}$ alkyl, $C_3$-$C_{20}$ alkyl, $C_4$-$C_{20}$ alkyl and so on. An embodiment can be $C_1$-$C_{30}$ alkyl, $C_2$-$C_{30}$ alkyl, $C_3$-$C_{30}$ alkyl, $C_4$-$C_{30}$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl, $C_3$-$C_{12}$ alkenyl, $C_2$-$C_{20}$ alkenyl, $C_3$-$C_{20}$ alkenyl, $C_2$-$C_{30}$ alkenyl, or $C_3$-$C_{30}$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl or $C_3$-$C_{12}$ alkynyl, $C_2$-$C_{20}$ alkynyl, $C_3$-$C_{20}$ alkynyl, $C_2$-$C_{30}$ alkynyl, or $C_3$-$C_{30}$ alkynyl.

As used herein, "aryl" is intended to mean any stable monocyclic or bicyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring. The substituted aryls included in this invention include substitution at any suitable position with amines, substituted amines, alkylamines, hydroxys and alkylhydroxys, wherein the "alkyl" portion of the alkylamines and alkylhydroxys is a $C_2$-$C_n$ alkyl as defined hereinabove. The substituted amines may be substituted with alkyl, alkenyl, alkynyl, or aryl groups as hereinabove defined.

The alkyl, alkenyl, alkynyl, and aryl substituents may be unsubstituted or unsubstituted, unless specifically defined otherwise. For example, a ($C_1$-$C_6$) alkyl may be substituted with one or more substituents selected from OH, oxo, halogen, alkoxy, dialkylamino, or heterocyclyl, such as morpholinyl, piperidinyl, and so on.

In the compounds of the present invention, alkyl, alkenyl, and alkynyl groups can be further substituted by replacing one or more hydrogen atoms by non-hydrogen groups described herein to the extent possible. These include, but are not limited to, halo, hydroxy, mercapto, amino, carboxy, cyano and carbamoyl.

The term "substituted" as used herein means that a given structure has a substituent which can be an alkyl, alkenyl, or aryl group as defined above. The term shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Examples of substituent groups include the functional groups described above, and halogens (i.e., F, Cl, Br, and I); alkyl groups, such as methyl, ethyl, n-propyl, isopropyl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethyl-benzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

In the compounds of the present invention, the substituents may be substituted or unsubstituted, unless specifically defined otherwise.

In the compounds of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, a "compound" is a small molecule that does not include proteins, peptides or amino acids.

As used herein, an "isolated" compound is a compound isolated from a crude reaction mixture or from a natural source following an affirmative act of isolation. The act of isolation necessarily involves separating the compound from the other components of the mixture or natural source, with some impurities, unknown side products and residual amounts of the other components permitted to remain. Purification is an example of an affirmative act of isolation.

"Administering to the subject" or "administering to the (human) patient" means the giving of, dispensing of, or application of medicines, drugs, or remedies to a subject/patient to relieve, cure, or reduce the symptoms associated with a condition, e.g., a pathological condition. The administration can be periodic administration. As used herein, "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times weekly and so on, etc.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

As used herein, "combination" means an assemblage of reagents for use in therapy either by simultaneous or contemporaneous administration. Simultaneous administration refers to administration of an admixture (whether a true mixture, a suspension, an emulsion or other physical combination) of the compound and the anti-cancer agent. The combination may be the admixture or separate containers that are combined just prior to administration. Contemporaneous administration refers to the separate administration, or at times sufficiently close together that a synergistic activity relative to the activity of either the alone is observed.

As used herein, "concomitant administration" or administering "concomitantly" means the administration of two agents given in close enough temporal proximately to allow the individual therapeutic effects of each agent to overlap.

As used herein, "add-on" or "add-on therapy" means an assemblage of reagents for use in therapy, wherein the subject receiving the therapy begins a first treatment regimen of one or more reagents prior to beginning a second treatment regimen of one or more different reagents in addition to the first treatment regimen, so that not all of the reagents used in the therapy are started at the same time.

The following delivery systems, which employ a number of routinely used pharmaceutical carriers, may be used but are only representative of the many possible systems envisioned for administering compositions in accordance with the invention.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's).

Other injectable drug delivery systems include solutions, suspensions, gels. Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

The compounds used in the method of the present invention may be in a salt form. As used herein, a "salt" is a salt of the instant compounds which has been modified by making acid or base salts of the compounds. In the case of compounds used to treat an infection or disease, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

As used herein, an "amount" or "dose" of an agent measured in milligrams refers to the milligrams of agent present in a drug product, regardless of the form of the drug product.

As used herein, the term "therapeutically effective amount" or "effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

Where a range is given in the specification it is understood that the range includes all integers and 0.1 units within that range, and any sub-range thereof. For example, a range of 77 to 90% is a disclosure of 77, 78, 79, 80, and 81% etc.

As used herein, "about" with regard to a stated number encompasses a range of +one percent to −one percent of the stated value. By way of example, about 100 mg/kg therefore includes 99, 99.1, 99.2, 99.3, 99.4, 99.5, 99.6, 99.7, 99.8, 99.9, 100, 100.1, 100.2, 100.3, 100.4, 100.5, 100.6, 100.7, 100.8, 100.9 and 101 mg/kg. Accordingly, about 100 mg/kg includes, in an embodiment, 100 mg/kg.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Abbreviations

ACN—Acetonitrile; $AUC_{last}$—Area under concentration-time curve from time 0 to the last quantifiable concentration; $AUC_{INF}$—Area under concentration-time curve from time 0 to infinity; BQL—Below quantifiable limit; CL—Clearance; $C_{max}$—Maximum plasma concentration; hr or Hr—Hour; IV Intravenous; kg—Kilogram; L—Liter; LC Liquid chromatography; LLOQ—Lower limit of quantification; MeOH Methanol; mg Milligram; MS—mass spectrometry; $NH_4OAc$—Ammonium acetate; PK—Pharmacokinetics PO—Oral; SD Standard deviation; $t_{1/2}$—Terminal half-life; $T_{max}$—Time to reach maximum plasma concentration; $V_{ss}$—Volume of distribution at steady-state Materials and Methods Representative Method for Preparation of Prodrugs:

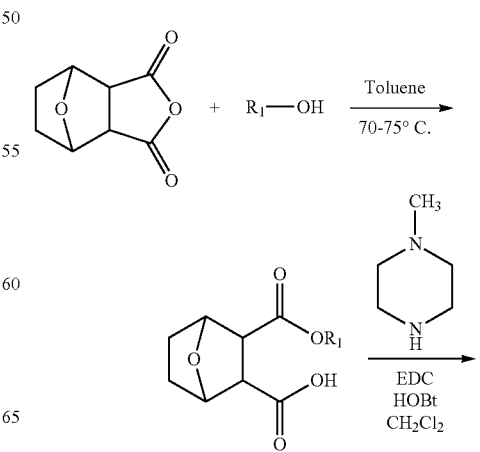

-continued

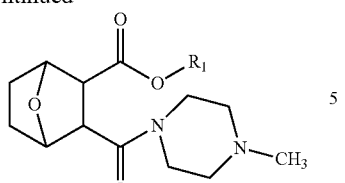

A mixture of exo-7-oxabicyclo[2.2.1]heptane-2,3-dicarboxylic anhydride (50.0 mmol) and the appropriate alkyl alcohol (110.0 mmol) in toluene is heated at 70-75° C. overnight. The reaction mixture is concentrated on rotary evaporator and the crude solid is triturated with 20 mL of isopropyl ether while heating, and filtered to give a solid. To the mixture of alkyl ester in methylene chloride is added N-hydroxybenzotriazole (5 mmol) followed by N-methylpiperazine (200 mmol) and EDC (75 mmol). The reaction mixture is stirred overnight at room temperature and evaporated to dryness. The product is purified by column chromatography and recrystallization.

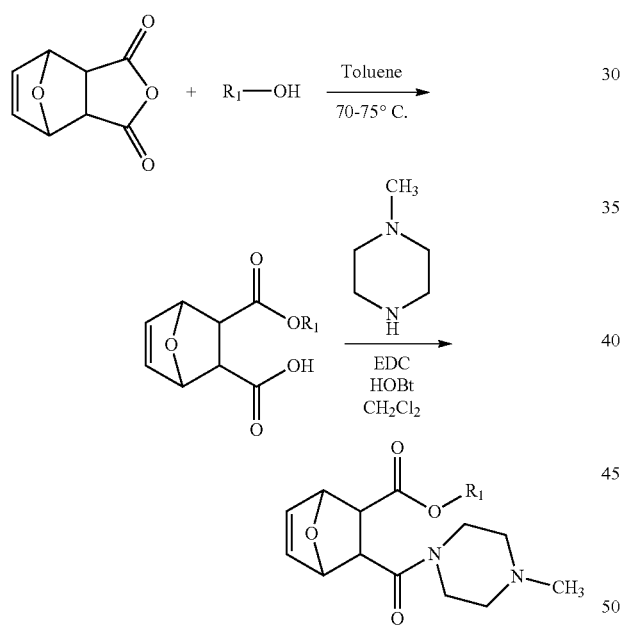

A mixture of exo-3,6-Epoxy-1,2,3,6-tetrahydrophthalic anhydride (50.0 mmol) and the appropriate alkyl alcohol (110.0 mmol) in toluene is heated at 70-75° C. overnight. The reaction mixture is concentrated on rotary evaporator and the crude solid is triturated with 20 mL of isopropyl ether while heating, and filtered to give a solid. To the mixture of alkyl ester in methylene chloride is added N-hydroxybenzotriazole (5 mmol) followed by N-methylpiperazine (200 mmol) and EDC (75 mmol). The reaction mixture is stirred overnight at room temperature and evaporated to dryness. The product is purified by column chromatography and recrystallization.

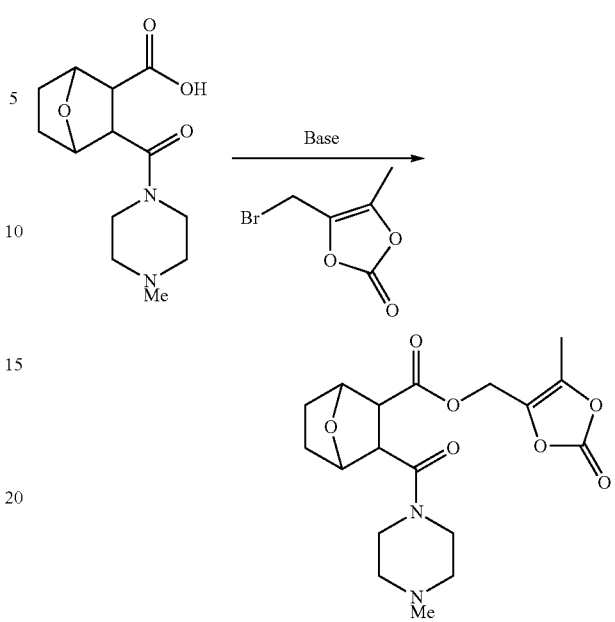

To the mixture of the acid in methylene chloride is added TEA (1 mmol) followed by the acid (1 mmol) and Alkyl bromide (1.5 mmol). The reaction mixture is stirred overnight at room temperature and evaporated to dryness. The product is purified by column chromatography and recrystallization to afford the pure prodrug.

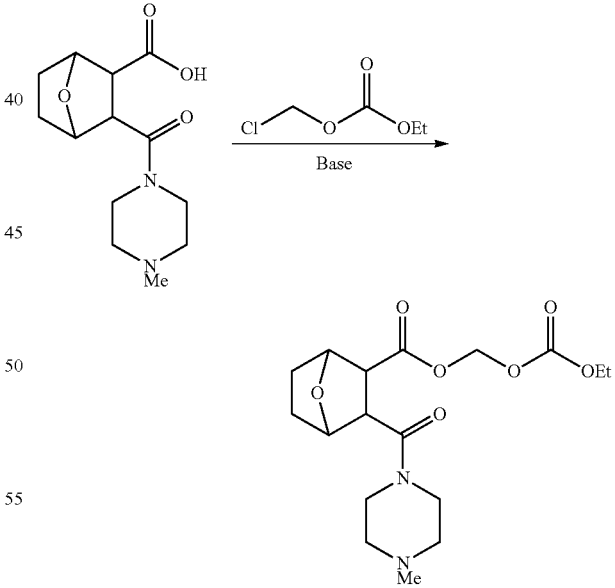

To the mixture of the acid in methylene chloride is added TEA (1 mmol) followed by the alkyl chloride (1.5 mmol). The reaction mixture is stirred overnight at room temperature and evaporated to dryness. The product is purified by column chromatography and recrystallization to afford the pure prodrug.

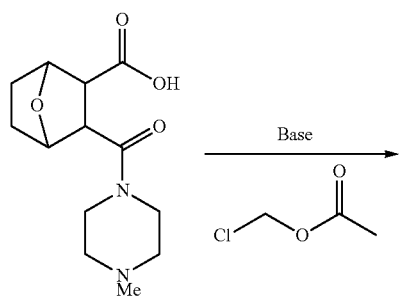

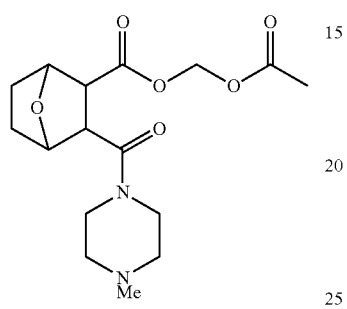

To the mixture of the acid in methylene chloride is added TEA (1 mmol) followed by the alkyl chloride (1.5 mmol). The reaction mixture is stirred overnight at room temperature and evaporated to dryness. The product is purified by column chromatography and recrystallization to afford the pure prodrug.

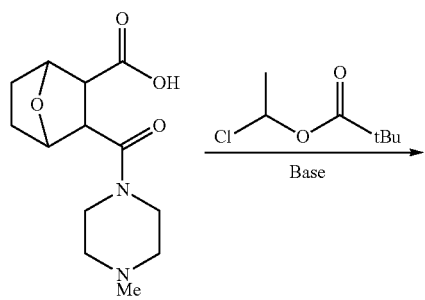

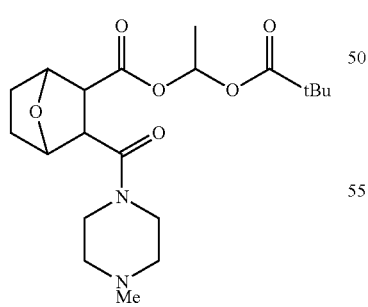

To the mixture of the acid in methylene chloride is added triethylamine (1 mmol) followed by the alkyl chloride (1 mmol). The reaction mixture is stirred overnight at room temperature and diluted with H₂O. The aqueous phase is extracted (3×) with dichloromethane. The combined organic layer are then washed (3×) with saturated sodium bicarbonate. The organic layer is then concentrated and purified by column chromatography and recrystallization to afford the pure prodrug.

Compound 100 has the structure:

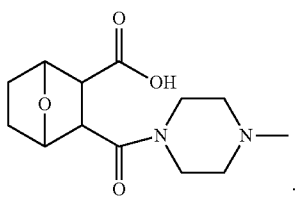

(LB100)

Compound 105 has the structure:

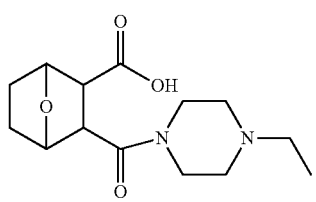

(LB105)

Compound 113 has the structure:

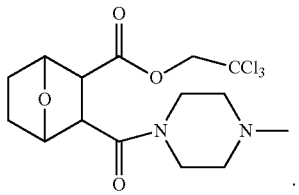

(LB113)

Compound 151 has the structure:

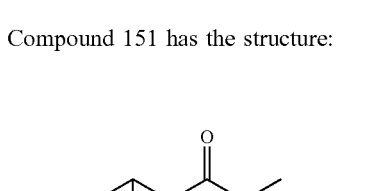

(LB151)

Compound 153 has the structure:

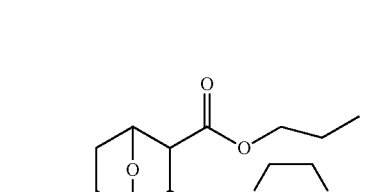

(LB153)

Compound 157 has the structure:

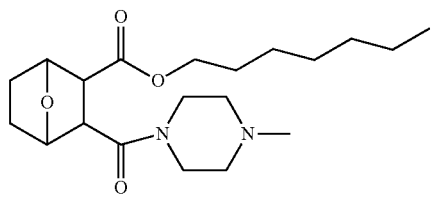
(LB157)

Example 1

Pharmacokinetic Study of Compounds 153 and 157

The pharmacokinetic studies on 153, 157 and its metabolite endothal were conducted in SD rats. 153 at 1.25 mg/kg and 157 at 1.5 mg/kg were administered via iv and po route into SD rats. The blood, liver and brain tissue samples were collected at predetermined times from rats. The LC/MS/MS methods were developed to determine 153, 157 and endothal in plasma, liver and brain samples. In the report, the concentrations of 153, 157 and endothal in plasma, liver and brain samples after iv dose were presented. The bioavailability of 153 and 157 was also calculated. Compound were diluted shortly before use in 4% sodium bicarbonate for sterile injection (this is the standard pediatric solution of NaHCO$_3$ with a pH of about 8.5).

A total of 30 female SD rats were assigned to this study as shown in the table below:

| Group | Cpds | Animal number | Route | Dose (mg/kg) | Volume (ml/kg) | 2 rats/Timepoint | Sampling |
|---|---|---|---|---|---|---|---|
| 1 | Control | 2 | | | | | |
| 2 | 153 | 12 | IV | 1.25 mg/kg | 5 ml/kg | 15 min, 1 hr, 2 hr, 6 hr 10 hr, 24 hr | Plasma, liver and brain tissue |
| 3 | 157 | 12 | IV | 1.5 mg/kg | 5 ml/kg | 15 min, 1 hr, 2 hr, 6 hr 10 hr, 24 hr | Plasma, liver and brain tissue |
| 4 | 153 | 2 | PO | 1.25 mg/kg | 5 ml/kg | 30 min, 1 hr, 2 hr, 6 hr 10 hr, 24 hr | Plasma |
| 5 | 157 | 2 | PO | 1.5 mg/kg | 5 ml/kg | 30 min, 1 hr, 2 hr, 6 hr 10 hr, 24 hr | Plasma |

Compound 153 was freshly prepared by diluting the drugs shortly before use in 4% sodium bicarbonate for sterile injection (this is the standard pediatric solution of NaHCO$_3$ with a pH of about 8.5). The final concentrations of 153 solutions were 0.25 mg/mL. The 153 solutions were administered via iv or po route at dose volume of 5 ml/kg according to the latest body weight. Compound 157 was freshly prepared by diluting the drugs shortly before use in 4% sodium bicarbonate for sterile injection (this is the standard pediatric solution of NaHCO$_3$ with a pH of about 8.5). The final concentrations of 153 solutions were 0.3 mg/mL. The 157 solutions were administered via iv or po route at dose volume of 5 ml/kg according to the latest body weight.

Twelve (12) female SD rats per group were dosed by iv with 153 or 157. The rats were fasted overnight prior to dosing, with free access to water. Foods were withheld for 2 hours post-dose. Blood, liver and brain tissue samples in two animals each group were collected at each time point, within 10% of the scheduled time for each time point. Two extra animals were used for analytic method development. Blood (>0.3 mL) were collected via aorta abdominalis in anaesthetic animals into tubes containing heparin at 15 min, 1, 2, 6, 10 and 24 hours after iv administration. Liver and brain tissues were collected immediately after animal death. The liver and brain tissues were excised and rinsed with cold saline to avoid blood residual. Upon collection, each sample was placed on ice and the blood samples were subsequently centrifuged (4° C., 11000 rpm, 5 min) to separate plasma. The obtained plasma, liver and brain tissue samples were stored at −70° C. until LC-MS/MS analysis.

Two (2) female SD rats per group were dosed by po with 153 or 157. The rats were fasted overnight prior to dosing, with free access to water. Foods were withheld for 2 hours post-dose. Blood samples (>0.3 mL) were collected via aorta abdominalis in anaesthetic animals into tubes containing heparin at 30 min, 1, 2, 6, 10 and 24 hours after po administration.

Preparation of Plasma, Liver and Brain Samples for Compound 153

Frozen unknown plasma samples were thawed at room temperature and vortexed thoroughly. With a pipette, 50 μL of plasma was transferred into a 1.5 mL Eppendorf tube. To each sample, 20 μL IS-D (for blank samples, 20 μL acetonitrile:water (1:1) was added) and 300 ul acetonitrile was added. The sample mixture was vortexed for approximately 3 min. After centrifugation at 10000 rpm for 5 min at 4° C., 100 μL of the upper layer was transferred to a new tube and added 200 μL 0.4% formic acid in water (pH 6.0). The mixture was vortexed for approximately 3 min before injected onto the LC/MS/MS system for analysis.

On the day of the assay, the frozen liver and brain samples were thawed unassisted at room temperature. An about 200 mg weighed sample of each thawed tissue was placed into a plastic tube with water (0.6 mL) to facilitate homogenization. Tissue processing was conducted using a homogenizer for approximately 1 min, 200 μl homogenate was transferred into a fresh Eppendorf tube. To each tube, 50 μL IS-D was added and mixed. Then 600 ul acetonitrile was added and the sample mixture was vortexed for approximately 3 min. After centrifugation at 10000 rpm for 5 min at 4° C., 400 μL of the upper layer was transferred to a new tube and evaporate the supernatant to dryness at 35° C. Reconstitute the residue with 200 μL of 0.4% formic acid in water (pH6.0), and vortex for 3 min, submit for LC-MS/MS analysis.

Preparation of Plasma, Liver and Brain Samples for Compound 157

Frozen unknown plasma samples were thawed at room temperature and vortexed thoroughly. With a pipette, 50 μL of plasma was transferred into a 1.5 mL Eppendorf tube. To each sample, 30 μL IS-D (for blank samples, 20 μL acetonitrile:water (1:1) was added) and 300 ul acetonitrile was added. The sample mixture was vortexed for approximately 3 min. After centrifugation at 10000 rpm for 5 min at 4° C., 100 µL of the upper layer was transferred to a new tube and added 200 µL 0.4% formic acid in water (pH6.0). The mixture was vortexed for approximately 3 min before injected onto the LC/MS/MS system for analysis.

On the day of the assay, the frozen liver and brain samples were thawed unassisted at room temperature. An about 200 mg weighed sample of each thawed tissue was placed into a plastic tube with water (0.6 mL) to facilitate homogenization. Tissue processing was conducted using a homogenizer for approximately 1 min, 100 µl homogenate was transferred into a fresh Eppendorf tube. To each tube, 50 µL IS-D was added and mixed. Then 500 ul acetonitrile was added and the sample mixture was vortexed for approximately 3 min. After centrifugation at 10000 rpm for 5 min at 4° C., 100 µL of the upper layer was transferred to a new tube and evaporate the supernatant to dryness at 35° C. Reconstitute the residue with 200 µL of 0.4% formic acid in water (pH 6.0), and vortex for 3 min, submit for LC-MS/MS analysis.

Preparation of Plasma, Liver and Brain Samples for Endothal

Frozen unknown plasma samples were completely thawed at room temperature and vortexed thoroughly. With a pipette, 50 µL of plasma was transferred into a 2.0 mL Eppendorf tube. 50 µL of 0.1N HCl and 800 µL ethyl acetate were added into each sample. The sample mixture was vortexed for approximately 3 min. After centrifugation at 10000 rpm for 5 min at 4° C., the 600 µl supernatant was transferred into a 1.5 mL Eppendorf tube. The precipitate were extracted with 800 µL ethyl acetate again and 600 µl supernatant was transferred into the same tube, and evaporated into dryness. The residue was reconstituted with 150 µL IS-D (for blank samples, 0.05% formic acid in acetonitrile), and vortexed for 3 min. submit for LC/MS/MS analysis. On the day of the assay, the frozen liver and brain tissues samples were thawed unassisted at room temperature. An about 200 mg weighed sample of each thawed tissue was placed into a plastic tube with water (0.6 mL) to facilitate homogenization. 150 µL of each homogenate was transferred into a fresh Eppendorf tube, 150 µL of 0.1N HCl and 800 µL of acetic ether were added into each homogenate sample. The sample mixture was vortexed and centrifuged at 10000 rpm for 5 min at 4° C. 600 µl supernatant was transferred into a 1.5 mL Eppendorf tube, the precipitate were extracted with 800 µL ethyl acetate again and 600 µl supernatant was transferred into the same tube, and evaporated into dryness. The residue was reconstituted with 200 µL IS-D (for blank samples, 0.05% formic acid in acetonitrile), and vortexed for 3 min. submit for LC/MS/MS analysis.

Preparation of Calibration Samples for Compound 153

1) Preparation of Calibration Samples for Plasma Samples Analysis

Calibration standards were prepared by spiking 25 µL of the 153 standard solutions into 25 µL of heparinized blank rat plasma. The nominal standard concentrations in mouse plasma were 2.00, 4.00, 10.0, 50.0, 100, 500, 900 and 1000 ng/mL.

2) Preparation of Calibration Samples for Liver and Brain Tissue Samples Analysis In order to quantify 153 in liver and brain tissue samples, a calibration curve consisting of 8 standard samples was prepared, using the same blank tissue homogenate as sample matrix analyzed (final concentrations: 1.00, 2.00, 5.00, 25.0, 50.0, 250, 450 and 500 ng/g).

Preparation of Calibration Samples for Compound 157

1) Preparation of Calibration Samples for Plasma Samples Analysis

Calibration standards were prepared by spiking 25 µL of the 157 standard solutions into 25 µL of heparinized blank rat plasma. The nominal standard concentrations in mouse plasma were 0.500, 1.00, 2.50, 12.5, 25.0, 125, 225 and 250 ng/mL.

2) Preparation of Calibration Samples for Liver and Brain Tissue Samples Analysis In order to quantify 157 in liver and brain tissue samples, a calibration curve consisting of 8 standard samples was prepared, using the same blank tissue homogenate as sample matrix analyzed (final concentrations: 0.500, 1.00, 2.50, 12.5, 25.0, 125, 225 and 250 ng/mL).

Preparation of Calibration Samples for Endothal

1) Preparation of Calibration Samples for Plasma Samples Analysis

Calibration standards were prepared by spiking 25 µL of the endothal standard solutions into 25 µL of heparinized blank rat plasma. The nominal standard concentrations in rat plasma were 20.0, 40.0, 100, 200, 400, 2000, 3600 and 4000 ng/mL.

2) Preparation of Calibration Samples for Liver Tissue Samples Analysis

In order to quantify endothal in liver tissue samples, a calibration curve consisting of 8 standard samples was prepared, using the same blank tissue homogenate as sample matrix analyzed (final concentrations: 20.0, 40.0, 100, 200, 400, 2000, 3600 and 4000 ng/g).

LC/MS/MS System

The analysis was performed using a LC-MS/MS system consisting of the following components: HPLC system: Shimadzu UFLC 20-AD XR; MS/MS system: API-5000 triple quadrupole mass spectrometer (Applied Biosystems); Data system: Watson LIMS version 7.2.

1) Chromatographic Conditions for Compound 153

| Analytical column: | Luna C18 5 µm, 50 × 2.0 mm |
|---|---|
| Mobile phase: | A: 0.4% formic acid in water (pH 6.0) |
| | B: Acetonitrile |
| Injection volume: | 20~30 µL |
| Run Time: | ~4.5 min |
| Flow Rate: | 0.5 mL/min |

| Time | 0 | 0.5 | 0.6 | 2.0 | 2.1 | 3.0 | 3.1 | 4.5 |
|---|---|---|---|---|---|---|---|---|
| % B | 15 | 15 | 45 | 45 | 95 | 95 | 15 | Stop |
| Divert Valve Position | Waste | MS | MS | MS | MS | Waste | | Waste |

2) Mass Spectrometric Conditions for Compound 153

| Parameters | 153 |
|---|---|
| Ion Spray (IS) | 5000 V |
| Curtain Gas (CUR) | 15 |
| Temperature (TEM) | 500° C. |
| Entrance Potential (EP) | 10 |
| Collision Gas (CAD) | 6 |
| Collision Cell Exit Potential (CXP) | 15 |
| Dwell Time (ms) | 100 |
| Gas 1 | 40 |
| Gas 2 | 40 |
| Declustering potential (DP) | 120 |
| Ionization Mode: | (+) ESI |

(CE):

| Compound | Precursor ion (m/z) | Product ion (m/z) | CE (eV) |
|---|---|---|---|
| 153 | 311.1 | 169.2 | 30 |
| Irbesartan (IS) | 429.4 | 207.2 | 30 |

1) Chromatographic Conditions for Compound 157

| | |
|---|---|
| Analytical column: | Luna C18 5 μm, 50 × 2.0 mm |
| Mobile phase: | A: 0.4% formic acid in water (pH 6.0) |
| | B: Acetonitrile |
| Injection volume: | 10 μL |
| Run Time: | ~4.5 min |
| Flow Rate: | 0.5 mL/min |

| Time | 0 | 0.5 | 2.0 | 2.1 | 3.0 | 3.1 | 4.0 |
|---|---|---|---|---|---|---|---|
| % B | 45 | 45 | 45 | 95 | 95 | 45 | Stop |
| Divert Valve Position | Waste | MS | MS | MS | Waste | | Waste |

2) Mass Spectrometric Conditions for Compound 157

| Parameters | 157 |
|---|---|
| Ion Spray (IS) | 5000 V |
| Curtain Gas (CUR) | 15 |
| Temperature (TEM) | 450° C. |
| Entrance Potential (EP) | 10 |
| Collision Gas (CAD) | 6 |
| Collision Cell Exit Potential (CXP) | 15 |
| Dwell Time (ms) | 100 |
| Gas 1 | 40 |
| Gas 2 | 40 |
| Declustering potential (DP) | 120 |
| Ionization Mode: | (+) ESI |

(CE):

| Compound | Precursor ion (m/z) | Product ion (m/z) | CE (eV) |
|---|---|---|---|
| 157 | 367.3 | 251.0 | 25 |
| Verapamil (IS) | 455.1 | 303.3 | 25 |

1) Chromatographic Conditions for Endothal

Chromatographic separation was carried out at room temperature.

| | |
|---|---|
| Analytical column: | Luna HILIC 5 μm, 100 × 2.0 mm |
| Mobile phase: | A: 0.1% formic acid in water |
| | B: Acetonitrile |
| Injection volume: | 5 μL |
| Run Time: | ~2.5 min |
| Flow Rate: | 0.6 mL/min |

| Time | 0 | 0.4 | 2.0 | 2.5 |
|---|---|---|---|---|
| % B | 88 | 88 | 88 | Stop |
| Divert Valve Position | Waste | MS | Waste | Waste |

2) Mass Spectrometric Conditions for Endothal

| Parameters | endothal |
|---|---|
| Ion Spray (IS) | −4500 V |
| Curtain Gas (CUR) | 20 |
| Temperature (TEM) | 450° C. |
| Entrance Potential (EP) | −10 |
| Collision Gas (CAD) | 6 |
| Collision Cell Exit Potential (CXP) | −10 |
| Dwell Time (ms) | 150 |
| Gas 1 | 45 |
| Gas 2 | 45 |
| Declustering potential (DP) | −80 |
| Ionization Mode: | (−) ESI |

(CE):

| Compound | Precursor ion (m/z) | Product ion (m/z) | CE (eV) |
|---|---|---|---|
| Endothal | 185 | 141 | −30 |
| PAH(IS) | 192.9 | 149 | −20 |

Quantification

Quantification was achieved by the external standard method for 153, 157 and endothal. Concentrations of the test article were calculated using a weighted least-squares linear regression ($W=1/x^2$).

Pharmacokinetic Interpretation

The pharmacokinetic parameters were evaluated using Watson LIMS (version 7.2), assuming a non-compartmental model for drug absorption and distribution.

$AUC_{0-t}$ ($AUC_{last}$) is the area under the plasma concentration-time curve from time zero to last sampling time, calculated by the linear trapezoidal rule.

$AUC_{0-\infty}$ ($AUC_{INF}$) is the area under the plasma concentration-time curve with last concentration extrapolated based on the elimination rate constant.

Results

The calibration curve of 153 in rat plasma was linear throughout the study in the range of 2.00-1000 ng/mL. The linear equation and the correlation coefficient of calibration curve is $y=0.0252x+0.0127$ and $R^2=0.9957$.

The calibration curve of 100 in the tested tissues was linear throughout the study in the range of 1.00-500 ng/g. The linear equation and the correlation coefficient of calibration curve is $y=0.0233x+0.0213$ and $R^2=0.9939$.

The calibration curve of 157 in rat plasma was linear throughout the study in the range of 0.50-250 ng/mL. The linear equation and the correlation coefficient of calibration curve is $y=0.333x-0.0136$ and $R^2=0.9986$.

The calibration curve of 157 in the tested tissues was linear throughout the study in the range of 0.50-250 ng/g. The linear equation and the correlation coefficient of calibration curve is $y=0.0467x+0.0034$ and $R^2=0.9989$.

The calibration curves of endothal in rat plasma were linear throughout the study in the range of 20.0-4000 ng/mL. The linear equation and the correlation coefficient of calibration curve is $y=0.00155x-0.00162$ and $R^2=0.9986$.

The calibration curves of endothal in rat liver tissues were linear throughout the study in the range of 20.0-4000 ng/g. The linear equation and the correlation coefficient of calibration curve are y=0.00349x+0.0177 and $R^2$=0.997.

Following single iv & po administration of 153 to SD rats, plasma, liver and brain tissue concentrations of both 153 and endothal were determined by the LC/MS/MS method described above. The plasma, liver and brain tissue concentrations at each sampling time are listed in Tables 6.1-6.8 and FIGS. 1A-1B. The calculated pharmacokinetic parameters are listed in Table 6.9-6.12.

153 was orally available at 1.25 mg/kg to SD rats, the $C_{max}$ was 239 ng/mL, AUC was 164 ng·h/ml, and the BA is 55.41%.

The mean $C_{max}$ in plasma was 557 ng/ml following iv administration of 153. The mean $C_{max}$ in liver and brain were 762.0 ng/kg and 42.7 ng/kg, respectively. $AUC_{last}$ in plasma was 295 ng·h/ml, with 500 ng·h/g in liver and 39.4 ng·h/g in brain, respectively. $T_{1/2}$ in plasma, liver and brain were 0.921 h, 0.626 h and 0.596 h, respectively.

As shown in Table 6.5-6.8 and FIG. 1B, endothal was detectable in plasma and liver samples following single iv administration of 153 at 1.25 mg/kg, whereas not detectable in brain samples. The mean $C_{max}$ in plasma and liver were 70.5 ng/ml and 2068 ng/ml, respectively. $AUC_{last}$ in plasma and liver were 378 ng·h/ml and 10820 ng·h/g, respectively. $T_{1/2}$ in plasma and liver were 5.20 h and 2.79 h, respectively.

Following single iv & po administration of 157 to SD rats, plasma, liver and brain tissue concentrations of both 157 and endothal were determined by the LC/MS/MS method described above. The plasma, liver and brain tissue concentrations at each sampling time are listed in Tables 6.13-6.20 and FIG. 1C-1D. The calculated pharmacokinetic parameters are listed in Table 6.21-6.24. 157 was poorly orally available at 1.5 mg/kg to SD rats, the $C_{max}$ was 6.14 ng/mL, AUC was 3.2 ng·h/ml, and the BA was 6.98%.

The mean $C_{max}$ in plasma was 115 ng/ml following iv administration of 157 at 1.5 mg/kg to SD rats. The mean Cmax in liver and brain were 297 ng/kg and 60.0 ng/kg, respectively. $AUC_{last}$ in plasma was 47.2 ng·h/ml, with 152 ng·h/g in liver and 24.6 ng·h/g in brain, respectively. $T_{1/2}$ in plasma, liver and brain were 0.391 h, 0.813 h and 0.162 h, respectively.

As shown in table 6.17-6.20 and FIG. 1D, endothal was detectable in plasma and liver samples following single iv administration of 157 at 1.5 mg/kg, whereas endothal was not detectable in brain samples. The mean $C_{max}$ in plasma and liver were 98.1 ng/ml and 3720 ng/ml, respectively. $AUC_{last}$ in plasma and liver were 374 ng·h/ml and 15025 ng·h/g, respectively. $T_{1/2}$ in plasma and liver were 5.94 h and 2.61 h, respectively.

153 was orally available at 1.25 mg/kg to SD rats, the $C_{max}$ was 239 ng/mL, AUC was 164 ng·h/ml, and the BA was 55.41%. The mean $C_{max}$ in plasma was 557 ng/ml following iv administration of 153. The mean $C_{max}$ in liver and brain were 762.0 ng/kg and 42.7 ng/kg, respectively. $AUC_{last}$ in plasma was 295 ng·h/ml, with 500 ng·h/g in liver and 39.4 ng·h/g in brain, respectively. $T_{1/2}$ in plasma, liver and brain were 0.921 h, 0.626 h and 0.596 h, respectively.

Endothal was detectable in plasma and liver samples following single iv administration of 153 at 1.25 mg/kg. The mean $C_{max}$ in plasma and liver were 70.5 ng/ml and 2068 ng/ml, respectively. $AUC_{last}$ in plasma and liver were 378 ng·h/ml and 10820 ng·h/g, respectively. $T_{1/2}$ in plasma and liver were 5.20 h and 2.79 h, respectively. However, endothal was undetectable in brain tissue.

157 was poorly orally available at 1.5 mg/kg to SD rats, the $C_{max}$ was 6.14 ng/mL, AUC was 3.2 ng·h/ml, and the BA was 6.98%.

The mean $C_{max}$ in plasma was 115 ng/ml following iv administration of 157 at 1.5 mg/kg to SD rats. The mean $C_{max}$ in liver and brain were 297 ng/kg and 60.0 ng/kg, respectively. $AUC_{last}$ in plasma was 47.2 ng·h/ml, with 152 ng·h/g in liver and 24.6 ng·h/g in brain, respectively. $T_{1/2}$ in plasma, liver and brain were 0.391 h, 0.813 h and 0.162 h, respectively.

Endothal was detectable in plasma and liver samples following single iv administration of 157 at 1.5 mg/kg. The mean $C_{max}$ in plasma and liver were 98.1 ng/ml and 3720 ng/ml, respectively. $AUC_{last}$ in plasma and liver were 374 ng·h/ml and 15025 ng·h/g, respectively. $T_{1/2}$ in plasma and liver were 5.94 h and 2.61 h, respectively. However, endothal was undetectable in brain tissue.

TABLE 6.1

Analytical data of 153 plasma concentration (ng/mL) in SD rats following PO administration.
1.25 mg/kg Liver concentration (ng/g)

| Time (hr) | Rat 1 | Rat 2 | Mean | SD |
|---|---|---|---|---|
| 0.25 | 872 | 652 | 762 | 155.6 |
| 1 | 131 | 121 | 126 | 7.1 |
| 2 | 42 | 41.2 | 41.6 | 0.6 |
| 6 | BLQ | BLQ | NA | NA |
| 10 | BLQ | ND | NA | NA |
| 24 | ND | ND | NA | NA |

TABLE 6.2

Analytical data of 153 plasma concentration (ng/mL) in SD rats following iv administration.
1.25 mg/kg Plasma concentration (ng/ml)

| Time (hr) | Rat 1 | Rat 2 | Mean | SD |
|---|---|---|---|---|
| 0.25 | 563 | 550 | 557 | 9.2 |
| 1 | 58 | 51.4 | 54.7 | 4.7 |
| 2 | 14.8 | 13 | 13.9 | 1.3 |
| 6 | 1.04 | 1.02 | 1.03 | 0 |
| 10 | ND | 9.42* | NA | NA |
| 24 | ND | ND | NA | NA |

*Conc. was 9.42 ng/mL, which was abnormal and did not include in the calculation.

TABLE 6.3

Analytical data of 153 liver concentration (ng/g) in SD rats following iv administration.
1.25 mg/kg Liver concentration (ng/g)

| Time (hr) | Rat 1 | Rat 2 | Mean | SD |
|---|---|---|---|---|
| 0.25 | 872 | 652 | 762 | 155.6 |
| 1 | 131 | 121 | 126 | 7.1 |
| 2 | 42 | 41.2 | 41.6 | 0.6 |
| 6 | BLQ | BLQ | NA | NA |
| 10 | BLQ | ND | NA | NA |
| 24 | ND | ND | NA | NA |

TABLE 6.4

Analytical data of 153 brain concentration (ng/g) in SD rats following iv administration.
1.25 mg/kg Brain concentration (ng/g)

| Time (hr) | Rat 1 | Rat 2 | Mean | SD |
|---|---|---|---|---|
| 0.25 | 45 | 40.3 | 42.7 | 3.3 |
| 1 | 13.9 | 14.3 | 14.1 | 0.3 |
| 2 | 4.05 | 4.75 | 4.4 | 0.5 |
| 6 | ND | ND | NA | NA |
| 10 | ND | ND | NA | NA |
| 24 | ND | ND | NA | NA |

TABLE 6.5

Analytical data of endothal plasma concentration (ng/ml) in SD rats following po administration of 153.
Endothal plasma concentration (ng/ml)

| Time (hr) | Rat 1 | Rat 2 | Mean | SD |
|---|---|---|---|---|
| 0.25 | 41.4 | 40.2 | 40.8 | 0.8 |
| 1 | 53.6 | 38.9 | 46.3 | 10.4 |
| 2 | 34.5 | 35.3 | 34.9 | 0.6 |
| 6 | 25.8 | 20.8 | 23.3 | 3.5 |
| 10 | BLQ | ND | NA | NA |
| 24 | ND | ND | NA | NA |

TABLE 6.6

Analytical data of endothal plasma concentration (ng/ml) in SD rats following iv administration of 153.
Endothal plasma concentration (ng/ml)

| Time (hr) | Rat 1 | Rat 2 | Mean | SD |
|---|---|---|---|---|
| 0.25 | 70.9 | 63.8 | 67.4 | 5 |
| 1 | 57.1 | 44.3 | 50.7 | 9.1 |
| 2 | 77.1 | 56.1 | 66.6 | 14.8 |
| 6 | 42.2 | 35.4 | 38.8 | 4.8 |
| 10 | 21.7 | BLQ | NA | NA |
| 24 | BLQ | BLQ | NA | NA |

TABLE 6.7

Analytical data of endothal liver concentration (ng/g) in SD rats following iv administration of 153.
Endothal liver concentration (ng/g)

| Time (hr) | Rat 1 | Rat 2 | Mean | SD |
|---|---|---|---|---|
| 0.25 | 1524 | 956 | 1240 | 401.6 |
| 1 | 1836 | 2012 | 1924 | 124.5 |
| 2 | 1912 | 2224 | 2068 | 220.6 |
| 6 | 492 | 980 | 736 | 345.1 |
| 10 | 301 | 256 | 279 | 31.8 |
| 24 | ND | ND | NA | NA |

TABLE 6.8

Analytical data of endothal brain concentration (ng/g) in SD rats following iv administration of 153.
Endothal brain concentration (ng/g)

| Time (hr) | Rat 1 | Rat 2 | Mean | SD |
|---|---|---|---|---|
| 0.25 | ND | ND | NA | NA |
| 1 | ND | ND | NA | NA |
| 2 | ND | ND | NA | NA |
| 6 | ND | ND | NA | NA |
| 10 | ND | ND | NA | NA |
| 24 | ND | ND | NA | NA |

TABLE 6.9

Main pharmacokinetic parameters of 153 in SD rats following iv or po administration.

| Dosage | Plasma PK Parameters | $C_{max}$ ng/mL | $T_{max}$ Hours | AUC ng*Hours/mL | $AUC_{0-\infty}$ ng*Hours/mL | MRT (0-t) Hours | $T_{1/2}$ Hours | F % |
|---|---|---|---|---|---|---|---|---|
| 1.25 mg/kg (PO Group) | 1 | 249 | 0.5 | 163 | 163 | 0.987 | 0.33 | |
| | 2 | 229 | 0.5 | 164 | 164 | 1.04 | 0.355 | |
| | Mean | 239 | 0.5 | 164 | 164 | 1.01 | 0.343 | 55.41 |
| 1.25 mg/kg (IV Group) | 1 | 563 | 0.25 | 303 | 303 | 0.666 | 0.907 | |
| | 2 | 550 | 0.25 | 288 | 288 | 0.647 | 0.934 | |
| | Mean | 557 | 0.25 | 295 | 296 | 0.657 | 0.921 | |

TABLE 6.10

Main pharmacokinetic parameters of 153 in liver & brain of SD rats following iv or po administration.

| TA | Dosage | Group | Plasma PK Parameters | $C_{max}$ ng/mL | $T_{max}$ Hrs | AUC ng*Hrs/mL | $AUC_{0-\infty}$ ng*Hrs/mL | MRT (0-t) Hrs | $T_{1/2}$ Hrs |
|---|---|---|---|---|---|---|---|---|---|
| End. | 153 1.25 | PO | 1 | 53.6 | 1 | 189 | 395 | 2.8 | 5.53 |
| | | | 2 | 40.2 | 0.5 | 169 | 333 | 2.72 | 5.45 |

TABLE 6.10-continued

Main pharmacokinetic parameters of 153 in liver &
brain of SD rats following iv or po administration.

| TA | Dosage | Group | Plasma PK Parameters | $C_{max}$ ng/mL | $T_{max}$ Hrs | AUC ng*Hrs/mL | $AUC_{0-\infty}$ ng*Hrs/mL | MRT (0-t) Hrs | $T_{1/2}$ Hrs |
|---|---|---|---|---|---|---|---|---|---|
| | mg/kg | | Mean | 46.9 | 0.75 | 179 | 364 | 2.76 | 5.49 |
| | 153 | IV | 1 | 77.1 | 2 | 482 | 618 | 3.93 | 4.37 |
| | 1.25 | | 2 | 63.8 | 0.25 | 274 | 581 | 2.74 | 6.02 |
| | mg/kg | | Mean | 70.5 | 1.13 | 378 | 600 | 3.34 | 5.2 |

TABLE 6.11

Main pharmacokinetic parameters of Endothal in SD rats
following single iv or po administration of 153.

| Group | PK Parameters | $C_{max}$ ng/mL | $T_{max}$ Hours | AUC ng*Hours/mL | $AUC_{0-\infty}$ ng*Hours/mL | MRT (0-t) Hours | $T_{1/2}$ Hours |
|---|---|---|---|---|---|---|---|
| Liver | 1 | 872 | 0.25 | 547 | 547 | 0.745 | 0.609 |
| 1.25 | 2 | 652 | 0.25 | 453 | 453 | 0.825 | 0.643 |
| mg/kg IV | Mean | 762 | 0.25 | 500 | 500 | 0.785 | 0.626 |
| Brain | 1 | 45 | 0.25 | 39.2 | 39.2 | 0.934 | 0.562 |
| 1.25 | 2 | 40.3 | 0.25 | 39.5 | 39.5 | 1.01 | 0.629 |
| mg/kg IV | Mean | 42.7 | 0.25 | 39.4 | 39.35 | 0.972 | 0.596 |

TABLE 6.12

Main pharmacokinetic parameters of Endothal in SD rats liver
& brain following single iv administration of 153.

| TA | Dosage | PK Parameters | $C_{max}$ ng/mL | $T_{max}$ Hrs | AUC ng*Hrs/mL | $AUC_{0-\infty}$ ng*Hrs/mL | MRT (0-t) Hrs | $T_{1/2}$ Hrs |
|---|---|---|---|---|---|---|---|---|
| End. | 153 | 1 | 1912 | 2 | 9528 | 10800 | 3.05 | 3 |
| | 1.25 mg/ | 2 | 2224 | 2 | 12112 | 13100 | 3.43 | 2.57 |
| | kg | Mean | 2068 | 2 | 10820 | 11950 | 3.24 | 2.79 |
| | (Liver Group) | | | | | | | |
| | 153 | 1 | NA | NA | NA | NA | NA | NA |
| | 1.25 mg/ | 2 | NA | NA | NA | NA | NA | NA |
| | kg | Mean | NA | NA | NA | NA | NA | NA |
| | (Brian Group) | | | | | | | |

TABLE 6.13

Analytical data of 157 plasma concentration (ng/mL)
in SD rats following PO administration.
1.5 mg/kg Plasma concentration (ng/ml)

| Time (hr) | Rat 1 | Rat 2 | Mean | SD |
|---|---|---|---|---|
| 0.5 | 5.92 | 6.35 | 6.14 | 0.3 |
| 1 | 1.48 | 1.26 | 1.37 | 0.2 |
| 2 | 0.303 | 0.194 | 0.249 | 0.1 |
| 6 | ND | ND | NA | NA |
| 10 | ND | ND | NA | NA |
| 24 | ND | ND | NA | NA |

TABLE 6.14

Analytical data of 157 plasma concentration (ng/mL)
in SD rats following iv administration.
1.5 mg/kg Plasma concentration (ng/ml)

| Time (hr) | Rat 1 | Rat 2 | Mean | SD |
|---|---|---|---|---|
| 0.25 | 116 | 114 | 115 | 1.4 |
| 1 | 2.67 | 3.57 | 3.12 | 0.6 |
| 2 | 0.491 | 0.556 | 0.524 | 0 |
| 6 | ND | ND | NA | NA |
| 10 | ND | ND | NA | NA |
| 24 | ND | ND | NA | NA |

TABLE 6.15

Analytical data of 157 liver concentration (ng/g) in SD rats following iv administration.
1.5 mg/kg Liver concentration (ng/g)

| Time (hr) | Rat 1 | Rat 2 | Mean | SD |
|---|---|---|---|---|
| 0.25 | 337 | 257 | 297 | 56.6 |
| 1 | 29.4 | 17.6 | 23.5 | 8.3 |
| 2 | 6.40 | 9.72 | 8.06 | 2.3 |
| 6 | ND | ND | NA | NA |
| 10 | ND | BLQ | NA | NA |
| 24 | ND | ND | NA | NA |

TABLE 6.16

Analytical data of 157 brain concentration (ng/g) in SD rats following iv administration.
1.5 mg/kg Brain concentration (ng/g)

| Time (hr) | Rat 1 | Rat 2 | Mean | SD |
|---|---|---|---|---|
| 0.25 | 60.0 | 60.0 | 60.0 | 0.0 |
| 1 | 1.99 | 2.80 | 2.40 | 0.6 |
| 2 | BLQ | BLQ | NA | NA |
| 6 | ND | ND | NA | NA |
| 10 | ND | ND | NA | NA |
| 24 | ND | ND | NA | NA |

TABLE 6.17

Analytical data of endothal plasma concentration (ng/ml) in SD rats following po administration of 157.
Endothal plasma concentration (ng/ml)

| Time (hr) | Rat 1 | Rat 2 | Mean | SD |
|---|---|---|---|---|
| 0.25 | 93.5 | 65.4 | 79.5 | 19.9 |
| 1 | 91.8 | 150 | 121 | 41.2 |
| 2 | 142 | 68.9 | 105 | 51.7 |
| 6 | 22.7 | 31.9 | 27.3 | 6.5 |
| 10 | BLQ | BLQ | NA | NA |
| 24 | ND | ND | NA | NA |

TABLE 6.18

Analytical data of endothal plasma concentration (ng/ml) in SD rats following iv administration of 157.
Endothal plasma concentration (ng/ml)

| Time (hr) | Rat 1 | Rat 2 | Mean | SD |
|---|---|---|---|---|
| 0.25 | 76.4 | 53.4 | 64.9 | 16.3 |
| 1 | 113 | 83.2 | 98.1 | 21.1 |
| 2 | 91.5 | 45.7 | 68.6 | 32.4 |
| 6 | 47.7 | 45 | 46.4 | 1.9 |
| 10 | BLQ | BLQ | NA | NA |
| 24 | BLQ | BLQ | NA | NA |

TABLE 6.19

Analytical data of endothal liver concentration (ng/g) in SD rats following iv administration of 157.
Endothal liver concentration (ng/g)

| Time (hr) | Rat 1 | Rat 2 | Mean | SD |
|---|---|---|---|---|
| 0.25 | 3676 | 3536 | 3606 | 99.0 |
| 1 | 3124 | 3764 | 3444 | 452.5 |
| 2 | 2484 | 2272 | 2378 | 149.9 |
| 6 | 1000 | 1076 | 1038 | 53.7 |
| 10 | 218 | 344 | 281 | 89.1 |
| 24 | ND | ND | NA | NA |

TABLE 6.20

Analytical data of endothal brain concentration (ng/g) in SD rats following iv administration of 157.
Endothal brain concentration (ng/g)

| Time (hr) | Rat 1 | Rat 2 | Mean | SD |
|---|---|---|---|---|
| 0.25 | ND | ND | NA | NA |
| 1 | ND | ND | NA | NA |
| 2 | ND | ND | NA | NA |
| 6 | ND | ND | NA | NA |
| 10 | ND | ND | NA | NA |
| 24 | ND | ND | NA | NA |

TABLE 6.21

Main pharmacokinetic parameters of 157 in SD rats following iv or po administration.

| Dosage | Group | Plasma PK Parameters | $C_{max}$ ng/mL | $T_{max}$ Hrs | AUC ng*Hrs/mL | $AUC_{0-\infty}$ ng*Hrs/mL | MRT (0-t) Hrs | $T_{1/2}$ Hrs | F % |
|---|---|---|---|---|---|---|---|---|---|
| 1.5 mg/kg | PO | 1 | 5.92 | 0.5 | 3.4 | 3.4 | 0.988 | 0.437 | |
| | | 2 | 6.35 | 0.5 | 3 | 3 | 0.903 | 0.37 | |
| | | Mean | 6.14 | 0.5 | 3.2 | 3.2 | 0.946 | 0.404 | 6.78 |
| | IV | 1 | 116 | 0.25 | 47.1 | 47.1 | 0.333 | 0.409 | |
| | | 2 | 114 | 0.25 | 47.3 | 47.3 | 0.349 | 0.373 | |
| | | Mean | 115 | 0.25 | 47.2 | 47.2 | 0.341 | 0.391 | |

TABLE 6.22

Main pharmacokinetic parameters of 157 in SD rats liver & brain following iv administration.

| Dosage | Tissues | PK Parameters | $C_{max}$ ng/mL | $T_{max}$ Hrs | AUC ng*Hrs/mL | $AUC_{0-\infty}$ ng*Hrs/mL | MRT (0-t) Hrs | $T_{1/2}$ Hrs |
|---|---|---|---|---|---|---|---|---|
| 1.5 mg/kg | Liver | 1 | 337 | 0.25 | 168 | 168 | 0.531 | 0.455 |
| | | 2 | 257 | 0.25 | 136 | 136 | 0.647 | 1.17 |

TABLE 6.22-continued

Main pharmacokinetic parameters of 157 in SD rats liver & brain following iv administration.

| Dosage | Tissues | PK Parameters | $C_{max}$ ng/mL | $T_{max}$ Hrs | AUC ng*Hrs/mL | $AUC_{0-\infty}$ ng*Hrs/mL | MRT (0-t) Hrs | $T_{1/2}$ Hrs |
|---|---|---|---|---|---|---|---|---|
| | | Mean | 297 | 0.25 | 152 | 152 | 0.589 | 0.813 |
| | Brain | 1 | 60 | 0.25 | 24.2 | 24.2 | 0.305 | 0.153 |
| | | 2 | 60 | 0.25 | 25 | 25 | 0.323 | 0.17 |
| | | Mean | 60 | 0.25 | 24.6 | 24.6 | 0.314 | 0.162 |

TABLE 6.23

Main pharmacokinetic parameters of Endothal in SD rats following single iv & po administration of 157.

| TA | Dosage | Group | Plasma PK Parameters | $C_{max}$ ng/mL | $T_{max}$ Hours | AUC ng*Hours/mL | $AUC_{0-\infty}$ ng*Hours/mL | MRT (0-t) Hours | $T_{1/2}$ Hours |
|---|---|---|---|---|---|---|---|---|---|
| Endothal | 157 (1.25 mg/kg) | PO | 1 | 142 | 2 | 492.6 | 542 | 2.15 | 1.51 |
| | | | 2 | 150 | 1 | 365 | 481 | 2.32 | 2.51 |
| | | | Mean | 146 | 1.5 | 429 | 512 | 2.24 | 2.01 |
| | 157 (1.25 mg/kg) | IV | 1 | 113 | 1 | 452 | 733 | 2.52 | 4.08 |
| | | | 2 | 83.2 | 1 | 297 | 803 | 2.85 | 7.8 |
| | | | Mean | 98.1 | 1 | 374 | 768 | 2.69 | 5.94 |

TABLE 6.24

Main pharmacokinetic parameters of Endothal in SD rats liver & brain following single iv administration of 157.

| TA | Dosage | Tissues | PK Parameters | $C_{max}$ ng/mL | $T_{max}$ Hrs | AUC ng*Hrs/mL | $AUC_{0-\infty}$ ng*Hrs/mL | MRT (0-t) Hrs | $T_{1/2}$ Hrs |
|---|---|---|---|---|---|---|---|---|---|
| Endothal | 157 (1.25 mg/kg IV) | Liver | 1 | 3676 | 0.25 | 14759 | 15500 | 2.97 | 2.28 |
| | | | 2 | 3764 | 1 | 15292 | 16700 | 3.12 | 2.94 |
| | | | Mean | 3720 | 0.625 | 15025 | 16100 | 3.05 | 2.61 |
| | | Brain | 1 | NA | NA | NA | NA | NA | NA |
| | | | 2 | NA | NA | NA | NA | NA | NA |
| | | | Mean | NA | NA | NA | NA | NA | NA |

Example 2

Pharmacokinetic Study of Compound 105

The purpose of this study was to determine the pharmacokinetics parameters of 105 and endothal in plasma and liver following single intravenous administration of 105 to male SD rats. 105 was dissolved in 4% $NaHCO_3$ in saline for IV administration. The detailed procedure of dosing solution preparation was presented in Appendix I.

Animal Source:

| Species | Gender | Vendor | Certificate No. |
|---|---|---|---|
| SD rats | Male | SLAC Laboratory Animal Co. LTD | SCXK (SH) 2007-0005 |

Thirteen (13) animals were placed on the study. The animals in IV arm were free access to food and water. One extra animal was used for blank liver and plasma generation (5 mL per animal). The resulting blank liver and plasma was then applied to the development of bioanalytical method and sample bioanalysis for the entire study.

| | | | | | | | In-life Study Design |
|---|---|---|---|---|---|---|---|

| Treatment Group | Body Weight (g) | No. of Animals | Route of Admin. | Dose Level* (mg/kg) | Dose Conc. (mg/mL) | Dose Volume (mL/kg) | Time points |
|---|---|---|---|---|---|---|---|
| 1 | 220-255 | 12 | IV | 1 | 1 | 1 | Sampling at 0.25, 1, 2, 6, 10 and 24 hr post dose. |

In-life Study Design

| Treatment Group | Body Weight (g) | No. of Animals | Route of Admin. | Dose Level* (mg/kg) | Dose Conc. (mg/mL) | Dose Volume (mL/kg) | Time points |
|---|---|---|---|---|---|---|---|
| | | | | | | | Terminally collect plasma and liver samples from the same animal. |

*Dose was expressed as free base of 105.

Dosing, Sampling, Sample Processing and Sample Storage

The IV injection was conducted via foot dorsal vein. Animals were free access to food and water before dose.

The animal is restrained manually. Approximately 150 μL of blood/time point is collected into sodium heparin tube via cardiac puncture for terminal bleeding (anesthetized under carbon dioxide). Blood sample will be put on ice and centrifuged to obtain plasma sample (2000 g, 5 min under 4° C.) within 10 minutes.

The animal will be euthanized with carbon dioxide inhalation. Open abdominal cavity with scissor to expose internal organs. Hold the carcass in an upright position and allow the organs to fall forward. Cut the connective tissues and remove the organs. Then the organs are rinsed with cold saline, dried on filtrate paper, placed into a screw-top tube and weighed, snap frozen by placing into dry-ice immediately.

Plasma and liver samples were stored at approximately −80° C. until analysis. The backup samples will be discarded after three weeks after in-life completion unless requested. The unused dosing solutions will be discarded within three weeks after completion of the study

LC-MS-MS Analysis Analytical Method for 105

| | |
|---|---|
| Instrument | UPLC/MS-MS-010 (API-4000) |
| Matrix | SD rat plasma and liver homogenate |
| Analyte(s) | Compound 105 |
| Internal standard(s) | Dexamethasone |
| MS conditions | ESI: Positive ion<br>MRM detection<br>LB-105: [M + H]$^+$ m/z 283.3→ 265.2<br>Dexamethasone: [M + H]$^+$ m/z 393.3 ® 373.1<br>Mobile Phase A: H$_2$0-0.1% FA-5 mM NH$_4$OAc<br>Mobile Phase B: ACN |

| Time (min) | Mobile Phase B (%) |
|---|---|
| 0.20 | 2.00 |
| 1.00 | 95.0 |
| 1.60 | 95.0 |
| 1.61 | 2.00 |
| 2.20 | stop |

| | |
|---|---|
| HPLC conditions | Column: ACQUITY UPLC HSS T3 (2.1 × 50 mm, 1.8 μm)<br>Flow rate: 0.60 mL/min<br>Column temperature: 60° C.<br>Retention time:<br>LB-105: 0.97 min<br>Dexamethasone: .1.25 min<br>For plasma samples: An aliquot of 30 μL sample was added with 100 μL IS (Dexamethasone, 100 ng/mL in ACN). The mixture was vortexed for 10 min at 750 rpm and centrifuged at 6000 rpm for 10 min. An aliquot of 3 μL supernatant was injected for LC-MS/MS analysis.<br>For diluted samples: An aliquot of 3 μL plasma sample was diluted with 27 μL blank plasma. |

LC-MS-MS Analysis Analytical Method for 105

| | |
|---|---|
| | The following processing procedure was the same as those un-diluted plasma samples. For all the samples preparation, allow calibration, quality control, blanks, and test samples to thaw at 4° C. (nominal). And keep each step on an ice bath or at 4° C. |
| Calibration curve | 10.00-3000 ng/mL for LB-105 in SD rat plasma and liver homogenate. |

LC-MS-MS Analysis Analytical Method for Endothal

| | |
|---|---|
| Instrument | UPLC/MS-MS-015 (API-5500, Q-trap) |
| Matrix | SD rat plasma and liver homogenate |
| Analyte(s) | Endothal |
| Internal standard(s) | Diclofenac |
| MS conditions | ESI: Negative ion<br>MRM detection<br>Endothal: [M − H]− m/z 184.9 → 141.0<br>Diclofenac: [M − H]− m/z 294.2 → 249.9<br>Mobile Phase A: H$_2$0-0.1% FA-5 mM NH$_4$OAc<br>Mobile Phase B: ACN |

| Time (min) | Mobile Phase B (%) |
|---|---|
| 0.40 | 2.00 |
| 1.00 | 85.0 |
| 1.50 | 85.0 |
| 1.51 | 2.00 |
| 2.00 | stop |

| | |
|---|---|
| HPLC conditions | Column: ACQUITY UPLC HSS T3 (2.1 × 50 mm, 1.8 μm)<br>Flow rate: 0.60 mL/min<br>Column temperature: 60° C.<br>Retention time:<br>Endothal: 0.87 min<br>Diclofenac: 1.28 min<br>For plasma samples:<br>An aliquot of 30 μL sample was added with 100 μL IS (Diclofenac, 100 ng/mL in ACN). The mixture was vortexed for 10 min at 750 rpm and centrifuged at 6000 rpm for 10 min. An aliquot of 3 μL supernatant was injected for LC-MS/MS analysis.<br>For liver homogenate samples:<br>The liver samples were homogenized with 3 volumes (v/w) of homogenizing solution PBS (pH 7.4) for 2 mins. An aliquot of 30 μL tissue homogenate sample was added with 100 μL IS (Diclofenac, 100 ng/mL in ACN). Vortex at 750 rpm for 10 min and centrifuged at 6000 rpm for 10 min. An aliquot of 3 μL supernatant was injected for LC-MS/MS analysis.<br>For all the samples preparation, allow calibration, quality control, blanks, and test samples to thaw at 4° C. (nominal). And keep each step on an ice bath or at 4° C. |
| Calibration curve | 20.00-3000 ng/mL for Endothal in SD rat plasma and liver homogenate.. |

Pharmacokinetic Analysis

Software: The PK parameters were determined by non-compartmental model of non-compartmental analysis tool, Pharsight Phoenix WinNonlin® 6.2 software.

"BQL" Rule: Concentration data under 80% of LLOQ (LLOQ=10.00 ng/mL in rat plasma and liver homogenate for 105, and 20.00 ng/mL for Endothal) was replaced with "BQL" and excluded from graphing and PK parameters estimation. Concentration data within 80%-120% of LLOQ was considered within normal instrumental variation and presented in the results.

Terminal $t_{1/2}$ Calculation: Time points were automatic selected by "best fit" model for terminal half life estimation as the first option. Manual selection was applied when "best fit" could not well define the terminal phase.

Clinical Observations

The concentration-time data and pharmacokinetic parameters of 105 and Endothal in rat plasma and liver after IV administration were listed in Tables 7.1 to 7.8, and illustrated in FIGS. 2A to 2C.

TABLE 7.1

Individual and mean plasma concentration-time data of 105 after an IV dose of 1 mg/kg in male SD rats

| Time (hr) | Individual | | Mean (ng/mL) |
|---|---|---|---|
| 0.25 | 1930 | 1530 | 1730 |
| 1 | 263 | 228 | 246 |
| 2 | 45.2 | 21.5 | 33.4 |
| 6 | BQL | BQL | BQL |
| 10 | BQL | BQL | BQL |
| 24 | BQL | BQL | BQL |

LLOQ of 105 in plasma sample is 10.0 ng/mL.
ULOQ of 105 in plasma sample is 3000 ng/mL.
BLQ: Below Limit of Quantitation

TABLE 7.2

Individual and mean liver concentration-time data of 105 after an IV dose of 1 mg/kg in male SD rats

| Time (hr) | Individual | | Mean (ng/g) |
|---|---|---|---|
| 0.25 | 1070 | 988 | 1029 |
| 1 | 576 | 446 | 511 |
| 2 | 99.2 | 131 | 115 |
| 6 | BQL | BQL | BQL |
| 10 | BQL | BQL | BQL |
| 24 | BQL | BQL | BQL |

The liver sample is homogenized with 3 volumes (v/w) of homogenizing solution (PBS PH7.4).

Liver concentration=liver homogenate conc.×4, assuming 1 g wet liver tissue equals to 1 mL.

LLOQ of 105 in liver homogenate sample is 10.0 ng/mL.
ULOQ of 105 in liver homogenate sample is 3000 ng/mL.
BLQ: Below Limit of Quantitation

TABLE 7.3

Liver-plasma concentration ratio of 105 after an IV dose of 1 mg/kg in male SD rats

| Time (hr) | Individual | | Mean |
|---|---|---|---|
| 0.25 | 0.554 | 0.646 | 0.600 |
| 1 | 2.19 | 1.96 | 2.07 |
| 2 | 2.19 | 6.09 | 4.14 |
| 6 | NA | NA | NA |

TABLE 7.3-continued

Liver-plasma concentration ratio of 105 after an IV dose of 1 mg/kg in male SD rats

| Time (hr) | Individual | | Mean |
|---|---|---|---|
| 10 | NA | NA | NA |
| 24 | NA | NA | NA |

NA: Not Applicable

TABLE 7.4

Individual and mean plasma concentration-time data of Endothal after an IV dose of 1 mg/kg 105 in SD rats

| Time (hr) | Individual | | Mean (ng/mL) |
|---|---|---|---|
| 0.25 | 263 | 188 | 226 |
| 1 | 69.7 | 45.2 | 57.5 |
| 2 | 23.2 | BQL | 23.2 |
| 6 | BQL | BQL | BQL |
| 10 | BQL | 21.9 | 21.9 |
| 24 | BQL | BQL | BQL |

LLOQ of Endothal in plasma sample is 20.0 ng/mL.
ULOQ of Endothal in plasma sample is 3000 ng/mL.
BLQ: Below Limit of Quantitation

TABLE 7.5

Individual and mean liver concentration-time data of Endothal after an IV dose of 1 mg/kg 105 in SD rats

| Time (hr) | Individual | | Mean (ng/g) |
|---|---|---|---|
| 0.25 | 475 | 462 | 469 |
| 1 | 541 | 386 | 464 |
| 2 | 151 | 304 | 228 |
| 6 | 76.9 | 163 | 120 |
| 10 | 70.0 | 156 | 113 |
| 24 | BQL | 63.8 | 63.8 |

The liver sample is homogenized with 3 volumes (v/w) of homogenizing solution (PBS PH7.4).

Liver concentration=liver homogenate conc.×4, assuming 1 g wet liver tissue equals to 1 mL.

LLOQ of Endothal in liver homogenate sample is 20.0 ng/mL.

ULOQ of Endothal in liver homogenate sample is 3000 ng/mL.

BLQ: Below Limit of Quantitation

TABLE 7.6

Liver-plasma concentration ratio of Endothal after an IV dose of 1 mg/kg 105 in SD rats

| Time (hr) | Individual | | Mean |
|---|---|---|---|
| 0.25 | 1.81 | 2.46 | 2.13 |
| 1 | 7.76 | 8.54 | 8.15 |
| 2 | 6.51 | NA | 6.51 |
| 6 | NA | NA | NA |
| 10 | NA | 7.12 | 7.12 |
| 24 | NA | NA | NA |

NA: Not Applicable

TABLE 7.7

Mean Pharmacokinetics Parameters of 105 after an IV dose of 1 mg/kg in male SD rats

| Matrix | Dosing Route (Dose) | $AUC_{(0-t)}$ h*ng/mL | $AUC_{(0-\infty)}$ h*ng/mL | $t_{1/2z}$ hr | $T_{max}$ hr | $C_{max}$ ng/mL | CL L/hr/kg | $V_{SS}$ L/kg | $MRT_{INF}$ hr | $AUC_{last-liver}/AUC_{last-plasma}$ |
|---|---|---|---|---|---|---|---|---|---|---|
| Plasma | IV (1 mg/kg) | 1511 | 1526 | 0.309 | NA | NA | 0.655 | 0.215 | 0.328 | NA |
| Liver | | 1019 | NA | NA | 0.25 | 1029 | NA | NA | NA | 67.4 |

NA: Not Applicable

TABLE 7.8

Mean Pharmacokinetics Parameters of Endothal after an IV dose of 1 mg/kg 105 in male SD rats

| Matrix | Dosing Route (Dose) | $AUC_{(0-t)}$ h*ng/mL | $AUC_{(0-\infty)}$ h*ng/mL | $t_{1/2}$ hr | $T_{max}$ hr | $C_{max}$ ng/mL | $AUC_{last-liver}/AUC_{last-plasma}$ |
|---|---|---|---|---|---|---|---|
| Plasma | IV (1 mg/kg) | 355 | 673 | 10.1 | 0.250 | 226 | NA |
| Liver | | 3152 | 4896 | 19.0 | 0.250 | 469 | 888 |

NA: Not Applicable

IV-1 mg/kg 105

After an IV dose of 105 at 1 mg/kg in male SD rats, concentration of 105 in rat plasma declined with a terminal half life ($T_{1/2}$) of 0.309 hours. The area under curve from time 0 to last time point ($AUC_{last}$) and from time 0 to infinity ($AUC_{INF}$) were 1511 and 1526 hr*ng/mL respectively. The total clearance CL and volume of distribution at steady state $V_{ss}$ were 0.655 L/hr/kg and 0.215 L/kg, respectively.

The mean values of $C_{max}$ in liver was 1029 ng/g and corresponding $T_{max}$ value was 0.25 hr. The mean value of $AUC_{(0-last)}$ was 1019 ng/g*hr. $AUC_{(0-t)}$ ratio of liver over plasma was 67.4.

Endothal

Following intravenous administration of 1 mg/kg 105 to Male SD rats, concentration of Endothal in rat plasma declined with a terminal half-life ($T_{1/2}$) of 10.1 hours. The area under curve from time 0 to last time point ($AUC_{last}$) and from time 0 to infinity ($AUC_{INF}$) were 355 and 673 hr*ng/mL respectively. The mean values of $C_{max}$ and $T_{max}$ in plasma were 226 ng/mL and 0.25 hr, respectively.

The mean values of $C_{max}$ in liver was 469 ng/g and corresponding $T_{max}$ value was 0.25 hr. The mean value of $AUC_{(0-last)}$ and $AUC_{(0-\infty)}$ were 3152 and 4896 ng/g*hr, respectively. $AUC_{(0-t)}$ ratio of liver over plasma was 888.

Example 3

Pharmacokinetic Study of Compound 113

The purpose of this study was to determine the pharmacokinetics parameters of 113, 100 and Endothal following single intravenous (IV) or oral (PO) administrations of 113 to male SD rats. 113 was dissolved in 4% NaHCO3 in saline for IV administration. The detailed procedure of dosing solution preparation was presented in Appendix I.

| Animal source | | | |
|---|---|---|---|
| Species | Gender | Vendor | Certificate No. |
| SD rats | Male | SLAC Laboratory Animal Co. LTD | SCXK (SH) 2007-0005 |

15 animals were placed on the study. The animals in IV arm were free access to food and water. For PO dose group, the animals were fasted overnight prior to dosing and the food was resumed 4 hours postdose.

One extra animal was used for blank liver, brain and plasma generation (5 mL per animal). The resulting blank liver, brain and plasma were then applied to the development of bioanalytical method and sample bioanalysis for the entire study.

| In-life Study Design | | | | | | | |
|---|---|---|---|---|---|---|---|
| Treatment Group | Body Weight (g) | No. of Animals | Route of Admin. | Dose Level* (mg/kg) | Dose Conc. (mg/mL) | Dose Volume (mL/kg) | Time points |
| 1 | 275-295 | 12 | IV | 1.4 | 1.4 | 1 | Sampling at 0.25, 1, 2, 6, 10 and 24 hr post dose. Terminally collect plasma, brain and liver samples from the same animal. |

In-life Study Design

| Treatment Group | Body Weight (g) | No. of Animals | Route of Admin. | Dose Level* (mg/kg) | Dose Conc. (mg/mL) | Dose Volume (mL/kg) | Time points |
|---|---|---|---|---|---|---|---|
| 2 | 275-295 | 2 | PO | 1.4 | 0.14 | 10 | Sampling at 0.25, 1, 2, 6, 10 and 24 hr post dose. Serial bleeding from the same animal for plasma only. |

*Dose was expressed as free base of 113.

Dosing, Sampling, Sample Processing and Sample Storage

The IV injection was conducted via foot dorsal vein. PO via oral gavage.

Blood Collection: The animal is restrained manually. Approximately 200 μL of blood/time point is collected into sodium heparin tube via cardiac puncture for terminal bleeding (anesthetized under carbon dioxide). Blood sample will be put on ice and centrifuged to obtain plasma sample (2000 g, 5 min under 4° C.) within 10 minutes.

Liver Collection: The animal will be euthanized with carbon dioxide inhalation. Open abdominal cavity with scissor to expose internal organs. Hold the carcass in an upright position and allow the organs to fall forward. Cut the connective tissues and remove the organs. Then the organs are rinsed with cold saline, dried on filtrate paper, placed into a screw-top tube and weighed, snap frozen by placing into dry-ice immediately.

Brain collection: Make a mid-line incision in the animals scalp and retract the skin. Using small bone cutters and rongeurs, remove the skull overlying the brain. Remove the brain using a spatula and rinse with cold saline, dried on filtrate paper, placed into a screw-top tube and weighed, snap frozen by placing into dry-ice immediately. Brain tissue will be homogenized for 2 min with 3 volumes (v/w) of homogenizing solution (PBS pH 7.4) right before analysis. Plasma, brain and liver samples were stored at approximately −80° C. until analysis. The backup samples will be discarded after three weeks after in-life completion unless requested. The unused dosing solutions will be discarded within three weeks after completion of the study.

LC-MS-MS Analysis Analytical Method for 113

| | |
|---|---|
| Instrument | UPLC/MS-MS-010 (API-4000) |
| Matrix | SD rat plasma, brain and liver homogenate |
| Analyte(s) | 113 |
| Internal standard(s) | Dexamethasone/Propranolol |
| MS conditions | ESI: Positive ion<br>MRM detection<br>LB-113: [M + H]$^+$ m/z 399.1→ 251.2<br>Dexamethasone: [M + H]$^+$ m/z 393.3 ® 373.1<br>Propranolol: [M + H]$^+$ m/z 260.2 → 116.1<br>Mobile Phase A: H$_2$0-0.1% FA-5 mM NH$_4$OAc<br>Mobile Phase B: ACN |

| Time (min) | Mobile Phase B (%) |
|---|---|
| 0.20 | 2.00 |
| 0.60 | 95.0 |
| 1.20 | 95.0 |
| 1.21 | 2.00 |
| 1.80 | stop |

| | |
|---|---|
| HPLC conditions | Column: ACQUITY UPLC HSS T3 (2.1 × 50 mm, 1.8 μm)<br>Flow rate: 0.60 mL/min<br>Column temperature: 60° C.<br>Retention time:<br>LB-113: 0.95 min<br>Dexamethasone: .1.02 min<br>Propranolol: 0.92 min<br>For plasma samples:<br>An aliquot of 30 μL sample was added with 100 μL IS (Dexamethasone, 100 ng/mL and Propranolol, 50 ng/mL in ACN). The mixture was vortexed for 10 min at 750 rpm and centrifuged at 6000 rpm for 10 min. An aliquot of 1 μL supernatant was injected for LC-MS/MS analysis.<br>For diluted plasma samples:<br>An aliquot of 3 μL plasma sample was diluted with 27 μL blank plasma. The following processing procedure was the same as those un-diluted plasma samples.<br>For brain homogenate samples:<br>The brain samples were homogenized with 3 volumes (v/w) of homogenizing solution PBS (pH 7.4) for 2 mins. An aliquot of 30 μL tissue homogenate sample was added with 100 μL IS (Dexamethasone, 100 ng/ml, and Propranolol, 50 ng/mL in ACN). Vortex at 750 rpm for 10 min and centrifuged at 6000 rpm for 10 min. An aliquot of 1 μL supernatant was injected for LC-MS/MS analysis.<br>For liver homogenate samples:<br>The liver samples were homogenized with 3 volumes (v/w) of homogenizing solution PBS (pH 7.4) for 2 mins. An aliquot of 30 μL tissue homogenate sample was added with 100 μL, IS (Dexamethasone, 100 ng/mL and Propranolol, 50 ng/mL in ACN). Vortex at 750 rpm for 10 min and centrifuged at 6000 rpm for 10 min. An aliquot of 1 μL supernatant was injected for LC-MS/MS analysis.<br>For all the samples preparation, allow calibration, quality control, blanks, and test samples to thaw at 4° C. (nominal). And keep each step on an ice bath or at 4° C. |
| Calibration curve | 1.00-3000 ng/mL for LB-113 in SD rat plasma, brain and liver homogenate. |

| | LC-MS-MS Analysis Analytical Method for Endothal |
|---|---|
| Instrument | UPLC/MS-MS-015 (API-5500, Q-trap) |
| Matrix | SD rat plasma, brain and liver homogenate |
| Analyte(s) | Endothal |
| Internal standard(s) | Diclofenac |
| MS conditions | ESI: Negative ion<br>MRM detection<br>Endothal: $[M - H]-$ m/z 184.9 → 141.0<br>Diclofenac: $[M - H]-$ m/z 294.2 → 249.9<br>Mobile Phase A: $H_2O$-0.1% FA-5 mM $NH_4OAc$<br>Mobile Phase B: ACN |
| | Time (min) / Mobile Phase B (%)<br>0.40 / 2.00<br>1.00 / 85.0<br>1.50 / 85.0<br>1.51 / 2.00<br>2.00 / stop<br>Column: ACQUITY UPLC HSS T3 (2.1 × 50 mm, 1.8 μm)<br>Flow rate: 0.60 mL/min<br>Column temperature: 60° C.<br>Retention time:<br>Endothal: 0.87 min<br>Diclofenac: 1.28 min |
| HPLC conditions | For plasma samples:<br>An aliquot of 30 μL sample was added with 100 μL IS (Diclofenac, 100 ng/mL in ACN). The mixture was vortexed for 10 min at 750 rpm and centrifuged at 6000 rpm for 10 min. An aliquot of 3 μL supernatant was injected for LC-MS/MS analysis.<br>For brain homogenate samples:<br>The brain samples were homogenized with 3 volumes (v/w) of homogenizing solution PBS (pH 7.4) for 2 mins. An aliquot of 30 μL tissue homogenate sample was added with 100 μL IS (Diclofenac, 100 ng/mL in ACN). Vortex at 750 rpm for 10 min and centrifuged at 6000 rpm for 10 min. An aliquot of 3 μL supernatant was injected for LC-MS/MS analysis.<br>For liver homogenate samples:<br>The liver samples were homogenized with 3 volumes (v/w) of homogenizing solution PBS (pH 7.4) for 2 mins. An aliquot of 30 μL tissue homogenate sample was added with 100 μL IS (Diclofenac, 100 ng/mL in ACN). Vortex at 750 rpm for 10 min and centrifuged at 6000 rpm for 10 min. An aliquot of 3 μL supernatant was injected for LC-MS/MS analysis.<br>For all the samples preparation, allow calibration, quality control, blanks, and test samples to thaw at 4° C. (nominal). And keep each step on an ice bath or at 4° C. |
| Calibration curve | 20.00-3000 ng/mL for Endothal in SD rat plasma, brain and liver homogenate. |

| | LC-MS-MS Analysis Analytical Method for Compound 100 |
|---|---|
| Instrument | DPLC/MS-MS-010 (API-4000) |
| Matrix | SD rat plasma, brain and liver homogenate |
| Analyte(s) | 100 |
| Internal standard(s) | Diclofenac/Propranolol |
| MS conditions | ESI: Positive ion<br>MRM detection<br>LB-100: $[M + H]^+$ m/z 269.3 → 101.1<br>Diclofenac: $[M + H]^+$ m/z 296.0 ® 250.3<br>Propranolol: $[M + H]^+$ m/z 260.2 → 116.1<br>Mobile Phase A: $H_2O$-0.1% FA-5 mM $NH_4OAc$<br>Mobile Phase B: ACN |

| Time (min) | Mobile Phase B (%) |
|---|---|
| 0.20 | 15.0 |
| 1.60 | 98.0 |
| 3.10 | 98.0 |
| 3.11 | 15.0 |
| 5.00 | stop |

-continued

| | LC-MS-MS Analysis Analytical Method for Compound 100 |
|---|---|
| HPLC conditions | Column: Agilent Eclipse XDB-C18 (4.6 × 150 mm, 5 μm)<br>Flow rate: 0.80 mL/min<br>Column temperature: 40° C.<br>Retention time:<br>LB-100: 1.75 min<br>Diclofenac: 3.56 min<br>Propranolol: 2.77 min<br>For plasma samples:<br>An aliquot of 30 μL sample was added with 100 μL IS (Diclofenac, 100 ng/mL and Propranolol, 50 ng/mL in ACN). The mixture was vortexed for 10 min at 750 rpm and centrifuged at 6000 rpm for 10 min. An aliquot of 5 μL supernatant was injected for LC-MS/MS analysis.<br>For brain homogenate samples:<br>The brain samples were homogenized with 3 volumes (v/w) of homogenizing solution PBS (pH 7.4) for 2 mins. An aliquot of 30 μL tissue homogenate sample was added with 100 μL IS (Diclofenac, 100 ng/mL and Propranolol, 50 ng/mL in ACN). Vortex at 750 rpm for 10 min and centrifuged at 6000 rpm for 10 min. An aliquot of 5 μL supernatant was injected for LC-MS/MS analysis.<br>For liver homogenate samples:<br>The liver samples were homogenized with 3 volumes (v/w) of homogenizing solution PBS (pH 7.4) for 2 mins. An aliquot of 30 μL tissue homogenate sample was added with 100 μL IS (Diclofenac, 100 ng/mL and Propranolol, 50 ng/mL in ACN). Vortex at 750 rpm for 10 min and centrifuged at 6000 rpm for 10 min. An aliquot of 5 μL supernatant was injected for LC-MS/MS analysis.<br>For all the samples preparation, allow calibration, quality control, blanks, and test samples to thaw at 4° C. (nominal). And keep each step on an ice bath or at 4° C. |
| Calibration curve | 3-3000 ng/mL for LB-100 in SD rat plasma;<br>6-3000 ng/mL for LB-100 in SD rat brain and liver homogenate. |

Pharmacokinetic Analysis

Software: The PK parameters were determined by non-compartmental model of non-compartmental analysis tool, Pharsight Phoenix WinNonlin® 6.2 software.

"BQL" Rule: Concentration data under 80% of LLOQ (LLOQ=1.00 ng/mL in rat plasma, brain and liver homogenate for 113. LLOQ=20.00 ng/mL in rat plasma, brain and liver homogenate for Endothal. LLOQ=3.00 ng/mL for 100 in rat plasma, 6.00 ng/mL for 100 in rat brain and liver homogenate) was replaced with "BQL" and excluded from graphing and PK parameters estimation. Concentration data within 80%-120% of LLOQ was considered within normal instrumental variation and presented in the results.

Terminal $t_{1/2}$ Calculation: Time points were automatic selected by "best fit" model for terminal half life estimation as the first option. Manual selection was applied when "best fit" could not well define the terminal phase.

Results

No abnormal clinical symptom was observed after IV and PO administrations.

The concentration-time data and pharmacokinetic parameters of 113, 100 and Endothal in rat plasma, brain and liver after IV or PO administrations were listed in Tables 8.1 to 8.19, and illustrated in FIGS. 3A-3D.

TABLE 8.1

Individual and mean plasma concentration-time data of 113 after an IV dose of 1.4 mg/kg in male SD rats

| Time (hr) | Individual | | Mean (ng/mL) |
|---|---|---|---|
| 0.25 | 173 | 193 | 183 |
| 1 | 10.8 | 9.96 | 10.4 |

TABLE 8.1-continued

Individual and mean plasma concentration-time data of 113 after an IV dose of 1.4 mg/kg in male SD rats

| Time (hr) | Individual | | Mean (ng/mL) |
|---|---|---|---|
| 2 | BQL | BQL | BQL |
| 6 | BQL | BQL | BQL |
| 10 | BQL | BQL | BQL |
| 24 | BQL | BQL | BQL |

LLOQ of 113 in plasma sample is 1.00 ng/mL.

ULOQ of 113 in plasma sample is 3000 ng/mL.

BLQ: Below Limit of Quantitation

TABLE 8.2

Individual and mean plasma concentration-time data of 113 after a PO dose of 1.4 mg/kg in male SD rats

| Time (hr) | Individual | | Mean (ng/mL) |
|---|---|---|---|
| 0.25 | 18.3 | 17.0 | 17.7 |
| 1 | 4.61 | 8.56 | 6.59 |
| 2 | BQL | 2.15 | 2.15 |
| 6 | BQL | BQL | BQL |
| 10 | BQL | BQL | BQL |
| 24 | BQL | BQL | BQL |

LLOQ of 113 in plasma sample is 1.00 ng/mL.

ULOQ of 113 in plasma sample is 3000 ng/mL.

BLQ: Below Limit of Quantitation

TABLE 8.3

Individual and mean liver concentration-time data of 113 after an IV dose of 1.4 mg/kg in male SD rats

| Time (hr) | Individual | | Mean (ng/g) |
|---|---|---|---|
| 0.25 | 55.5 | 36.9 | 46.2 |
| 1 | 14.6 | 11.8 | 13.2 |
| 2 | BQL | BQL | BQL |
| 6 | BQL | BQL | BQL |
| 10 | BQL | BQL | BQL |
| 24 | BQL | BQL | BQL |

The liver sample is homogenized with 3 volumes (v/w) of homogenizing solution (PBS PH7.4).
Liver concentration=liver homogenate conc.×4, assuming 1 g wet liver tissue equals to 1 mL.
LLOQ of 113 in liver homogenate sample is 1.00 ng/mL.
ULOQ of 113 in liver homogenate sample is 3000 ng/mL.
BLQ: Below Limit of Quantitation

TABLE 8.4

Liver-plasma concentration ratio of 113 after an IV dose of 1.4 mg/kg in male SD rats

| Time (hr) | Individual | | Mean |
|---|---|---|---|
| 0.25 | 0.321 | 0.191 | 0.256 |
| 1 | 1.35 | 1.18 | 1.27 |
| 2 | NA | NA | NA |
| 6 | NA | NA | NA |
| 10 | NA | NA | NA |
| 24 | NA | NA | NA |

NA: Not Applicable

TABLE 8.5

Individual and mean brain concentration-time data of 113 after an IV dose of 1.4 mg/kg in male SD rats

| Time (hr) | Individual | | Mean (ng/g) |
|---|---|---|---|
| 0.25 | 86.2 | 94.5 | 90.4 |
| 1 | 5.80 | 6.42 | 6.11 |
| 2 | BQL | BQL | BQL |
| 6 | BQL | BQL | BQL |
| 10 | BQL | BQL | BQL |
| 24 | BQL | BQL | BQL |

The brain sample is homogenized with 3 volumes (v/w) of homogenizing solution (PBS PH7.4).
Brain concentration=brain homogenate conc.×4, assuming 1 g wet brain tissue equals to 1 mL.
LLOQ of 113 in brain homogenate sample is 1.00 ng/mL.
ULOQ of 113 in brain homogenate sample is 3000 ng/mL.
BLQ: Below Limit of Quantitation

TABLE 8.6

Brain-plasma concentration ratio of 113 after an IV dose of 1.4 mg/kg in male SD rats

| Time (hr) | Individual | | Mean |
|---|---|---|---|
| 0.25 | 0.498 | 0.490 | 0.494 |
| 1 | 0.537 | 0.645 | 0.591 |
| 2 | NA | NA | NA |
| 6 | NA | NA | NA |
| 10 | NA | NA | NA |
| 24 | NA | NA | NA |

NA: Not Applicable

TABLE 8.7

Individual and mean plasma concentration-time data of Endothal after an IV dose of 1.4 mg/kg 113 in SD rats

| Time (hr) | Individual | | Mean (ng/mL) |
|---|---|---|---|
| 0.25 | 24.9 | 61.2 | 43.1 |
| 1 | 41.6 | 36.1 | 38.9 |
| 2 | 43.3 | 17.4 | 30.4 |
| 6 | BQL | BQL | BQL |
| 10 | BQL | BQL | BQL |
| 24 | BQL | BQL | BQL |

LLOQ of Endothal in plasma sample is 20.0 ng/mL.
ULOQ of Endothal in plasma sample is 3000 ng/mL.
BLQ: Below Limit of Quantitation

TABLE 8.8

Individual and mean liver concentration-time data of Endothal after an IV dose of 1.4 mg/kg 113 in SD rats

| Time (hr) | Individual | | Mean (ng/g) |
|---|---|---|---|
| 0.25 | 727 | 988 | 858 |
| 1 | 902 | 1230 | 1066 |
| 2 | 998 | 795 | 897 |
| 6 | 526 | 477 | 502 |
| 10 | 288 | 157 | 223 |
| 24 | 66.9 | 68.8 | 67.9 |

The liver sample is homogenized with 3 volumes (v/w) of homogenizing solution (PBS PH7.4).
Liver concentration=liver homogenate conc.×4, assuming 1 g wet liver tissue equals to 1 mL.
LLOQ of Endothal in liver homogenate sample is 20.0 ng/mL.
ULOQ of Endothal in liver homogenate sample is 3000 ng/mL.
BLQ: Below Limit of Quantitation

TABLE 8.9

Liver-plasma concentration ratio of Endothal after an IV dose of 1.4 mg/kg 113 in SD rats

| Time (hr) | Individual | | Mean |
|---|---|---|---|
| 0.25 | 29.2 | 16.1 | 22.7 |
| 1 | 21.7 | 34.1 | 27.9 |
| 2 | 23.0 | 45.7 | 34.4 |
| 6 | NA | NA | NA |
| 10 | NA | NA | NA |
| 24 | NA | NA | NA |

NA: Not Applicable

TABLE 8.10

Individual and mean brain concentration-time data of Endothal after an IV dose of 1.4 mg/kg 113 in SD rats

| Time (hr) | Individual | | Mean (ng/g) |
|---|---|---|---|
| 0.25 | BQL | BQL | BQL |
| 1 | BQL | BQL | BQL |
| 2 | BQL | BQL | BQL |
| 6 | BQL | BQL | BQL |
| 10 | BQL | BQL | BQL |
| 24 | BQL | BQL | BQL |

The brain sample is homogenized with 3 volumes (v/w) of homogenizing solution (PBS PH7.4).

Brain concentration=brain homogenate conc.×4, assuming 1 g wet brain tissue equals to 1 mL.

LLOQ of Endothal in brain homogenate sample is 20.0 ng/mL.

ULOQ of Endothal in brain homogenate sample is 3000 ng/mL.

BLQ: Below Limit of Quantitation

TABLE 8.11

Brain-plasma concentration ratio of Endothal after an IV dose of 1.4 mg/kg 113 in SD rats

| Time (hr) | Individual | | Mean |
|---|---|---|---|
| 0.25 | NA | NA | NA |
| 1 | NA | NA | NA |
| 2 | NA | NA | NA |
| 6 | NA | NA | NA |
| 10 | NA | NA | NA |
| 24 | NA | NA | NA |

NA: Not Applicable

TABLE 8.12

Individual and mean plasma concentration-time data of 100 after an IV dose of 1.4 mg/kg 113 in SD rats

| Time (hr) | Individual | | Mean (ng/mL) |
|---|---|---|---|
| 0.25 | 510 | 598 | 554 |
| 1 | 273 | 170 | 222 |
| 2 | 135 | 45.3 | 90.2 |
| 6 | 3.25 | BQL | 3.25 |
| 10 | BQL | BQL | BQL |
| 24 | BQL | BQL | BQL |

LLOQ of 100 in plasma sample is 3.00 ng/mL.
ULOQ of 100 in plasma sample is 3000 ng/mL.
BLQ: Below Limit of Quantitation

TABLE 8.13

Individual and mean liver concentration-time data of 100 after an IV dose of 1.4 mg/kg 113 in SD rats

| Time (hr) | Individual | | Mean (ng/g) |
|---|---|---|---|
| 0.25 | 2090 | 1700 | 1895 |
| 1 | 1360 | 690 | 1025 |
| 2 | 425 | 306 | 366 |
| 6 | 23.8 | 21.8 | 22.8 |

TABLE 8.13-continued

Individual and mean liver concentration-time data of 100 after an IV dose of 1.4 mg/kg 113 in SD rats

| Time (hr) | Individual | | Mean (ng/g) |
|---|---|---|---|
| 10 | BQL | BQL | BQL |
| 24 | BQL | BQL | BQL |

The liver sample is homogenized with 3 volumes (v/w) of homogenizing solution (PBS pH7.4).

Liver concentration=liver homogenate conc.×4, assuming 1 g wet liver tissue equals to 1 mL.

LLOQ of 100 in liver homogenate sample is 6.00 ng/mL.
ULOQ of 100 in liver homogenate sample is 3000 ng/mL.
BLQ: Below Limit of Quantitation

TABLE 8.14

Liver-plasma concentration ratio of 100 after an IV dose of 1.4 mg/kg 113 in SD rats

| Time (hr) | Individual | | Mean |
|---|---|---|---|
| 0.25 | 4.10 | 2.84 | 3.47 |
| 1 | 4.98 | 4.06 | 4.52 |
| 2 | 3.15 | 6.75 | 4.95 |
| 6 | 7.32 | NA | 7.32 |
| 10 | NA | NA | NA |
| 24 | NA | NA | NA |

NA: Not Applicable

TABLE 8.15

Individual and mean brain concentration-time data of 100 after an IV dose of 1.4 mg/kg 113 in SD rats

| Time (hr) | Individual | | Mean (ng/g) |
|---|---|---|---|
| 0.25 | BQL | BQL | BQL |
| 1 | BQL | BQL | BQL |
| 2 | BQL | BQL | BQL |
| 6 | BQL | BQL | BQL |
| 10 | BQL | BQL | BQL |
| 24 | BQL | BQL | BQL |

The brain sample is homogenized with 3 volumes (v/w) of homogenizing solution (PBS PH7.4).

Brain concentration=brain homogenate conc.×4, assuming 1 g wet brain tissue equals to 1 mL.

LLOQ of 100 in brain homogenate sample is 6.00 ng/mL.
ULOQ of 100 in brain homogenate sample is 3000 ng/mL.
BLQ: Below Limit of Quantitation

TABLE 8.16

Brain-plasma concentration ratio of 100 after an IV dose of 1.4 mg/kg 113 in SD rats

| Time (hr) | Individual | | Mean |
|---|---|---|---|
| 0.25 | NA | NA | NA |
| 1 | NA | NA | NA |
| 2 | NA | NA | NA |
| 6 | NA | NA | NA |
| 10 | NA | NA | NA |
| 24 | NA | NA | NA |

NA: Not Applicable

TABLE 8.17

Mean Pharmacokinetics Parameters of 113 after an IV dose of 1.4 mg/kg in male SD rats

| Matrix | Dosing Route (Dose) | $AUC_{(0-t)}$ h*ng/mL | $AUC_{(0-\infty)}$ h*ng/mL | $t_{1/2}$ hr | $T_{max}$ hr | $C_{max}$ ng/mL | CL L/hr/kg | $V_{SS}$ L/kg | $MRT_{INF}$ hr | F % | $AUC_{last-liver(brain)}/AUC_{last-plasma}$ |
|---|---|---|---|---|---|---|---|---|---|---|---|
| Plasma | PO (1.4 mg/kg) | 15.7 | NA | NA | 0.25 | 17.7 | NA | NA | NA | 10.1 | NA |
| Plasma | IV | 155 | NA | NA | NA | NA | NA | NA | NA | NA | NA |
| Liver | (1.4 | 28.1 | NA | NA | 0.25 | 46.2 | NA | NA | NA | NA | 18.1 |
| Brain | mg/kg) | 47.5 | NA | NA | 0.25 | 90.4 | NA | NA | NA | NA | 30.6 |

TABLE 8.18

Mean Pharmacokinetics Parameters of Endothal after an IV dose of 1.4 mg/kg 113 in male SD rats

| Matrix | Dosing Route (Dose) | $AUC_{(0-t)}$ h*ng/mL | $AUC_{(0-\infty)}$ h*ng/mL | $t_{1/2}$ hr | $T_{max}$ hr | $C_{max}$ ng/mL | $AUC_{last-liver}/AUC_{last-plasma}$ |
|---|---|---|---|---|---|---|---|
| Plasma | IV | 70.7 | NA | NA | 0.25 | 43.1 | NA |
| Liver | (1.4 | 8086 | 8678 | 6.04 | 1 | 1066 | 11438 |
| Brain | mg/kg) | NA | NA | NA | NA | NA | NA |

TABLE 8.19

Mean Pharmacokinetics Parameters of 100 after an IV dose of 1.4 mg/kg 113 in male SD rats

| Matrix | Dosing Route (Dose) | $AUC_{(0-t)}$ h*ng/mL | $AUC_{(0-\infty)}$ h*ng/mL | $t_{1/2z}$ hr | $T_{max}$ hr | $C_{max}$ ng/mL | $AUC_{last-liver}/AUC_{last-plasma}$ |
|---|---|---|---|---|---|---|---|
| Plasma | IV (1 | 703 | 707 | 0.825 | 0.25 | 554 | NA |
| Liver | mg/kg) | 2804 | 2834 | 0.934 | 0.25 | 1895 | 399 |
| Brain | | NA | NA | NA | NA | NA | NA |

IV-1.4 mg/kg 113

After an IV dose of 113 at 1.4 mg/kg in male SD rats, the area under curve from time 0 to last time point ($AUC_{last}$) was 155 hr*ng/mL.

The mean values of $C_{max}$ in liver was 46.2 ng/g and corresponding $T_{max}$ value was 0.25 hr. The mean value of $AUC_{(0-last)}$ was 28.1 ng/g*hr. $AUC_{(0-t)}$ ratio of liver over plasma was 18.1.

The mean values of $C_{max}$ in brain was 90.4 ng/g and corresponding $T_{max}$ value was 0.25 hr. The mean value of $AUC_{(0-last)}$ was 47.5 ng/g*hr. $AUC_{(0-t)}$ ratio of liver over plasma was 30.6.

PO-1.4 mg/kg 113

After a PO dose of 113 at 1.4 mg/kg, the $C_{max}$ value in rat plasma was 17.7 ng/mL, and corresponding mean $T_{max}$ value was 0.250 hr. The area under curve from time 0 to last time point $AUC_{last}$ was 15.7 hr*ng/mL. After the IV dose of 1.4 mg/kg and the PO dose of 1.4 mg/kg, the bioavailability of this compound in SD rat was estimated to be 10.1%.

Endothal

Following intravenous administration of 1.4 mg/kg 113 to Male SD rats, the area under curve from time 0 to last time point ($AUC_{last}$) was 70.7 hr*ng/mL. The mean values of $C_{max}$ and $T_{max}$ in plasma were 43.1 ng/mL and 0.25 hr, respectively.

The mean values of $C_{max}$ in liver was 1066 ng/g and corresponding $T_{max}$ value was 1.00 hr. The mean value of $AUC_{(0-last)}$ and $AUC_{(0-\infty)}$ were 8086 and 8678 ng/g*hr, respectively. $AUC_{(0-t)}$ ratio of liver over plasma was 11438.

Compound 100

The mean values of $C_{max}$ and $T_{max}$ in plasma were 554 ng/mL and 0.25 hr, respectively. The mean value of $AUC_{(0-last)}$ and $AUC_{(0-\infty)}$ were 703 ng/mL*hr and 707 ng/mL*hr, respectively.

The mean values of $C_{max}$ in liver was 1895 ng/g and corresponding $T_{max}$ value was 0.25 hr. The mean value of $AUC_{(0-last)}$ and $AUC_{(0-\infty)}$ were 2804 ng/g*hr and 2834 ng/g*hr, respectively. $AUC_{(0-t)}$ ratio of liver over plasma was 399.

Example 4

Pharmacokinetic Study of Compound 151

A pharmacokinetic study of 151 was conducted in SD rats. The study consisted of two dose levels at 1.0 (iv) and 10 (oral) mg/kg. The blood samples were collected at predetermined times from rats and centrifuged to separate plasma. An LC/MS/MS method was developed to determine the test article in plasma samples. The pharmacokinetic parameters of 151 following iv and oral administration to SD rats were calculated. The absolute bioavailability was evaluated.

Study Design

A total of 5 male SD rats were assigned to this study as shown in the table below:

| Groups | Number of rats (male) | Route of administration | Dose level (mg/kg) | Dose volume (ml/kg) |
|---|---|---|---|---|
| 1 | 3 | oral | 10 | 10 |
| 2 | 2 | iv | 1.0 | 5.0 |

Dose Preparation and Dose Administration 151 (MW 282.34, purity 99.2%, lot no. 20110512) was prepared by dissolving the article in PBS (pH 7.4) on the day of dosing. The final concentration of the test article was 0.2 mg/mL for iv administration and 1.0 mg/mL for oral administration. The test article solutions were administered using the most recent body weight for each animal.

Sample Collection

Blood (approximately 0.3 mL) were collected via orbital plexus into tubes containing sodium heparin at 0.25, 0.5, 1, 2, 3, 5, 7, 9, and 24 hours after oral administration; at 5 min, 15 min, 0.5, 1, 2, 3, 5, 7, 9 and 24 hours after iv administration. Samples were centrifuged for 5 min, at 4° C. with the centrifuge set at 11,000 rpm to separate plasma. The obtained plasma samples were stored frozen at a temperature of about −70° C. until analysis.

Preparation of Plasma Samples

Frozen plasma samples were thawed at room temperature and vortexed thoroughly. With a pipette, an aliquot (30 μL) of plasma was transferred into a 1.5-mL conical polypropylene tube. To each sample, 160 μL of acetonitrile were added. The samples were then vigorously vortex-mixed for 1 min. After centrifugation at 11000 rpm for 5 min, a 15 μL aliquot of the supernatant was injected into the LC-MS/MS system for analysis.

Preparation of Calibration Samples

Calibration standards were prepared by spiking 30 μL of the 151 standard solutions into 30 μL of heparinized blank rat plasma. The nominal standard concentrations in the standard curve were 1.00, 3.00, 10.0, 30.0, 100, 300, 1000 and 3000 ng/mL.

LC/MS/MS System

The analysis was performed using an LC-MS/MS system consisting of the following components—HPLC system: Agilent 1200 series instrument consisting of G1312B vacuum degasser, G1322A binary pump, G1316B column oven and G1367D autosampler (Agilent, USA); MS/MS system: Agilent 6460 triple quadrupole mass spectrometer, equipped with an APCI Interface (Agilent, USA); Data system: MassHunter Software (Agilent, USA).

Chromatographic Conditions

Chromatographic separation was carried out at room temperature—Analytical column: $C_8$ column (4.6 mm×150 mm I.D., 5 μm, Agilent, USA); Mobile phase: Acetonitrile: 10 mM ammonium acetate (75:25, v/v); Flow rate: 0.80 mL/min; Injection volume: 15 μL.

Mass Spectrometric Conditions

The mass spectrometer was operated in the positive mode. Ionization was performed applying the following parameters: gas temperature, 325° C.; vaporizer temperature, 350° C.; gas flow, 4 L/min; nebulizer, 20 psi; capillary voltage, 4500 V; corona current, 4 μA. 151 was detected using MRM of the transitions m/z 283→m/z 123 and m/z 283→m/z 251, simultaneously. The optimized collision energies of 25 eV and 10 eV were used for m/z 123 and m/z 251, respectively.

Quantification

Quantification was achieved by the external standard method. Concentrations of the test article were calculated using a weighted least-squares linear regression ($W=1/x^2$).

Pharmacokinetic Interpretation

The pharmacokinetic parameters were evaluated using WinNonlin version 5.3 (Pharsight Corp., Mountain View, Calif., USA), assuming a non-compartmental model for drug absorption and distribution.

$AUC_{0-t}$ is the area under the plasma concentration-time curve from time zero to last sampling time, calculated by the linear trapezoidal rule.

$AUC_{0-\infty}$ is the area under the plasma concentration-time curve from time zero extrapolating to infinity.

$T_{1/2}$ is the elimination half-life associated with the terminal (log-linear) elimination phase, which is estimated via linear regression of time vs. log concentrations.

CL is the total body clearance.

$V_{ss}$ is the volume of distribution at steady-state.

Calibration Curve for Plasma Samples

The calibration curve for L151 in rat plasma was linear throughout the study in the range of 1.00-3000 ng/mL. The linear regression equation of the calibration curve was y=885.6448 x+791.9622, $r^2$=0.9927, where y represents the peak area of 151 and x represents the plasma concentrations of 151.

Plasma Concentrations of 151 in SD Rats

Following iv (1.0 mg/kg) and oral (10 mg/kg) administration of 151 to SD rats, plasma concentrations of the test articles were determined by the LC/MS/MS method described above. The plasma concentrations at each sampling time are listed in Tables 9.1 and 9.2.

Interpretation of Pharmacokinetics

The major pharmacokinetic parameters of 151 in plasma are summarized in Tables 9.3 and 9.4. Following oral administration of 10 mg/kg to SD rats (n=3), 151 was rapidly absorbed with peak plasma concentration occurring at 0.5 h after dose. The elimination of 151 was fast with mean half-life of 1.26 h. Following iv administration of 1.0 mg/kg (n=2), the elimination half-life of 151 was 0.89 h. The mean clearance of 151 from rat plasma and the volume of distribution at steady state were 859 ml/h/kg and 736 ml/kg. Based on the exposure ($AUC_{0-\infty}$), the absolute bioavailability (F) of 151 was 54.6% following oral administration at 10 mg/kg to SD rats.

TABLE 9.1

Analytical data of 151 plasma concentration (ng/mL) in SD rats following PO administration at 10 mg/kg.

| Rat No. | Time (h) | | | | | | | | |
|---|---|---|---|---|---|---|---|---|---|
| | 0.25 | 0.50 | 1.0 | 2.0 | 3.0 | 5.0 | 7.0 | 9.0 | 24 |
| 1 | 2231 | 2451 | 2204 | 1100 | 521 | 125 | 42.6 | 52.1 | BLQ |
| 2 | 2029 | 3934 | 2581 | 1237 | 660 | 99.4 | 20.7 | 38.2 | BLQ |
| 3 | 2731 | 3343 | 2538 | 1582 | 794 | 192 | 68.0 | 66.1 | BLQ |
| Mean | 2330 | 3243 | 2441 | 1306 | 658 | 139 | 43.8 | 52.1 | |
| SD | 361 | 747 | 206 | 248 | 136 | 48 | 23.6 | 13.9 | |

BLQ: Below the lower limit of quantification 1.00 ng/mL.

TABLE 9.2

Analytical data of 151 plasma concentration (ng/mL)
in SD rats following IV administration at 1.0 mg/kg.

| Rat No. | Time (h) | | | | | | | | | |
|---|---|---|---|---|---|---|---|---|---|---|
| | 0.083 | 0.250 | 0.50 | 1.0 | 2.0 | 3.0 | 5.0 | 7.0 | 9.0 | 24 |
| 4 | 1677 | 1160 | 760 | 381 | 95.8 | 39.6 | 9.75 | 12.2 | BLQ | BLQ |
| 5 | 1301 | 949 | 607 | 314 | 103 | 28.1 | 3.63 | 1.83 | 2.01 | BLQ |
| Mean | 1489 | 1055 | 683 | 348 | 99.6 | 33.8 | 6.69 | 7.02 | 1.00 | |

TABLE 9.3

The main pharmacokinetic parameters of 151 in SD
rats following PO administration at 10 mg/kg.

| Rat No. | Tmax (ng/ml) | Cmax (ng/ml) | $AUC_{0-t}$ (ng·h/ml) | $AUC_{0-\infty}$ (ng·h/ml) | $T_{1/2}$ (h) | MRT (h) | F (%) |
|---|---|---|---|---|---|---|---|
| 1 | 0.50 | 2451 | 5399 | 5499 | 1.33 | 1.86 | |
| 2 | 0.50 | 3934 | 6423 | 6484 | 1.10 | 1.62 | |
| 3 | 0.50 | 3343 | 7199 | 7328 | 1.35 | 1.95 | |
| Mean | 0.50 | 3243 | 6340 | 6437 | 1.26 | 1.81 | 54.6 |
| SD | 0.00 | 747 | 903 | 916 | 0.14 | 0.17 | |
| CV (%) | 0.0 | 23.0 | 14.2 | 14.2 | 11.0 | 9.4 | |

TABLE 9.4

The main pharmacokinetic parameters of 151 in SD
rats following IV administration at 1.0 mg/kg.

| Rat No. | $AUC_{0-t}$ (ng·h/ml) | $AUC_{0-\infty}$ (ng·h/ml) | $T_{1/2}$ (h) | MRT (h) | $V_{ss}$ (ml/kg) | CL (ml/h/kg) |
|---|---|---|---|---|---|---|
| 4 | 1293 | 1309 | 0.91 | 0.91 | 696 | 764 |
| 5 | 1045 | 1047 | 0.87 | 0.81 | 775 | 955 |
| Mean | 1169 | 1178 | 0.89 | 0.86 | 736 | 859 |

LB100 concentrations of the LB151 plasma samples were also measured and pharmacokinetic parameters were calculated. LB151 was converted to LB100 (see Tables 9.5-9.8).

TABLE 9.5

Plasma Concentrations of 100 after PO administration
of 10 mg/kg 151 to SD rat (ng/mL)

| Group | Rat No. | Time (h) | | | | | | | | |
|---|---|---|---|---|---|---|---|---|---|---|
| | | 0.25 | 0.50 | 1.0 | 2.0 | 3.0 | 5.0 | 7.0 | 9.0 | 24 |
| PO-10 mg/kg | 1 | 966 | 1426 | 882 | 734 | 236 | 81.1 | 37.9 | 31.6 | BLQ |
| | 2 | 522 | 1489 | 1141 | 645 | 396 | 79.4 | 20.3 | 22.5 | BLQ |
| | 3 | 1056 | 1439 | 1447 | 963 | 624 | 185 | 56.0 | 39.6 | BLQ |
| | Mean | 848 | 1451 | 1156 | 781 | 419 | 115 | 38.1 | 31.3 | |
| | SD | 286 | 33 | 283 | 164 | 195 | 61 | 17.9 | 8.6 | |

BLQ: Below the lower limit of quantification 10.0 ng/mL

TABLE 9.6

Plasma Concentrations of 100 after iv administration
of 1.0 mg/kg 151 to SD rat (ng/mL)

| Group | Rat No. | Time (h) | | | | | | | | | |
|---|---|---|---|---|---|---|---|---|---|---|---|
| | | 0.083 | 0.25 | 0.5 | 1.0 | 2.0 | 3.0 | 5.0 | 7.0 | 9.0 | 24 |
| IV-1 mg/kg | 4 | 646 | 345 | 308 | 257 | 125 | 32.2 | 10.2 | BLQ | BLQ | BLQ |
| | 5 | 430 | 239 | 231 | 182 | 114 | 33.3 | BLQ | BLQ | BLQ | BLQ |
| | Mean | 538 | 292 | 270 | 219 | 120 | 32.7 | 5.10 | | | |

BLQ: Below the lower limit of quantification 10.0 ng/ml.

TABLE 9.7

PK parameters of 100 after PO administration of 10 mg/kg 151 to SD rat

| Group | Rat No. | $T_{max}$ (h) | $C_{max}$ (ng/ml) | $AUC_{0-t}$ (ng · h/ml) | $AUC_{0-\infty}$ (ng · h/ml) | $T_{1/2}$ (h) | MRT (h) |
|---|---|---|---|---|---|---|---|
| PO-10 mg/kg | 1 | 0.50 | 1426 | 2795 | 2862 | 1.45 | 2.06 |
| | 2 | 0.50 | 1489 | 3006 | 3046 | 1.25 | 1.96 |
| | 3 | 1.00 | 1447 | 4309 | 4391 | 1.43 | 2.29 |
| | Mean | 0.67 | 1454 | 3370 | 3433 | 1.38 | 2.10 |
| | SD | 0.29 | 32 | 820 | 835 | 0.11 | 0.17 |
| | CV (%) | 43.3 | 2.2 | 24.3 | 24.3 | 8.1 | 8.1 |

TABLE 9.8

PK parameters of 100 after iv administration of 1.0 mg/kg 151 to SD rat

| Group | Rat No. | $T_{max}$ (h) | $C_{max}$ (ng/ml) | $AUC_{0-t}$ (ng · h/ml) | $AUC_{0-\infty}$ (ng · h/ml) | $T_{1/2}$ (h) | MRT (h) |
|---|---|---|---|---|---|---|---|
| IV-1 mg/kg | 4 | 0.083 | 646 | 681 | 694 | 0.88 | 1.16 |
| | 5 | 0.083 | 430 | 481 | 526 | 0.93 | 1.27 |
| | Mean | 0.083 | 538 | 581 | 610 | 0.91 | 1.21 |

Example 5

Pharmacokinetic Study of Compound 100

The pharmacokinetic studies on 100 and its metabolite endothal were conducted in SD rats. 100 was administrated via iv route at 0.5, 1.0 and 1.5 mg/kg into SD rats. The blood, liver and brain tissue samples were collected at predetermined times from rats. The LC/MS/MS methods were developed to determine 100 and endothal in plasma, liver and brain samples. In the report, the concentrations of 100 and endothal in plasma, liver and brain samples were presented.

Sample Collection

Twelve (12) female SD rats per group were dosed by iv with 100. The rats were fasted overnight prior to dosing, with free access to water. Foods were withheld for 2 hours post-dose. Blood, liver and brain tissue samples in two animals each group were collected at each time point, within 10% of the scheduled time for each time point. Two extra animals were used for analytic method development. Blood (>0.3 mL) were collected via aorta abdominalis in anaesthetic animals into tubes containing heparin at 15 min, 1, 2, 6, 10 and 24 hours after iv administration. Liver and brain tissues were collected immediately after animal death. The liver and brain tissues were excised and rinsed with cold saline to avoid blood residual. Upon collection, each sample was placed on ice and the blood samples were subsequently centrifuged (4° C., 11000 rpm, 5 min) to separate plasma. The obtained plasma, liver and brain tissue samples were stored at −70° C. until LC-MS/MS analysis.

Pharmacokinetic Interpretation

The pharmacokinetic parameters were evaluated using WinNonlin version 5.3 (Pharsight Corp., Mountain View, Calif., USA), assuming a non-compartmental model for drug absorption and distribution. $AUC_{0-t}$ ($AUC_{last}$) is the area under the plasma concentration-time curve from time zero to last sampling time, calculated by the linear trapezoidal rule. $AUC_{0-\infty}$ ($AUC_{INF}$) is the area under the plasma concentration-time curve with last concentration extrapolated based on the elimination rate constant.

Plasma, Liver and Brain Tissue Concentrations of Test Articles in SD Rats

Following single iv administration of 100 to SD rats, plasma, liver and brain tissue concentrations of both 100 and endothal were determined by the LC/MS/MS method described above. The plasma, liver and brain tissue concentrations at each sampling time are listed in Tables 10.1-10.6 and FIG. 4A-4D. The calculated pharmacokinetic parameters are listed in Table 10.7-10.8. 100 could pass through blood-brain barrier (BBB) following iv administration at 0.5, 1.0 and 1.5 mg/kg to SD rats. The mean $C_{max}$ in plasma was 1110~3664 ng/ml. The mean $C_{max}$ in liver and brain were 586~2548 ng/kg and 17.4~43.5 ng/kg, respectively. $AUC_{Last}$ in plasma was 695.8~7399.6 ng·h/ml, with 758.6~9081.0 ng·h/g in liver and 10.8~125.5 ng·h/g in brain, respectively. $T_{1/2}$ in plasma, liver and brain were 0.31~2.20 h, 0.78~2.01 h and 1.67~1.93 h, respectively.

Figure 4E:
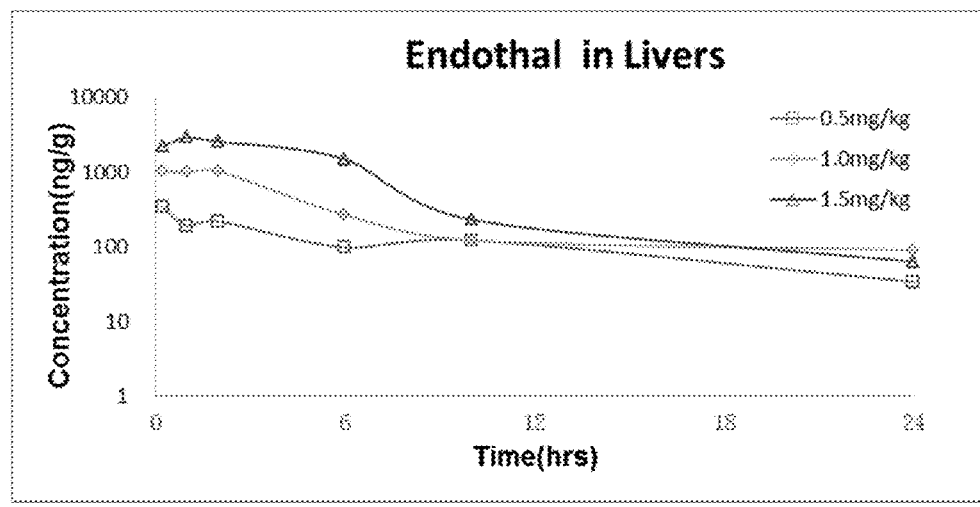
FIG. 4E: Concentration versus time curves of endothal in liver following iv administration of 100 to SD rats.
Figure 6A:
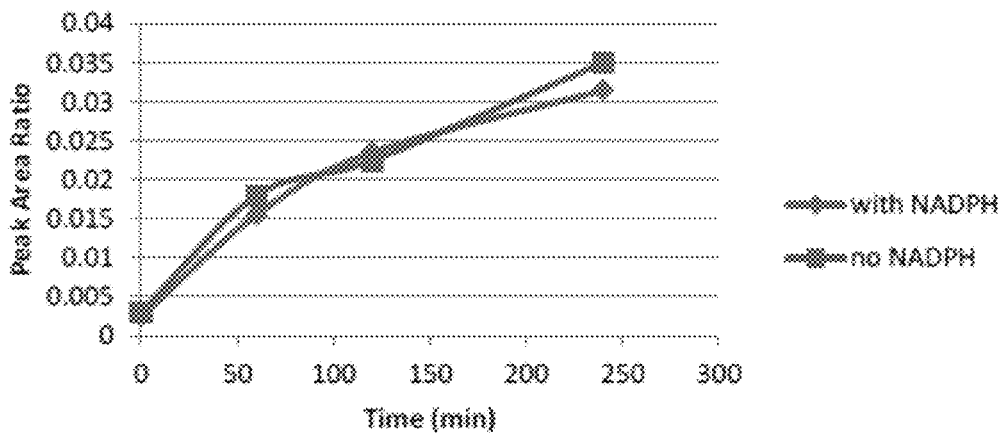
FIG. 6A: Chart showing formation of endothal in monkey liver S9 study.
Figure 6B:
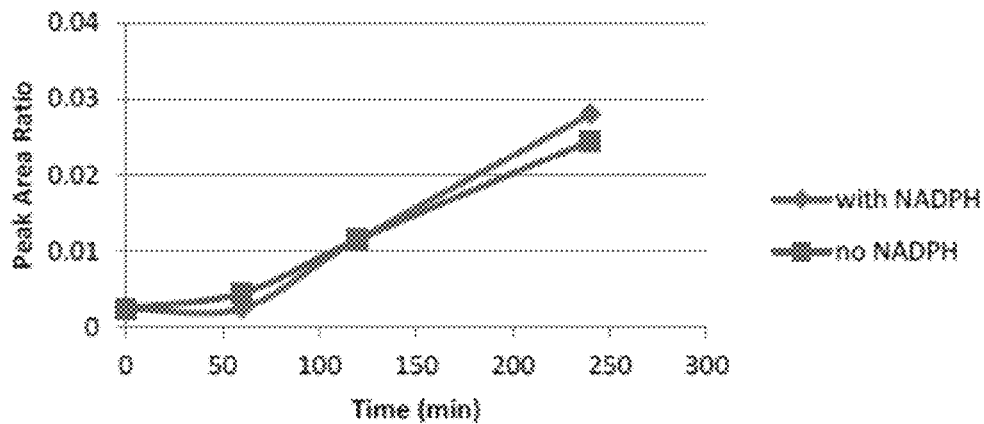
FIG. 6B: Chart showing formation of endothal in human liver S9 study.
Figure 6C:
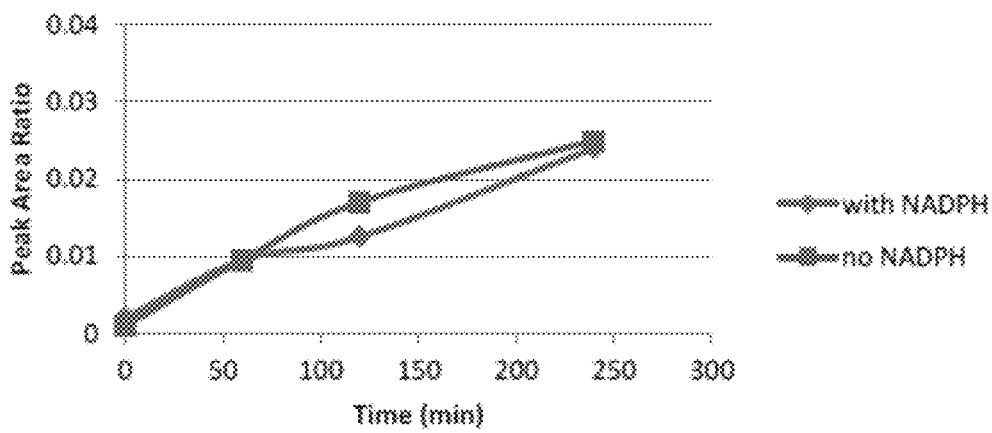
FIG. 6C: Chart showing formation of endothal in rat liver S9 study.
Figure 6D:
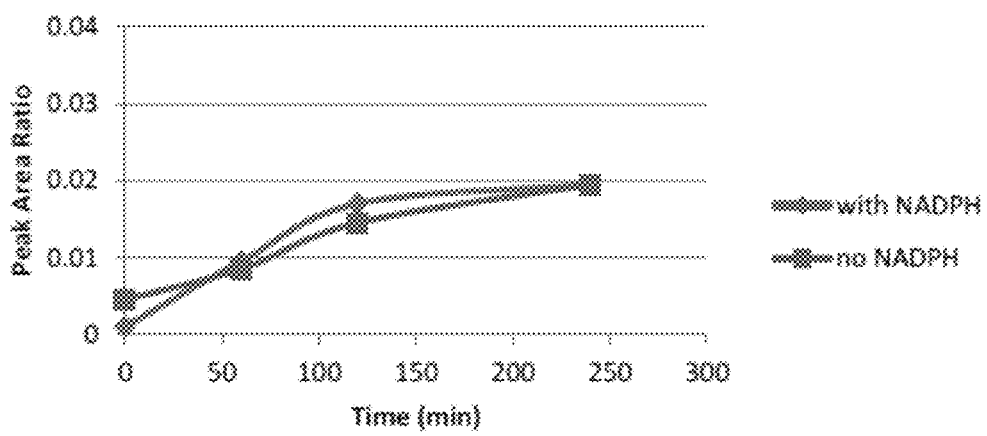
FIG. 6D: Chart showing formation of endothal in monkey liver S9 study.
Figure 6E:
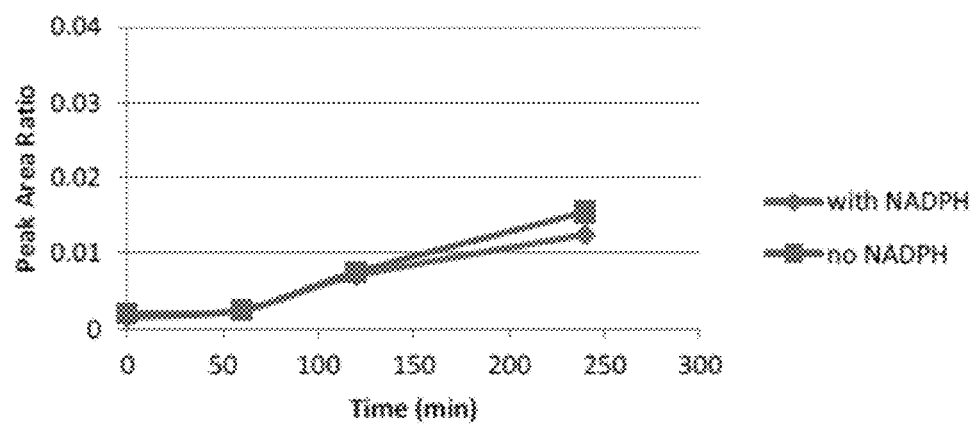
FIG. 6E: Chart showing formation of endothal in human liver S9 study.
Figure 6F:
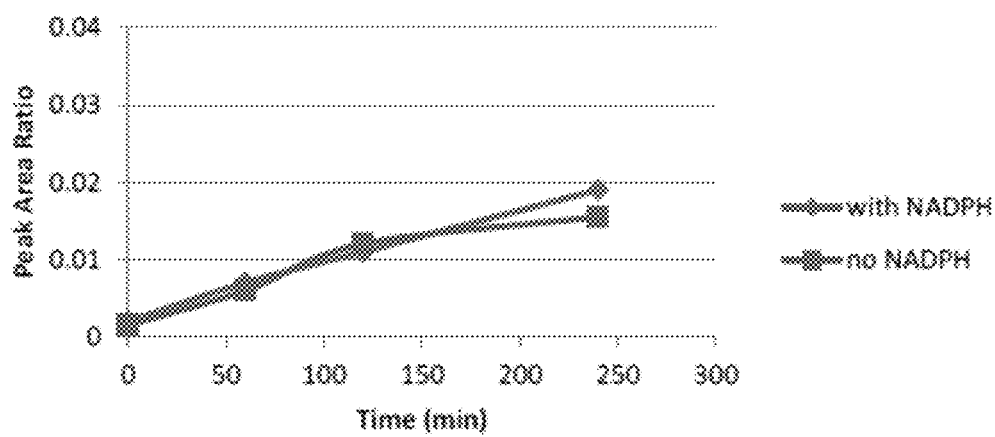
FIG. 6F: Chart showing formation of endothal in rat liver S9 study.
Figure 6G:
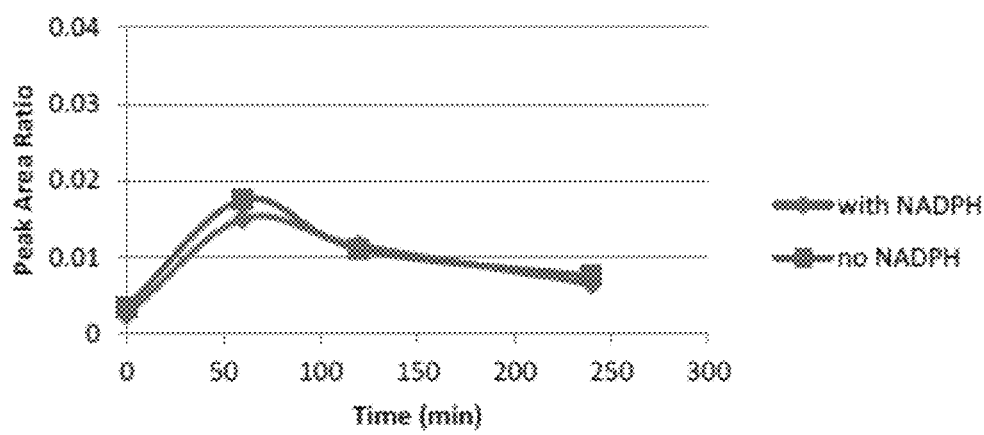
FIG. 6G: Chart showing formation of LB100 in monkey liver S9 study.
Figure 6H:
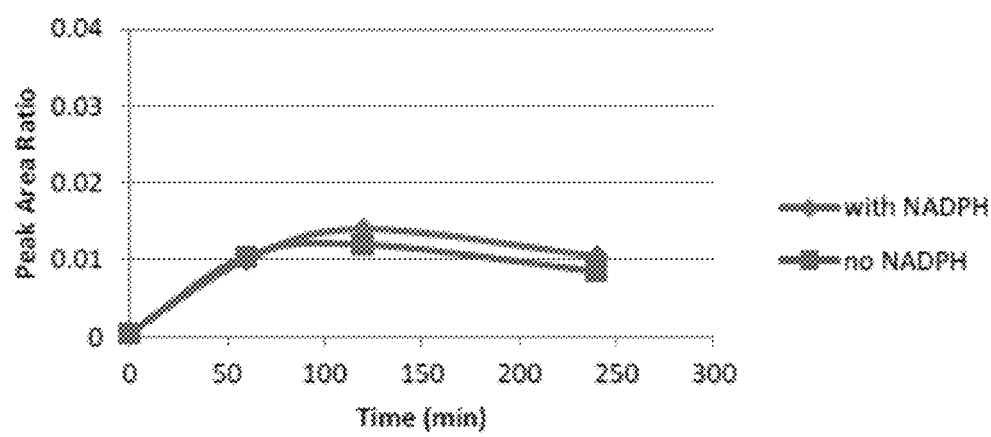
FIG. 6H: Chart showing formation of LB100 in human liver S9 study.
Figure 6I:
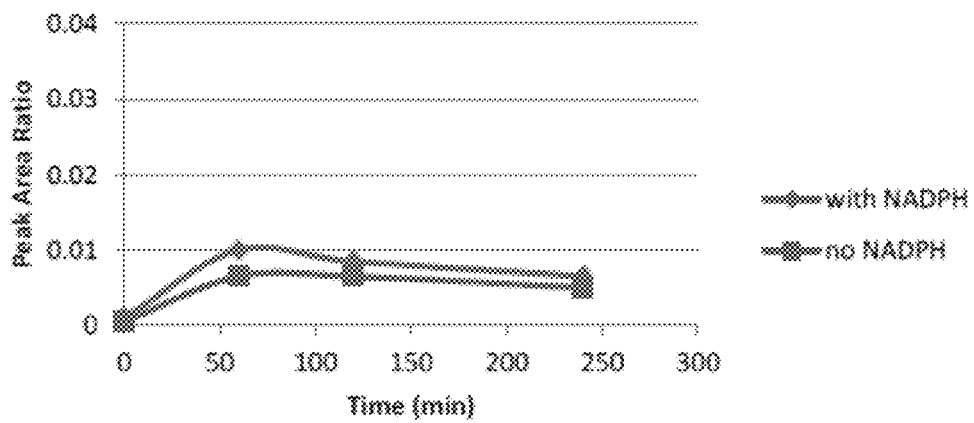
FIG. 6I: Chart showing formation of LB100 in rat liver S9 study.
Figure 6J:
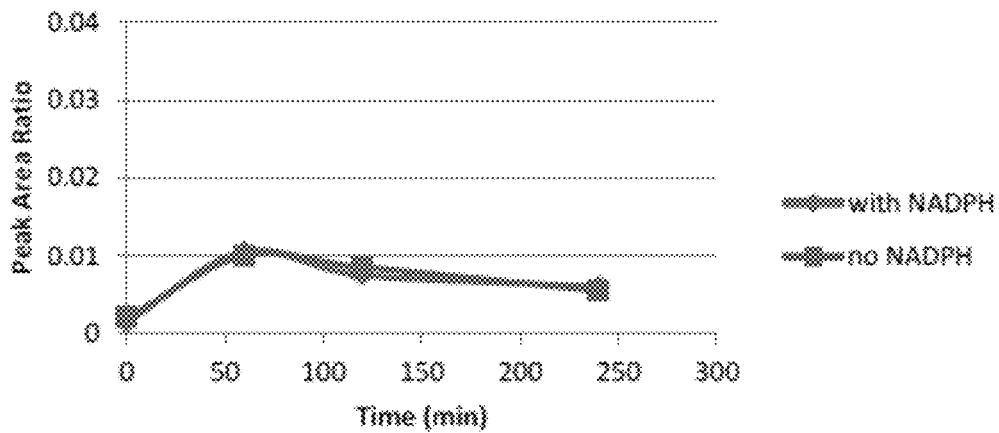
FIG. 6J: Chart showing formation of LB100 in monkey liver S9 study.
Figure 6K:
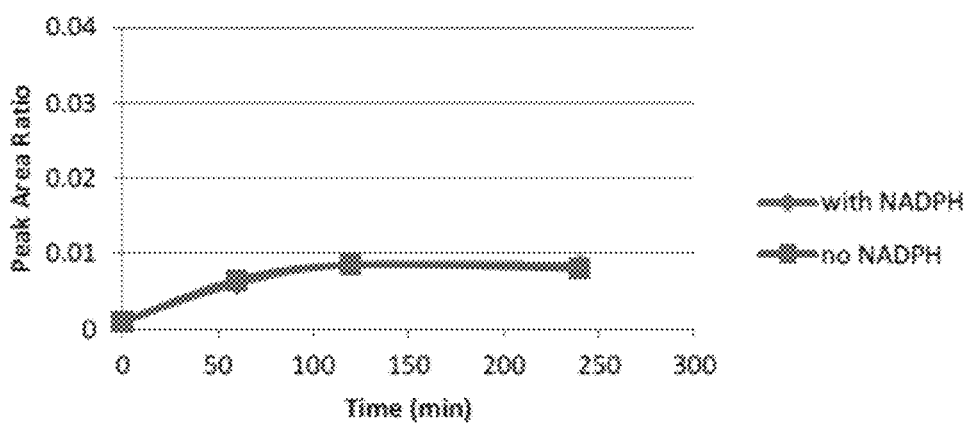
FIG. 6K: Chart showing formation of LB100 in human liver S9 study.
Figure 6L:
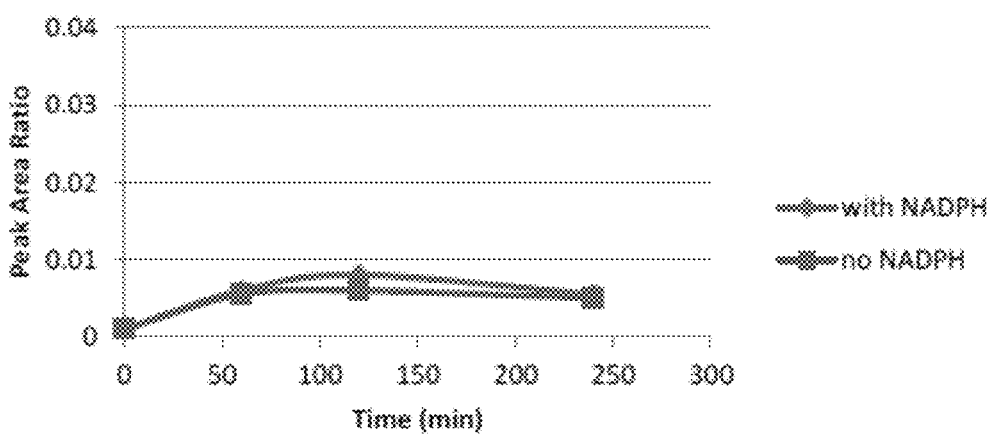
FIG. 6L: Chart showing formation of LB100 in rat liver S9 study.
Figure 8A:
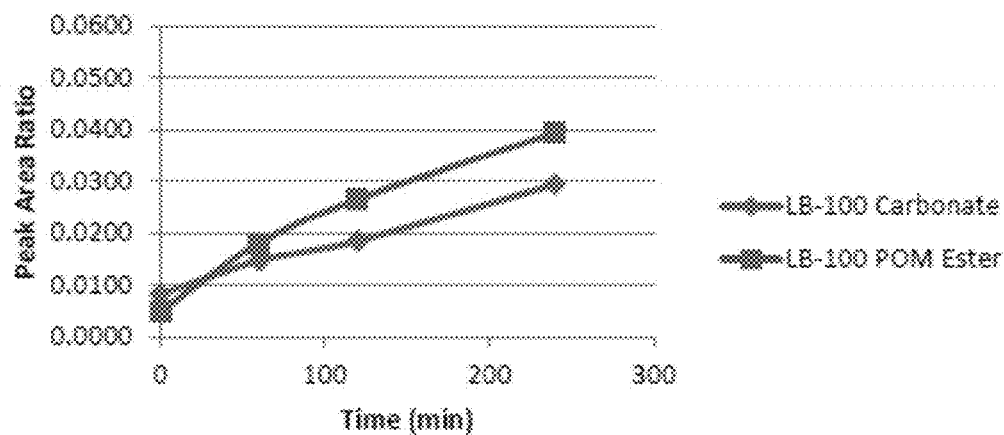
FIG. 8A: Chart showing formation of endothal in Dog whole blood study.
Figure 8B:
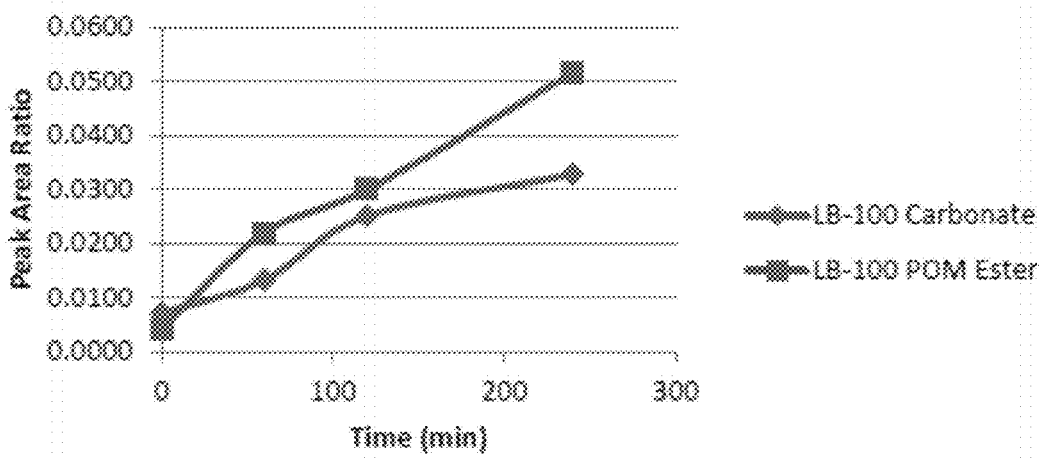
FIG. 8B: Chart showing formation of endothal in Human whole blood study.
Figure 8C:
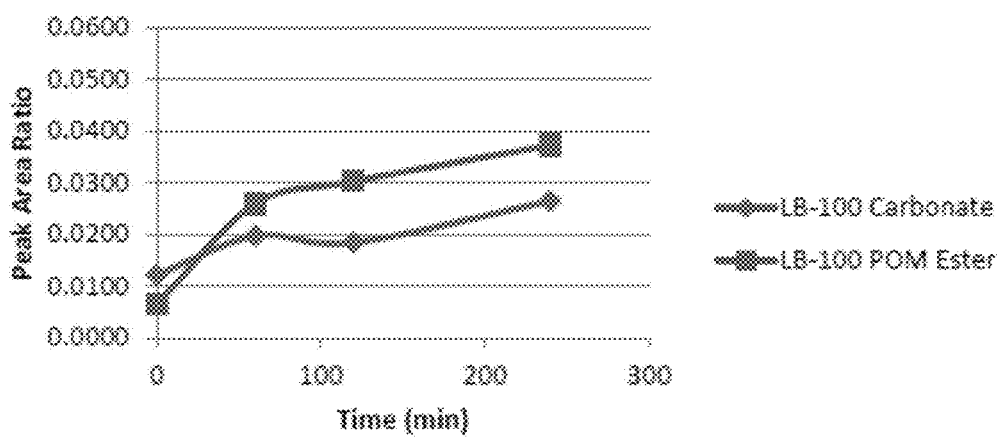
FIG. 8C: Chart showing formation of endothal in monkey whole blood study.
Figure 8D:
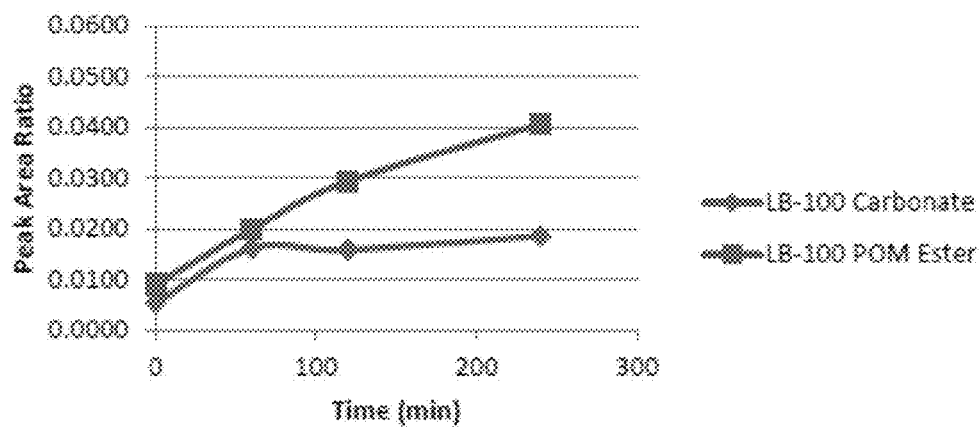
FIG. 8D: Chart showing formation of endothal in rat whole blood study.
Figure 8E:
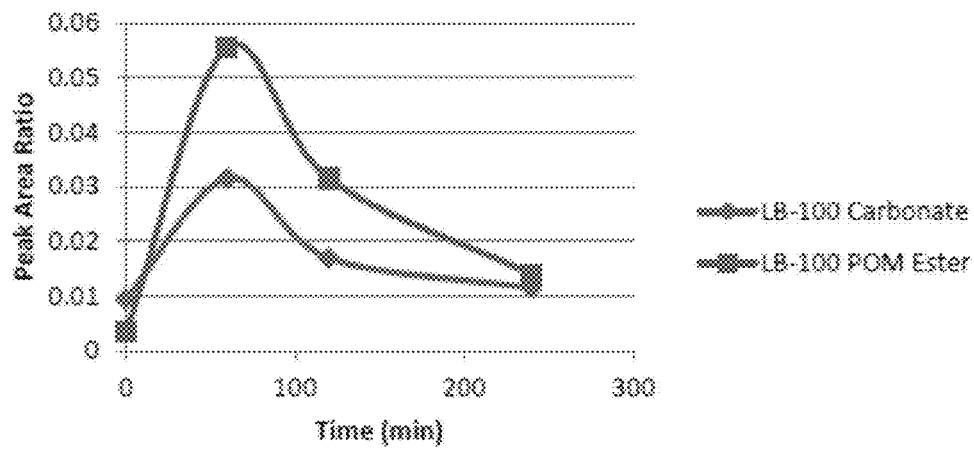
FIG. 8E: Chart showing formation of LB100 in dog whole blood study.
Figure 8F:
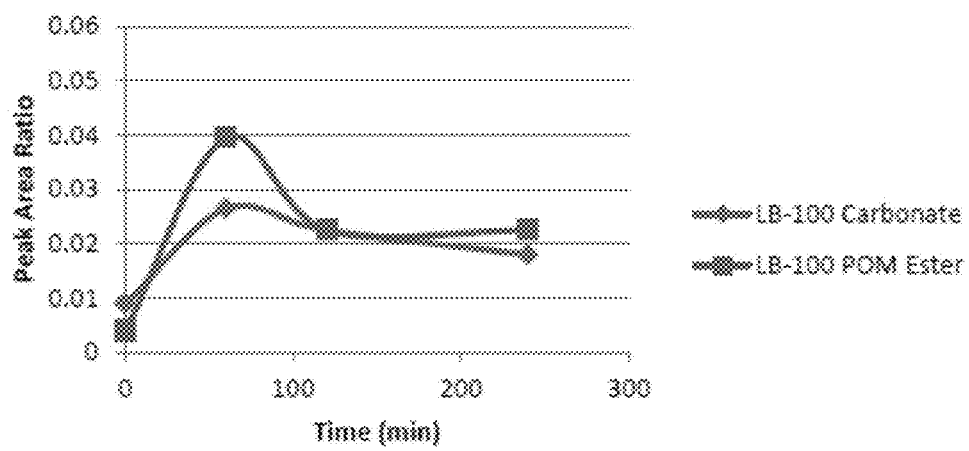
FIG. 8F: Chart showing formation of LB100 in human whole blood study.
Figure 8G:
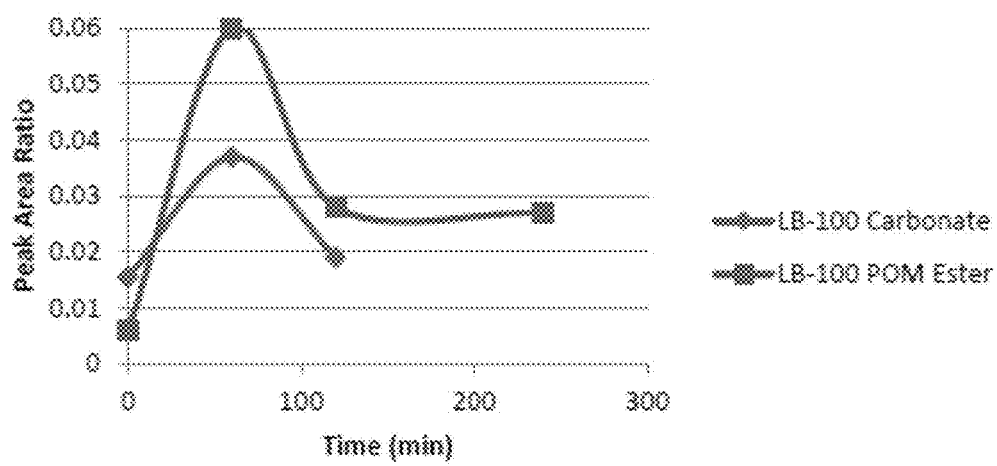
FIG. 8G: Chart showing formation of LB100 in monkey whole blood study.
Figure 8H:
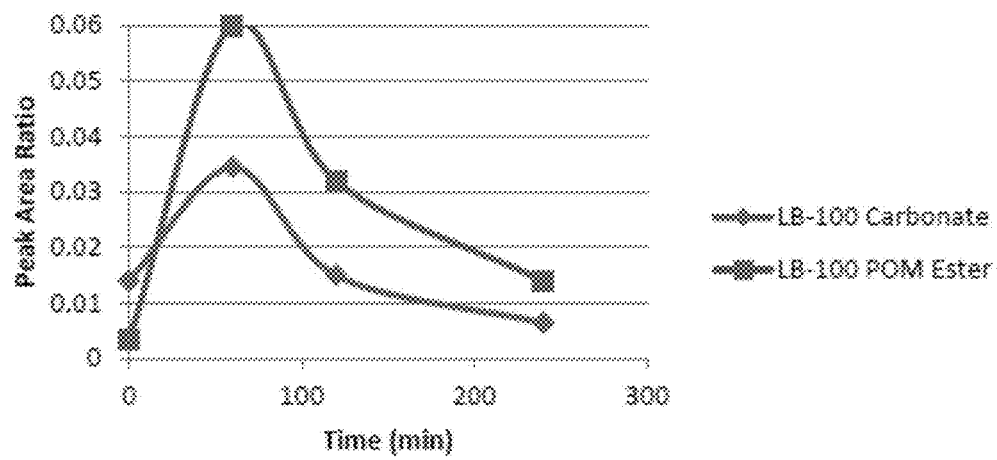
FIG. 8H: Chart showing formation of LB100 in rat whole blood study.

As shown in Table 10.4-10.6 and FIG. 4D-4E, endothal was detectable in plasma and liver samples following single iv administration of 100 at 0.5, 1.0 and 1.5 mg/kg, and the concentrations in plasma and liver increased with dose level of 100, whereas endothal was not detectable in brain samples. The mean $C_{max}$ in plasma and liver were 577-1230 ng/ml and 349-2964 ng/ml, respectively. $AUC_{last}$ in plasma and liver were 546-4476 ng·h/ml and 2598-18434 ng·h/g, respectively. $T_{1/2}$ in plasma and liver were 6.25-7.06 h and 4.57-10.1 h, respectively.

Following single iv administration, the mean $C_{max}$ of 100 in plasma was 1110~3664 ng/ml and $T_{1/2}$ in plasma was 0.31~2.20 h. $AUC_{last}$ in plasma was 695.8~7399.6 ng·h/ml, and AUC increased proportionally with the dose level of 100. Following single iv administration, 100 was both detectable in liver and brain tissue samples. The concentration of 100 in liver samples was much higher than that in brain samples at same sampling time point, but 100 in liver and brain tissues was both below limit of quantification 24 hours after iv administration. Following single iv administration of 100, endothal was detectable and stay a long time in plasma and liver tissue. The mean $C_{max}$ in plasma and liver were 577-1230 ng/ml and 349-2964 ng/ml, respectively. $AUC_{last}$ in plasma and liver were 546-4476 ng·h/ml and 2598-18434 ng·h/g, respectively. $T_{1/2}$ in plasma and liver were 6.25-7.06 h and 4.57-10.1 h, respectively. However, endothal was undetectable in brain tissue.

TABLE 10.1

Analytical data of 100 plasma concentration (ng/mL) in SD rats following iv administration.

| Time (hr) | Rat 1 | Rat 2 | Mean | SD |
|---|---|---|---|---|
| 0.5 mg/kg Plasma concentration (ng/ml) | | | | |
| 0.25 | 1000 | 1219 | 1110 | 154.68 |
| 1 | 192 | 103 | 148 | 62.78 |
| 2 | 25.8 | 19.4 | 22.6 | 4.58 |
| 6 | BLQ | BLQ | BLQ | N/A |
| 10 | BLQ | BLQ | BLQ | N/A |
| 24 | BLQ | BLQ | BLQ | N/A |
| 1.0 mg/kg Plasma concentration (ng/ml) | | | | |
| 0.25 | 2118 | 2648 | 2383 | 374.46 |
| 1 | 354 | 595 | 474 | 170.92 |
| 2 | 1030 | 239 | 634.4 | 559.22 |
| 6 | 3.27 | BLQ | BLQ | N/A |
| 10 | BLQ | BLQ | BLQ | N/A |
| 24 | BLQ | BLQ | BLQ | N/A |

TABLE 10.1-continued

Analytical data of 100 plasma concentration (ng/mL) in SD rats following iv administration.

| Time (hr) | Rat 1 | Rat 2 | Mean | SD |
|---|---|---|---|---|
| 1.5 mg/kg Plasma concentration (ng/ml) | | | | |
| 0.25 | 3779 | 3548 | 3664 | 162.94 |
| 1 | 1758 | 2273 | 2015 | 364.20 |
| 2 | 1314 | 1104 | 1209 | 148.70 |
| 6 | 263 | 519 | 391 | 180.40 |
| 10 | BLQ | BLQ | BLQ | N/A |
| 24 | BLQ | BLQ | BLQ | N/A |

TABLE 10.2

Analytical data of 100 liver concentration (ng/g) in SD rats following iv administration.

| Time (hr) | Rat 1 | Rat 2 | Mean | SD |
|---|---|---|---|---|
| 0.5 mg/kg Liver concentration (ng/g) | | | | |
| 0.25 | 520 | 651 | 586 | 92.76 |
| 1 | 695 | 223 | 459 | 333.91 |
| 2 | 109 | 148 | 128 | 27.06 |
| 6 | BLQ | 4.80 | BLQ | N/A |
| 10 | BLQ | BLQ | BLQ | N/A |
| 24 | BLQ | BLQ | BLQ | N/A |
| 1.0 mg/kg Liver concentration (ng/g) | | | | |
| 0.25 | 1299 | 1442 | 1371 | 101.47 |
| 1 | 865 | 682 | 773 | 129.61 |
| 2 | 1318 | 398 | 858 | 650.73 |
| 6 | 13.9 | 5.73 | 9.83 | 5.81 |
| 10 | BLQ | BLQ | BLQ | N/A |
| 24 | BLQ | BLQ | BLQ | N/A |
| 1.5 mg/kg Liver concentration (ng/g) | | | | |
| 0.25 | 1980 | 1709 | 1844 | 191.66 |
| 1 | 2144 | 2953 | 2548 | 571.97 |
| 2 | 2404 | 1585 | 1995 | 579.17 |
| 6 | 407 | 536 | 471 | 91.77 |
| 10 | BLQ | 5.25 | BLQ | N/A |
| 24 | BLQ | BLQ | BLQ | N/A |

TABLE 10.3

Analytical data of 100 brain concentration (ng/g) in SD rats following iv administration.

| Time (hr) | Rat 1 | Rat 2 | Mean | SD |
|---|---|---|---|---|
| 0.5 mg/kg Brain concentration (ng/g) | | | | |
| 0.25 | 15.3 | 19.5 | 17.42 | 3.02 |
| 1 | 6.31 | 4.77 | 5.54 | 1.09 |
| 2 | BLQ | BLQ | BLQ | N/A |
| 6 | BLQ | BLQ | BLQ | N/A |
| 10 | BLQ | BLQ | BLQ | N/A |
| 24 | BLQ | BLQ | BLQ | N/A |
| 1.0 mg/kg Brain concentration (ng/g) | | | | |
| 0.25 | 21.9 | 45.8 | 33.90 | 16.90 |
| 1 | 16.3 | 8.05 | 12.20 | 5.84 |
| 2 | 24.3 | 6.60 | 15.40 | 12.49 |
| 6 | BLQ | BLQ | BLQ | N/A |
| 10 | BLQ | BLQ | BLQ | N/A |
| 24 | BLQ | BLQ | BLQ | N/A |

TABLE 10.3-continued

Analytical data of 100 brain concentration (ng/g) in SD rats following iv administration.

| Time (hr) | Rat 1 | Rat 2 | Mean | SD |
|---|---|---|---|---|
| 1.5 mg/kg Brain concentration (ng/g) | | | | |
| 0.25 | 46.9 | 40.1 | 43.49 | 4.82 |
| 1 | 28.2 | 36.9 | 32.56 | 6.18 |
| 2 | 27.2 | 24.1 | 25.66 | 2.16 |
| 6 | 4.23 | 6.77 | 5.50 | 1.79 |
| 10 | BLQ | BLQ | BLQ | N/A |
| 24 | BLQ | BLQ | BLQ | N/A |

TABLE 10.4

Analytical data of endothal plasma concentration (ng/g) in SD rats following iv administration.

| Time (hr) | Rat 1 | Rat 2 | Mean | SD |
|---|---|---|---|---|
| 0.5 mg/kg Endothal plasma concentration (ng/ml) | | | | |
| 0.25 | 355 | 798 | 576 | 313.25 |
| 1 | 104 | 59.5 | 81.75 | 31.47 |
| 2 | 44.6 | 28.1 | 36.35 | 11.67 |
| 6 | 20.3 | BLQ | 20.3 | N/A |
| 10 | 48.1 | 25.3 | 36.70 | 16.12 |
| 24 | BLQ | BLQ | BLQ | N/A |
| 1.0 mg/kg Endothal plasma concentration (ng/ml) | | | | |
| 0.25 | 1310 | 1150 | 1230 | 113.14 |
| 1 | 164 | 456 | 310 | 206.48 |
| 2 | 699 | 213 | 456 | 343.65 |
| 6 | 33.6 | 38.2 | 35.90 | 3.25 |
| 10 | 32.9 | 31.8 | 32.35 | 0.78 |
| 24 | 29.4 | 22.0 | 25.70 | 5.23 |
| 1.5 mg/kg Endothal plasma concentration (ng/ml) | | | | |
| 0.25 | 1610 | 745 | 1177 | 611.65 |
| 1 | 760 | 458 | 609 | 213.55 |
| 2 | 539 | 600 | 569.50 | 43.13 |
| 6 | 373 | 444 | 408.50 | 50.20 |
| 10 | 22.3 | 33.1 | 27.70 | 7.64 |
| 24 | 21.5 | 34.1 | 27.80 | 8.91 |

TABLE 10.5

Analytical data of endothal liver concentration (ng/g) in SD rats following iv administration of 100.

| Time (hr) | Rat 1 | Rat 2 | Mean | SD |
|---|---|---|---|---|
| 0.5 mg/kg Endothal liver concentration (ng/g) | | | | |
| 0.25 | 316 | 382 | 349 | 46.67 |
| 1 | 256 | 131 | 193.50 | 88.39 |
| 2 | 168 | 273 | 220.50 | 74.25 |
| 6 | 85.8 | 112 | 98.90 | 18.53 |
| 10 | 129 | 118 | 123.50 | 7.78 |
| 24 | 32.0 | 36.4 | 34.20 | 3.11 |
| 1.0 mg/kg Endothal liver concentration (ng/g) | | | | |
| 0.25 | 768 | 1320 | 1044 | 390.32 |
| 1 | 1380 | 618 | 999 | 538.82 |
| 2 | 1530 | 542 | 1036 | 698.62 |
| 6 | 298 | 241 | 269.50 | 40.31 |
| 10 | 151 | 94.2 | 122.60 | 40.16 |
| 24 | 66.6 | 115 | 90.80 | 34.22 |

TABLE 10.5-continued

Analytical data of endothal liver concentration (ng/g) in SD rats following iv administration of 100.

| Time (hr) | Rat 1 | Rat 2 | Mean | SD |
|---|---|---|---|---|
| 1.5 mg/kg Endothal liver concentration (ng/g) | | | | |
| 0.25 | 2298 | 2160 | 2229 | 97.58 |
| 1 | 2874 | 2976 | 2925 | 72.12 |
| 2 | 2952 | 2226 | 2589 | 513.36 |
| 6 | 1686 | 1326 | 1506 | 254.56 |
| 10 | 137 | 329 | 233 | 135.76 |
| 24 | 75.0 | 52.1 | 63.55 | 16.19 |

TABLE 10.6

Analytical data of endothal brain concentration (ng/g) in SD rats following iv administration of 100.

| Time (hr) | Rat 1 | Rat 2 | Mean | SD |
|---|---|---|---|---|
| 0.5 mg/kg Endothal brain concentration (ng/g) | | | | |
| 0.25 | BLQ | BLQ | BLQ | N/A |
| 1 | BLQ | BLQ | BLQ | N/A |
| 2 | BLQ | BLQ | BLQ | N/A |
| 6 | BLQ | BLQ | BLQ | N/A |
| 10 | BLQ | BLQ | BLQ | N/A |
| 24 | BLQ | BLQ | BLQ | N/A |
| 1.0 mg/kg Endothal brain concentration (ng/g) | | | | |
| 0.25 | BLQ | BLQ | BLQ | N/A |
| 1 | BLQ | BLQ | BLQ | N/A |
| 2 | BLQ | BLQ | BLQ | N/A |
| 6 | BLQ | BLQ | BLQ | N/A |
| 10 | BLQ | BLQ | BLQ | N/A |
| 24 | BLQ | BLQ | BLQ | N/A |
| 1.5 mg/kg Endothal brain concentration (ng/g) | | | | |
| 0.25 | BLQ | BLQ | BLQ | N/A |
| 1 | BLQ | BLQ | BLQ | N/A |
| 2 | BLQ | BLQ | BLQ | N/A |
| 6 | BLQ | BLQ | BLQ | N/A |
| 10 | BLQ | BLQ | BLQ | N/A |
| 24 | BLQ | BLQ | BLQ | N/A |

TABLE 10.7

Main pharmacokinetic parameters of 100 in SD rats following iv administration.

| Analyte | Dose of LB-100 mg/kg | Tissue | T½ h | Tmax h | Cmax ng/ml or ng/g | AUClast ng · h/ml or ng · h/g | AUCINF ng · h/ml or ng · h/g | MRT h |
|---|---|---|---|---|---|---|---|---|
| 100 | 0.5 | Brain | / | 0.25 | 17.4 | 10.8 | / | / |
| | | Liver | 0.78 | 0.25 | 586 | 758.6 | 902.2 | 1.17 |
| | | Plasma | 0.31 | 0.25 | 1110 | 695.8 | 706.0 | 0.45 |
| | 1.0 | Brain | 1.67 | 0.25 | 33.9 | 35.3 | 72.5 | 2.68 |
| | | Liver | 0.79 | 0.25 | 1371 | 3526.5 | 3537.7 | 1.51 |
| | | Plasma | 0.99 | 0.25 | 2383 | 1923.5 | 2830.2 | 1.57 |
| | 1.5 | Brain | 1.93 | 0.25 | 43.5 | 125.5 | 140.8 | 2.57 |
| | | Liver | 2.01 | 1.0 | 2548 | 9081.0 | 10449.1 | 2.90 |
| | | Plasma | 2.20 | 0.25 | 3664 | 7399.6 | 8641.4 | 2.82 |

TABLE 10.8

Main pharmacokinetic parameters of Endothal in SD rats following single iv administration of 100.

| Analyte | Dose of LB-100 mg/kg | Tissue | T½ h | Tmax h | Cmax ng/ml or ng/g | AUClast ng · h/ml or ng · h/g | AUCINF ng · h/ml or ng · h/g | MRT h |
|---|---|---|---|---|---|---|---|---|
| Endothal | 0.5 | Brain | / | / | / | / | / | / |
| | | Liver | 10.1 | 0.25 | 349 | 2598 | 3095 | 7.90 |
| | | Plasma | 6.65 | 0.25 | 577 | 546 | 828 | 2.96 |
| | 1.0 | Brain | / | / | / | / | / | / |
| | | Liver | 6.10 | 0.25 | 1425 | 6673 | 7370 | 6.14 |
| | | Plasma | 7.06 | 0.25 | 1230 | 2487 | 2750 | 4.38 |
| | 1.5 | Brain | / | / | / | / | / | / |
| | | Liver | 4.57 | 0.25 | 2964 | 18434 | 18850 | 4.54 |
| | | Plasma | 6.25 | 0.25 | 1178 | 4476 | 4730 | 4.57 |

Endothal concentrations of the 100 plasma samples were measured and pharmacokinetic parameters were calculated. LB100 was converted to endothal.

Example 6

Administration of Compound

Compounds 100, 105, 113, 153 and 157 are PP2A inhibitors. The present invention provides analogues of 100, 105, 113, 153 and 157, which are inhibitors of PP2A in vitro in human cancer cells and in xenografts of human tumor cells in mice when given parenterally in mice. These compounds inhibit the growth of cancer cells in mouse model systems. The analogues of 100, 105, 113, 153 and 157 are intraperitoneally administered to mice and PP2A activity is measured in the liver and brain. The analogues of 100, 105, 113, 153 and 157 reduce PP2A activity in the liver and brain.

An amount of any one of the compounds of the present invention is administered to a subject afflicted with brain cancer. The amount of the compound is effective to treat the subject.

An amount of any one of the compounds of the present invention is administered to a subject afflicted with diffuse intrinsic pontine glioma. The amount of the compound is effective to treat the subject.

An amount of any one of the compounds of the present invention is administered to a subject afflicted with glioblastoma multiforme. The amount of the compound is effective to treat the subject.

An amount of any one of the compounds of the present invention is administered to a subject afflicted with brain cancer. The amount of the compound is effective to cross the blood brain barrier of the subject and treat the subject.

An amount of any one of the compounds of the present invention is administered to a subject afflicted with diffuse intrinsic pontine glioma. The amount of the compound is effective to cross the blood brain barrier of the subject and treat the subject.

An amount of any one of the compounds of the present invention is administered to a subject afflicted with glioblastoma multiforme. The amount of the compound is effective to cross the blood brain barrier of the subject and treat the subject.

Example 7

Administration of Compound in Combination with an Anti-Cancer Agent

An amount of any one of the compounds of the present invention in combination with an anti-cancer agent is administered to a subject afflicted with brain cancer. The amount of the compound is effective to enhance the anti-cancer activity of the anti-cancer agent.

An amount of any one of the compounds of the present invention in combination with ionizing radiation, x-radiation, docetaxel or temozolomide is administered to a subject afflicted with brain cancer. The amount of the compound is effective to enhance the anti-cancer activity of the ionizing radiation, x-radiation, docetaxel or temozolomide.

An amount of any one of the compounds of the present invention in combination with an anti-cancer agent is administered to a subject afflicted with diffuse intrinsic pontine glioma or glioblastoma multiforme. The amount of the compound is effective to enhance the anti-cancer activity of the anti-cancer agent.

An amount of any one of the compounds of the present invention in combination with ionizing radiation, x-radiation, docetaxel or temozolomide is administered to a subject afflicted with diffuse intrinsic pontine glioma or glioblastoma multiforme. The amount of the compound is effective to enhance the anti-cancer activity of the ionizing radiation, x-radiation, docetaxel or temozolomide.

Example 8

Endothal Prodrugs

As demonstrated in the data contained herein Compounds 105, 113, 153 and 157 are metabolized to endothal in vivo. The analogues of 105, 113, 153 and 157 contained herein are also metabolize to endothal in vivo and act as prodrugs of endothal. The endothal dimer analogs contained herein are also metabolized to endothal in vivo and act as prodrugs of endothal.

In addition, while not wishing to be bound to a theory, it is believed that the prodrugs of the present application allow for targeted delivery of endothal to specific cells, i.e. cancer cells, in a subject. Direct administration of endothal is undesirable due to toxicity. The prodrugs provide improved absorption leading to greater bioavailability of the active compound.

An amount of any one of the compounds of the present invention is administered to a subject afflicted with cancer. The amount of the compound is effective to deliver endothal to cancers cells in the subject.

An amount of any one of the compounds of the present invention is administered to a subject afflicted with brain cancer. The amount of the compound is effective to deliver endothal to brain cancers cells in the subject.

An amount of any one of the compounds of the present invention is administered to a subject afflicted with diffuse intrinsic pontine glioma or glioblastoma multiforme. The amount of the compound is effective to deliver endothal to diffuse intrinsic pontine glioma cells or glioblastoma multiforme cells in the subject.

An amount of any one of the compounds of the present invention is administered to a subject afflicted with brain cancer. The amount of the compound is effective to deliver endothal across the blood brain barrier of the subject.

Example 9

Dual Endothal/Chemotherapeutic Agent Prodrug

As demonstrated in the data contained herein Compounds 105, 113, 153 and 157 are metabolized to endothal in vivo. The analogues of 105, 113, 153 and 157 contained herein are also metabolized to endothal in vivo and act as dual endothal/chemotherapeutic agents prodrugs. The dual prodrugs contained herein are also metabolized to endothal in vivo and act as prodrugs of endothal. However, the metabolism to endothal simultaneously releases a chemotherapeutic agent.

In addition, while not wishing to be bound to a theory, it is believed that the dual prodrugs of the present application allow for targeted delivery of endothal and a chemotherapeutic agent to specific cells, i.e. cancer cells, in a subject. Direct administration of endothal and/or a chemotherapeutic agent is undesirable due to toxicity.

In addition, while not wishing to be bound to a theory, it is believed that the dual prodrugs of the present application allow for targeted delivery of endothal and a chemotherapeutic agent to specific cells, i.e. cancer cells, in a subject. Furthermore, the dual prodrugs have the advantage of having two bioactive compounds combined into one drug (novel structure). That structures alone have their own advantages, e.g., improved absorption leading to greater bioavailability of either constituent. Furthermore, direct administration of endothal and/or a chemotherapeutic agent could be undesirable due to either's intrinsic toxicity.

Example 10

Synthesis of LB-100 POM Ester and LB-100 Carbonate

LB-100 POM Ester

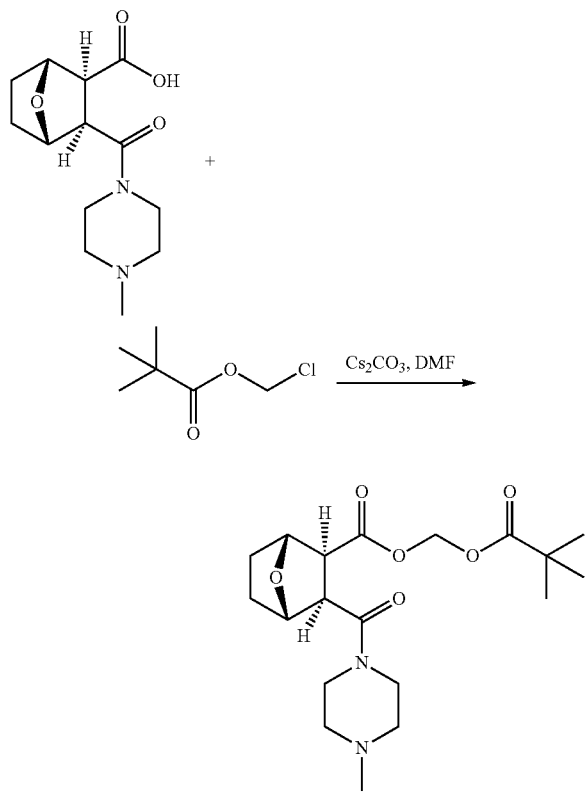

To a solution of LB-100 (106 mg, 0.4 mmol) in DMF (5 mL) is added Cs$_2$CO$_3$ (386 mg, 1.2 mmol) at room temperature. After stirring for 5 min., chloromethyl pivalate (178 mmg, 1.2 mmol) is added. The resulting mixture is stirred at room temperature overnight. Water (10 ml) is added, the mixture is extracted with ethyl acetate (5×10 ml). The organic phase is dried over MgSO$_4$, filtered and the solvent is removed. The residue is titrated with hexane, and filtered to give white solid (103 mg, 68% yield). $^1$H NMR (CDCl$_3$) 1.20 (s, 9H), 1.52 (d, 2H), 1.84 (d, 2H), 2.28-2.52 (m, 7H), 2.88 (d, 1H), 3.16 (d, 1H), 3.36-3.52 (m, 3H), 3.72 (m, 1H), 4.80 (s, 1H), 5.00 (s, 1H), 5.68 (d, 1H), 5.72 (d, 1H)

LB-100 Carbonate

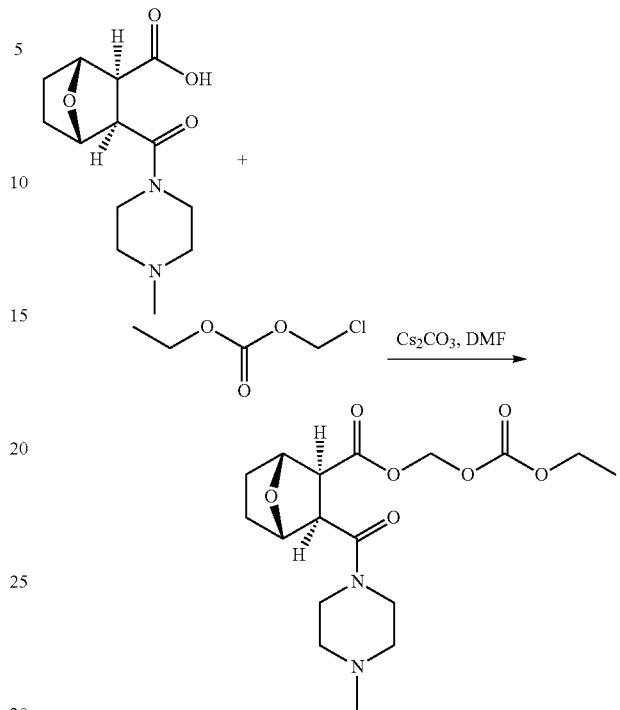

To a solution of LB-100 (150 mg, 0.56 mmol) in DMF (5 mL) is added Cs$_2$CO$_3$ (546 mg, 1.7 mmol) at room temperature. After stirring for 5 min., chloromethyl ethyl carbonate (232 mmg, 1.7 mmol) is added. The resulting mixture is stirred at room temperature overnight. Water (10 ml) is added, the mixture is extracted with ethyl acetate (5×10 ml). The organic phase is dried over MgSO$_4$, filtered and the solvent is removed. The residue is titrated with hexane, and filtered to give white solid (124 mg, 60% yield). $^1$HNMR (CDCl3) 1.23 (t, 3H), 1.52 (d, 2H), 1.84 (d, 2H), 2.28-2.52 (m, 7H), 2.84 (d, 1H), 3.18 (d, 1H), 3.36-3.52 (m, 3H), 3.72 (m, 1H), 4.20 (q, 2H), 4.80 (s, 1H), 5.00 (s, 1H), 5.62 (d, 1H), 5.80 (d, 1H).

Example 12

Administration of LB-100 Carbonate or LB-100 POM

An amount of LB-100 Carbonate or LB-100 POM is administered to a subject afflicted with brain cancer. The amount of the compound is effective to treat the subject.

An amount of LB-100 Carbonate or LB-100 POM is administered to a subject afflicted with diffuse intrinsic pontine glioma. The amount of the compound is effective to treat the subject.

An amount of LB-100 Carbonate or LB-100 POM is administered to a subject afflicted with glioblastoma multiforme. The amount of the compound is effective to treat the subject.

An amount of LB-100 Carbonate or LB-100 POM is administered to a subject afflicted with brain cancer. The amount of the compound is effective to cross the blood brain barrier of the subject and treat the subject.

An amount of LB-100 Carbonate or LB-100 POM is administered to a subject afflicted with diffuse intrinsic pontine glioma. The amount of the compound is effective to cross the blood brain barrier of the subject and treat the subject.

An amount of LB-100 Carbonate or LB-100 POM is administered to a subject afflicted with glioblastoma multiforme. The amount of the compound is effective to cross the blood brain barrier of the subject and treat the subject.

An amount of LB-100 Carbonate or LB-100 POM in combination with an anti-cancer agent is administered to a subject afflicted with brain cancer. The amount of the compound is effective to enhance the anti-cancer activity of the anti-cancer agent.

An amount of LB-100 Carbonate or LB-100 POM in combination with ionizing radiation, x-radiation, docetaxel or temozolomide is administered to a subject afflicted with brain cancer. The amount of the compound is effective to enhance the anti-cancer activity of the ionizing radiation, x-radiation, docetaxel or temozolomide.

An amount of LB-100 Carbonate or LB-100 POM in combination with an anti-cancer agent is administered to a subject afflicted with diffuse intrinsic pontine glioma or glioblastoma multiforme. The amount of the compound is effective to enhance the anti-cancer activity of the anti-cancer agent.

An amount of LB-100 Carbonate or LB-100 POM in combination with ionizing radiation, x-radiation, docetaxel or temozolomide is administered to a subject afflicted with diffuse intrinsic pontine glioma or glioblastoma multiforme. The amount of the compound is effective to enhance the anti-cancer activity of the ionizing radiation, x-radiation, docetaxel or temozolomide.

Example 13

LB-100 Carbonate and LB-100 POM Prodrugs

As demonstrated in the data contained herein LB-100 Carbonate and LB-100 POM are metabolized to endothal in vivo and act as prodrugs of endothal. In addition, while not wishing to be bound to a theory, it is believed that the prodrugs of the present application allow for targeted delivery of endothal to specific cells, i.e. cancer cells, in a subject. Direct administration of endothal is undesirable due to toxicity. The prodrugs provide improved absorption leading to greater bioavailability of the active compound.

An amount of LB-100 Carbonate or LB-100 POM is administered to a subject afflicted with cancer. The amount of the compound is effective to deliver endothal to cancers cells in the subject.

An amount of LB-100 Carbonate or LB-100 POM is administered to a subject afflicted with brain cancer. The amount of the compound is effective to deliver endothal to brain cancers cells in the subject.

An amount of LB-100 Carbonate or LB-100 POM is administered to a subject afflicted with diffuse intrinsic pontine glioma or glioblastoma multiforme. The amount of the compound is effective to deliver endothal to diffuse intrinsic pontine glioma cells or glioblastoma multiforme cells in the subject.

An amount of LB-100 Carbonate or LB-100 POM is administered to a subject afflicted with brain cancer. The amount of the compound is effective to deliver endothal across the blood brain barrier of the subject.

Example 14

Liver and Whole Blood Assays

The stability (whole blood, liver S9, SGF, SIF, and PBS buffer) and MDCK-MDR1 monolayer permeability of LB100, LB-100 Carbonate and LB-100 POM were evaluated.

Analytical Method Development

The analyte signal was optimized for each compound by ESI positive or negative ionization mode. An MS2 scan or an SIM scan was used to optimize the fragmenter voltage and a product ion analysis was used to identify the best fragment for analysis, and the collision energy was optimized using a product ion or MRM scan. An ionization ranking was assigned indicating the compound's ease of ionization.

3.3 Sample Analysis (Chemical Stability, Whole Blood Stability, and S9 Stability Assays)

Sample Analysis (Chemical Stability, Whole Blood Stability, and S9 Stability Assays)

Samples were analyzed by LC-MS/MS using a SCIEX QTrap 5500 mass spectrometer coupled with an Agilent 1290 HPLC Infinity series, a CTC PAL chilled autosampler, all controlled by Analyst software. After separation on a C18 reverse phase HPLC column (Acquity UPLC HSS T3, 1.8, 2.1×50 mm) using an acetonitrile-water gradient system, peaks were analyzed by mass spectrometry (MS) using ESI ionization in MRM mode.

Sample Analysis (MDCK-MDR1 Permeability Assay)

Samples were analyzed by LC/MS/MS using an Xevo II mass spectrometer coupled with an Acquity HPLC and a CTC PAL chilled autosampler, all controlled by MassLynx (Waters). After separation on a C18 reverse phase HPLC column (Waters Acquity UPLC HSS T3 1.8 um 1×50 mM) using an acetonitrile-water gradient system, peaks were analyzed by mass spectrometry (MS) using ESI ionization in MRM mode.

| HPLC Gradient (Chemical Stability, Whole Blood Stability, and S9 Stability Assays) | | | |
|---|---|---|---|
| Time (min) | Flow rate (mL/min) | % A Mobile Phase | % B Mobile Phase |
| 0.05 | 0.6 | 100 | 0 |
| 1.0 | 0.6 | 5 | 95 |
| 1.40 | 0.6 | 5 | 95 |
| 1.41 | 0.6 | 100 | 0 |
| 1.8 | 0.6 | 100 | 0 |

Solution A: $H_2O$ with 0.1% Formic acid;
Solution B: Acetonitrile with 0.1% Formic acid

| HPLC Gradient (MDCK-MDR1 Permeability) | | | |
|---|---|---|---|
| Time (min) | Flow rate (mL/min) | % A Mobile Phase | % B Mobile Phase |
| 0.00 | 0.600 | 99.9 | 0.1 |
| 0.01 | 0.600 | 99.9 | 0.1 |
| 1.0 | 0.600 | 5 | 95 |
| 1.4 | 0.600 | 99.9 | 0.1 |
| 1.8 | 0.600 | 99.9 | 0.1 |

Solution A: $H_2O$ with 0.1% Formic acid;
Solution B: Acetonitrile with 0.1% Formic acid

| Chemical Stability: Experimental Conditions | | | | | |
|---|---|---|---|---|---|
| Test Article | Test conc. | Test conditions | Incubation | Reference compounds | Analytical method |
| LB-151 | 5 μM | PBS buffer (pH 7.4) | 0, 1, 2, and 4 hrs (37° C.) | omeprazole warfarin | LC-MS/MS |
| LB-100 POM Ester | | SGF (pH 1.2) | | | |

-continued

| Chemical Stability: Experimental Conditions | | | | | |
|---|---|---|---|---|---|
| Test Article | Test conc. | Test conditions | Incubation | Reference compounds | Analytical method |
| LB-100 Carbonate | | SIF (pH 6.5) | | | |

| Test Article | Test Conc. | Species | Incubation | Analytical Method |
|---|---|---|---|---|
| LB-151 LB-100 POM Ester LB-100 Carbonate | 5 µM | rat, dog, monkey, and human | 0, 1, 2, and 4 hr (37° C.) | LC-MS/MS |

Experimental Procedure: The compound was incubated in duplicate with either PBS buffer (pH 7.4), SGF (pH 1.2) or SIF (pH 6.5) at 37° C. At the indicated times, an aliquot was removed from each experimental reaction and mixed with three volumes of ice-cold Stop Solution (methanol containing propranolol/diclofenac/bucetin as analytical internal standards). Stopped reactions were incubated for ten minutes at −20° C. The samples were centrifuged, and the supernatants were analyzed by LC/MS/MS to quantitate the remaining parent as well as the formation of metabolites. Data was converted to % remaining by dividing by the time zero concentration value. Data were fit to a first-order decay model to determine half-life.

Liver S9 Stability: Experimental Conditions

Experimental Procedure: Test agent is incubated in duplicate with liver S9 at 37° C. The reaction contains liver S9 protein in 100 mM potassium phosphate, 2 mM NADPH, 3 mM $MgCl_2$, pH 7.4. A control is run for each test agent omitting NADPH to detect NADPH-free degradation. At indicated times, an aliquot is removed from each experimental and control reaction and mixed with an equal volume of ice-cold Stop Solution (methanol, containing internal standard propranolol). Stopped reactions are incubated for 10 minutes at −20° C. Samples are centrifuged to remove precipitated protein, and supernatants are analyzed by LC/MS/MS to quantitate remaining parent and the formation of metabolites. Data are reported as % remaining by dividing by the time zero concentration value.

MDCK-MDR1 Permeability: Experimental Conditions

Experimental Procedure: MDCK-MDR1 cells grown in tissue culture flasks are trypsinized, suspended in medium, and the suspensions were applied to wells of a Millipore 96 well plate. The cells are allowed to grow and differentiate for three weeks, feeding at 2-day intervals. For Apical to Basolateral (A-B) permeability, the test agent is added to the apical (A) side and amount of permeation is determined on the basolateral (B) side; for Basolateral to Apical (B-A) permeability, the test agent is added to the B side and the amount of permeation is determine on the A side. The A-side buffer contains 100 µM Lucifer yellow dye, in Transport Buffer (1.98 g/L glucose in 10 mM HEPES, 1× Hank's Balanced Salt Solution) pH 7.4, and the B-side buffer is Transport Buffer at pH 7.4. MDCK-MDR1 cells are incubated with these buffers for 2 hr, and the receiver side buffer is removed for analysis by LC/MS/MS (using propranolol as an analytical internal standard). To verify the MDCK-MDR1 cell monolayers are properly formed, aliquots of the cell buffers are analyzed by fluorescence to determine the transport of the impermeable dye Lucifer Yellow. Any deviations from control values are reported.

Mass Spectrometry Method Development: MS/MS

Metabolites of LB-151 (LB-100, Endothal, and Endothal methyl ester), LB-100 Carbonate (LB-100 and Endothal) and LB-100 POM (LB-100 and Endothal) were monitored.

| Test Article | Test Conc | S9 Species | Protein Conc | Incubation | Reference Compound | Analytical Method |
|---|---|---|---|---|---|---|
| LB-151 LB-100 POM Ester LB-100 Carbonate | 1 µM | Rat, monkey, and human | 1.0 mg/mL | 0, 1, 2, and 4 hr (37° C.) | verapamil warfarin | LC-MS/MS |

Whole Blood Stability: Experimental Conditions

Experimental Procedure: The stock solution was first diluted in acetonitrile at a concentration that is 100× of the desired final concentration. It was incubated in duplicate with whole blood at 37° C. At indicated times, an aliquot was removed from each experimental and control reaction and mixed with three volumes of ice-cold Stop Solution (methanol containing propranolol as internal standard). Stopped reactions were incubated at least ten minutes at −20° C. The samples were centrifuged to remove precipitated protein, and the supernatants were analyzed by LC-MS/MS to quantitate the remaining parent and the formation of metabolites.

Data were converted to % remaining by dividing by the time zero concentration value. Data were fit to a first-order decay model to determine half-life.

| Test Article | MW | ESI Polarization | Precursor m/z | Product m/z | Ionization Classification |
|---|---|---|---|---|---|
| LB-151 | 282.34 | positive | 283.15 | 251.153 | 1 |
| LB-100 POM Ester | 382.46 | positive | 383.196 | 251.17 | 1 |
| LB-100 Carbonate | 370.4 | positive | 371.153 | 251.137 | 1 |
| Monitored Metabolites | | | | | |
| LB-100 | 268.31 | positive | 269.171 | 251.138 | 1 |
| Eudothall | 186.16 | negative | 184.986 | 140.92 | 1 |
| Eudothall methyl ester | 200.19 | negative | 198.94 | 110.89 | 1 |

1 = highly ionizable,
2 = intermediate,
3 = pooly ionizable
m/z: mass-to-charge ratio of analyte In the liver S9 Stability study, metabolites LB-100 and endothal were observed in both LB-100 carbonate and LB-100 POM ester in the presence and absence of NADPH (cross species), suggesting that these metabolites were formed by non-NADPH dependent enzymes (e.g. esterases and amidases). No metabolites were observed in LB-151 samples (see FIG. 5). The LB-100 carbonate and LB-100 POM ester metabolites were studied in rat, dog, monkey and human (see FIG. 6).

In the whole blood half-life study, formation of endothall and LB-100 were observed in LB-100 carbonate and LB-100 POM ester (cross species). No metabolites were detected in LB-151 (see FIG. 7). In the whole blood metabolite study, LB-100 carbonate and LB-100 POM ester were metabolized to endothall and LB-100 in rat, dog, monkey and human (see FIG. 8).

In the MDCK-MDR1 permeability study, no metabolites were observed in all samples (see FIG. 9).

DISCUSSION

Inhibition of PP2A interferes with multiple aspects of the DNA damage repair (DDR) mechanisms and with exit from mitosis. These mechanisms sensitize cancer cells to cancer treatments that cause acute DNA injury. Compound 100 (see U.S. patent publication No. 7,998,957 B2) has anti-cancer activity when used alone (Lu et al. 2009a) and significantly potentiates in vivo, without observable increase in toxicity, the anti-tumor activity of standard cytotoxic anti-cancer drugs including temozolomide (Lu et al. 2009b, Martiniova et al. 2010), doxorubicin (Zhang et al. 2010), and docetaxel. 100 was recently approved for Phase I clinical evaluation alone and in combination with docetaxel and is in clinical trial.

Compound 100 is a serine-threonine phosphatase inhibitor that potentiates the activity of standard chemotherapeutic drugs and radiation. The mechanism of potentiation is impairment of multiple steps in a DNA-damage repair process and inhibition of exit from mitosis. Compound 100 has been shown to potentiate the activity of temozolomide, doxorubicin, taxotere, and radiation against a variety of human cancer cell lines growing as subcutaneous xenografts. Compound 100 treatment yields a radiation dose enhancement factor of 1.45. Mice bearing subcutaneous (sc) xenografts of U251 human GBM cells were treated with compound 100 intraperitoneally together with radiation, each given daily for 5 days×3 courses. The drug/radiation combination was no more toxic that radiation alone and eliminated 60% of the xenografts (6 months plus follow-up). The remaining 40% of xenografts treated with the combination recurred two months later than xenografts treated with radiation alone. Wei et al. (2013) showed that inhibition of PP2A by compound 100 enhanced the effectiveness of targeted radiation in inhibiting the growth of human pancreatic cancer xenografts in an animal model. Thus, 100 would seem to be an ideal agent to combine with radiation to treat localized cancers such as brain tumors.

Compound 100 is highly effective against xenografts of human gliomas in combination with temozolomide and/or radiation. Compound 100, which has an $IC_{50}$ of 1-3 µM for a broad spectrum of human cancer cell lines, is a highly water soluble zwitterion that does not readily pass the blood brain barrier (BBB) as determined in rats and non-human primates. GLP toxokinetic studies of compound 100 given intravenously daily×5 days were performed in the rat and dog. The major expected toxicities at clinically tolerable doses expected to inhibit the target enzyme, PP2A, in vivo (3-5 mg/m$^2$) are reversible microscopic renal proximal tubule changes and microscopic alterations in epicardial cells. It is of interest that fostriecin, a natural-product selective inhibitor of PP2A, was evaluated given iv daily for 5 days in phase I trials several years ago. Dose limiting toxicity was not achieved before the studies were terminated for lack of a reliable drug supply. In those studies, the major toxicities were reversible non-cumulative increases in serum creatinine and hepatic enzymes.

Compound 100 is considered stable relative to verapamil in the presence of mouse, rat, dog, monkey, and human microsomes. Compound 100 is poorly absorbed from or broken down in the gut so that little is present in plasma after oral administration. In glp studies in the male and female Sprague Dawley rat, the PK parameters for compound 100 given by slow iv bolus daily×5 days were also dose dependent and comparable on day 1 and day 4. The values for female rats after drug at 0.5, 0.75, and 1.25 mg/kg on day 4 were respectively: $C_o$ (ng/ml) 1497, 2347, and 3849; $AUC_{last}$ (ng·h/ml) 452, 691, and 2359; SC $AUC_{last}$ (ng·h/ml) 17.7, 54.0, and 747; DN $AUC_{last}$ 904, 921, and 1887; AUC* (ng·h/ml) 479, 949, and 2853; % AUC* Extrapolated 5.6, 27, and 17; $T_{1/2}$ (h) 0.25, 0.59, and 1.8; Cl (mL/h/kg) 1045, 790, 438 (MALE 1071, 1339, 945); $V_z$ (ml/kg) 378, 677, and 1138. In GLP studies in the male and female dog, the toxicokinetic parameters for compound 100 given iv over 15 minutes daily for 5 days were dose dependent and comparable on day 1 and day 4. The values for the female dogs on after drug at 0.15, 0.30, and 0.50 mg/kg on day 4 were respectively: $C_o$ (ng/ml) 566, 857, and 1930; $AUC_{last}$ (ng·h/ml) 335, 1020, and 2120; $C_{max}$ (ng/ml) 370, 731, 1260; $T_{max}$ (hr) 0.25, 0.35, and 0.25; and, $T_{1/2}$ (h) 0.47, 0.81, and 1.2 (IND No. 109,777: compound 100 for Injection). Inhibition of the abundant PP2A in circulating white blood cells (isolated by Ficoll-Hypaque) has been shown to be dose dependent in the rat following slow iv administration of 100 at 0.375, 0.75, and 1.5 mg/kg resulting 9, 15 and 25% inhibition, respectively.

The methyl ester of 100, compound 151, which has an oral bioavailability of about 60% versus 1% for compound 100, was given by mouth to rats. Compound 151 treatment resulted in substantial levels of compound 100 in the plasma with an apparently much greater half life compared with 100 given intravenously.

Based on the data contained in Examples 8-11, compounds 105, 113, 153 and 157 are converted to endothal in the plasma when administered to rats. Accordingly, compounds 105, 113, 151, 153 and 157 and derivative thereof are useful as prodrugs of endothal. The compounds of the present application contain different substituents which are cleaved in vivo when administered to a subject thereby releasing endothall. These compound contain X or Y groups which are more efficiently cleaved in vivo.

Diffuse Intrinsic Pontine Glioma (DIPG) is a uniformly fatal brain tumor of children for which no standard treatment other that radiation is available. Pediatric neurooncologists believe it is appropriate to treat even previously untreated patients on an investigational protocol that offers a new approach. There has been no advance in overall survival in Glioblastoma Multiforme (GBM) patients since the definite but marginal improvement shown years ago by the addition of temozolomide to radiation after surgery. Recurrent GBM is often treated with Avastin as second line therapy but following relapse after Avastin, experimental treatment is the standard. Of interest concerning inhibition of PP2A in brain tumors is the recent report that increased levels of PP2A are present in GBM and that patients with the highest levels of PP2A in their gliomas have the worst prognosis (Hoffstetter et al., 2012).

As shown in PK and PD studies presented herein, LB-100 itself enters tissues and is converted in part to endothall in tissues. As an inhibitor of the purified target protein of LB-100, protein phosphatase PP2A, endothal is potent with an $IC_{50}$ of ~90 nM. In vivo, endothall has a longer half-life that LB-100 on the order of 6 hours compared to about 1 hour or less for LB-100. Thus LB-100 is both an active anti-cancer agent in itself and by its in vivo conversion to endothal increases the effective duration of inhibition of the intended target, PP2A, in tissue. A half-life of several hours of activity is clinically more desirable that much shorter durations. Modification of substituents of LB-100 provide opportunities to further enhance the clinical usefulness of LB-100 by for example improving oral absorption, uptake into specific organs bearing the disease process, for example, the brain, and further modifying the the rate of conversion for effective delivery of parent compound and/or endothall to tissue.

REFERENCES

Bastien et al. (2004), Gene, Vol. 328, pp. 1-16.
Giannini, R. and Cvallini, A. (2005) Anticancer Research Vol. 36, No. 6B, pp. 4287-4292.
Graziano, M. J. and Casida, J. E. (1987) Toxicol Lett. 37, 143-148.
Havrilesky, L J et al. (2001) J. Soc. Gynecology. Investig. Vol. 8, pp. 104-113.
Hawkins C E et al (2011) Journal of Clinical Oncology, Vol 29, No. 30, 3954-3956.
Hermanson et al. (2002) Nature, Vol. 419, pp. 934-939.
Hofstetter C P et al (2012) PLoS ONE 7(1):1-11.
Honkanan, R. E. et al. (1993) FEBS Lett. 330, 283-286.
Li, Y. M. et al. (1992) Proc. Natl. Acad. Sci. USA, 89, 11867-11870.
Li, Y. M. et al. (1993) Biochem. Pharmacol. 46, 1435-1443.
Lu J et al (2009a) J Neurosurgery Vol. 113, No. 2, Pages 225-233.
Lu J et al (2009b) PNAS 106(28), 11697-11702.
Martiniova L et al (2011) PLoS ONE 6(2):1-8.
Myers, E. et al. (2005) Clin. Cancer Res. Vol. 11, pp. 2111-2122.
Park D M et al (2007) Cell Cycle 6(4):467-470.
Stupp R et al (2009) Lancet Oncol 10:459-466.
Thiery J P, et al. (1999) Hepatology, 29, 1406-17.
Tsauer, W. et al. (1997) Anticancer Research 17, 2095-2098.
Wang, D. S. (1989) Journal of Ethnopharmacology 26, 147-162.
Warren K et al (2012) Cancer 118:3607-3613.
Waters, C E et al. (2004) J. Endocrinol. Vol. 183, pp. 375-383.
Wei et al (2013) Clin. Cancer Res. 19, 4422-4432.
Ynag, Y. et al. (2011) Acta Pharmaceutica Sinica B, 1(3), 143-159.
Zhang C et al (2010) Biomaterials 31, 9535-9543.
Zhuang Z et al (2009) Cell Cycle 8(20):3303-3306.

What is claimed is:

1. A compound having the structure:

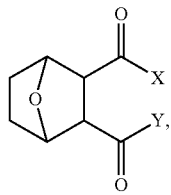

wherein
X is

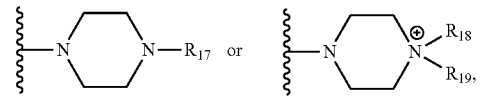

$R_{17}$ is H, alkyl, hydroxyalkyl, alkenyl, alkenyl, alkynyl, aryl, alkylaryl, heteroaryl, alkylaryheteroaryl, C(O)O-t-Bu or —$CH_2CN$;
$R_{18}$ is H or alkyl;
$R_{19}$ is ($C_1$-$C_4$ alkyl)-O(CO)$R_4$, ($C_1$-$C_4$ alkyl)-O(CO)O$R_4$, ($C_1$-$C_4$ alkyl)-OP(O)(O$R_4$)$_2$, ($C_1$-$C_4$ alkyl)-OP(O)(O($C_1$-$C_4$ alkyl)-O(CO)O$R_4$)$_2$, ($C_1$-$C_4$ alkyl)-OP(O)(O($C_1$-$C_4$ alkyl)-O(CO)$R_4$)$_2$, ($C_1$-$C_4$ alkyl)NR$_4$R$_5$, ($C_1$-$C_4$ alkyl)NC(O)R$_4$, ($C_1$-$C_4$alkyl)C(O)OR$_4$, ($C_1$-$C_4$ alkyl)OC(O)aryl($C_1$-$C_4$ alkyl)P(O)(OR$_4$)$_2$, ($C_1$-$C_4$ alkyl)OC(O)($C_2$-$C_4$ alkenyl)CO$_2$R$_4$, ($C_1$-$C_4$ alkyl)OC(O)($C_1$-$C_4$ alkyl)NH$_2$, ($C_1$-$C_4$ alkyl)C(O)NR$_4$R$_5$,

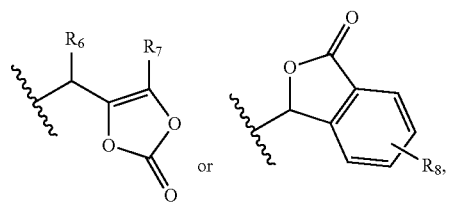

wherein each occurrence of $R_4$ is, independently, H, alkyl, alkenyl, alkynyl, aryl or heteroaryl;
wherein each occurrence of $R_5$ is, independently, H, alkyl, alkenyl, alkynyl, aryl or heteroaryl;
wherein each occurrence of $R_6$ and $R_7$ is, independently, H, alkyl, alkenyl, alkynyl, aryl or heteroaryl;
wherein each occurrence of $R_8$ is, independently, H, halogen, alkyl, alkenyl, alkynyl, aryl or heteroaryl; and
Y is OR$_9$ or NR$_{10}$R$_{11}$,
wherein
$R_9$ is ($C_1$-$C_4$ alkyl)-O(CO)R$_{12}$, ($C_1$-$C_4$ alkyl)-O(CO)OR$_{12}$, ($C_1$-$C_4$ alkyl)-OP(O)(OR$_{12}$)$_2$, ($C_1$-$C_4$ alkyl)-OP(O)(O($C_1$-$C_4$ alkyl)-O(CO)OR$_{12}$)$_2$, ($C_1$-$C_4$ alkyl)-OP(O)(O($C_1$-$C_4$ alkyl)-O(CO)R$_{12}$)$_2$, ($C_1$-$C_4$ alkyl)NR$_{12}$R$_{13}$, ($C_1$-$C_4$ alkyl)NHC(O)R$_{12}$, ($C_1$-$C_4$ alkyl)C(O)OR$_{12}$, ($C_1$-$C_4$ alkyl)OC(O)aryl($C_1$-$C_4$ alkyl)P(O)(OR$_{12}$)$_2$, ($C_1$-$C_4$ alkyl)OC(O)($C_2$-$C_4$ alkenyl)CO$_2$R$_{12}$, ($C_1$-$C_4$ alkyl)OC(O)($C_1$-$C_4$ alkyl)NH$_2$, ($C_1$-$C_4$ alkyl)C(O)NR$_{12}$R$_{13}$,

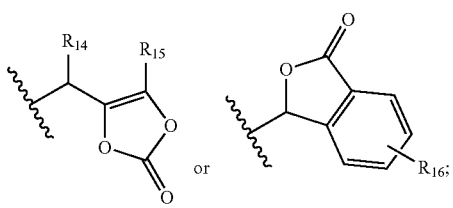

$R_{10}$ is H; and
$R_{11}$ is ($C_1$-$C_4$ alkyl)-O(CO)R$_{12}$, ($C_1$-$C_4$ alkyl)-O(CO)OR$_{12}$, ($C_1$-$C_4$ alkyl)-OP(O)(OR$_{12}$)$_2$, ($C_1$-$C_4$ alkyl)-

OP(O)(O(C$_1$-C$_4$ alkyl)-O(CO)OR$_{12}$)$_2$, (C$_1$-C$_4$ alkyl)-OP(O)(O(C$_1$-C$_4$ alkyl)-O(CO)R$_{12}$)$_2$, (C$_1$-C$_4$ alkyl)NR$_{12}$R$_{13}$, (C$_1$-C$_4$ alkyl)NHC(O)R$_{12}$, (C$_1$-C$_4$ alkyl)C(O)OR$_{12}$, (C$_1$-C$_4$ alkyl)OC(O)aryl(C$_1$-C$_4$ alkyl)P(O)(OR$_{12}$)$_2$, (C$_1$-C$_4$ alkyl)OC(O)(C$_2$-C$_4$ alkenyl)CO$_2$R$_{12}$, (C$_1$-C$_4$ alkyl)OC(O)(C$_1$-C$_4$ alkyl)NH$_2$, (C$_1$-C$_4$ alkyl)C(O)NR$_{12}$R$_{13}$,

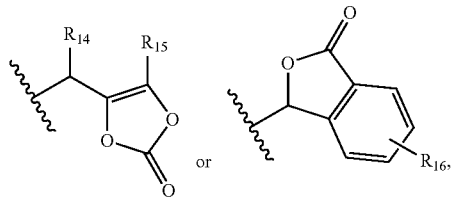

wherein each occurrence of R$_{12}$ is, independently, H, alkyl, alkenyl, alkynyl, aryl or heteroaryl;

wherein each occurrence of R$_{13}$ is, independently, H, alkyl, alkenyl, alkynyl, aryl or heteroaryl;

wherein each occurrence of R$_{14}$ and R$_{15}$ is, independently, H, alkyl, alkenyl, alkynyl, aryl or heteroaryl; and wherein each occurrence of R$_{16}$ is, independently, H, halogen, alkyl, alkenyl, alkynyl, aryl or heteroaryl, wherein when X is

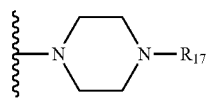

where R$_{17}$ is CH$_3$, then Y is other than —O(C$_4$ alkyl)-OP(O)(OEt)$_2$ or —NH(C$_4$ alkyl)-OP(O)(OEt)$_2$, or a salt or ester of the compound.

2. The compound of claim 1 having the structure:

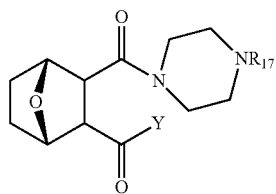

wherein

R$_{17}$ is H, alkyl, hydroxyalkyl, alkenyl or alkylaryl;

Y is OR$_9$ or NR$_{10}$R$_{11}$, wherein R$_9$ is (C$_1$-C$_4$ alkyl)-O(CO)R$_{12}$, (C$_1$-C$_4$ alkyl)-O(CO)OR$_{12}$, (C$_1$-C$_4$ alkyl)-OP(O)(OR$_{12}$)$_2$, (C$_1$-C$_4$ alkyl)-OP(O)(O(C$_1$-C$_4$ alkyl)-O(CO)OR$_{12}$)$_2$, (C$_1$-C$_4$ alkyl)-OP(O)(O(C$_1$-C$_4$ alkyl)-O(CO)R$_{12}$)$_2$, (C$_1$-C$_4$ alkyl)NR$_{12}$R$_{13}$, (C$_1$-C$_4$ alkyl)NHC(O)R$_{12}$, (C$_1$-C$_4$ alkyl)C(O)OR$_{12}$, (C$_1$-C$_4$ alkyl)OC(O)aryl(C$_1$-C$_4$ alkyl)P(O)(OR$_{12}$)$_2$, (C$_1$-C$_4$ alkyl)OC(O)(C$_2$-C$_4$ alkenyl)CO$_2$R$_{12}$, (C$_1$-C$_4$ alkyl)OC(O)(C$_1$-C$_4$ alkyl)NH$_2$, (C$_1$-C$_4$ alkyl)C(O)NR$_{12}$R$_{13}$,

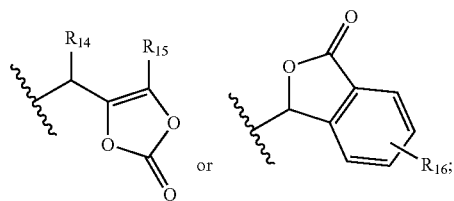

R$_{10}$ is H; and

R$_{11}$ is (C$_1$-C$_4$ alkyl)-O(CO)R$_{12}$, (C$_1$-C$_4$ alkyl)-O(CO)OR$_{12}$, (C$_1$-C$_4$ alkyl)-OP(O)(OR$_{12}$)$_2$, (C$_1$-C$_4$ alkyl)-OP(O)(O(C$_1$-C$_4$ alkyl)-O(CO)OR$_{12}$)$_2$, (C$_1$-C$_4$ alkyl)-OP(O)(O(C$_1$-C$_4$ alkyl)-O(CO)R$_{12}$)$_2$, (C$_1$-C$_4$ alkyl)NR$_{12}$R$_{13}$, (C$_1$-C$_4$ alkyl)NC(O)R$_{12}$, (C$_1$-C$_4$ alkyl)C(O)OR$_{12}$, (C$_1$-C$_4$ alkyl)OC(O)aryl(C$_1$-C$_4$ alkyl)P(O)(OR$_{12}$)$_2$, (C$_1$-C$_4$ alkyl)OC(O)(C$_2$-C$_4$ alkenyl)CO$_2$R$_{12}$, (C$_1$-C$_4$ alkyl)OC(O)(C$_1$-C$_4$ alkyl)NH$_2$, (C$_1$-C$_4$ alkyl)C(O)NR$_{12}$R$_{13}$,

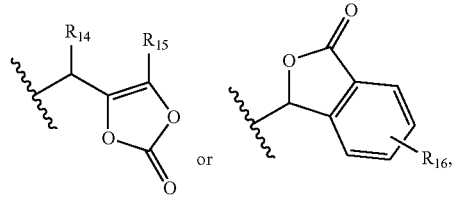

wherein each occurrence of R$_{12}$ is, independently, H, halogen, alkyl, alkenyl, alkynyl, aryl or heteroaryl;

wherein each occurrence of R$_{13}$ is, independently, H, alkyl, alkenyl, alkynyl, aryl or heteroaryl;

wherein each occurrence of R$_{14}$ and R$_{15}$ is, independently, H, alkyl, alkenyl, alkynyl, aryl or heteroaryl;

wherein each occurrence of R$_{16}$ is, independently, H, halogen, alkyl, alkenyl, alkynyl, aryl or heteroaryl.

3. The compound of claim 2 wherein the compound has the structure:

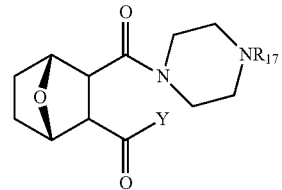

wherein

R$_{17}$ is H, alkyl, hydroxyalkyl, alkenyl or alkylaryl; and

Y is OR$_9$, wherein R$_9$ is

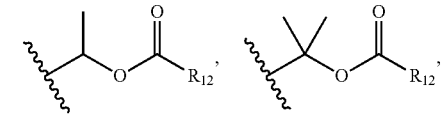

-continued

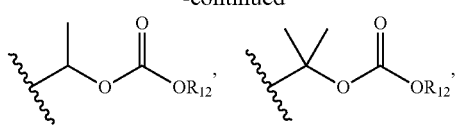
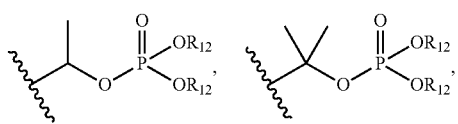
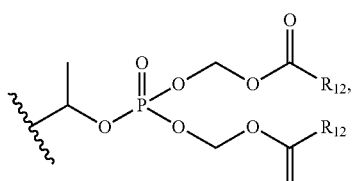
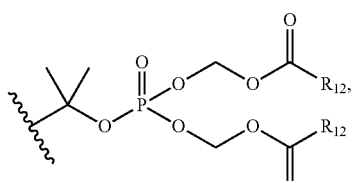
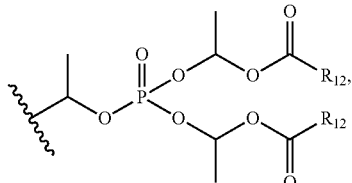
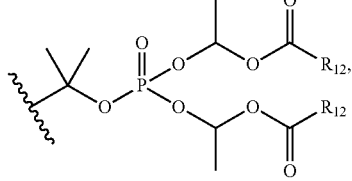
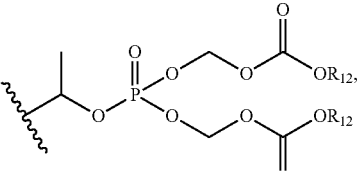
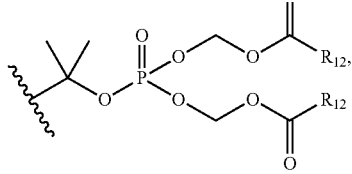
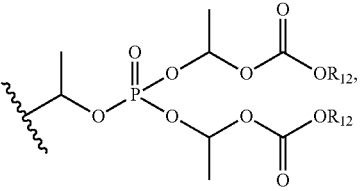

-continued

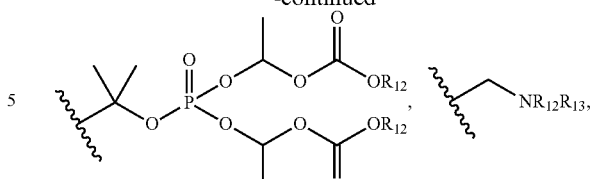
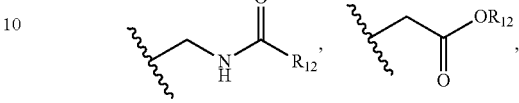
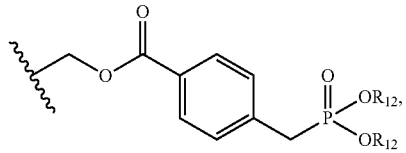
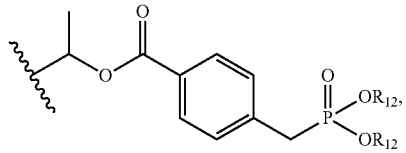
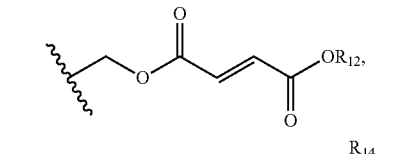
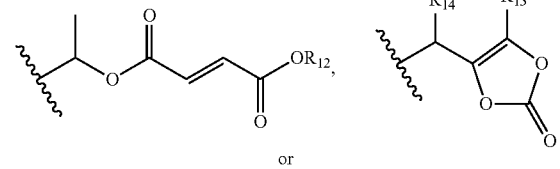

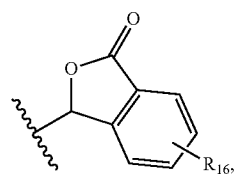

or

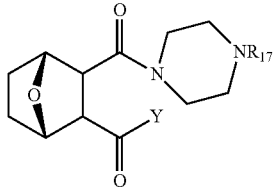

wherein each occurrence of $R_{12}$ is, independently, H, halogen, alkyl, alkenyl, alkynyl, aryl or heteroaryl;

wherein each occurrence of $R_{13}$ is, independently, H, alkyl, alkenyl, alkynyl, aryl or heteroaryl;

wherein each occurrence of $R_{14}$ and $R_{15}$ is, independently, H, alkyl, alkenyl, alkynyl, aryl or heteroaryl;

wherein each occurrence of $R_{16}$ is, independently, H, halogen, alkyl, alkenyl, alkynyl, aryl or heteroaryl.

4. The compound of claim 3 wherein the compound has the structure:

wherein $R_{17}$ is H, methyl, ethyl, $CH_2CH_2OH$, $CH_2(phenyl)$; and

Y is $OR_9$, wherein $R_9$ is

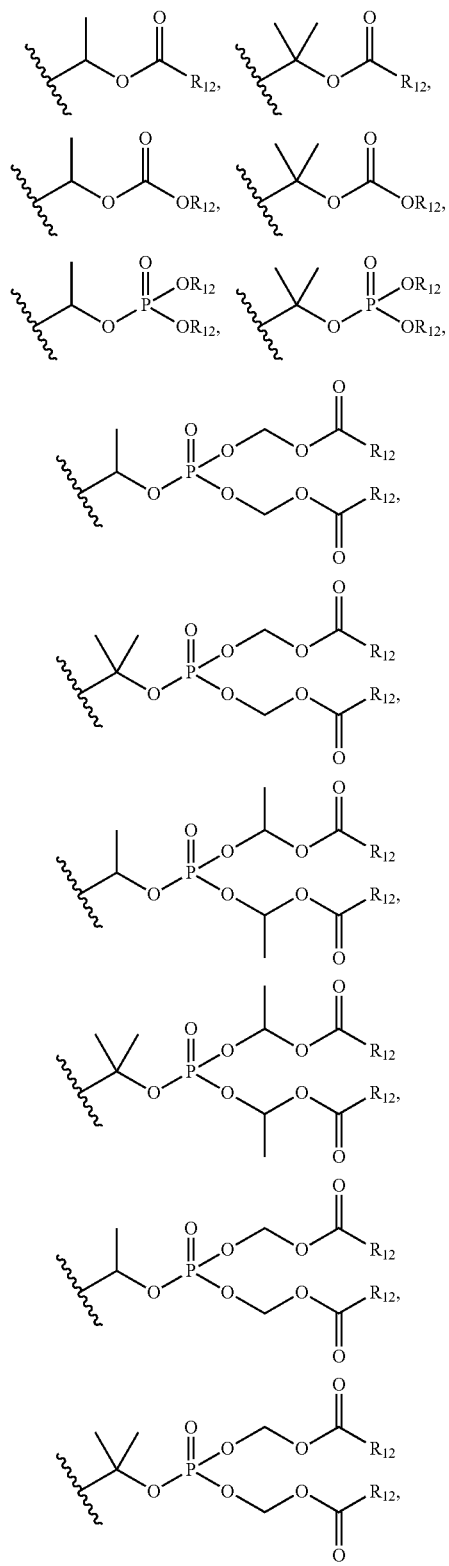

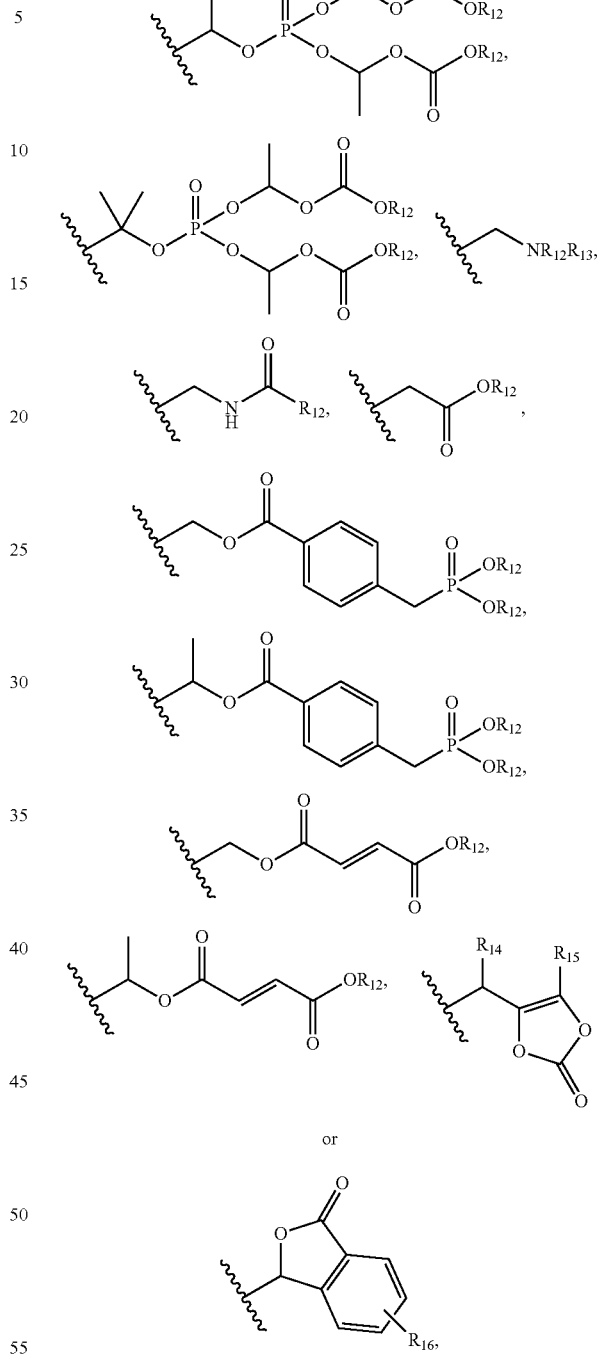

wherein each occurrence of $R_{12}$ is, independently, H, alkyl, alkenyl, alkynyl, aryl or heteroaryl;

wherein each occurrence of $R_{13}$ is, independently, H, alkyl, alkenyl, alkynyl, aryl or heteroaryl;

wherein each occurrence of $R_{14}$ and $R_{15}$ is, independently, H, alkyl, alkenyl, alkynyl, aryl or heteroaryl;

wherein each occurrence of $R_{16}$ is, independently, H, halogen, alkyl, alkenyl, alkynyl, aryl or heteroaryl.

5. The compound of claim 4 having the structure:
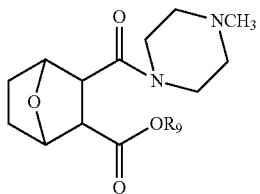
wherein
R₉ is
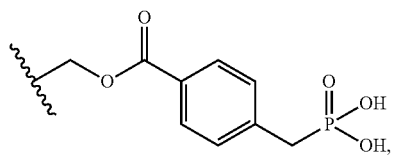
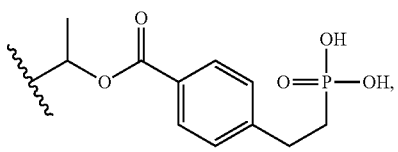
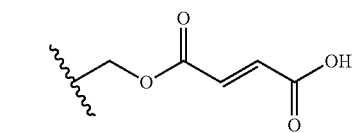
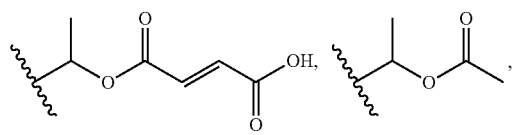
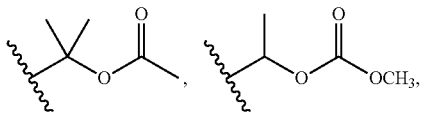
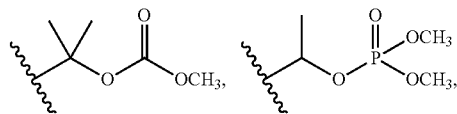
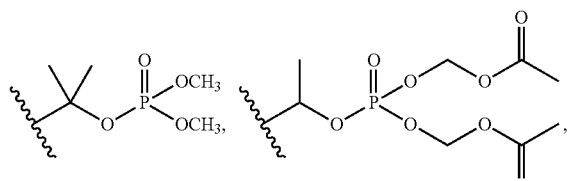
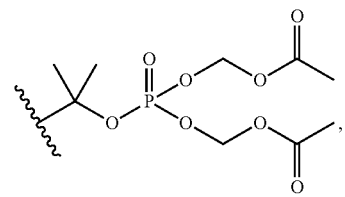
-continued
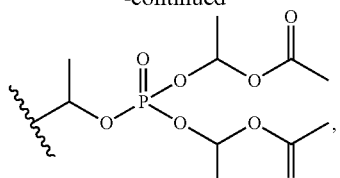
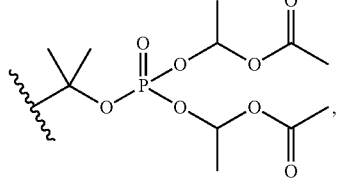
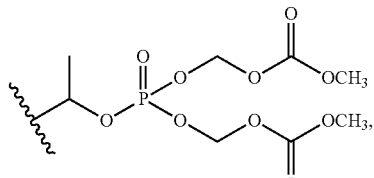
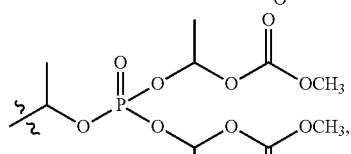
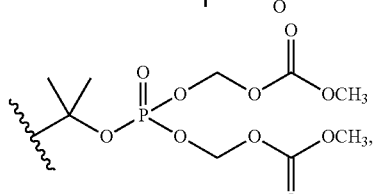
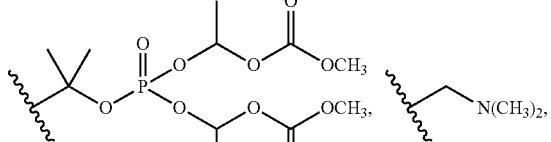
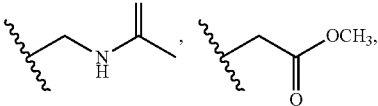
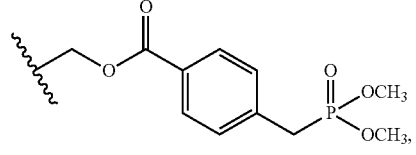
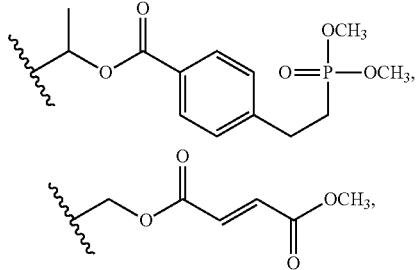

171
-continued
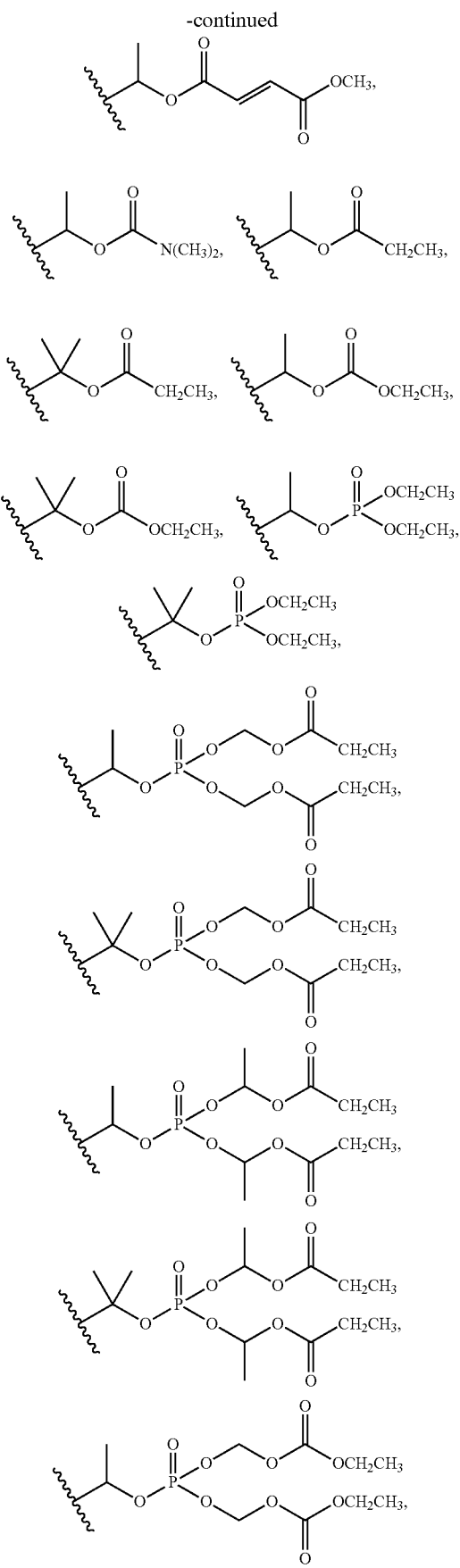
172
-continued
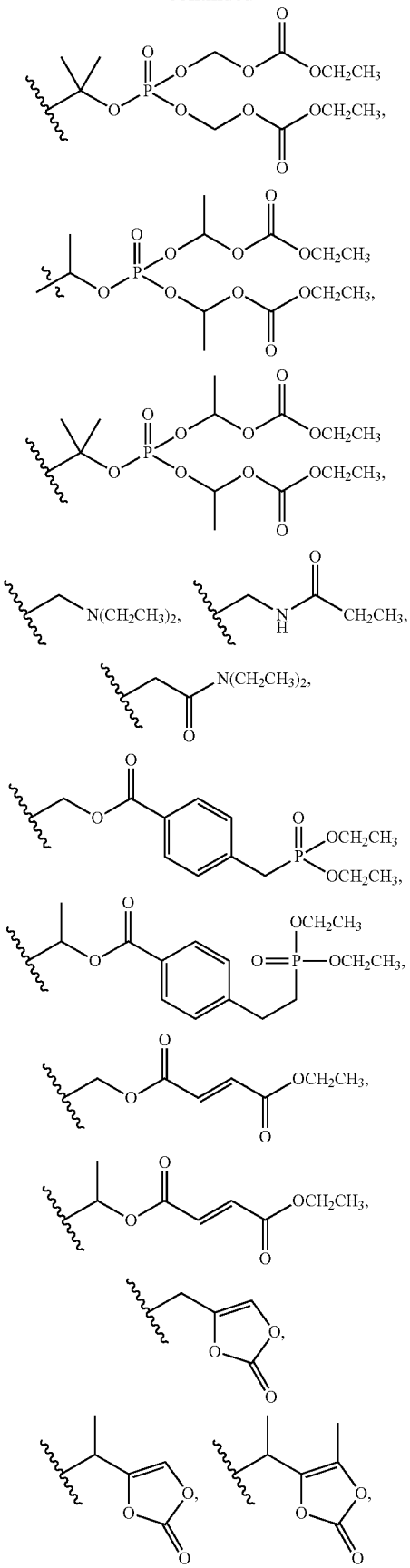

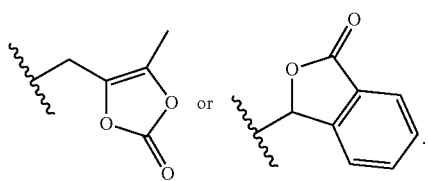 or 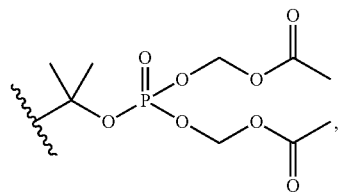
6. The compound of claim 4 having the structure:
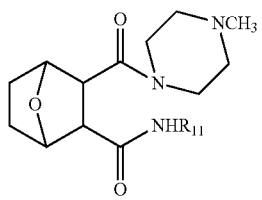
wherein
$R_{11}$ is
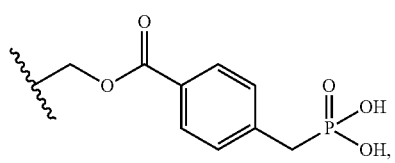
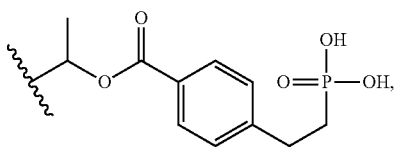
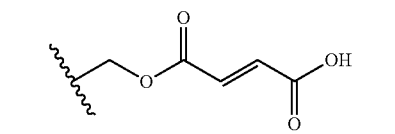
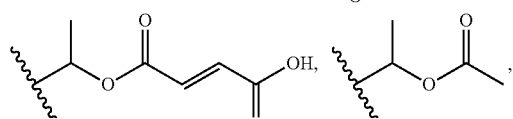
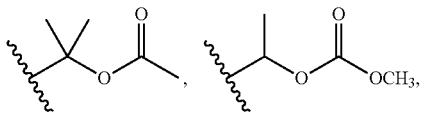
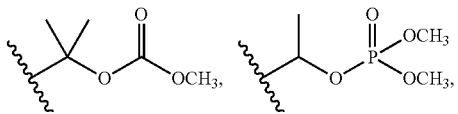
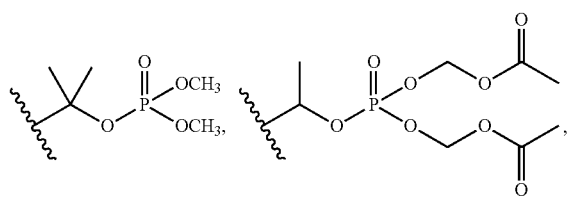
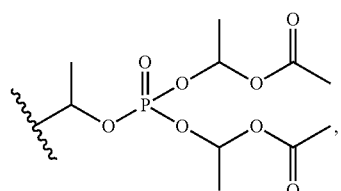
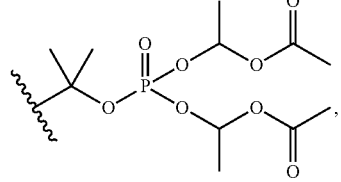
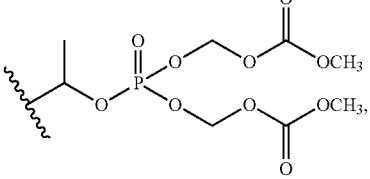
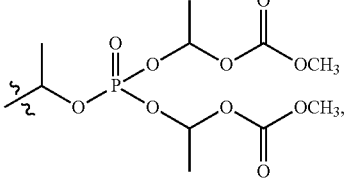
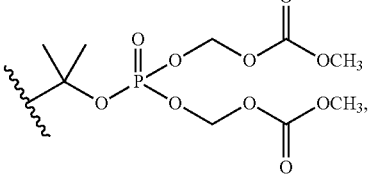
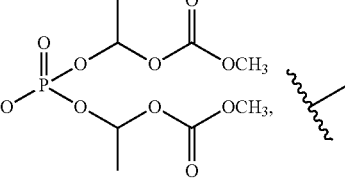
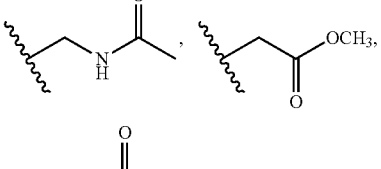
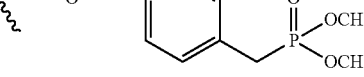

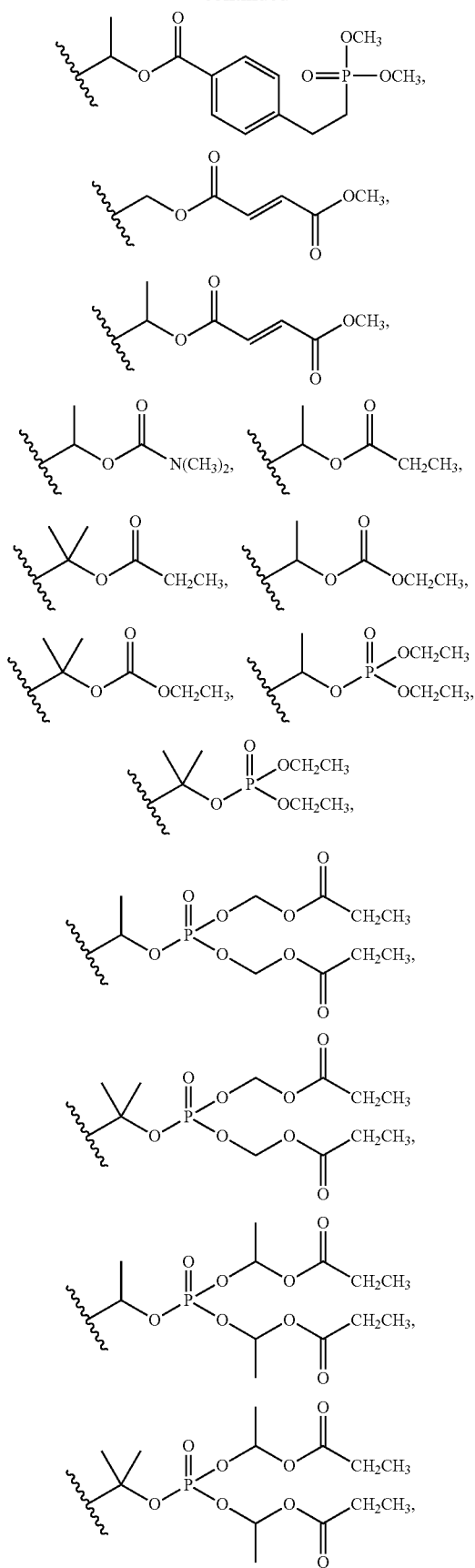
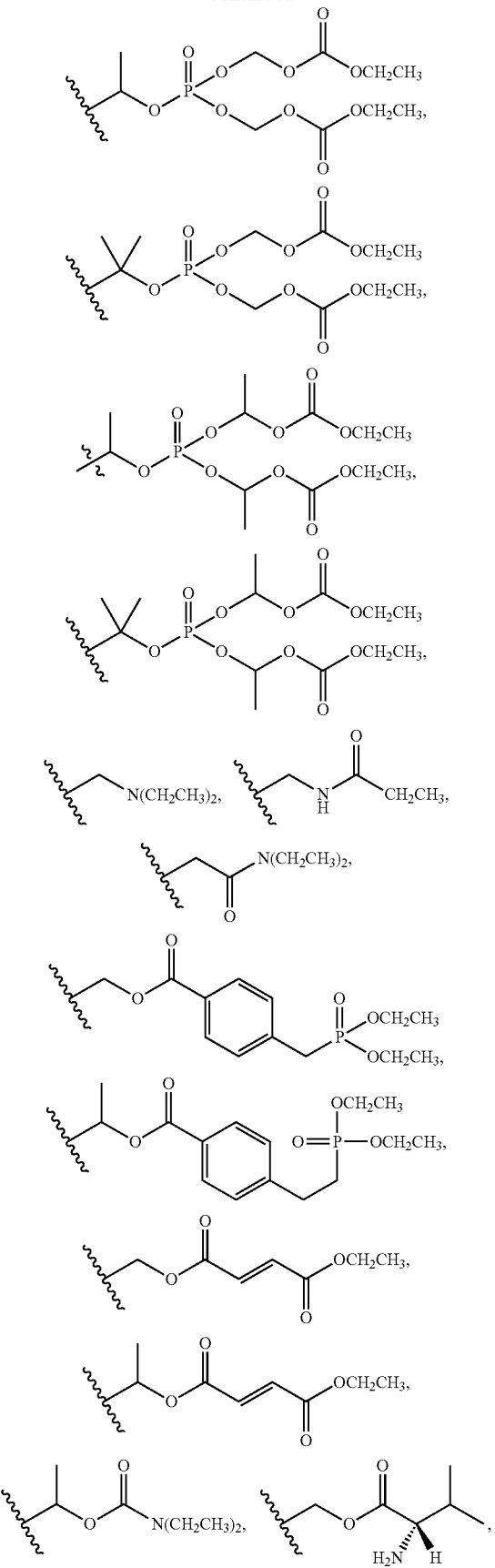

-continued

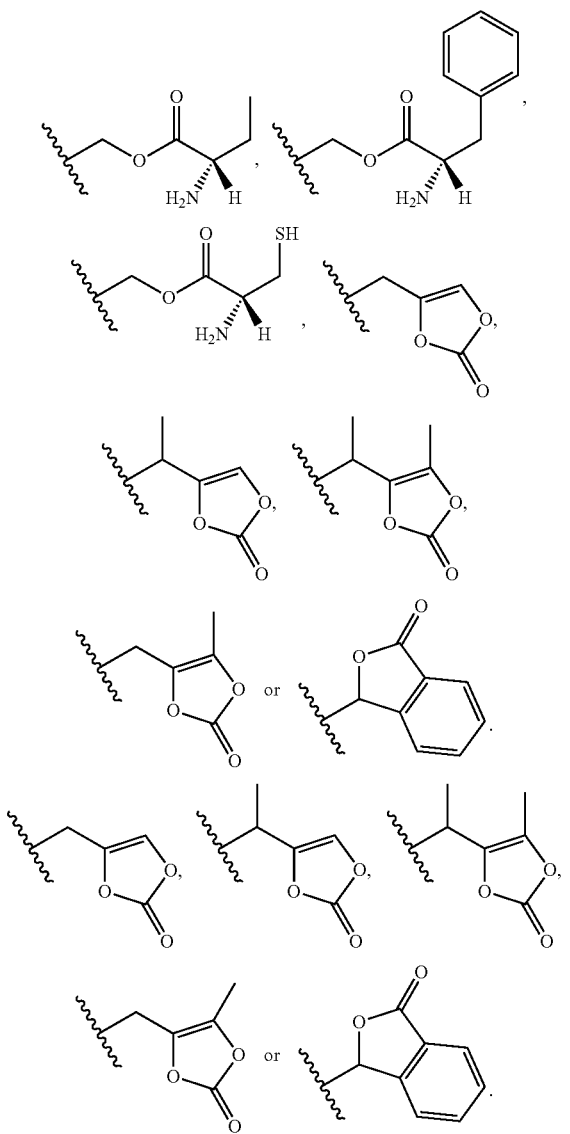

7. The compound of claim 1 having the structure:

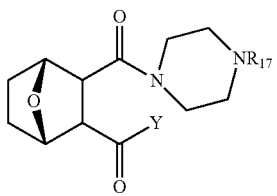

wherein

R$_{17}$ is H, alkyl, hydroxyalkyl, alkenyl, alkenyl, alkynyl, aryl, alkylaryl, heteroaryl, alkylheteroaryl, C(O)O-t-Bu or —CH$_2$CN;

Y is OR$_9$, wherein R$_9$ is (C$_1$-C$_4$ alkyl)-O(CO)R$_{12}$ or (C$_1$-C$_4$ alkyl)-O(CO)OR$_{12}$, wherein each occurrence of R$_{12}$ is, independently, H, alkyl, alkenyl, alkynyl, aryl or heteroaryl.

8. The compound of claim 7 having the structure

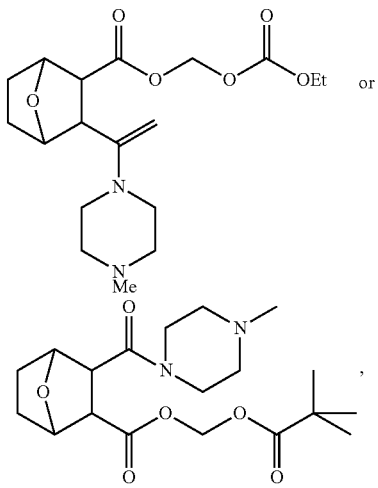

or a salt of the compound.

9. A pharmaceutical composition comprising the compound of claim 1 and a pharmaceutically acceptable carrier.

10. A pharmaceutical composition comprising the compound of claim 1 or a pharmaceutically acceptable salt thereof and an anticancer agent, and at least one pharmaceutically acceptable carrier.

11. The compound of claim 7,
wherein
R$_{17}$ is H, methyl, ethyl, CH$_2$CH$_2$OH, CH$_2$(phenyl); and
Y is OR$_9$, wherein R$_9$ is (C$_1$-C$_4$ alkyl)-O(CO)R$_{12}$ or (C$_1$-C$_4$ alkyl)-O(CO)OR$_{12}$,
wherein each occurrence of R$_{12}$ is, independently, H, alkyl, alkenyl, alkynyl, aryl or heteroaryl.

12. The compound of claim 11,
wherein
R$_{17}$ is H, methyl, ethyl, CH$_2$CH$_2$OH, CH$_2$(phenyl); and
Y is OR$_9$, wherein R$_9$ is (C$_1$-C$_4$ alkyl)-O(CO)R$_{12}$ or (C$_1$-C$_4$ alkyl)-O(CO)OR$_{12}$,
wherein each occurrence of R$_{12}$ is an alkyl.

13. The compound of claim 12,
wherein
R$_{17}$ is methyl; and
Y is OR$_9$, wherein R$_9$ is (C$_1$-C$_4$ alkyl)-O(CO)R$_{12}$ or (C$_1$-C$_4$ alkyl)-O(CO)OR$_{12}$,
wherein each occurrence of R$_{12}$ is an alkyl.

14. The compound of claim 7, wherein Y is OR$_9$, wherein R$_9$ is (C$_1$-C$_4$ alkyl)-O(CO)R$_{12}$.

15. The compound of claim 14, wherein said compound is:

or a pharmaceutically acceptable salt thereof.

16. The compound according to claim 1, wherein said compound is selected from any of the following, or a pharmaceutically acceptable salt thereof:

179
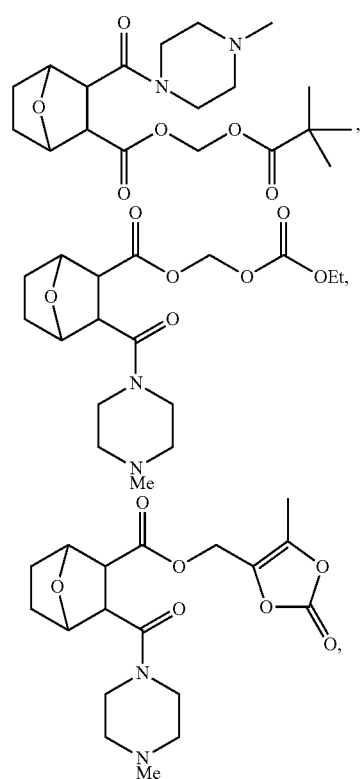
180
-continued
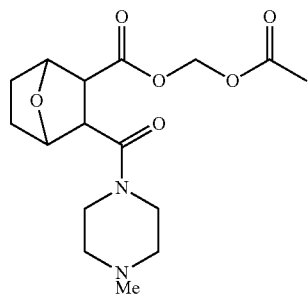
or
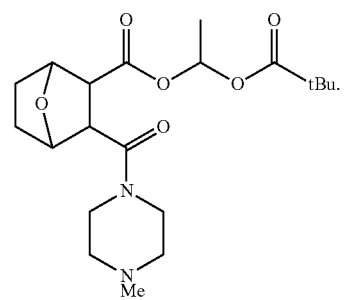
* * * * *

UNITED STATES PATENT AND TRADEMARK OFFICE
CERTIFICATE OF CORRECTION

PATENT NO. : 9,988,394 B2
APPLICATION NO. : 15/154304
DATED : June 5, 2018
INVENTOR(S) : Kovach et al.

Page 1 of 2

It is certified that error appears in the above-identified patent and that said Letters Patent is hereby corrected as shown below:

In the Claims

At Column 169, Line 1, replace "claim 4" with -- claim 1 --

At Column 173, Line 11, replace "claim 4" with -- claim 1 --

At Column 176, Lines 62-66, delete " 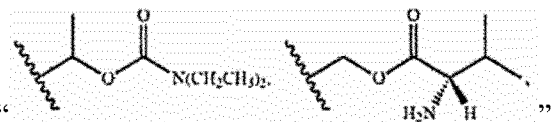 "

At Column 177, Lines 1-9, delete " 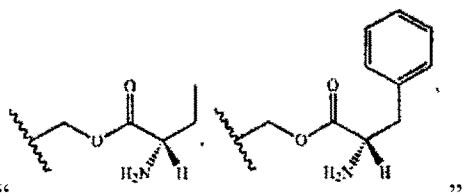 "

At Column 177, Lines 10-15, delete " 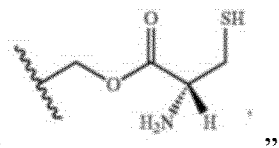 "

Signed and Sealed this
Sixth Day of September, 2022

Katherine Kelly Vidal
*Director of the United States Patent and Trademark Office*

CERTIFICATE OF CORRECTION (continued)
U.S. Pat. No. 9,988,394 B2

At Column 177, Lines 32-44, delete " 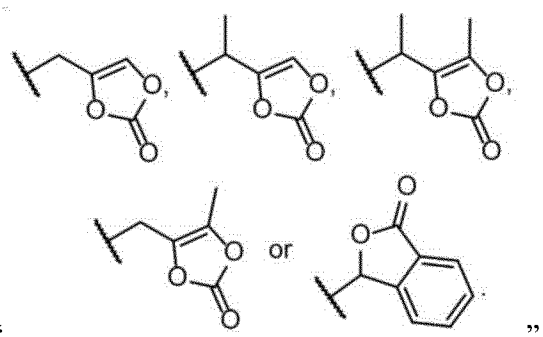 "

At Column 178, Line 1, replace "claim 7" with -- claim 1 --

At Column 178, Lines 2-14, replace " 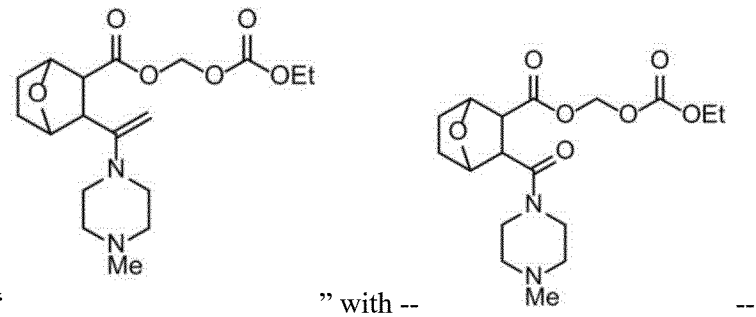 " with -- --

At Column 178, Line 52, replace "claim 14" with -- claim 1 --